(12) United States Patent
LaVon et al.

(10) Patent No.: US 11,925,537 B2
(45) Date of Patent: *Mar. 12, 2024

(54) BEAMED ELASTOMERIC LAMINATE STRUCTURE, FIT, AND TEXTURE

(71) Applicant: The Procter & Gamble Company, Cincinnati, OH (US)

(72) Inventors: Gary D. LaVon, Liberty Township, OH (US); Bret D. Seitz, West Chester, OH (US); Uwe Schneider, Springfield Township, OH (US); Joseph A. Eckstein, Sunman, IN (US); Vanessa M. Melendez, Cincinnati, OH (US); Monica R. Tournoux, Columbus, OH (US); Corinne A. Rowley, Columbus, OH (US); Elizabeth J. Bruns, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/475,577

(22) Filed: Sep. 15, 2021

(65) Prior Publication Data

US 2022/0008255 A1 Jan. 13, 2022

Related U.S. Application Data

(63) Continuation of application No. 16/117,579, filed on Aug. 30, 2018, now Pat. No. 11,147,718, which is a (Continued)

(51) Int. Cl.
*A61F 13/00* (2006.01)
*A61F 13/15* (2006.01)
(Continued)

(52) U.S. Cl.
CPC .. *A61F 13/15601* (2013.01); *A61F 13/15699* (2013.01); *A61F 13/49012* (2013.01);
(Continued)

(58) Field of Classification Search
CPC .......... A61F 13/00; A61F 13/10; A61F 13/15; A61F 13/156; A61F 13/15601;
(Continued)

(56) References Cited

U.S. PATENT DOCUMENTS 3,113,225 A 12/1963 Claus
3,434,189 A 3/1969 Buck et al.
(Continued)

FOREIGN PATENT DOCUMENTS

CA 2158790 A1 3/1996
CN 1461634 A 12/2003
(Continued)

OTHER PUBLICATIONS

3D Nonwovens Developments for textured nonwovens; Sep. 19, 2017, pp. 1-2.
(Continued)

*Primary Examiner* — Jacob T Minskey
*Assistant Examiner* — Matthew Hoover
(74) *Attorney, Agent, or Firm* — Charles R. Matson; Richard L. Alexander

(57) ABSTRACT

The present disclosure relates to stranded elastomeric laminates (including bi-laminates and tri-laminates) comprising beamed elastics and may have inventive Dtex-to-Nonwoven-Basis-Weight-Ratios, Dtex-to-Spacing-Ratios, and/or Void-Area-to-Strand-Area-Ratios. The stranded laminates of the present disclosure may be used for disposable absorbent article components (including pant belts) and may comprise inventive bonding arrangements that yield inventive textures and texture arrangements. When the inventive stranded
(Continued)

elastomeric laminates are used for pant belts, the pants may have inventive Application-Forces, Sustained-Fit-Load-Forces, and Sustained-Fit-Unload-Forces. Further, when absorbent articles are packaged under compression at inventive In-Bag-Stack-Heights, the stranded elastomeric laminates of the present disclosure maintain their inventive properties and characteristics, including their inventive textures.

13 Claims, 74 Drawing Sheets

Related U.S. Application Data continuation-in-part of application No. 16/115,617, filed on Aug. 29, 2018, now Pat. No. 11,129,753, and a continuation-in-part of application No. 15/846,360, filed on Dec. 19, 2017, now Pat. No. 10,987,253, and a continuation-in-part of application No. 15/846,391, filed on Dec. 19, 2017, now Pat. No. 10,966,874, and a continuation-in-part of application No. 15/846,382, filed on Dec. 19, 2017, now Pat. No. 10,966,873, and a continuation-in-part of application No. 15/846,409, filed on Dec. 19, 2017, now Pat. No. 11,000,421, and a continuation-in-part of application No. 15/846,341, filed on Dec. 19, 2017, now Pat. No. 11,000,420, and a continuation-in-part of application No. 15/846,745, filed on Dec. 19, 2017, now abandoned, and a continuation-in-part of application No. 15/846,349, filed on Dec. 19, 2017, now Pat. No. 11,000,426, and a continuation-in-part of application No. 15/846,371, filed on Dec. 19, 2017, and a continuation-in-part of application No. 15/846,433, filed on Dec. 19, 2017, now Pat. No. 10,993,851, and a continuation-in-part of application No. 15/839,896, filed on Dec. 13, 2017, now Pat. No. 11,141,322, and a continuation-in-part of application No. 15/838,405, filed on Dec. 12, 2017, now Pat. No. 11,219,555, and a continuation-in-part of application No. 15/832,929, filed on Dec. 6, 2017, now Pat. No. 11,141,321, and a continuation-in-part of application No. 15/833,057, filed on Dec. 6, 2017, now Pat. No. 11,147,717.

(60) Provisional application No. 62/687,031, filed on Jun. 19, 2018, provisional application No. 62/686,896, filed on Jun. 19, 2018, provisional application No. 62/685,429, filed on Jun. 15, 2018, provisional application No. 62/581,278, filed on Nov. 3, 2017, provisional application No. 62/553,171, filed on Sep. 1, 2017, provisional application No. 62/553,149, filed on Sep. 1, 2017, provisional application No. 62/553,538, filed on Sep. 1, 2017.

(51) Int. Cl.

| | | |
|---|---|---|
| *A61F 13/49* | (2006.01) | |
| *B29C 65/00* | (2006.01) | |
| *B29C 65/48* | (2006.01) | |
| *B32B 5/00* | (2006.01) | |
| *B32B 5/04* | (2006.01) | |
| *D04H 3/00* | (2012.01) | |
| *D04H 3/12* | (2006.01) | |
| *A61F 13/493* | (2006.01) | |
| *A61F 13/513* | (2006.01) | |
| *A61F 13/514* | (2006.01) | |
| *A61F 13/64* | (2006.01) | |
| *B29C 65/08* | (2006.01) | |
| *B29L 31/48* | (2006.01) | |
| *B32B 27/12* | (2006.01) | |
| *B32B 37/12* | (2006.01) | |
| *B32B 37/20* | (2006.01) | |
| *D02G 3/32* | (2006.01) | |

(52) U.S. Cl.
CPC .. *A61F 13/49015* (2013.01); *A61F 13/49017* (2013.01); *A61F 13/49019* (2013.01); *A61F 13/4902* (2013.01); *B29C 65/48* (2013.01); *B29C 66/344* (2013.01); *B29C 66/83411* (2013.01); *B32B 5/04* (2013.01); *D04H 3/12* (2013.01); *A61F 2013/1591* (2013.01); *A61F 2013/49031* (2013.01); *A61F 13/493* (2013.01); *A61F 2013/51322* (2013.01); *A61F 13/51464* (2013.01); *A61F 13/51478* (2013.01); *A61F 13/64* (2013.01); *B29C 65/083* (2013.01); *B29K 2995/0046* (2013.01); *B29L 2031/4878* (2013.01); *B32B 27/12* (2013.01); *B32B 37/12* (2013.01); *B32B 37/20* (2013.01); *B32B 2305/34* (2013.01); *D02G 3/32* (2013.01)

(58) Field of Classification Search
CPC ............ A61F 13/1569; A61F 13/15699; A61F 13/40; A61F 13/49; A61F 13/4901; A61F 13/46901; A61F 13/49015; A61F 13/49017; A61F 13/49019; A61F 13/4902; B29C 65/00; B29C 65/40; B29C 65/48; B29C 66/00; B29C 66/30; B29C 66/34; B29C 66/344; B29C 66/80; B29C 66/83; B29C 66/834; B29C 66/8341; B29C 66/83411; B32B 5/00; B32B 5/04; D04H 3/00; D04H 3/10; D04H 3/12
See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-land |
| 4,610,678 A | 9/1986 | Weisman |
| 4,640,859 A | 2/1987 | Hansen |
| 4,657,539 A | 4/1987 | Hasse |
| 4,673,402 A | 6/1987 | Weisman |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany |
| 4,854,984 A | 8/1989 | Ball |
| 4,888,231 A | 12/1989 | Angstadt |
| 4,909,803 A | 3/1990 | Aziz |
| 4,940,464 A | 7/1990 | Van Gompel et al. |
| 4,984,584 A | 1/1991 | Hansen |
| 5,003,676 A | 4/1991 | Mcfalls |
| 5,060,881 A | 10/1991 | Bogucki-land |
| 5,092,861 A | 3/1992 | Nomura |
| 5,110,403 A | 5/1992 | Ehlert |
| 5,167,897 A | 12/1992 | Weber et al. |
| 5,246,433 A | 9/1993 | Hasse |
| 5,334,289 A | 8/1994 | Trokhan et al. |
| 5,342,341 A | 8/1994 | Igaue |

(56) References Cited

U.S. PATENT DOCUMENTS

| | | |
|---|---|---|
| 5,360,420 A | 11/1994 | Cook et al. |
| 5,393,360 A | 2/1995 | Bridges |
| 5,413,849 A | 5/1995 | Austin et al. |
| 5,514,523 A | 5/1996 | Trokhan |
| 5,531,729 A | 7/1996 | Coles |
| 5,558,658 A | 9/1996 | Menard et al. |
| 5,562,646 A | 10/1996 | Goldman et al. |
| 5,569,234 A | 10/1996 | Buell |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson |
| 5,643,588 A | 7/1997 | Roe |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete |
| 5,827,259 A | 10/1998 | Laux |
| 5,858,504 A | 1/1999 | Fitting |
| 5,887,322 A | 3/1999 | Hartzheim |
| 5,895,623 A | 4/1999 | Trokhan |
| 5,897,545 A | 4/1999 | Kline |
| 5,904,673 A | 5/1999 | Roe et al. |
| 5,916,661 A | 6/1999 | Benson |
| 5,957,908 A | 9/1999 | Kline |
| 5,964,973 A | 10/1999 | Heath et al. |
| 5,968,025 A | 10/1999 | Roe |
| 5,993,433 A | 11/1999 | St. Louis |
| 5,997,521 A | 12/1999 | Robles et al. |
| 6,036,796 A | 3/2000 | Halbert |
| 6,043,168 A | 3/2000 | Colman |
| 6,107,537 A | 8/2000 | Elder |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe |
| 6,319,239 B1 | 11/2001 | Daniels |
| 6,361,638 B2 | 3/2002 | Takai |
| 6,383,431 B1 | 5/2002 | Dobrin et al. |
| 6,395,957 B1 | 5/2002 | Chen |
| 6,410,129 B2 | 6/2002 | Zhang |
| 6,426,444 B2 | 7/2002 | Roe et al. |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie |
| 6,645,330 B2 | 11/2003 | Pargass |
| 6,673,418 B1 | 1/2004 | Deolivera et al. |
| 6,676,054 B2 | 1/2004 | Heaney |
| 6,790,798 B1 | 9/2004 | Suzuki et al. |
| 6,821,301 B2 | 11/2004 | Azuse |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu |
| 7,465,367 B2 | 12/2008 | Day |
| 7,569,039 B2 | 8/2009 | Matsuda |
| 7,582,348 B2 | 9/2009 | Ando |
| 7,642,398 B2 | 1/2010 | Jaerpenberg |
| 7,708,849 B2 | 5/2010 | Mccabe |
| 7,777,094 B2 | 8/2010 | Mori |
| 7,861,756 B2 | 1/2011 | Jenquin |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani |
| 8,093,161 B2 | 1/2012 | Bansal |
| 8,143,177 B2 | 3/2012 | Noda et al. |
| 8,186,296 B2 | 5/2012 | Brown et al. |
| 8,226,625 B2 | 7/2012 | Turner et al. |
| 8,277,430 B2 | 10/2012 | Tabor et al. |
| 8,308,706 B2 | 11/2012 | Fukae |
| 8,377,554 B2 | 2/2013 | Martin |
| 8,388,594 B2 | 3/2013 | Turner et al. |
| 8,440,043 B1 | 5/2013 | Schneider |
| 8,551,608 B2 | 10/2013 | Kawakami et al. |
| 8,585,666 B2 | 11/2013 | Weisman |
| 8,647,319 B2 | 2/2014 | Een |
| 8,729,332 B2 | 5/2014 | Takahashi |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck |
| 9,370,775 B2 | 6/2016 | Harvey |
| 9,732,454 B2 | 8/2017 | Davis et al. |
| 9,758,339 B2 | 9/2017 | Yanez, Jr. |
| 9,795,520 B2 | 10/2017 | Kaneko |
| 9,877,876 B2 | 1/2018 | Huang et al. |
| 10,190,244 B2 | 1/2019 | Ashraf |
| 10,596,045 B2 | 3/2020 | Koshijima |
| 10,792,194 B2 | 10/2020 | Hohm |
| 10,966,874 B2* | 4/2021 | LaVon ................ A61F 13/4902 |
| 10,987,253 B2* | 4/2021 | LaVon ............... A61F 13/49061 |
| 11,147,718 B2* | 10/2021 | LaVon .................... B29C 65/48 |
| 11,547,613 B2* | 1/2023 | Ashraf ............. A61F 13/15764 |
| 2001/0030014 A1 | 10/2001 | Kwok |
| 2002/0026660 A1 | 3/2002 | Goda |
| 2002/0046802 A1 | 4/2002 | Tachibana |
| 2002/0072723 A1 | 6/2002 | Ronn |
| 2002/0099347 A1 | 7/2002 | Chen et al. |
| 2002/0103469 A1 | 8/2002 | Chen et al. |
| 2002/0134067 A1 | 9/2002 | Heaney |
| 2002/0153271 A1 | 10/2002 | McManus |
| 2002/0177829 A1 | 11/2002 | Fell |
| 2003/0022582 A1 | 1/2003 | Cree et al. |
| 2003/0044585 A1 | 3/2003 | Taylor |
| 2003/0070780 A1 | 4/2003 | Chen |
| 2003/0087056 A1 | 5/2003 | Ducker |
| 2003/0089447 A1 | 5/2003 | Molee et al. |
| 2003/0093045 A1 | 5/2003 | Erdman |
| 2003/0119404 A1 | 6/2003 | Belau et al. |
| 2003/0125687 A1 | 7/2003 | Gubernick et al. |
| 2003/0144643 A1 | 7/2003 | Jarpenberg |
| 2003/0199841 A1 | 10/2003 | Ashton et al. |
| 2003/0203162 A1 | 10/2003 | Fenwick et al. |
| 2003/0233082 A1 | 12/2003 | Kline |
| 2004/0006323 A1 | 1/2004 | Hall et al. |
| 2004/0030317 A1 | 2/2004 | Torigoshi |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 | 7/2004 | Mori |
| 2004/0158212 A1 | 8/2004 | Ponomarenko et al. |
| 2004/0158217 A1* | 8/2004 | Wu .................. A61F 13/15593 604/385.01 |
| 2004/0219854 A1* | 11/2004 | Groitzsch ........... A61F 13/4902 442/352 |
| 2004/0230171 A1 | 11/2004 | Ando |
| 2005/0013975 A1 | 1/2005 | Brock |
| 2005/0107764 A1 | 5/2005 | Matsuda et al. |
| 2005/0148971 A1 | 7/2005 | Kuroda et al. |
| 2005/0230037 A1 | 10/2005 | Jenquin |
| 2005/0244640 A1 | 11/2005 | Riswick et al. |
| 2005/0267431 A1 | 12/2005 | Sasaki |
| 2006/0047260 A1 | 3/2006 | Ashton |
| 2006/0069373 A1 | 3/2006 | Schlinz |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando |
| 2007/0026753 A1 | 2/2007 | Neely et al. |

(56) References Cited

U.S. PATENT DOCUMENTS

| | | |
|---|---|---|
| 2007/0045143 A1 | 3/2007 | Clough et al. |
| 2007/0045144 A1 | 3/2007 | Wheeler et al. |
| 2007/0131335 A1 | 6/2007 | Zhou |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba |
| 2008/0287897 A1 | 11/2008 | Guzman |
| 2009/0177176 A1 | 7/2009 | Saito |
| 2009/0204093 A1 | 8/2009 | Vasic |
| 2009/0312730 A1 | 12/2009 | LaVon et al. |
| 2010/0022151 A1 | 1/2010 | Malowaniec |
| 2010/0036346 A1 | 2/2010 | Hammons et al. |
| 2010/0048072 A1 | 2/2010 | Kauschke |
| 2010/0075103 A1 | 3/2010 | Miyamoto |
| 2010/0076394 A1 | 3/2010 | Hayase |
| 2010/0248575 A1 | 9/2010 | Malz |
| 2010/0307668 A1 | 12/2010 | Lange |
| 2011/0092943 A1 | 4/2011 | Bishop |
| 2011/0118689 A1 | 5/2011 | Een |
| 2011/0120897 A1 | 5/2011 | Takahashi |
| 2011/0250378 A1 | 10/2011 | Eaton |
| 2012/0004633 A1 | 1/2012 | R. Marcelo et al. |
| 2012/0061015 A1 | 3/2012 | Lavon et al. |
| 2012/0061016 A1 | 3/2012 | Lavon et al. |
| 2012/0071852 A1 | 3/2012 | Tsang et al. |
| 2012/0095429 A1 | 4/2012 | Kobayashi |
| 2012/0271267 A1 | 10/2012 | Love |
| 2012/0277713 A1 | 11/2012 | Raycheck |
| 2012/0323206 A1 | 12/2012 | Mcmorrow |
| 2013/0032656 A1 | 2/2013 | Yamamoto |
| 2013/0072887 A1 | 3/2013 | Lavon |
| 2013/0102982 A1 | 4/2013 | Nakano |
| 2013/0112584 A1 | 5/2013 | Gaspari |
| 2013/0139960 A1 | 6/2013 | Maruyama et al. |
| 2013/0171421 A1 | 7/2013 | Weisman et al. |
| 2013/0199696 A1 | 8/2013 | Schneider |
| 2013/0199707 A1 | 8/2013 | Schneider |
| 2013/0211356 A1 | 8/2013 | Nishikawa et al. |
| 2013/0211363 A1 | 8/2013 | Lavon |
| 2013/0255861 A1 | 10/2013 | Schneider et al. |
| 2013/0255862 A1 | 10/2013 | Schneider et al. |
| 2013/0255863 A1 | 10/2013 | Lavon et al. |
| 2013/0255864 A1 | 10/2013 | Schneider et al. |
| 2013/0255865 A1 | 10/2013 | Brown et al. |
| 2013/0261589 A1 | 10/2013 | Fujkawa |
| 2013/0306226 A1 | 11/2013 | Zink |
| 2014/0000794 A1 | 1/2014 | Hamilton |
| 2014/0005621 A1 | 1/2014 | Roe |
| 2014/0018759 A1 | 1/2014 | Jayasinghe |
| 2014/0041797 A1 | 2/2014 | Schneider |
| 2014/0107605 A1 | 4/2014 | Schroer, Jr. |
| 2014/0127460 A1 | 5/2014 | Xu et al. |
| 2014/0136893 A1 | 5/2014 | Xie et al. |
| 2014/0148773 A1 | 5/2014 | Brown |
| 2014/0234575 A1 | 8/2014 | Mitsuno |
| 2014/0235127 A1 | 8/2014 | Dejesus |
| 2014/0257231 A1 | 9/2014 | Wang |
| 2014/0276517 A1 | 9/2014 | Chester et al. |
| 2014/0288521 A1 | 9/2014 | Wade |
| 2014/0296815 A1 | 10/2014 | Takken et al. |
| 2014/0302286 A1 | 10/2014 | Okuda |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie |
| 2015/0083309 A1 | 3/2015 | Long |
| 2015/0126956 A1 | 5/2015 | Raycheck |
| 2015/0136893 A1 | 5/2015 | Koskol |
| 2015/0164708 A1 | 6/2015 | Hashimoto |
| 2015/0167207 A1 | 6/2015 | Bongartz et al. |
| 2015/0173967 A1 | 6/2015 | Kreuzer et al. |
| 2015/0230995 A1 | 8/2015 | Kaneko |
| 2015/0245958 A1 | 9/2015 | Chmielewski |
| 2015/0257941 A1 | 9/2015 | Eckstein |
| 2015/0282999 A1 | 10/2015 | Arizti et al. |
| 2015/0320612 A1 | 11/2015 | Seitz |
| 2015/0320613 A1 | 11/2015 | Seitz et al. |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een et al. |
| 2015/0351972 A1 | 12/2015 | Bing-wo |
| 2016/0058624 A1 | 3/2016 | Hohm |
| 2016/0058627 A1* | 3/2016 | Barnes ............ A61F 13/49011 604/385.3 |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman |
| 2016/0228305 A1 | 8/2016 | Gualtieri |
| 2016/0270977 A1 | 9/2016 | Surushe et al. |
| 2016/0331600 A1 | 11/2016 | Polidori et al. |
| 2017/0000659 A1* | 1/2017 | Autran ............ A61F 13/49012 |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith |
| 2017/0065461 A1 | 3/2017 | Schneider |
| 2017/0079852 A1 | 3/2017 | Fujima et al. |
| 2017/0119595 A1 | 5/2017 | Carla |
| 2017/0191198 A1 | 7/2017 | Ashraf et al. |
| 2018/0140473 A1 | 5/2018 | Koshijima |
| 2018/0168880 A1 | 6/2018 | Schneider |
| 2018/0168887 A1 | 6/2018 | Lavon |
| 2018/0168888 A1 | 6/2018 | Zink |
| 2018/0168889 A1 | 6/2018 | Lavon |
| 2018/0168890 A1 | 6/2018 | Lavon |
| 2018/0168891 A1 | 6/2018 | Wise |
| 2018/0168892 A1 | 6/2018 | Lavon |
| 2018/0168893 A1 | 6/2018 | Ashraf et al. |
| 2018/0169964 A1 | 6/2018 | Schneider |
| 2018/0170026 A1 | 6/2018 | Schneider |
| 2018/0170027 A1 | 6/2018 | Schneider |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1 | 11/2018 | Maki |
| 2019/0003079 A1 | 1/2019 | Ashraf et al. |
| 2019/0003080 A1 | 1/2019 | Ashraf et al. |
| 2019/0070041 A1 | 3/2019 | Schneider |
| 2019/0070042 A1 | 3/2019 | Beck |
| 2019/0112737 A1 | 4/2019 | Ashraf |
| 2019/0246196 A1 | 8/2019 | Han |
| 2019/0254881 A1 | 8/2019 | Ishikawa |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |
| 2020/0298545 A1 | 9/2020 | Andrews |
| 2021/0205148 A1* | 7/2021 | LaVon et al. ..... A61F 13/49061 |

FOREIGN PATENT DOCUMENTS

| | | |
|---|---|---|
| CN | 1685099 A | 10/2005 |
| CN | 1276196 C | 9/2006 |
| CN | 101001591 A | 7/2007 |
| CN | 101746057 | 6/2010 |
| CN | 104203180 A | 12/2014 |
| CN | 104869955 A | 8/2015 |
| CN | 105555240 A | 5/2016 |
| CN | 105997351 | 10/2016 |

(56) References Cited

FOREIGN PATENT DOCUMENTS

| | | |
|---|---|---|
| EP | 0989218 | 3/2000 |
| EP | 1305248 | 5/2003 |
| EP | 1452157 | 9/2004 |
| EP | 1473148 | 11/2004 |
| EP | 1393701 B1 | 7/2013 |
| EP | 3056176 | 8/2016 |
| EP | 3092997 B1 | 8/2017 |
| EP | 3251642 A1 | 12/2017 |
| EP | 3257488 A1 | 12/2017 |
| EP | 3563817 A1 | 11/2019 |
| JP | 3213543 A | 9/1991 |
| JP | H03213543 | 9/1991 |
| JP | H04030847 | 2/1992 |
| JP | H06254117 | 9/1994 |
| JP | 8071107 A | 3/1996 |
| JP | H08071107 | 3/1996 |
| JP | H08132576 | 5/1996 |
| JP | 2000026015 | 1/2000 |
| JP | 2000160460 A | 6/2000 |
| JP | 3086141 B2 | 9/2000 |
| JP | 2001276120 A | 10/2001 |
| JP | 2002035029 | 2/2002 |
| JP | 2002178428 | 6/2002 |
| JP | 2002238934 A | 8/2002 |
| JP | 2002248127 | 9/2002 |
| JP | 2003521949 A | 7/2003 |
| JP | 2004081365 A | 3/2004 |
| JP | 2004229857 | 8/2004 |
| JP | 2004237410 | 8/2004 |
| JP | 2004254862 | 9/2004 |
| JP | 2004298362 | 10/2004 |
| JP | 2004330777 A | 11/2004 |
| JP | 2005320636 | 11/2005 |
| JP | 2006149747 | 6/2006 |
| JP | 2006149749 | 6/2006 |
| JP | 2006204673 | 12/2006 |
| JP | 3913051 B2 | 2/2007 |
| JP | 2007190397 | 8/2007 |
| JP | 2008029749 | 2/2008 |
| JP | 2008055198 | 3/2008 |
| JP | 2008104853 A | 5/2008 |
| JP | 2008105425 | 5/2008 |
| JP | 2008148942 | 7/2008 |
| JP | 2008154998 A | 7/2008 |
| JP | 2008179128 | 8/2008 |
| JP | 2008194493 | 8/2008 |
| JP | 2008229006 | 10/2008 |
| JP | 2008229007 | 10/2008 |
| JP | 2008253290 | 10/2008 |
| JP | 2008260131 | 10/2008 |
| JP | 2008264480 | 11/2008 |
| JP | 2008272250 | 11/2008 |
| JP | 2008272253 | 11/2008 |
| JP | 2008296585 | 12/2008 |
| JP | 2009000161 | 1/2009 |
| JP | 2009039341 | 2/2009 |
| JP | 2009056156 | 3/2009 |
| JP | 2009106667 A | 5/2009 |
| JP | 2009172231 | 8/2009 |
| JP | 2009240804 | 10/2009 |
| JP | 2009241607 | 10/2009 |
| JP | 2010005918 A | 1/2010 |
| JP | 2010131833 | 6/2010 |
| JP | 2011015707 A | 1/2011 |
| JP | 2011111165 A | 6/2011 |
| JP | 2011178124 | 9/2011 |
| JP | 2011225000 | 11/2011 |
| JP | 2012050882 | 3/2012 |
| JP | 2012050883 | 3/2012 |
| JP | 2012115358 | 6/2012 |
| JP | 2012521498 A | 9/2012 |
| JP | 5124187 B2 | 11/2012 |
| JP | 5124188 B2 | 11/2012 |
| JP | 2013111326 A | 6/2013 |
| JP | 2013138795 | 7/2013 |
| JP | 2014097257 A | 5/2014 |
| JP | 2014111222 A | 6/2014 |
| JP | 2014188042 A | 10/2014 |
| JP | 2015510831 A | 4/2015 |
| JP | 2015104606 A | 6/2015 |
| JP | 2015521499 A | 7/2015 |
| JP | 2015171501 A | 10/2015 |
| JP | 2016013687 | 1/2016 |
| JP | 2016016536 | 2/2016 |
| JP | 5942819 | 6/2016 |
| JP | 2016193199 | 11/2016 |
| JP | 6149635 | 6/2017 |
| JP | 2019081304 A | 5/2019 |
| JP | 2019166804 A | 10/2019 |
| JP | 2019181807 A | 10/2019 |
| JP | 2020054741 A | 4/2020 |
| JP | 2020054742 A | 4/2020 |
| JP | 2020054744 A | 4/2020 |
| JP | 2020054745 A | 4/2020 |
| JP | 2022117131 A | 8/2022 |
| WO | 9925296 A1 | 5/1999 |
| WO | 2003015681 | 2/2003 |
| WO | 20030059603 | 7/2003 |
| WO | 2008123348 | 10/2008 |
| WO | 2011137962 A1 | 11/2011 |
| WO | 2012125344 A1 | 9/2012 |
| WO | 2013084977 A1 | 6/2013 |
| WO | 2014084168 A1 | 6/2014 |
| WO | 2014098683 A1 | 6/2014 |
| WO | 2014196669 A2 | 9/2014 |
| WO | 2016056092 A1 | 4/2016 |
| WO | 2016056093 A1 | 4/2016 |
| WO | 2016063346 A1 | 4/2016 |
| WO | 2016067387 A1 | 5/2016 |
| WO | 2016071981 A1 | 5/2016 |
| WO | 2016075974 A1 | 5/2016 |
| WO | 2016098416 A1 | 6/2016 |
| WO | 2016104412 A1 | 6/2016 |
| WO | 2016104422 A1 | 6/2016 |
| WO | 2016158499 A1 | 10/2016 |
| WO | 2016158746 A1 | 10/2016 |
| WO | 2016208502 A1 | 12/2016 |
| WO | 2016208513 A1 | 12/2016 |
| WO | 2017105997 A1 | 6/2017 |
| WO | 2018061288 A1 | 4/2018 |
| WO | 2018084145 A1 | 5/2018 |
| WO | 2018154680 A1 | 8/2018 |
| WO | 2018154682 A1 | 8/2018 |
| WO | 2018167836 A1 | 9/2018 |
| WO | 2019046363 A1 | 3/2019 |
| WO | 2019111203 A1 | 6/2019 |
| WO | 2019150802 A1 | 8/2019 |
| WO | 2020006996 A1 | 1/2020 |

OTHER PUBLICATIONS

All Office Actions, U.S. Appl. No. 15/846,745.
All Office Actions, U.S. Appl. No. 15/846,341.
All Office Actions, U.S. Appl. No. 15/846,360.
All Office Actions, U.S. Appl. No. 15/846,371.
All Office Actions, U.S. Appl. No. 15/846,391.
All Office Actions, U.S. Appl. No. 15/846,409.
All Office Actions, U.S. Appl. No. 15/846,433.
All Office Actions, U.S. Appl. No. 16/117,579.
American Cancer Society-What Cancer Patients Their Families and Caregivers Need to Know About COVID 19—Is Impacting Our Patient Services.
ASTM—Standard Tables of Body Measurements for Children Infant Size—Preemie to 24 Months.
International Search Report and Written Opinion, PCT/US2018/048800.
Extended EP Search Report and Written Opinion for 22176316.2 dated Nov. 2, 2022, 10pages.

* cited by examiner

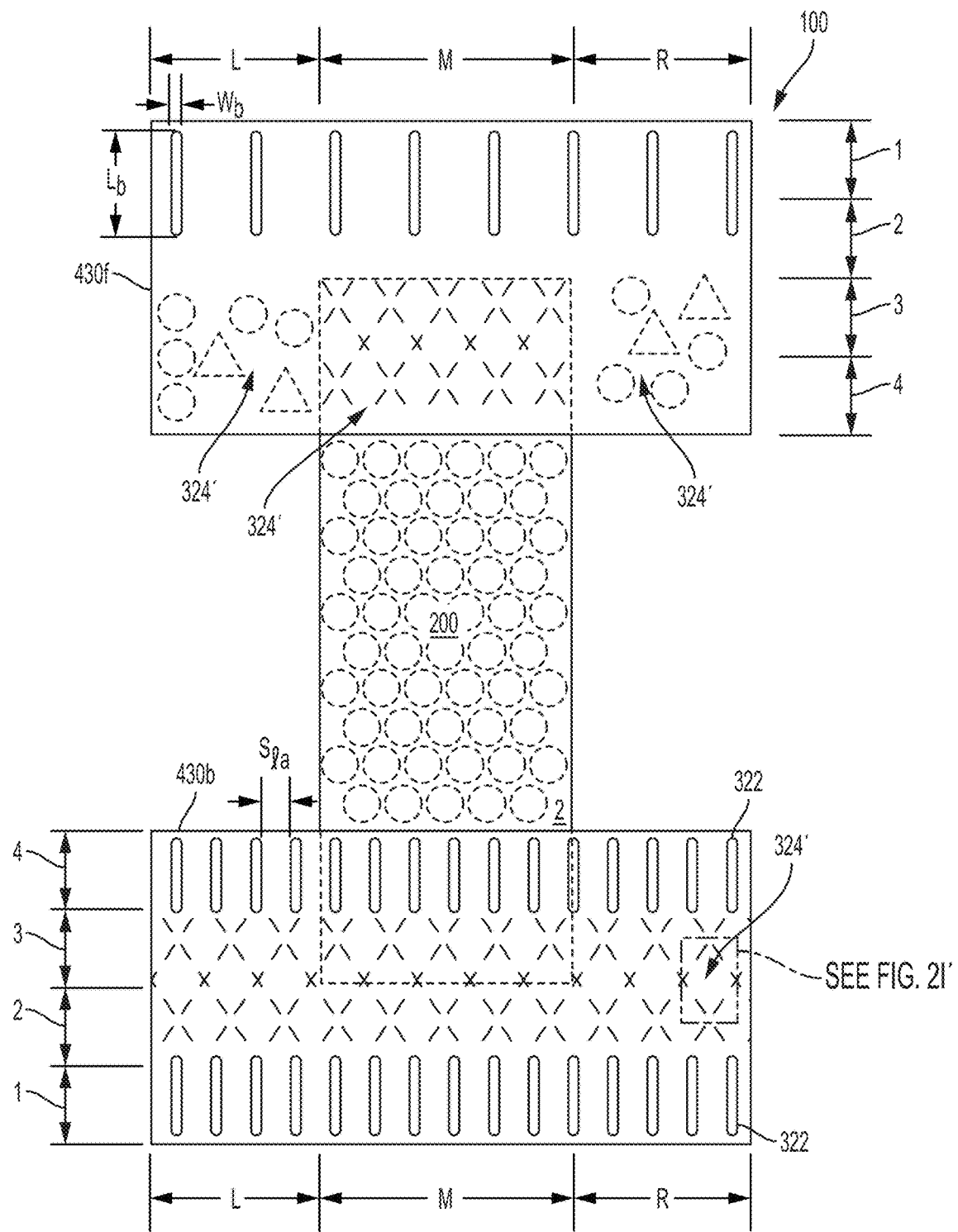
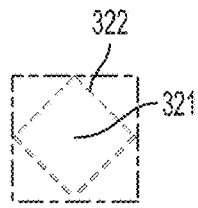
FIG. 2I
FIG. 2I'

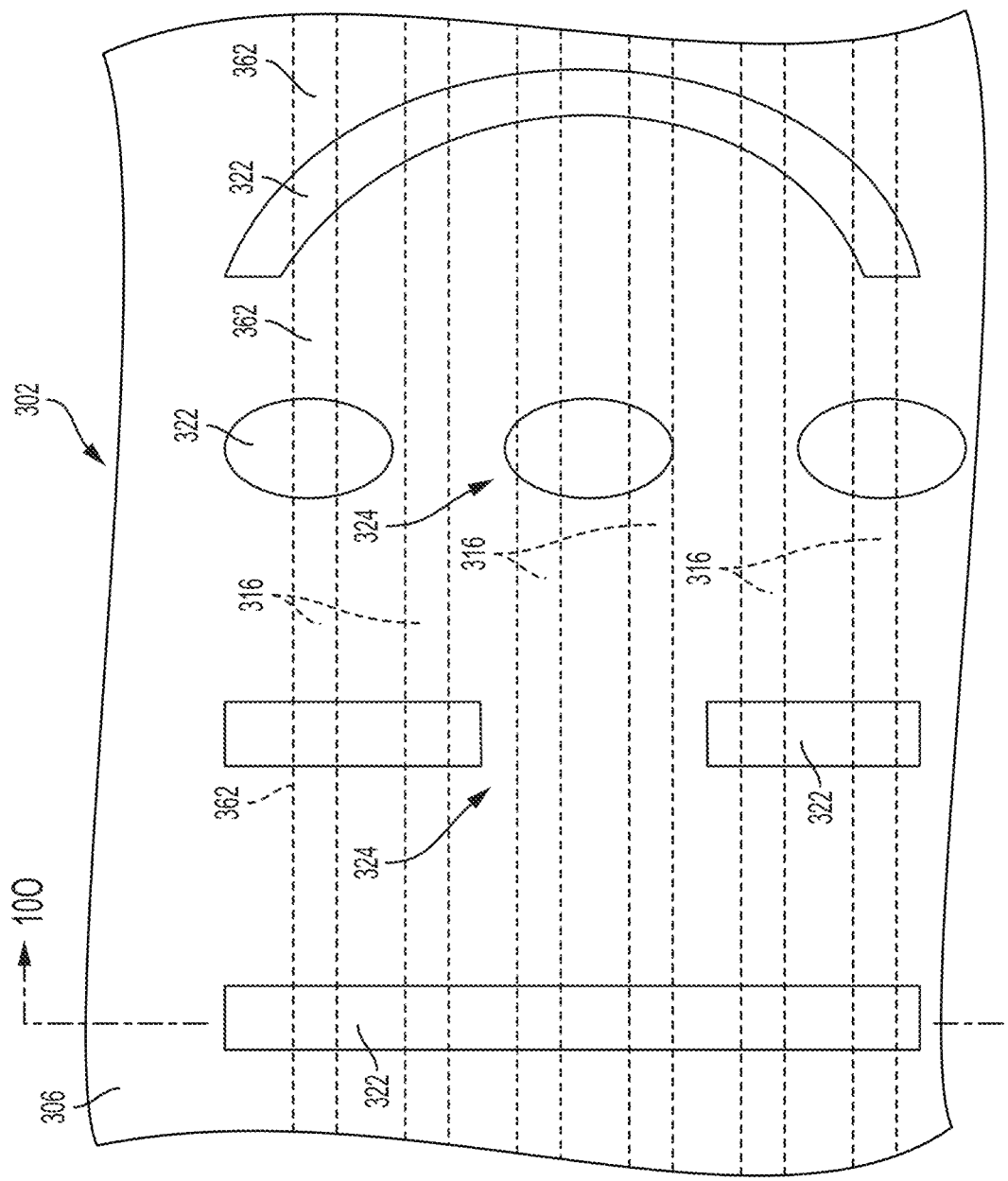

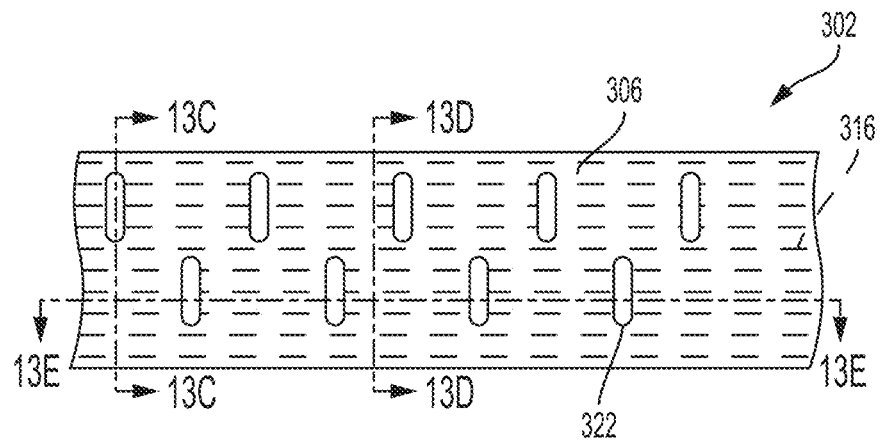
FIG. 13A
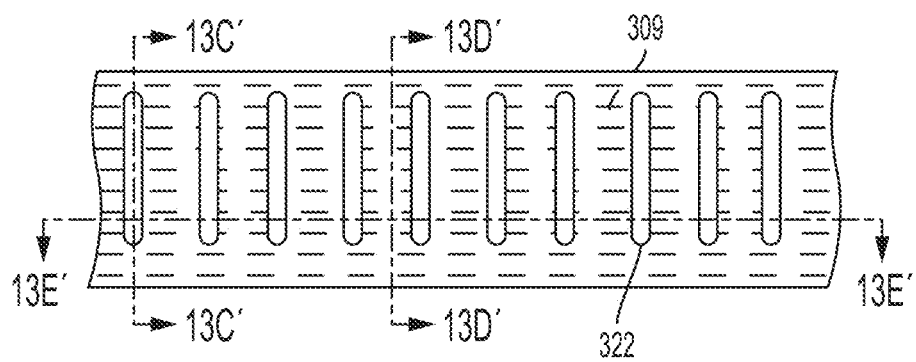
FIG. 13B
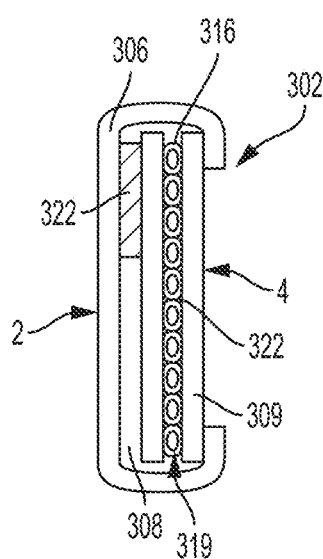 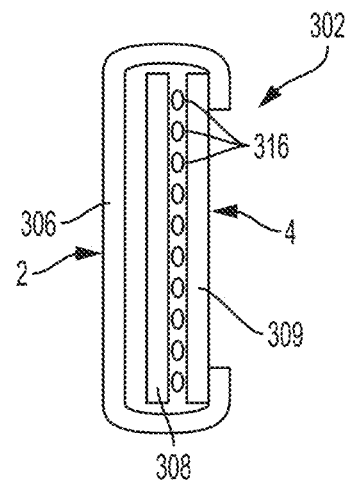
FIG. 13C          FIG. 13D

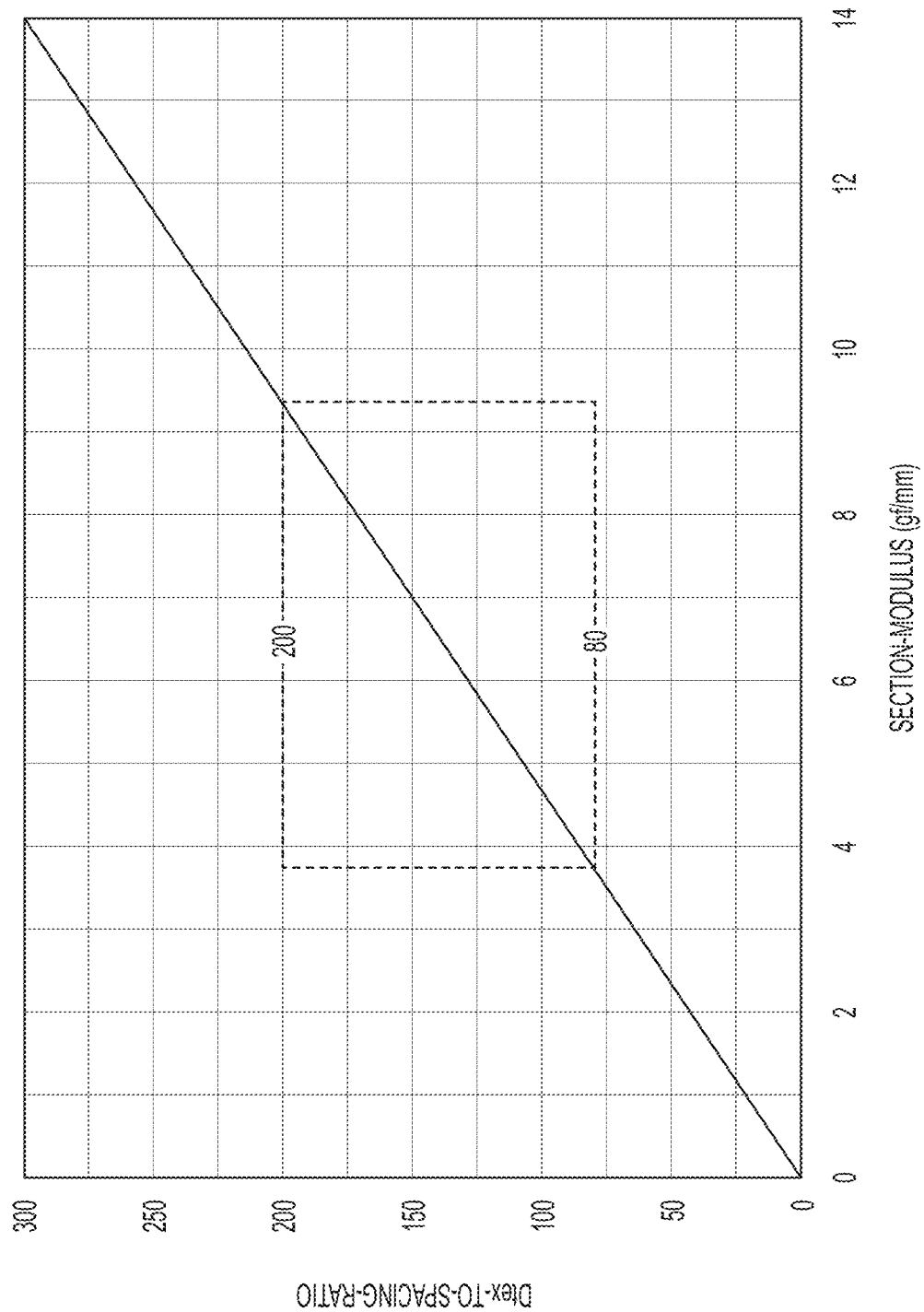

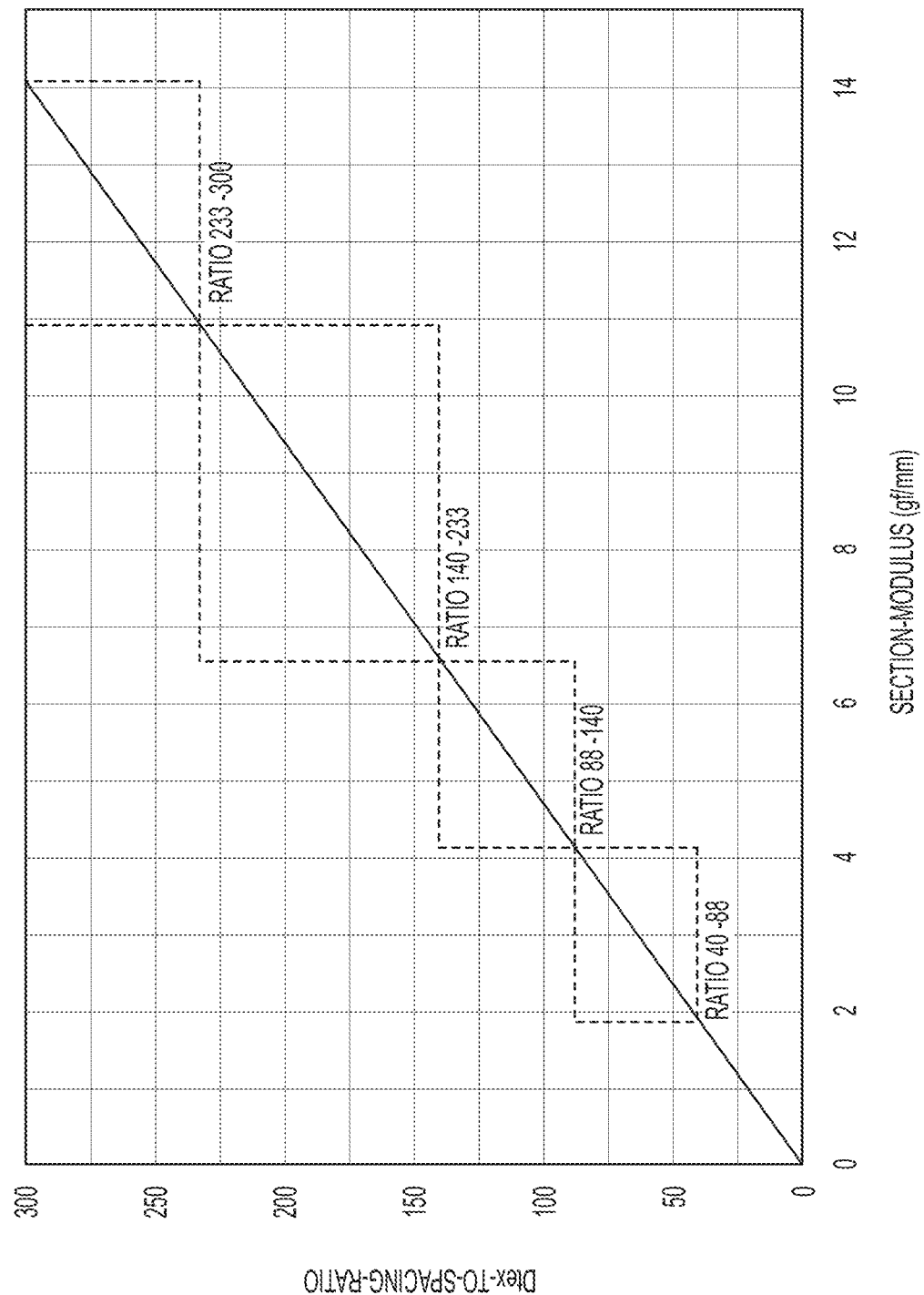

BEAMED ELASTOMERIC LAMINATE STRUCTURE, FIT, AND TEXTURE

CROSS-REFERENCE TO RELATED APPLICATIONS

This application is a continuation of U.S. application Ser. No. 16/117,579, filed on Aug. 30, 2018, which claims the benefit, under 35 USC 119(e), to U.S. Provisional Patent Application No. 62/553,538, filed on Sep. 1, 2017; U.S. Provisional Patent Application No. 62/553,149, filed on Sep. 1, 2017; U.S. Provisional Patent Application No. 62/553,171, filed on Sep. 1, 2017; U.S. Provisional Patent Application No. 62/581,278, filed on Nov. 30, 2017; U.S. Provisional Patent Application No. 62/685,429, filed on Jun. 15, 2018; U.S. Provisional Patent Application No. 62/687,031, filed on Jun. 19, 2018; U.S. Provisional Patent Application No. 62/686,896, filed on Jun. 19, 2018; each of which are herein incorporated by reference in their entirety.

U.S. application Ser. No. 16/117,579 is also a continuation-in-part of, and claims priority under 35 U.S.C. § 120, to U.S. Nonprovisional patent application Ser. No. 15/832,929, filed on Dec. 6, 2017; U.S. Nonprovisional patent application Ser. No. 15/833,057, filed on Dec. 6, 2017; U.S. Nonprovisional patent application Ser. No. 15/838,405, filed on Dec. 12, 2017; U.S. Nonprovisional patent application Ser. No. 15/839,896, filed on Dec. 13, 2017; U.S. Nonprovisional patent application Ser. No. 15/846,341, filed on Dec. 19, 2017; U.S. Nonprovisional patent application Ser. No. 15/846,360, filed on Dec. 19, 2017; U.S. Nonprovisional patent application Ser. No. 15/846,371, filed on Dec. 19, 2017; U.S. Nonprovisional patent application Ser. No. 15/846,391, filed on Dec. 19, 2017; U.S. Nonprovisional patent application Ser. No. 15/846,409, filed on Dec. 19, 2017; U.S. Nonprovisional patent application Ser. No. 15/846,433, filed on Dec. 19, 2017; U.S. Nonprovisional patent application Ser. No. 15/846,349, filed on Dec. 19, 2017; U.S. Nonprovisional patent application Ser. No. 15/846,382, filed on Dec. 19, 2017; U.S. Nonprovisional patent application Ser. No. 16/115,617, filed on Aug. 29, 2018; and U.S. Nonprovisional patent application Ser. No. 15/846,745, filed on Dec. 19, 2017; each of which are herein incorporated by reference in their entirety.

FIELD OF THE INVENTION

The present disclosure relates to absorbent articles, more particularly, to disposable absorbent articles comprising improved elastomeric laminates configured to perform in various components of the disposable absorbent articles.

BACKGROUND OF THE INVENTION

Traditional stranded elastomeric laminates as disclosed in the art are often used to make disposable pant belts. Because traditional stranded elastomeric laminates use larger elastic strands (e.g., Average-Dtex greater than 400) with larger spaces between the elastic strands (e.g., Average-Strand-Spacing greater than 4 mm) at higher pre-strains (e.g., Average-Pre-Strain greater than 200%) they have many undesirable performance parameters. Specifically, traditional laminates have high strand pressure (e.g., Pressure-Under-Strand greater than 1 psi) and modulus (e.g., Section-Modulus greater than 10 gf/mm) that result in poor sustained fit and red marking. Further, the force required to open many belts made with traditional stranded elastomeric laminates can be much too high (e.g., Application-Force greater than 2,500 gf), making it difficult for caretakers and wearers to don the disposable pants.

The elastomeric laminates of the present disclosure overcome many of the deficiencies of traditional stranded elastomeric laminates by using closely spaced (e.g., Average-Strand-Spacing less than 4 mm), fine elastomeric strands (Average-Dtex less than 400), resulting in low strand pressure (Pressure-Under-Strand less than 1 psi) and modulus (e.g., Section-Modulus less than 10 gf/mm). These new stranded elastomeric laminates disclosed herein provide ease of application/donning, improved sustained fit and without marking the wearer's skin because of the way they distribute force. The elastomeric laminates of the present disclosure also lend themselves to having multiple texture zones that help to make the disposable pant more textile garment-like and communicate comfortable fit or signal performance zones and a contoured fit. Overall, the elastomeric laminates of the present disclosure look and perform unlike any previously disclosed or marketed elastomeric laminate.

It has also been found that the inventive stranded elastomeric laminates of the present disclosure may be subjected to the process of being incorporated into absorbent article and of being packaged at high compressions over a substantial shelf life and still retain the beneficial and desirable properties described herein.

Much of the focus of the present disclosure is directed toward disposable pants and pant belts, but please note that the new laminates of the present disclosure have many applications to disposable absorbent articles (e.g., diapers, pads, liners, etc.) and article components (e.g., topsheets, backsheets, cuffs, side panels, belts etc.).

Greater details of the design ambitions of the new stranded elastomeric laminates follow in the sections below.

SUMMARY OF THE INVENTION

In a disclosed example of the present disclosure, an elastomeric laminate may comprise a plurality of elastic strands between of first and second nonwovens, where the plurality of elastic strands has an Average-Strand-Spacing from about 0.25 mm to about 4 mm, an Average-Dtex from about 10 to about 400, and an Average-Pre-Strain from about 50% to about 300%. Alternatively, the plurality of elastic strands may have an Average-Strand-Spacing from about 0.25 mm to about 2.5 mm, an Average-Dtex from about 40 to about 250, and an Average-Pre-Strain from about 75% to about 250%. A plurality of densified bonds join the first and second nonwovens together, are discrete and spaced from each other, and overlap and at least partially surround portions of the plurality of elastic strands. The laminate has a Peel-Strength between the first and second nonwovens from about 1 N/cm to about 15 N/cm or may have about 1.5N/cm to 10N/cm. A Dtex-to-Nonwoven-Basis-Weight-Ratio of a first elastic strand and of at least one of the first and second nonwovens is from about 1.5 to about 15 or may be about 3 to about 10. The first nonwoven layer has a basis weight from about 6 grams per square meter to about 35 grams per square meter, and the second nonwoven layer has a basis weight from about 6 grams per square meter to about 35 grams per square meter. Alternatively, the first nonwoven layer may have a basis weight from about 8 grams per square meter to about 25 grams per square meter, and the second nonwoven layer may have a basis weight from about 8 grams per square meter to about 25 grams per square meter.

In a disclosed example of the present disclosure, an elastomeric laminate comprises a plurality of elastic strands between of first and second nonwovens, where the plurality of elastic strands has an Average-Strand-Spacing from about 0.25 mm to about 4 mm and an Average-Dtex from about 10 to about 400. Alternatively, the plurality of elastic strands may have an Average-Strand-Spacing from about 0.25 mm to about 2.5 mm, an Average-Dtex from about 40 to about 250, and an Average-Pre-Strain from about 75% to about 250%. The first and second nonwovens may be joined together, and a third nonwoven is joined to the second nonwoven, such that the second nonwoven is an intermediate nonwoven. A Dtex-to-Spacing-Ratio of the plurality of elastic strands is from about 65:1 to about 200:1 or may be from about 75:1 to about 150:1. The first and second nonwovens may be joined together via an adhesive, where the adhesive overlaps and at least partially surrounds a portion of the plurality of elastic strands. The second and third nonwovens may be joined together via a plurality of bonds, where the plurality of bonds are discrete and laterally spaced from each other. Elastic strands may not be present between the second and third nonwovens. The exterior surface of the third nonwoven and an exterior surface of the first nonwoven may have different Percent-Contact-Areas. The Percent-Contact-Area of the exterior surface of the third nonwoven may be less than about 35% and the Percent-Contact-Area of the exterior surface of the first nonwoven may be greater than about 40%.

In a disclosed example of the present disclosure, a disposable absorbent pant article comprises a chassis, a front waist region, and a back waist region. The chassis comprises a topsheet, a backsheet and an absorbent core disposed between the topsheet and the backsheet. A first plurality of elastic strands is disposed in the front waist region and a second plurality of elastic strands is disposed in the back waist region. The front and back waist regions are joined together at laterally opposed side seams to form a waist and leg openings. The front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams. The back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams. The front waist region comprises a front component region disposed between and including a front distal most elastic strand of the front waist region and a proximal most elastic strand of the front waist region, where the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand. The front component region is then divided into 4 equal component sections, defined by first, second, and third component section lines, each disposed parallel to the lateral axis and disposed at 25%, 50% and 75% of the distance between the front distal component region line and front proximal component region line. The front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4. The absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, where any portion of the article to one lateral side or the other of the Section M defines Section L and the laterally opposed Section R. Each of the first and second pluralities of elastics have an Average-Strand-Spacing from about 0.25 mm to about 4 mm and an Average-Dtex is from about 10 to about 400. Alternatively, the plurality of elastic strands may have an Average-Strand-Spacing from about 0.25 mm to about 2.5 mm, an Average-Dtex from about 40 to about 250, and an Average-Pre-Strain from about 75% to about 250%. At least a portion of each of the first and second pluralities of elastics has a Pressure-Under-Strand of from about 0.1 to about 1.2 psi or may be less than about 1 psi or less than about 0.75 psi or less than about 0.5 psi. The pant article has an Application-Force of from about 900 gf to about 1600 gf, or may have from about 1,000 gf to about 1,400 gf and a Sustained-Fit-Load-Force greater than about 30% of the Application-Force, and a Sustained-Fit-Unload-Force greater than about 25% of the Application-Force.

In a disclosed example of the present disclosure, a packaged product comprises a package and a plurality of disposable absorbent articles. The package has height, width and depth dimensions, an interior space and an exterior surface, and the package comprises a film. The plurality of disposable absorbent articles are folded, and may be bi-folded, and arranged to form a stack of disposable absorbent articles. The stack of disposable absorbent articles is compressed along a compression axis and disposed within the interior space of the package such that the compression axis of the stack of disposable absorbent articles is oriented substantially along the width dimension of the package. Each of the folded disposable absorbent articles comprise a topsheet, a backsheet, and an absorbent core located between the topsheet and the backsheet. Each of the disposable absorbent articles comprise an elastomeric laminate comprising a plurality of elastic strands between first and second nonwovens, where the plurality of elastic strands has an Average-Strand-Spacing from about 0.25 mm to about 4 mm, an Average-Dtex from about 10 to about 400, an Average-Pre-Strain from about 50% to about 300%. Alternatively, the plurality of elastic strands may have an Average-Strand-Spacing from about 0.25 mm to about 2.5 mm, an Average-Dtex from about 40 to about 250, and an Average-Pre-Strain from about 75% to about 250%. The packaged product exhibits an In-Bag-Stack-Height from 70 mm to 110 mm wherein the In-Bag Stack-Height is the width of the package divided by the number of the disposable articles per stack and then multiplied by ten.

In each of these disclosed examples in the Summary of the Invention, one or more of the following may be true:

a) greater than 70% of the elastic strands in one of the L and R article sections extends at least 50% of a lateral width (laid out flat, i.e., extended) of the respective L and R sections;

b) less than 20% of the elastic filaments of the first plurality of strands are broken between adjacent bonds of the first plurality of bonds that are transversely spaced less than 20 mm from each other;

c) the elastomeric laminate has a Section-Modulus of from about 3 gf/mm to about 10 gf/mm, or from about 4 gf/mm to about 9 gf/mm;

d) the elastomeric laminate forms at least one of an article component selected from the group consisting of a side panel, a belt panel, a waistband, a leg cuff, and an ear panel;

e) the elastomeric laminate may form an article component that is divided into four equal sections according to the Section-Modulus Method, and wherein at least one of the sections comprises at least a portion of the first plurality of elastics and has a Section-Modulus of from about 3 gf/mm to about 10 gf/mm or from about 4 gf/mm to about 9 gf/mm;

f) the Basis-Weight of the first nonwoven is from about 6 gsm to about 35 gsm;

g) the Basis-Weight of the second nonwoven is from about 6 gsm to about 35 gsm;

h) portions of the elastomeric laminate comprises a TS7-Value of less than about 12 and a TS750-Value of less than 60;

i) the elastomeric laminate has an Air-Permeability of at least one of: a) greater than about 40 cubic meters/square meter/minute Air-Permeability at 0 gf/mm (no extension); b) greater than about 60 cubic meters/square meter/minute Air-Permeability at 3 gf/mm (slight extension); and c) greater than about 80 cubic meters/square meter/minute Air-Permeability at 7 gf/mm (moderate extension); j) the elastomeric laminate has a Cantilever-Bending of less than about 40 mm;

k) the elastomeric laminate has a Rugosity-Frequency of from about 0.2 $mm^{-1}$ to about 1 $mm^{-1}$, and a Rugosity-Wavelength of from about 0.5 mm to about 5 mm;

l) the elastomeric laminate has a Percent-Contact-Area of at least one of: 1) greater than about 10% at 100 um, 2) greater than about 20% at 200 um, and 3) greater than about 30% at 300 um;

m) the elastomeric laminate has a 2%-98%-Height-Value of <1.6 mm;

n) the Force-Relaxation-Over-Time of the elastomeric laminate is from about 5% to about 30%; and o) a Peel-Strength between the first and second nonwoven layers of at least about 1 N/cm to about 5N/cm or from about 2 N/cm up to about 10 N/cm or up to and including substrate failure of one or both of the nonwoven substrates.

BRIEF DESCRIPTION OF THE DRAWINGS

FIG. 2H' is an expanded image of a portion of the bond arrangement of FIG. 2H.

FIG. 2I is a plan view of a garment-facing surface of a pant comprising multiple texture zones, prior to joining side edges of the belt to form the waist and leg openings.

FIG. 2I' is an expanded image of a portion of the bond arrangement of FIG. 2I.

FIG. 5D' is a perspective front view of the final fit of the comparative market product of FIG. 5C (Easy Ups (Size 4)).

FIG. 5E' is a perspective front view of the final fit of the inventive product of FIG. 5C (Adhesively Bonded Beamed Elastic (Size 4)).

FIG. 5F' is a perspective back view of the final fit of the comparative market product of FIG. 5C (Easy Ups (Size 4)).

FIG. 5G' is a perspective back view of the final fit of the inventive product of FIG. 5C (Adhesively Bonded Beamed Elastic (Size 4)).

FIG. 10N is a detailed view of multiple elastic strands in a stretched state bonded between the first and second substrates, illustrating multiple bonds that may be used to form various textures.

FIG. 13A is a plan view of a garment-facing surface of an elastomeric tri-laminate.

FIG. 13B is a plan view of a wearer-facing surface of the elastomeric tri-laminate of FIG. 13A.

FIG. 13C is a cross-sectional view of the tri-laminate of FIG. 13A taken along line 13C-13C and is a cross-sectional view of the tri-laminate of FIG. 13B taken along line 13'-13C'.

FIG. 13D is a sectional view of the tri-laminate of FIG. 13A taken along line 13D-13D and is a sectional view of the tri-laminate of FIG. 13B taken along line 13D'-13D'.

FIG. 15A is a graph illustrating the relationship between Dtex-to-Spacing-Ratio and Section-Modulus.

FIG. 15B is a graph illustrating the relationship between Dtex-to-Spacing-Ratio and Section-Modulus.

DETAILED DESCRIPTION

Figure 1A:
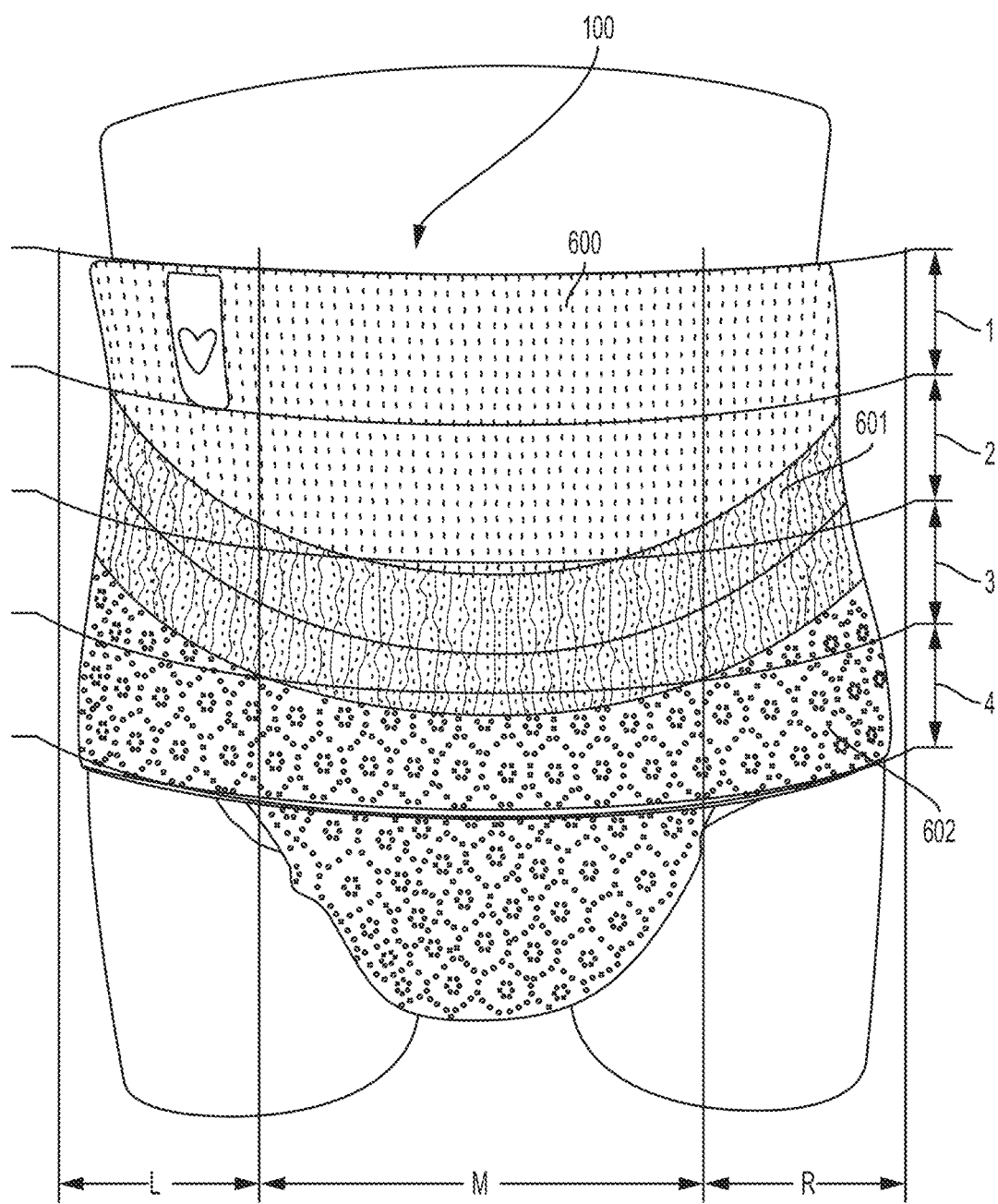
FIG. 1A is a perspective front view of a pant fitted onto a mannequin wearer comprising multiple texture zones.
Figure 1B:
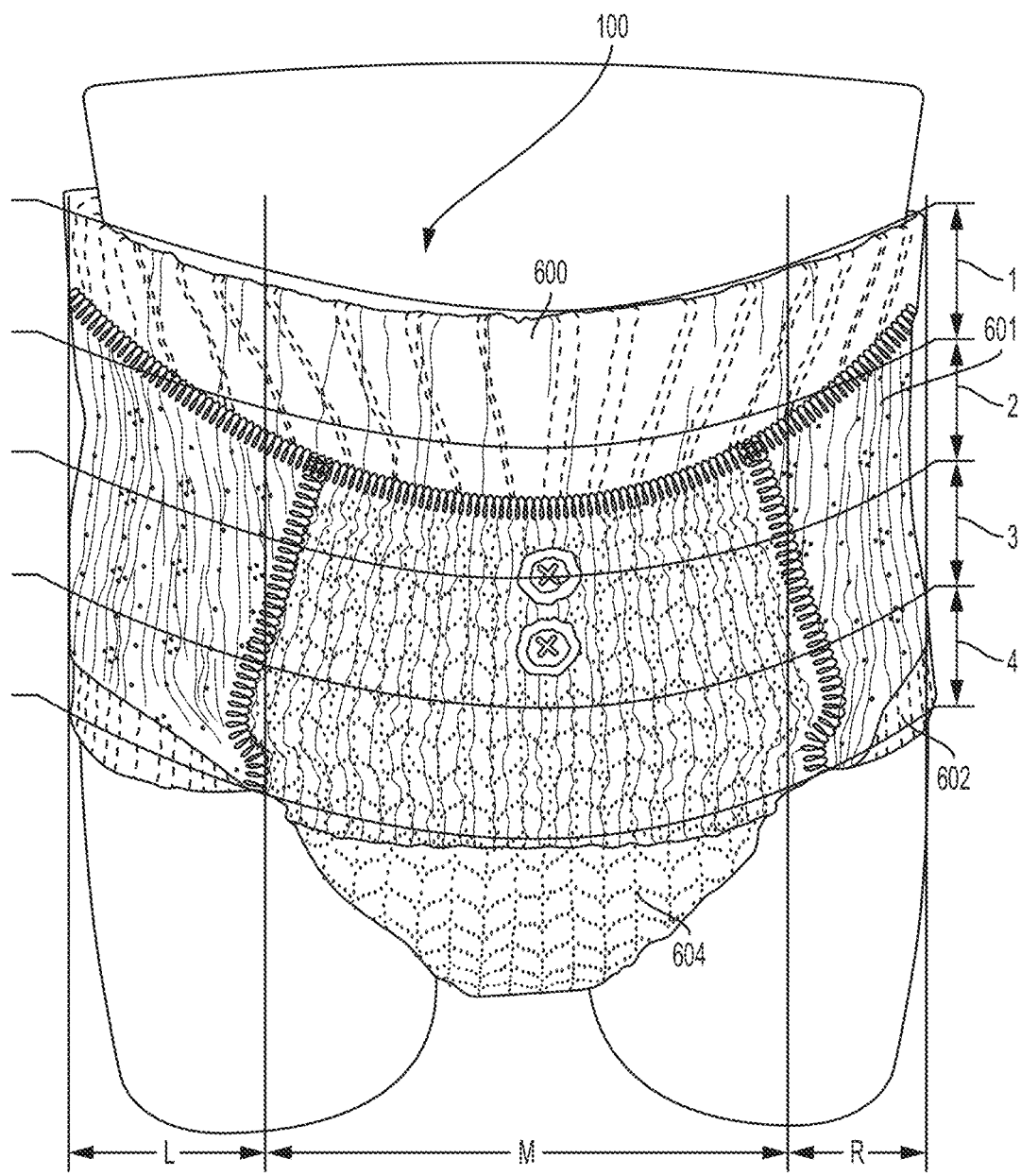
FIG. 1B is a perspective front view of a pant fitted onto a mannequin wearer comprising multiple texture zones.

The present disclosure details improved stranded elastomeric laminates (also referred to as "beamed laminates" comprising "beamed elastics") comprising a greater number of elastic strands having a greater fineness (i.e., lower decitex) and a closer spacing than has been previously disclosed or practiced in disposable absorbent articles. These improved stranded elastomeric laminates can be used as disposable absorbent article (e.g., disposable taped diapers, pants, pads, liners, etc.) components (e.g., topsheets, backsheets, belts, ears, side panels, cuffs, etc.) for improved fit and gasketing at the waist, legs, crotch, and sides of the wearer to generally provide the greatest level of extensibility, ease of application, the most comfortable wearing conditions, improved leakage protection and a better sustained fit. Further, the stranded elastomeric laminates of the present disclosure lend themselves to having different bonding zones via different bonding arrangements and/or different types of bonds.

Definitions

The following term explanations may be useful in understanding the present disclosure:

"Disposable," in reference to absorbent articles, means that the absorbent articles, are generally not intended to be laundered or otherwise restored or reused as absorbent articles (i.e., they are intended to be discarded after a single use and, preferably, to be recycled, composted or otherwise discarded in an environmentally compatible manner). Disposable absorbent articles often comprise adhesive between the layers and/or elements to hold the article together (e.g., ear panels, side panels, and belts are joined to the chassis via adhesive and the layers of the ear panels, side panels, belts, and chassis are joined together using adhesive). Alternatively, heat and/or pressure bonding are used with the adhesive or in place of the adhesive. In such instances portions of the material layers may become partially melted and pressed together such that once cooled they are physically bonded together. Nonwovens (including, for example, polypropylene, polyethylene, etc.) adhesives (including, for example, styrenic block copolymers (e.g., SIS, SBS)), and absorbent gelling material (AGM 26—see FIGS. 16C and 16D) make up more than 50%, more than 75%, and often more than 90% of the disposable absorbent article weight. And, a core comprising the AGM 26 is often held within the chassis in a manner that would encapsulate and contain the AGM 26 under normal conditions. Such disposable absorbent articles typically have an absorbent capacity of greater than about 100 mL of fluid and can have capacities of up to about 500 mL of fluid or more. Stitching (including the use of thread) and/or woven materials are typically not used to make a disposable absorbent article. If stitching or woven materials are used, they make up an extremely small percentage of the disposable absorbent article. Some landing zones of disposable absorbent articles for fasteners can comprise a woven material, but no other part of a disposable absorbent article typically comprises woven materials.

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, feminine pads, absorbent inserts, absorbent pad and panty (disposable and semi-durable) systems and the like.

"Proximal" and "Distal" refer respectively to the location of an element relatively near to or far from the longitudinal or lateral centerline of a structure (e.g., the proximal edge of a longitudinally extending element is located nearer to the longitudinal axis than the distal edge of the same element is located relative to the same longitudinal axis).

"Wearer-facing" and "garment-facing" refer respectively to the relative location of an element or a surface of an element or group of elements. "Wearer-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinally extending side edge to an opposing longitudinally extending side edge of the article and generally at a right angle to the longitudinal direction. Directions within 45 degrees of the lateral direction are considered to be "lateral."

"Disposed" refers to an element being located in a particular place or position.

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Elastic," "elastomer," or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry for measuring yarns or filaments. 1 Decitex=1 gram per 10,000 meters. In other words, if 10,000 linear meters of a relaxed yarn or filament weights 500 grams that yarn or filament would have a decitex of 500.

"Substrate" is used herein to describe a material which is primarily two-dimensional (i.e. in an XY plane) and whose thickness (in a Z direction) is relatively small (i.e. ¹/₁₀ or less) in comparison to its length (in an X direction) and width (in a Y direction). Non-limiting examples of substrates include a web, layer or layers of fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is generally perpendicular to the machine direction.

"Taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

"Pant" (also referred to as "training pant", "pre-closed diaper", "diaper pant", "pant diaper", "panty", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or prefastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Side Seam" is the area connecting the front waist region to the back waist region to form the waist and leg openings. Side seams may be formed as permanent seams via thermal, pressure, heat or ultrasonic bonding. Side seams may also be formed via fastening elements to create a refastenable side seam. In such cases the length of the side seam is determined by the length of the fastener or fasteners. Side seams need to have sufficient strength as to not open during use but to be easily opened for removal.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

"Channel," as used herein, is a region or zone in an absorbent material layer that has a substantially lower basis weight (e.g., less than 50%, less than 70%, less than 90%) than the surrounding material in the material layer. The channel may be a region in a material layer that is substantially absorbent material-free (e.g., 90% absorbent material-free, 95% absorbent material-free, or 99% absorbent material-free, or completely absorbent material-free). A channel may extend through one or more absorbent material layers. The channel generally has a lower bending modulus than the surrounding regions of the absorbent material layer, enabling the material layer to bend more easily and/or rapidly distribute more bodily exudates within the channel than in the surrounding areas of the absorbent material layer. Thus, a channel is not merely an indentation in the material layer that does not create a reduced basis weight in the material layer in the area of the channel.

"Cross-Sectional-Bond-Void-Area" is the cross-sectional area of the void space created by the pre-strained elastic material when the nonwoven substrates are compressed or densified to form the bond. The shape of the void is defined substantially by the shape and dimensions of the elongated elastic present when the bond is formed (see FIG. 10K). Elastomeric laminates of the present disclosure may comprise densified bonds joining substrates and overlapping elastic strands such that a Cross-Sectional-Bond-Void-Area of the densified bond is from about 0.001 $mm^2$ to about 0.03 $mm^2$, or from about 0.005 $mm^2$ to about 0.015 $mm^2$.

"Cross-Sectional-Strand-Area" is the combined cross-sectional area of the individual filaments forming the strand. The Cross-Sectional-Strand-Area is determined by measuring the cross-sectional area of each of the filaments forming the strand in the fully relaxed state and adding the individual filament cross-sectional areas together to determine the cross-sectional area of the strand in its relaxed state. Elastomeric laminates of the present disclosure may have strands having a Cross-Sectional-Strand-Area in its relaxed disposition from about 0.004 $mm^2$ to about 0.04 $mm^2$ or from about 0.008 to about 0.03.

"Void-Area-to-Strand-Area-Ratio" is the ratio required to form the dimensional lock and is determined by dividing the Cross-Sectional-Bond-Void-Area of the bond by the Cross-Sectional-Strand-Area of the relaxed elastic strand. Elastomeric laminates of the present disclosure may have Void-Area-to-Strand-Area-Ratios of less than about 1, or from about 0.25 to about 0.9, or from about 0.3 to about 0.7.

"Bond-Length" or "$L_b$" is defined as the longest dimension of the bond. The measurement is taken from a first end of a bond to a second end of the bond along the pathlength of the bond itself. For substantially linear bonds, the length measurement will be perpendicular to the width measurement of the bond. For circular bonds the length is considered to be the diameter of the circular bond. Elastomeric laminates of the present disclosure may have a Bond-Length from about 1 mm to about 300 mm, from 3 mm to about 150 mm, or from about 5 mm to about 100 mm. See FIGS. 2H, 2H', 10A and 10I.

Figure 2A:
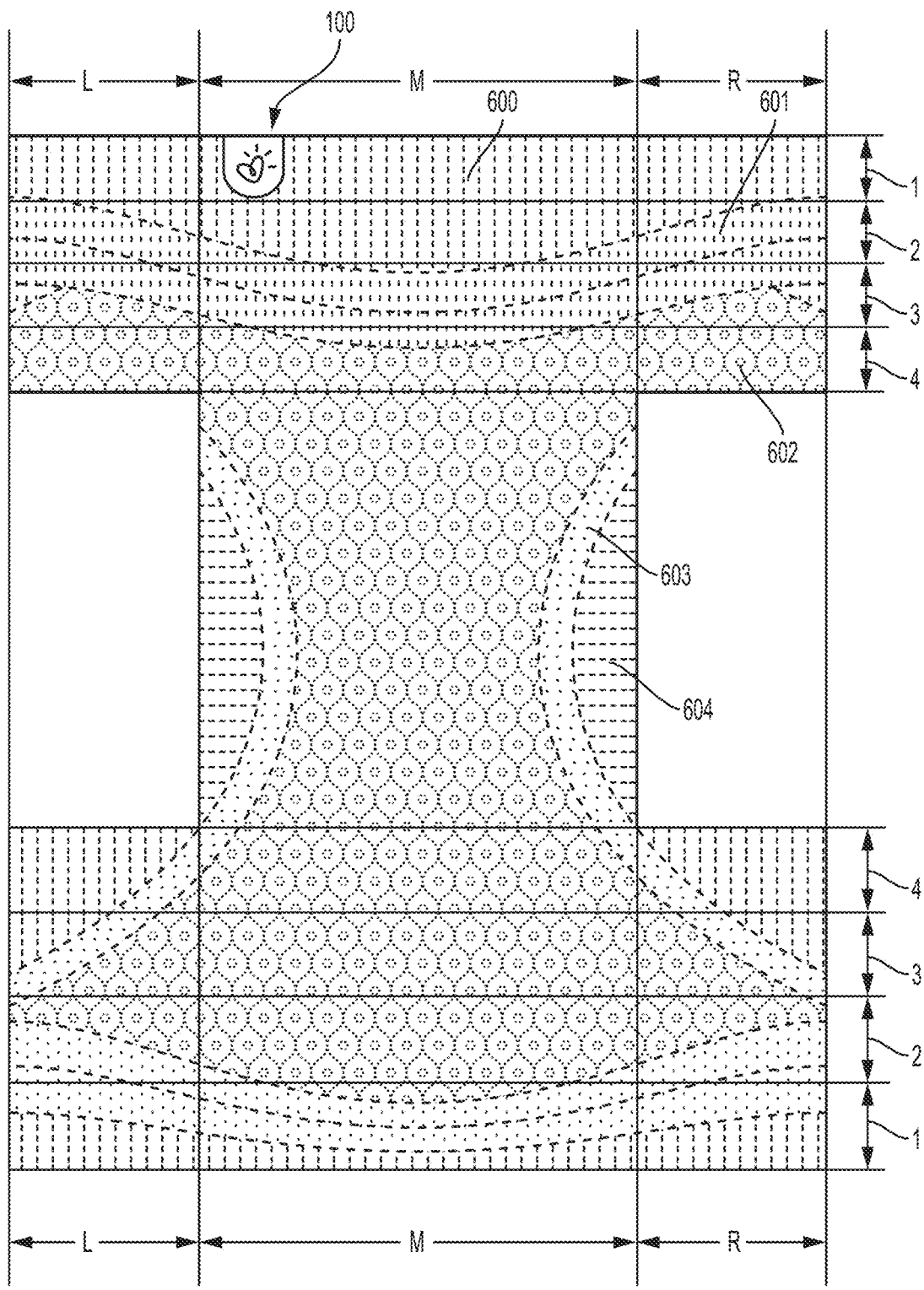
FIG. 2A is a plan view of a garment-facing surface of the pant of FIG. 1A comprising texture, prior to joining side edges of the belt to form the waist and leg openings.

"Average-Bond-Length" is defined as the average of the Bond-Length of a representative plurality of bonds forming the elastomeric laminates of the present disclosure. Such elastomeric laminates may have an Average-Bond-Length from about 3 mm to about 300 mm, from about 5 mm to about 100 mm, or from about 10 mm to about 50 mm. The bonds 322 may be continuous and may longitudinally overlap from about 2 to about 200 elastic strands, from about 5 to about 150 elastic strands, or from about 10 to about 100 elastic strands. FIGS. 2H, 2I, and 10N illustrate densified bonds 322 overlapping a plurality of elastic strands 316.

"Bond-Width" or "$W_b$" is defined as the shortest dimension of the bond. The measurement from a first side of a bond to a second side of the bond intersecting the bond length measurement. For substantially linear bonds the measurement is perpendicular to the length measurement of the bond.

For circular bonds the width is considered to be the diameter of the circular bond. Elastomeric laminates of the present disclosure may have a Bond-Width from about 0.25 mm to about 5 mm, from 0.5 mm to about 3 mm, or from about 0.5 mm to about 2 mm. See FIGS. 2H, 2I, and 10A.

"Average-Bond-Width" is defined as the average of the Bond-Width of a representative plurality of bonds forming the elastomeric laminates of the present disclosure. Elastomeric laminates of the present disclosure may have an Average-Bond-Width from about 0.25 mm to about 5 mm, from about 0.5 mm to about 4 mm, or from about 1 mm to about 3 mm.

As used in this disclosure, "Bond-Region-Width" or "$W_{br}$" is defined as the width from a first laterally opposing bond to a second laterally opposing bond measured parallel to the lateral axis. Elastomeric laminates of the present disclosure may have a Bond-Region-Width from about 0.25 mm to about 5 mm, from about 0.5 mm to about 4 mm, or from about 1 mm to about 3 mm. See FIGS. 2H and 2I.

"Average-Bond-Region-Width" is defined as the average of the Bond-Region-Width of a representative plurality of bond regions forming the elastomeric laminates of the present disclosure. Elastomeric laminates of the present disclosure may have an Average-Bond-Region-Width from about 0.25 mm to about 5 mm, from about 0.5 mm to about 4 mm, or from about 1 mm to about 3 mm.

"Bond-Region-Length" or "$L_{br}$" is defined as the length from a first longitudinally opposing bond to a second longitudinally opposing bond measured parallel to the longitudinal axis. Elastomeric laminates of the present disclosure may have a Bond-Region-Length from about 10 mm to about 300 mm. See FIGS. 2H and 2I.

"Average-Bond-Region-Length" is defined as the average of the Bond-Region-Length of a representative plurality of bond regions forming the elastomeric laminates of the present disclosure. Elastomeric laminates of the present disclosure may have an Average-Bond-Region-Length from about 10 mm to about 300 mm or from about 25 mm to about 200 mm.

"Longitudinal-Bond-Spacing" or "$S_b$" is defined as the spacing between a first bond and a second bond measured parallel to the longitudinal axis—See FIG. 2H. Elastomeric laminates of the present disclosure may have a Longitudinal-Bond-Spacing from about 1 mm to about 20 mm or from about 2 mm to about 15 mm.

"Average-Longitudinal-Bond-Spacing" is defined as the average of the Longitudinal-Bond-Spacing of a representative plurality of bonds forming the elastomeric laminates of the present disclosure. Elastomeric laminates of the present disclosure may have an Average-Longitudinal-Bond-Spacing from about 1 mm to about 20 mm.

"Lateral-Bond-Spacing" or "$S_{la}$" is defined as the spacing between a first bond and a second bond measured parallel to the lateral axis—See FIG. 2H. Elastomeric laminates of the present disclosure may have a Lateral-Bond-Spacing from about 2 mm to about 30 mm.

"Average-Lateral-Bond-Spacing" is defined as the average of the Lateral-Bond-Spacing of a representative plurality of bonds forming the elastomeric laminates of the present disclosure. Elastomeric laminates of the present disclosure may have an Average-Lateral-Bond-Spacing from about 2 mm to about 30 mm.

"Dtex-to-Spacing-Ratio" is determined by dividing the elastic decitex by the elastic spacing of the plurality of elastics being examined. Elastomeric laminates of the present disclosure may have Dtex-to-Spacing-Ratios of from about 65:1 to about 300:1, or from about 80:1 to about 200:1.

"Dtex-to-Nonwoven-Basis-Weight-Ratio" is determined by dividing the elastic decitex by the nonwoven basis weight of the one or more nonwoven substrates of the elastomeric laminate disposed on one side (garment facing side or wearer-facing side) of the elastic strand, i.e. the inner or outer elastomeric laminate substrate layers. Elastomeric laminates of the present disclosure may have Dtex-to-Nonwoven-Basis-Weight-Ratios of from about 1.5 to about 15, from about 3 to about 12, or from about 4 to about 10.

"Peel-Strength" is the force required to separate the first and second nonwoven substrate layers forming the elastomeric laminate. Elastomeric laminates of the present disclosure may have a Peel-Strength of at least about 1 N/cm to about 5N/cm or from about 2 N/cm up to about 10 N/cm or up to and including substrate failure of one or both of the nonwoven substrates.

"Melting-Point" is the temperature at which a material or substance changes state from solid to liquid at atmospheric pressure. At the melting point the solid and liquid phase exist in equilibrium. The Melting-Point of the first and second substrates may be from about 100 to about 170, or from about 110 to about 160, or from about 120 to about 150 degrees Celsius. The Melting-Point for the elastic strands of elastomeric laminates of the present disclosure may be greater than about 170 degrees Celsius.

"Application-Force" is the force that a wearer of caretaker might encounter while donning the absorbent article. The Application-Force is derived from a two cycle Hip Hoop Test.

"Sustained-Fit-Load-Force" is the force that an article applies to the wearer when the wearer's waist extends for example during respiration or during wearer movement like when a wearer goes from a standing position to a sitting position or from a prone position to a sitting position. The Sustained-Fit-Load-Force is derived from a two cycle Hip Hoop Test.

"Sustained-Fit-Unload-Force" is the force that an article applies to the wearer when the wearer's waist contracts for example during respiration or during wearer movement like when a wearer goes from a sitting position to a standing position or from a sitting position to a prone position. The Sustained-Fit-Unload-Force is derived from a two cycle Hip Hoop Test.

Other definitions may be presented herein.

Textures of the Present Disclosure

Absorbent articles comprising traditional stranded elastomeric laminates, i.e., those having elastics with a decitex above 400, elastic spacing greater than 4 mm and elastic pre-strain above 200% have a texture comprising large, random rugosities that are present on the wearer-facing surface as well as the garment facing surface. The texture formed by such large, random, rugosities does not provide the appearance of a textile garment and the size and harshness can adversely impact the skin of the wearer leaving marks and indentations.

Absorbent articles comprising beamed elastics and elastomeric laminates formed from beamed elastic have much more intentional, well-defined and deliberate textures enabled by the beamed elastics incorporated into the elastomeric laminate. These intentional, well-defined and deliberate textures and zones of texture can be used to communicate the intended use of the article, the function of the article, as well as the intended wearer. For example, an intentional texture that is blousy and soft may communicate a comfortable fitting design intended for overnight wear, low activity wear times, or may be desirable for younger less mobile babies or those with more sensitive skin. On the other hand, an intentional design that is smoother and closer fitting to the skin may communicate a contour fitting design intended for daytime wear, times of high activity such as walking, hiking, or playing sports. A contour fitting design may also be intended for use on older more mobile children for example toddlers or walking/running children. The intentional, well-defined and deliberate textures and zones of texture enabled by beamed elastic based laminates are consistent with textile garments that typically have such identifiable textural patterns as well as patterns to communicate function. For example, it is easy to differentiate between leggings meant for lounging and leggings meant for high activity endeavors like aerobics, running or sports because of the visual nature of the design and in particular the textures and/or zones of texture.

The intentional, well-defined and deliberate textures and textural zones enabled by beamed elastic laminates also can impact distribution of forces in the belt as well as sustained fit by providing structural features, for example vertically oriented gathers, enabled by the textures themselves that increase bucking resistance and prevent rollover, sagging, collapse and slippage of the elastomeric laminate in use.

General

As shown in FIGS. 2H and 2I, an article component (e.g., a belt, a side panel, and ear panel, etc.) may comprise a plurality of the same or different type and/or arrangement of bonds 322 or bond regions 324 that may be of similar shape, scale, disposition, and/or pattern in various sections (e.g., Sections 1, 2, 3, 4, L, R, or M). The bonds 322 or bond regions 324 may be formed using an adhesive or may be formed mechanically, including heat, pressure, and/or ultrasonically, and may join the first and second substrate layers 306 and 308 together, with elastic strands 316 therebetween, to form the absorbent article component. Each of the sections may comprise a plurality of the same type and/or arrangement of bonds 322 or bond regions 324 to form the same or similar texture zone (i.e., the same or substantially the same presentation of texture). Alternatively, the bonds 322 or bond regions 324 in one or more Sections 1, 2, 3, or 4 may be different from the bonds 322 or bond regions 324 in another section to form different texture zones. Different texture zones may also be formed by adjusting the spacing, Dtex, and pre-strain of the elastic strands between the layers of the laminate. It should also be noted that the texture and/or bond pattern may be mirrored across one or both of the longitudinal and/or lateral centerlines to create a balanced more holistic textural appearance.

FIG. 2H illustrates linear, longitudinally extending, continuous ultrasonic (comprising densified portions) bonds 322 disposed in Sections 1 and 2 in the front waist region 36, arcuate ultrasonic bonds in Sections 1 and 2 in the back waist region 38, arcuate ultrasonic bond regions 324 in Sections 1, 2, and 3 of the back waist region 38, and spiral adhesive 319 in Section 4 in the back waist region 38. Each of these described bonds 322 and bond regions 324 join the first and second substrate layers 306 and 308 together. These differences in bonding type, pattern and shape will contribute to providing distinct and visually discernible well-defined textural differences in the various Sections 1, 2, 3, 4, L, M, and/or R.

The garment-facing surface 2 of a substrate in the area where a wearer-facing surface 4 of the article component is joined to the chassis, often by spiral or slot-coated adhesive, may have a discernable textural difference even when it comprises the same bonding arrangement and the same elastic profile as adjacent areas of the article component because the adhesive joining the article component to the chassis may partially deaden the impact of elastics 316 in that area; further, the elastic strands may be severed so that they do not run continuously across the chassis 200.

The bonds 322 or bond regions 324 joining the first and second substrate layers 306 and 308 together, where elastic strands 316 are there-between, translate substantially the same texture on the garment-facing surface 2 as of the elastomeric laminate 302 as the wearer-facing surface 4.

The elastomeric laminate 302 may comprise continuous bonds 322 (for example, in the article of FIG. 2H, in the front waist region 36, several of the bonds extend continuously (longitudinally) across multiple component sections—some bonds 322 extend continuously from Component Section 1 to 4, but are laterally discrete in that that they are laterally spaced (Sea)) along a given shape or pattern. Alternatively bond regions 324 may be formed from a plurality of bond sites disposed in a particular pattern or shape (see, for example, FIG. 2H, back waist region 38, Sections 1-3). Examples of the shapes or patterns that can be formed from a plurality of discrete bond sites include lines disposed parallel to one or both of the longitudinal or lateral axis or lines disposed angularly relative to one or both of the longitudinal or lateral axis. The bond or bond regions may form various open shapes 324" (e.g., arcs, curves, etc.—see FIG. 2H) and closed shapes 324' (e.g., circles, triangles, squares, diamonds, etc.—see FIG. 2H). Regarding closed shapes 324', bonding leaves a center portion 321 unbonded, while the perimeter is bonded via bonds 322, and the two cooperate to form the appearance of the closed shape 324' (see FIG. 2H).

Bond Regions

Regarding bond regions 324, the discrete bonds forming a pattern or shape may be disposed within 5 mm or less of each other and more typically within 3 mm of each other or less of one another (S1) (see FIG. 2H'). These closely spaced bonds 322 may be considered part of the same bond region 324.

With regard to particular bonding arrangements for yielding desirable textures, an article component selected from an ear panel, a side panel, and/or a belt panel may, in Section 1, comprises longitudinally extending bonds or bond regions transversely spaced from each other at an Average-Lateral-Bond-Spacing, and may, in Sections 2 or 3, comprise longitudinally extending bonds or bond regions transversely spaced from each other at a different Average-Lateral-Bond-Spacing than Section 1. The bonds or bond regions in these sections may have an Average-Longitudinal-Bond-Length from about 20 mm to about 200 mm and an Average-Lateral-Bond-Spacing from about 2 mm to about 20 mm.

Extend/Cooperate

The bonds 322 or bond regions 324 from one section may "extend into" another section or "cooperate" with bonds in various sections to form a larger composite shape. For instance, an end edge of a bond or bond region in a section may substantially align with an end edge of the bond or bond region in an adjacent section such that the bond or bond region is, or appears to be, continuous through multiple sections or such that a larger composite shape is formed (e.g., an arc, serpentine curves, etc.). For example, a bond or bond region in Section 1 may have an end edge that is substantially aligned with an end edge of a bond or bond region in Section 2. In this way, a bond element may extend or appear to extend through Sections 1, 2, 3, 4 and/or L, R, and M. Furthermore, an end edge of a bond or bond region in a section disposed in a first waist region may substantially align with an end edge of the bond or bond region in an adjacent section disposed in a second waist region such that the bond or bond region is, or appears to be, continuous from a first waist region to a second waist region such that a larger composite shape is formed (e.g., an arc, serpentine curves, etc.).

General Texture Example

It may be desirable that each of the Sections 1, 2, 3, 4, and Sections L, M, and R consist of a plurality of densified bonds 322 or bond regions 324 joining first and second nonwoven layers each having a basis weight from about 6 gsm to about 35 gsm, the densified bonds 322 or bond regions 324 overlapping a plurality of elastic strands 316 having an Average-Strand-Spacing from about 0.25 mm to about 4 mm, or from about 0.5 mm to about 2.5 mm, an Average-Dtex of from about 20 to about 300, or from about 40 to about 220, and an Average-Pre-Strain from about 50% to about 300%, or from about 75% to about 250% to form an elastomeric laminate that may be used as an article component, such as a belt flap. Said bonds 322 or bond regions 324 may have an Average-Bond-Width or Average-Bond-Region-Width of from about 0.25 mm to about 5 mm, or from about 0.5 mm to about 2 mm, an Average-Bond-Length or an Average-Bond-Region-Length of from about 5 mm to about 300 mm, or from about 20 mm to about 200 mm, and having an Average-Lateral-Bond-Spacing from about 2 mm to about 20 mm, or from about 4 mm to about 10 mm. The densified bonds 322 or bond regions 324 may overlap and dimensionally lock at least 15 elastic strands. One or more of the densified bonds overlapping one or more of said elastic strands may have a Cross-Sectional-Strand-Area in its relaxed disposition from about 0.002 mm$^2$ to about 0.04 mm$^2$, and a Cross-Sectional-Bond-Void-Area of the bond from about 0.001 mm$^2$ to about 0.02 mm$^2$. A ratio of Bond-Width to Bond-Length of at least two bonds of said plurality of densified bonds may be between 4:1 and 300:1, or between 20:1 to about 200:1. And, further, a Dtex-to-Nonwoven-Basis-Weight-Ratio of a first elastic strand (of the plurality of elastic strands) and first and second nonwoven layers may be from about 1.5 to about 7; a Dtex-to-Spacing-Ratio of the plurality of elastic strands may be from about 65:1 to about 300:1; a ratio of Average-Lateral-Bond-Spacing to Average-Bond-Width may be between 1:1 to 50:1; a ratio of Average-Bond-Length to Average-Bond-Width may be between 1:1 to 300:1; a ratio of Average-Longitudinal-Bond-Spacing to Average-Bond-Width may be between 1:2 to 20:1; a ratio of Average-Bond-Length to Average-Longitudinal-Bond-Spacing may be between 1:1 to 300:1.

Adhesive

One or more of Sections 1, 2, 3, 4, and Sections L, M, and R of an article component may be adhesive free. For example, sections having densified bonds joining first and second substrates together may be adhesive free. However, it may be desirable that these sections comprising densified bonds may also comprise adhesive, for example, in a tri-laminate or quad-laminate configuration as described hereinafter. In other words, the sections of the elastomeric laminate may comprise 2 or more substrate layers and may comprise one or more bonding means including, mechanical, thermal, ultrasonic, pressure, adhesive, cohesive and combinations thereof. It may also be desirable that the component article sections consist only of adhesive bonds holding the substrate layers, as well as the elastic strands therebetween. Areas that comprise substantially continuous fields or areas of adhesive joining the elastics and/or substrates of an elastomeric laminate, may result in a smoother texture. These smoother sections may be desirable in high-motion zone areas and wearer-facing surfaces in contact with the wearer. These smoother textures signal body-conforming contoured fit. These smoother adhesive sections may also be used to contrast macro textures created by sections comprising intermittent bonds (e.g., discrete ultrasonic bonds).

Figure 1C:
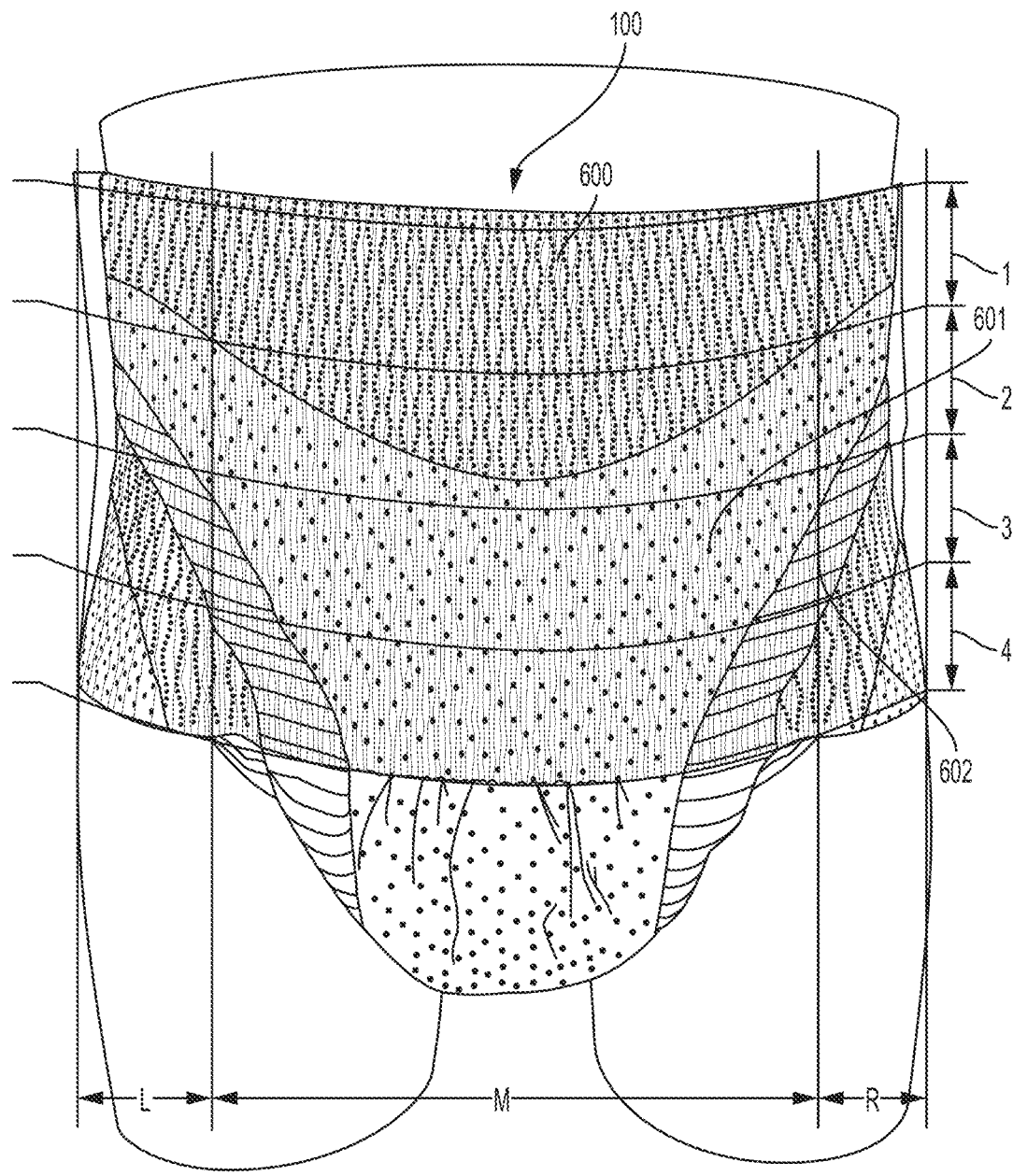
FIG. 1C is a perspective front view of a pant fitted onto a mannequin wearer comprising multiple texture zones.
Figure 1D:
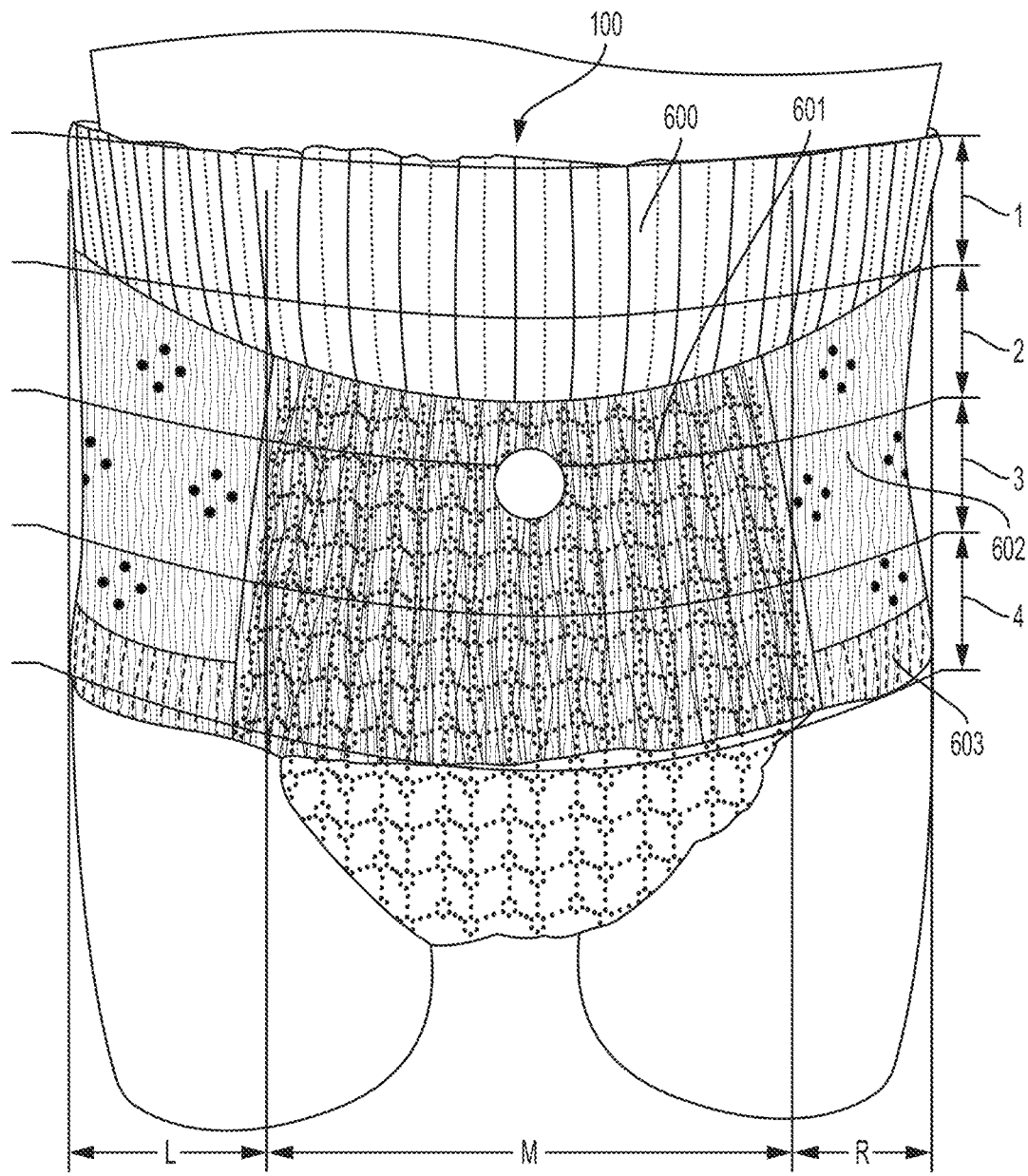
FIG. 1D is a perspective front view of a pant fitted onto a mannequin wearer comprising multiple texture zones.
Figure 1E:
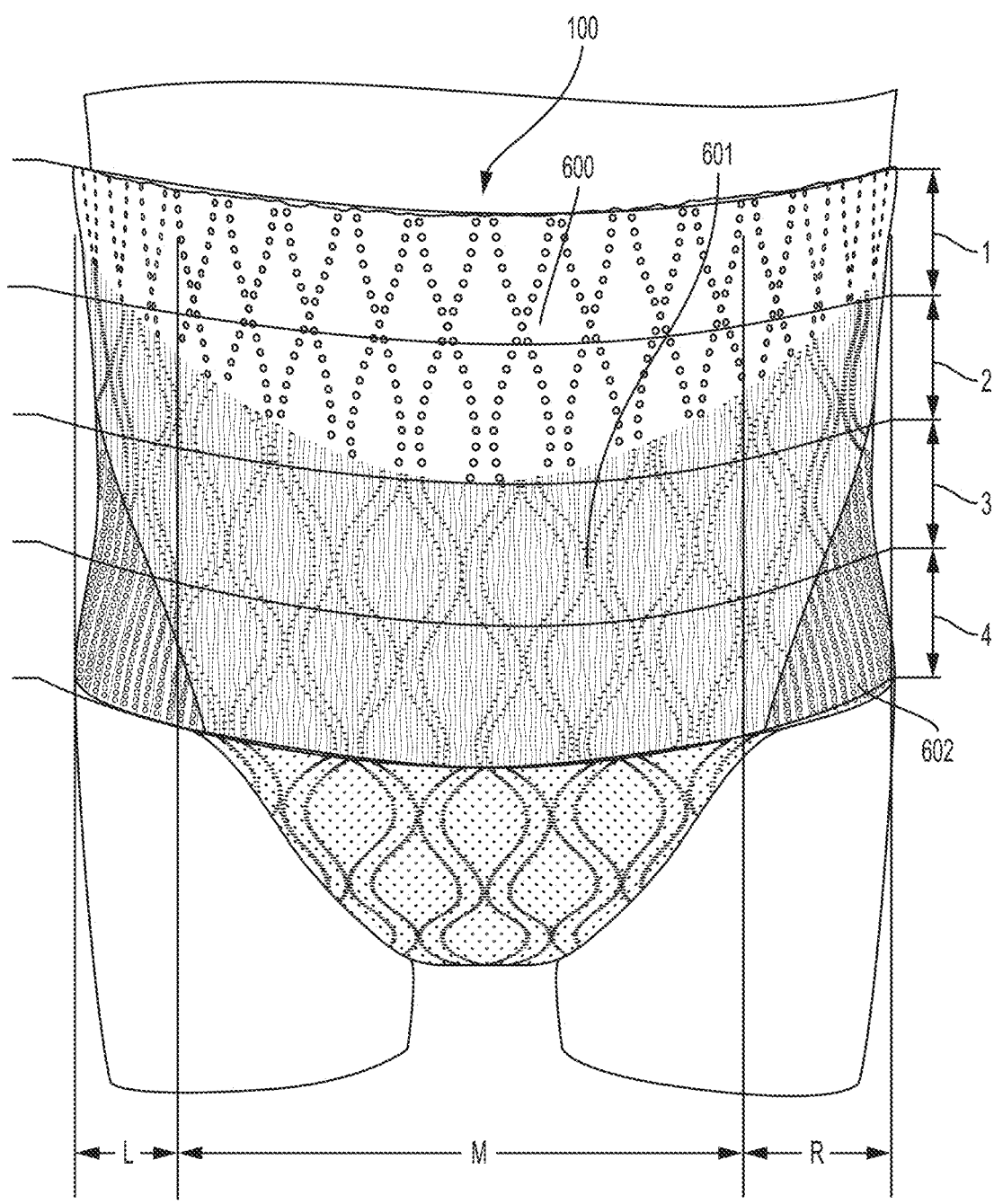
FIG. 1E is a perspective front view of a pant fitted onto a mannequin wearer comprising multiple texture zones.
Figure 1F:
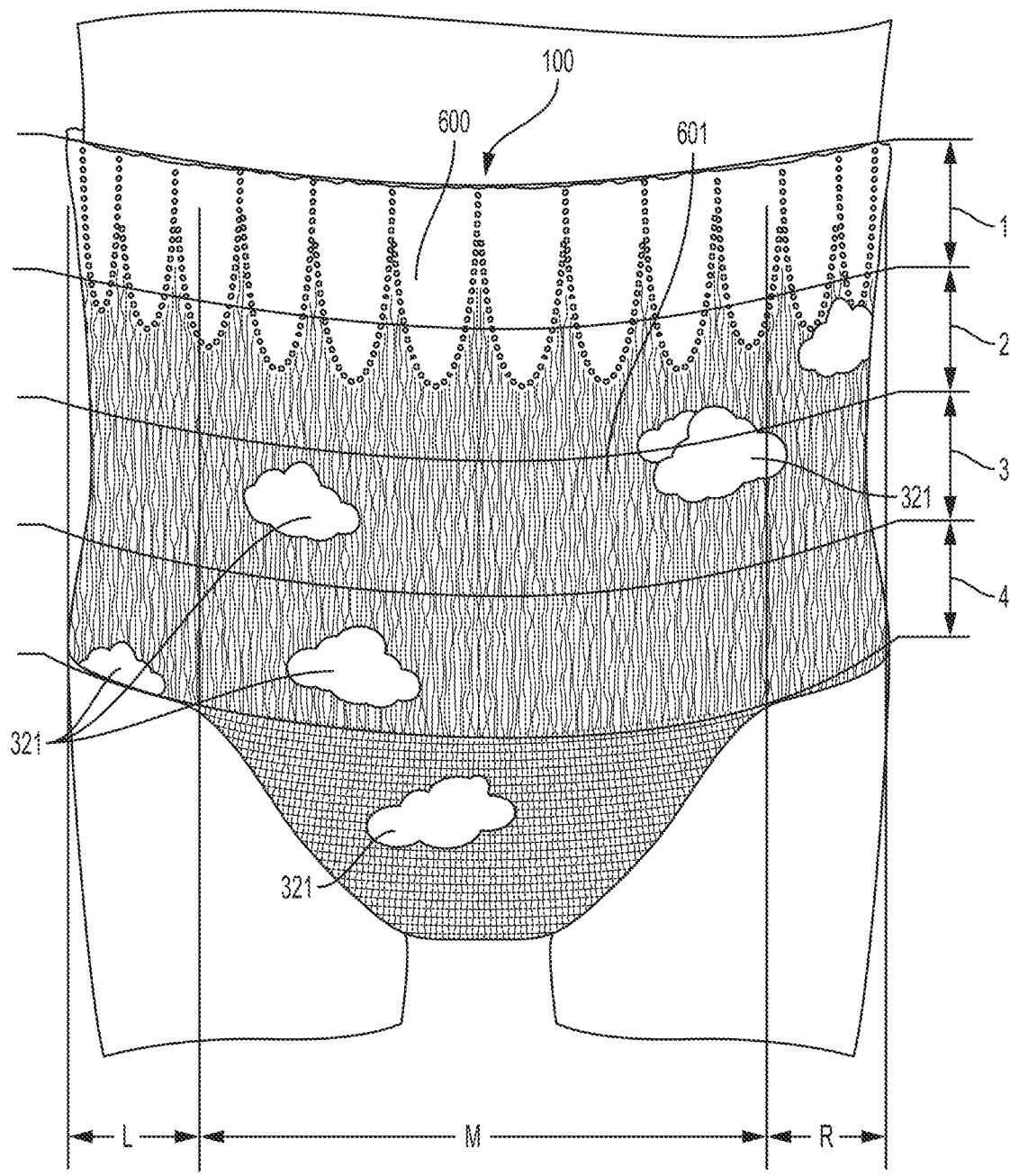
FIG. 1F is a perspective front view of a pant fitted onto a mannequin wearer comprising multiple texture zones.

It should also be understood that one or more of the component sections may comprise a single texture as illustrated in FIG. 1A Section 1 showing a single texture with a heart tag graphic. Alternatively one or more of the component sections may comprise 2 or more distinct textures as illustrated in FIG. 1C Section 2. In certain embodiments, one or more of the component sections in a first waist region may comprise the same texture as one or more of the component sections in a second waist region. In other embodiments the textures in a first waist region may be distinctly different than the textures in a second waist region.

Section L and R, in one or both waist regions, may have a relatively smooth texture enabled by application of a continuous field of adhesive joining the elastics to the substrate layers of the elastomeric laminate, while Section M may have an intentional, well-defined texture enabled by an intermittent bond pattern formed by mechanical bonds, thermal bonds, ultrasonic bonds, pressure bonds, and/or bonds formed from adhesive, cohesive and combinations thereof. Alternatively, Section M may comprise an outer nonwoven material comprising zones of varying basis weight and/or thickness—the outer nonwoven material comprising zones of varying basis weight and/or varying thickness may extend from a first waist edge through the crotch to the opposing waist edge or may be present only in the crotch region of the article. In certain embodiments, the outer nonwoven material comprising zones of varying basis weight and/or varying thickness may overlap with a portion of the elastomeric laminate and/or may form a portion of the elastomeric laminate.

Alternatively, Sections L and R, in one or both waist regions, may have a relatively smooth texture enabled by a tightly spaced pattern of intermittent bonds or a continuous surface bond joining the elastics to the substrate layers of the elastomeric laminate, while Section M may have an different texture enabled by an intermittent bond pattern having a different spacing or pattern from the bond pattern in Sections L and R.

Different Texture Zones

When textures vary (via different bonding arrangements, including one or more of different Average-Bond-Width, Average-Bond-Length, Average-Longitudinal-Bond-Spacing, and Average-Lateral-Bond-Spacing in one or more of Sections 1, 2, 3, 4, L, M, and R), they may have different parametric values, including one or more of Percent-Contact-Area, Rugosity-Frequency, Rugosity-Wavelength, 2-98%-Height-Value, Emtec-TS7-Value, and/or Emtec-TS750-Value. Different texture zones may have at least a 10%, 15%, or 20% different value of each of these parameters in one or more of Sections 1, 2, 3, 4, L, M, and R. Sections 1 and 4, which may include the appendix region (i.e., the portion of a flap below a side seam), may have different textures versus other sections of the component or the article because of the desire to make the sections along the waist and leg openings appear more finished or to communicate a greater level of elasticity or stretch along these openings. Further, it may be desirable that the texture zones adjacent to the waist and leg openings are the same or similar, at least in Sections L and R. Further, it may be desirable that Sections L and R have a Percent-Contact-Area greater than Section M. It may also be desirable if a first texture zone has a Percent-Contact-Area of less than about 30% and the second texture zone has a Percent-Contact-Area of greater than about 35%. Alternatively, it may be desirable if a first texture zone has a Percent-Contact-Area of less than about 40% and the second texture zone has a Percent-Contact-Area of greater than about 50%.

It may be desirable to compliment the distinct texture zones with common (i.e., similarly shaped and sized and disposed) graphic zones and/or color zones, each of the texture, color/graphic zones being disposed to overlap each other on the absorbent article. More particularly, a common color field and/or graphic pattern (e.g., 700) may overlap a similarly shaped, sized, and disposed bonding arrangements (e.g., 600). FIGS. 3A-F illustrate different color fields and/or graphic patterns, wherein many of the different color field and/or graphic pattern 700, 701, 702, 703, 704, etc. are in the shape and size and disposition of a different texture zone 600, 601, 602, 603, 604, etc. in FIGS. 2A-G. For instance color field and/or the graphic pattern of 700 may be a distinctly different color and/or pattern versus 701, 702, 703, and 704, just as texture zone 600 may be a distinctly different bonding pattern or arrangement versus 601, 602, 603, and 604.

It may, however, also be desirable to have color fields and/or graphic patterns zones or that do not compliment or coordinate with distinct texture zones, such that certain color fields and/or graphic patterns are larger or smaller or differently shaped versus the texture zones that they overlap with. For instance, in FIGS. 2A versus 3A, 601 is a distinct texture field, while the common area of the color field and/or graphic pattern 701 and 701' is two distinct zones.

Figure 2B:
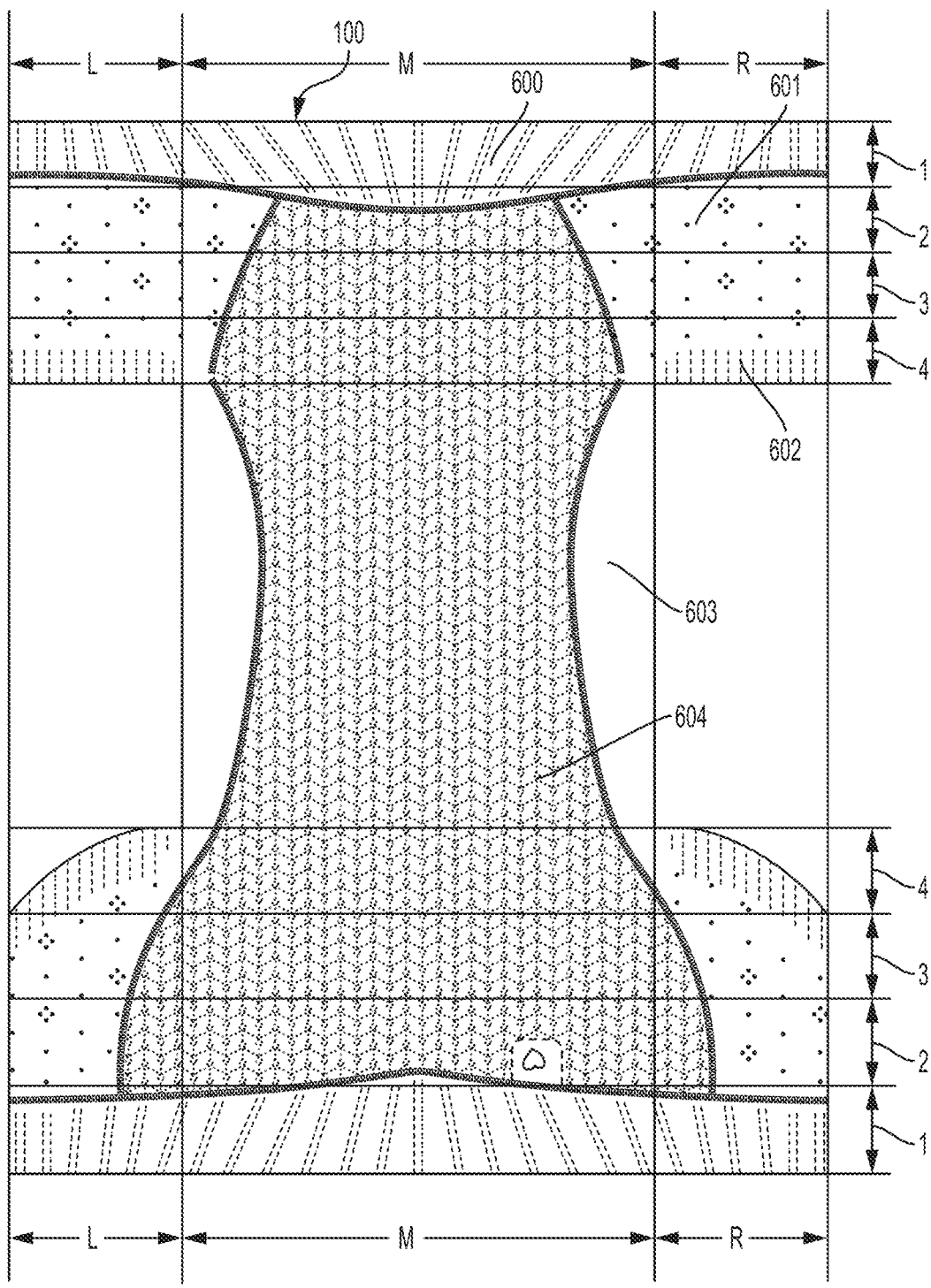
FIG. 2B is a plan view of a garment-facing surface of the pant of FIG. 1B comprising texture, prior to joining side edges of the belt to form the waist and leg openings.
Figure 2C:
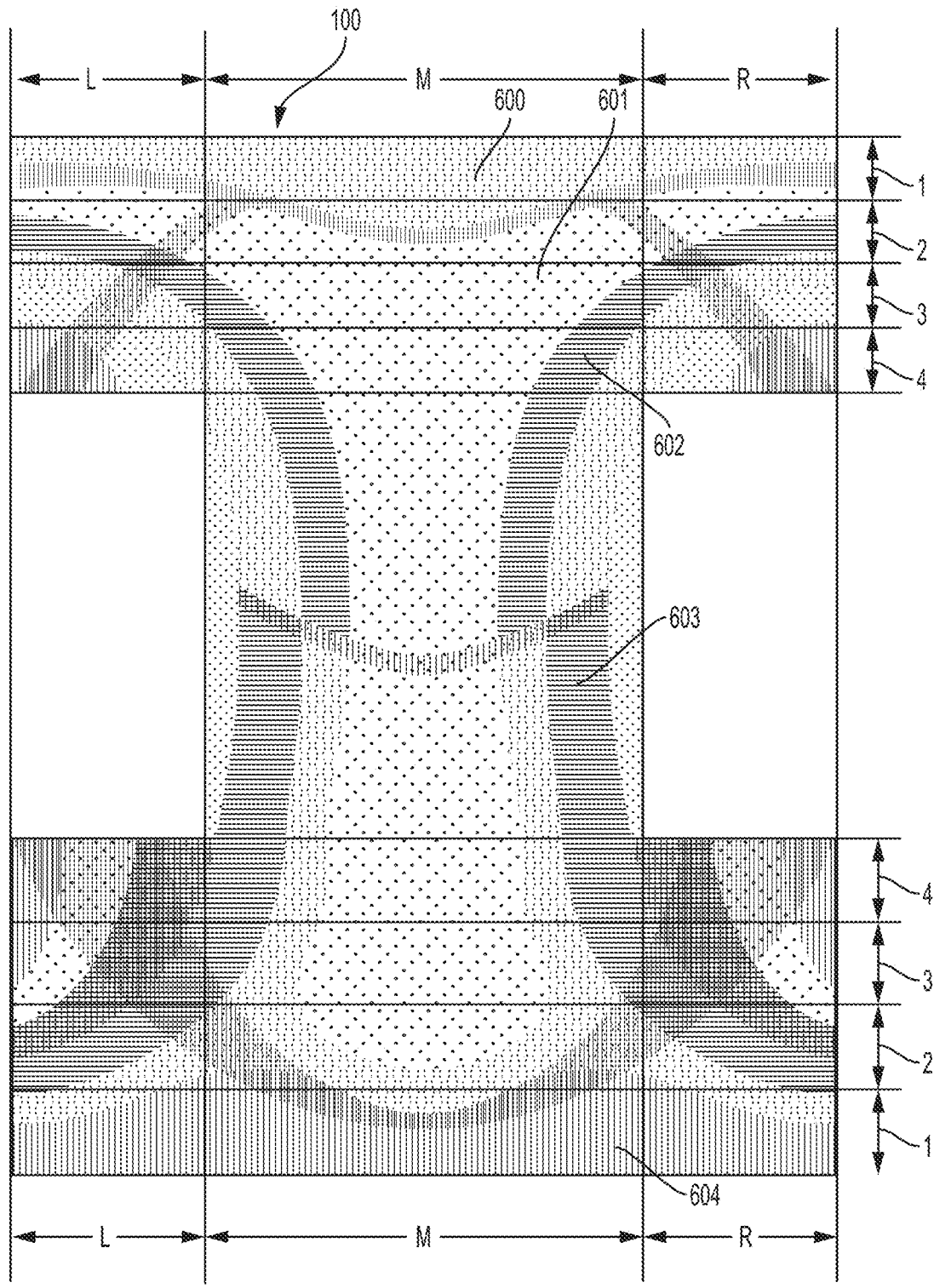
FIG. 2C is a plan view of a garment-facing surface of the pant of FIG. 1C comprising texture, prior to joining side edges of the belt to form the waist and leg openings.
Figure 2D:
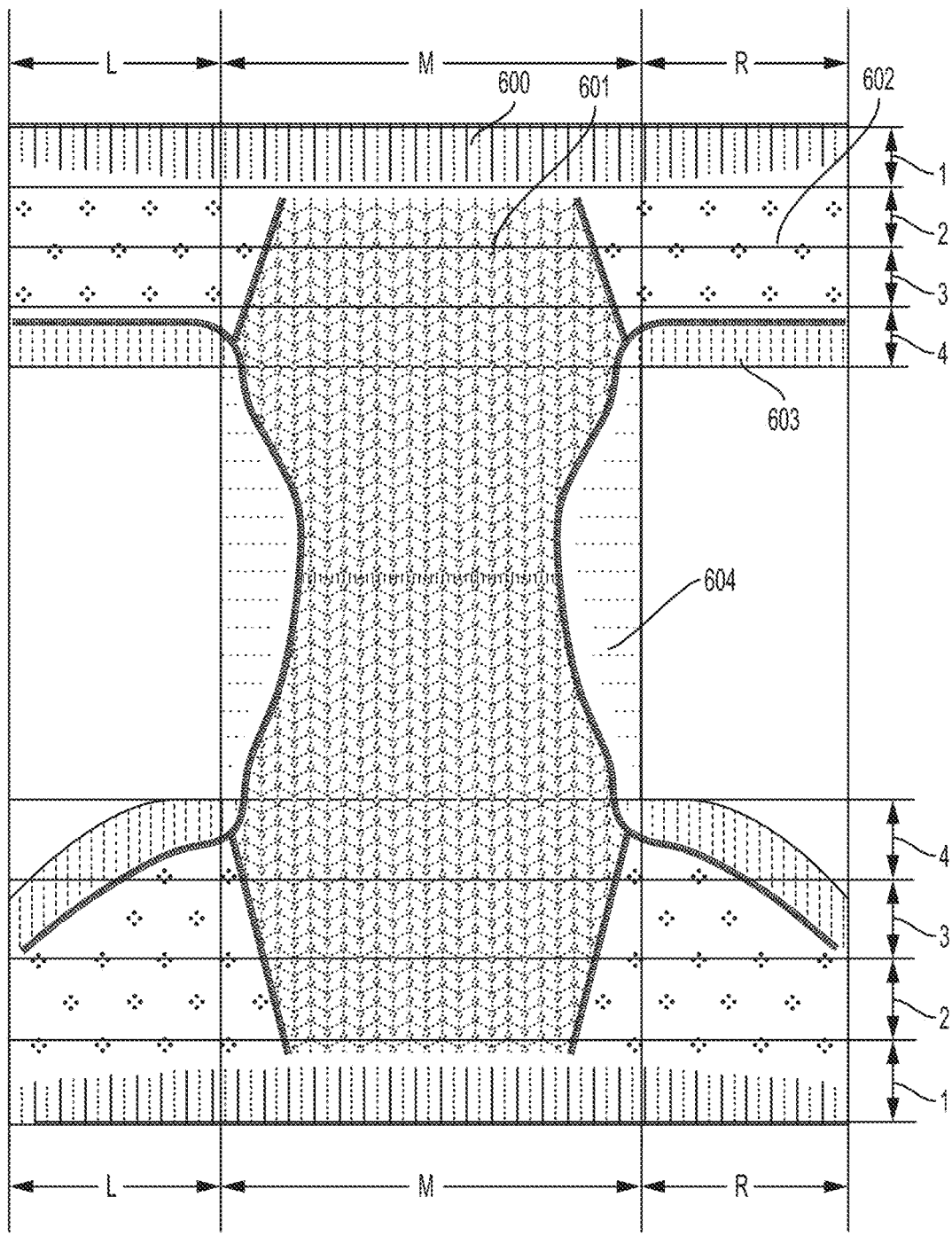
FIG. 2D is a plan view of a garment-facing surface of the pant of FIG. 1D comprising texture, prior to joining side edges of the belt to form the waist and leg openings.
Figure 2E:
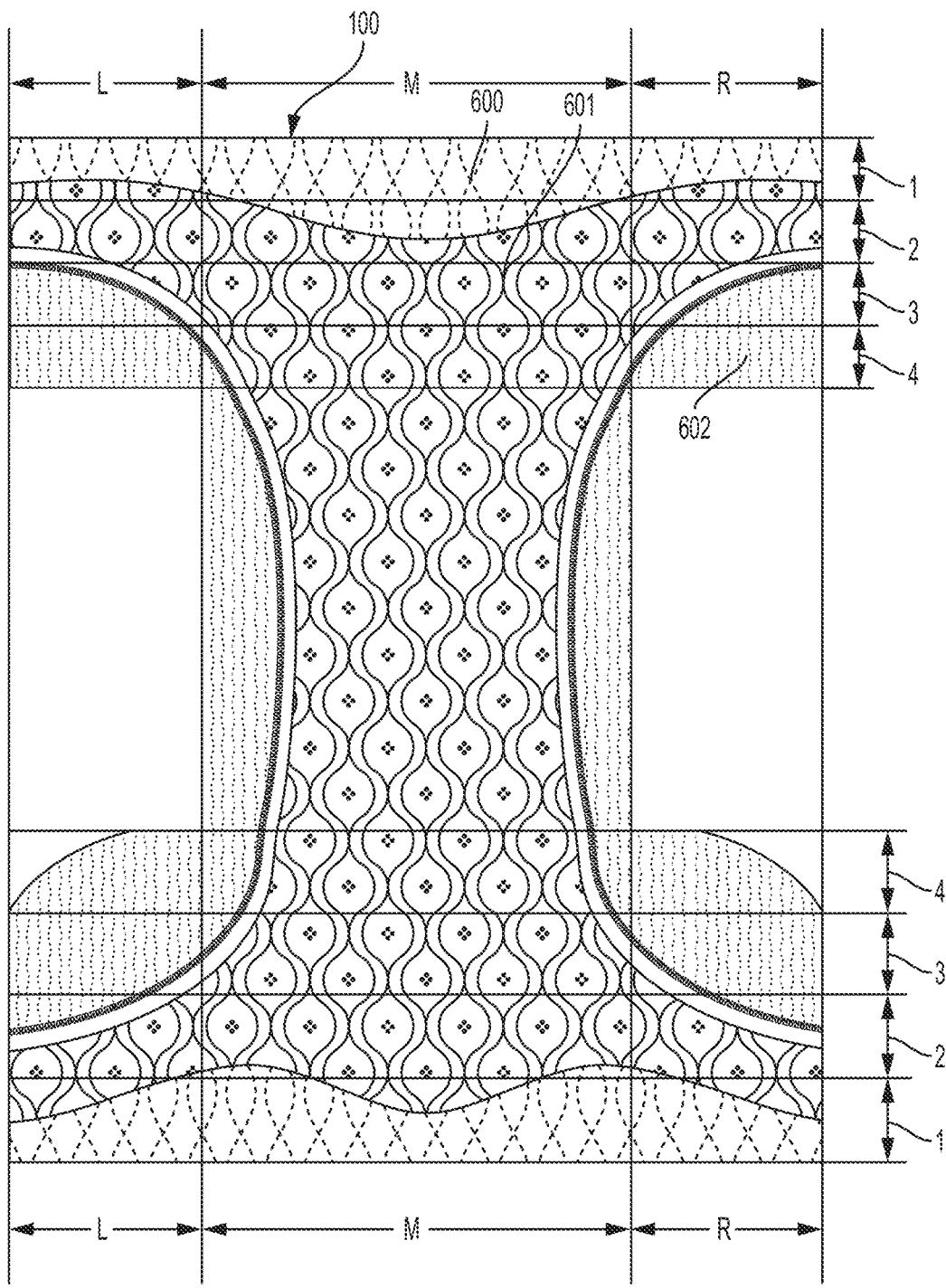
FIG. 2E is a plan view of a garment-facing surface of the pant of FIG. 1E comprising texture, prior to joining side edges of the belt to form the waist and leg openings.
Figure 2F:
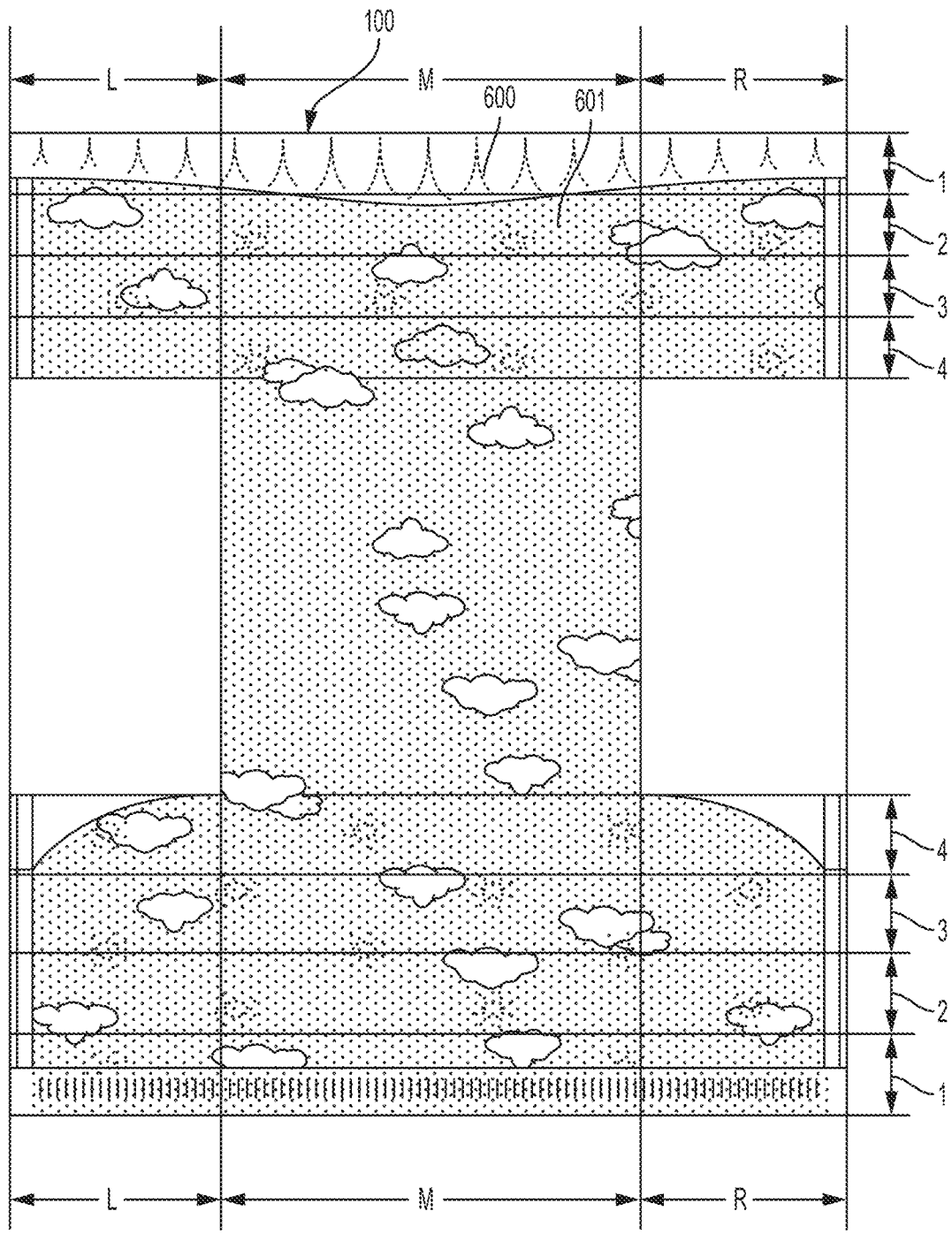
FIG. 2F is a plan view of a garment-facing surface of the pant of FIG. 1F comprising texture, prior to joining side edges of the belt to form the waist and leg openings.
Figure 2G:
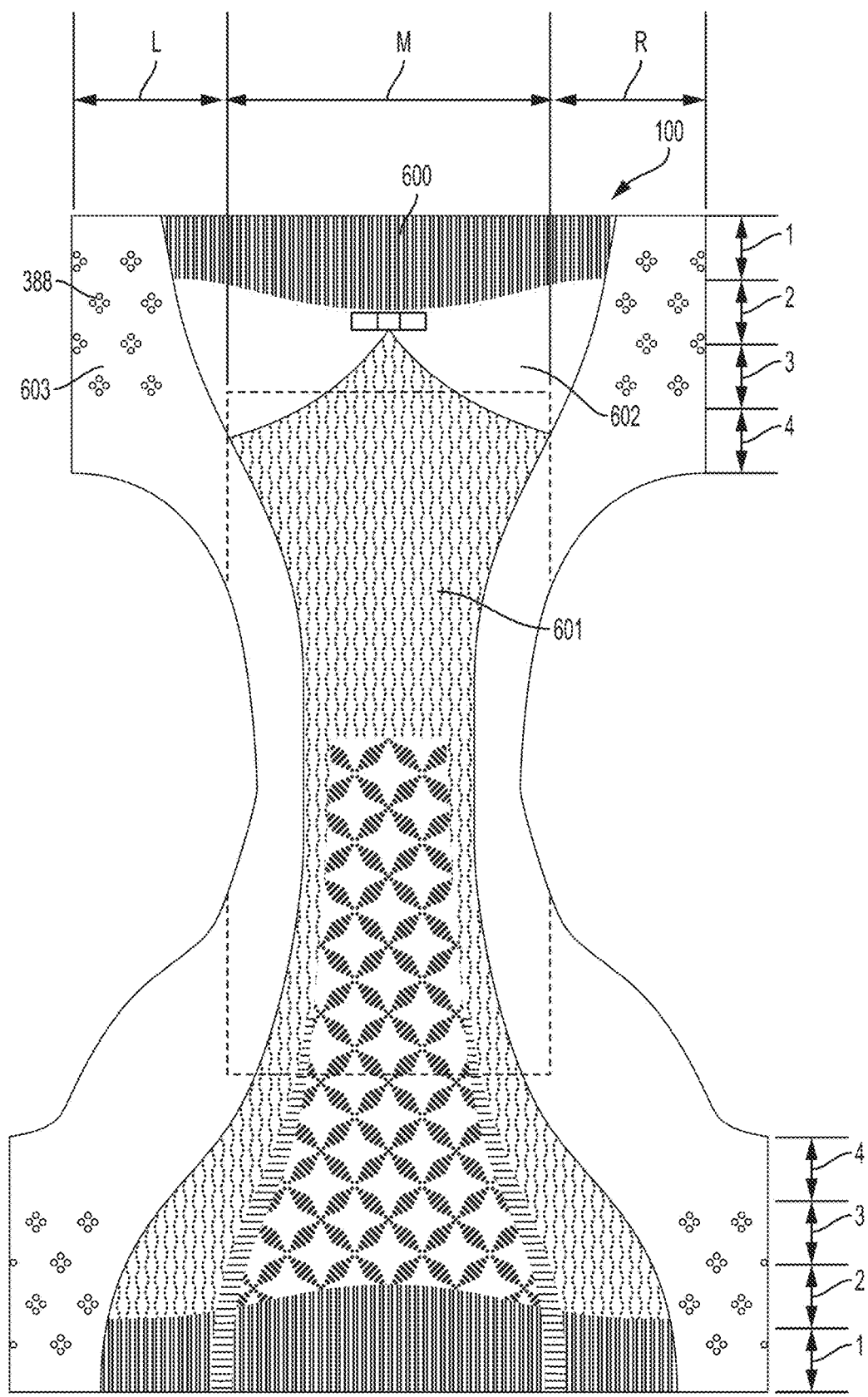
FIG. 2G is a plan view of a garment-facing surface of the pant of FIG. 1G comprising texture, prior to joining side edges of the belt to form the waist and leg openings.
Figure 2H:
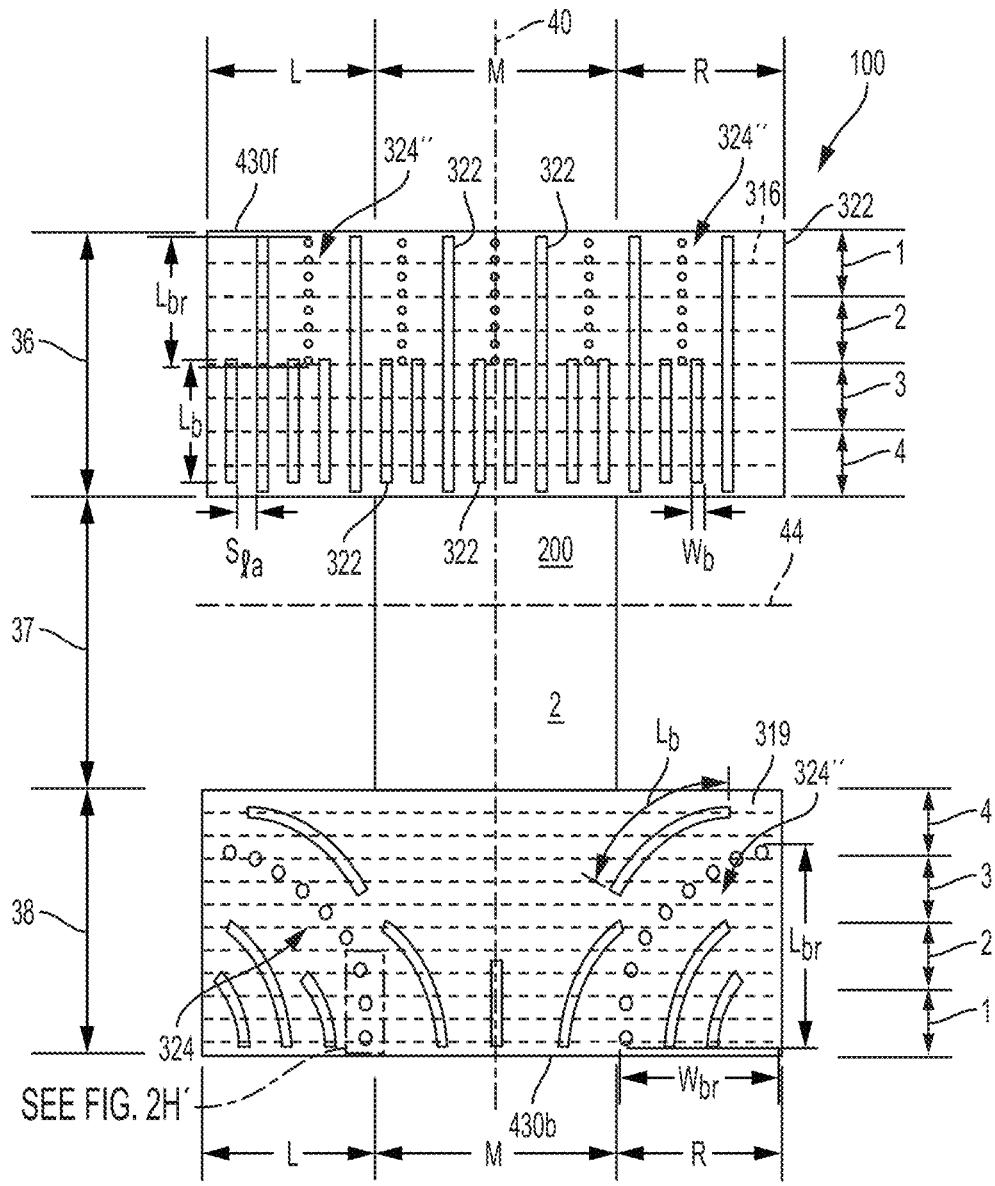
FIG. 2H is a plan view of a garment-facing surface of a pant comprising multiple texture zones, prior to joining side edges of the belt to form the waist and leg openings.
Figure 2H:
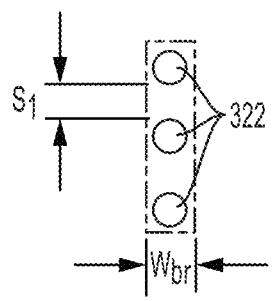
Figure 3A:
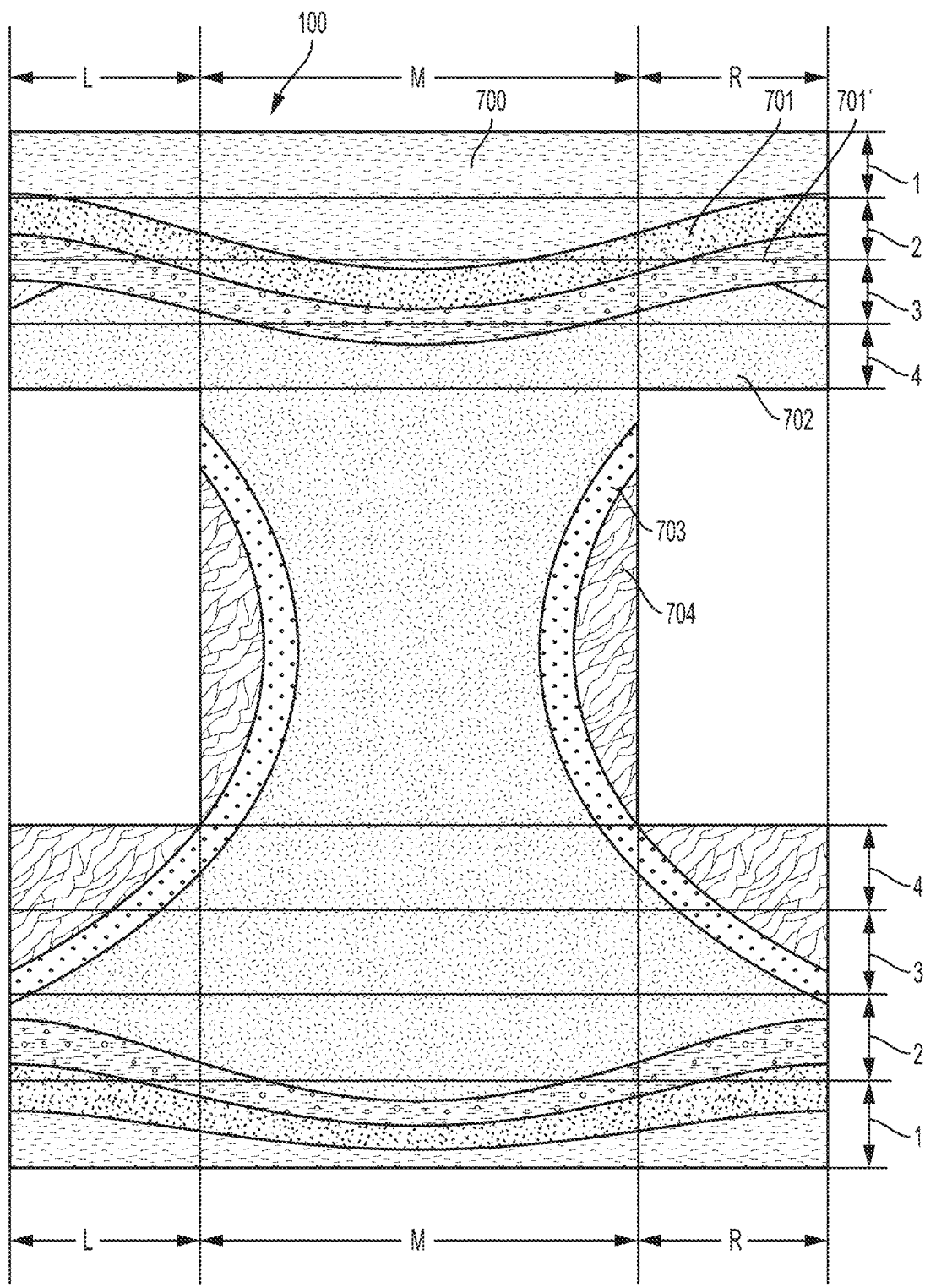
FIG. 3A is a plan view of a garment-facing surface of an optional embodiment of the pant of FIG. 1A comprising color fields and/or color patterns that compliment the different textures of FIG. 1A, prior to joining side edges of the belt to form the waist and leg openings.
Figure 3B:
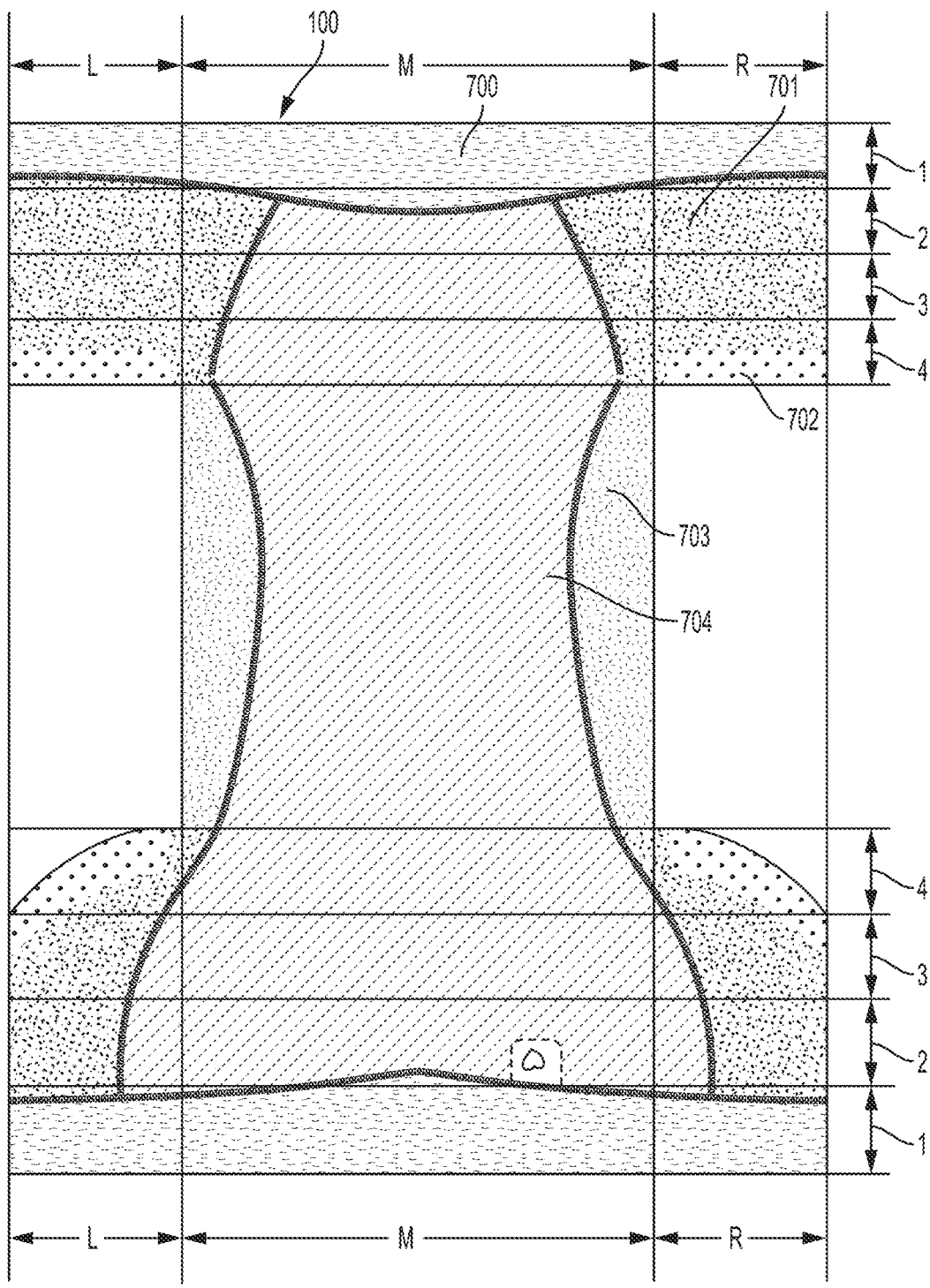
FIG. 3B is a plan view of a garment-facing surface of an optional embodiment of the pant of FIG. 1B comprising color fields and/or color patterns that compliment the different textures of FIG. 1B, prior to joining side edges of the belt to form the waist and leg openings.
Figure 3C:
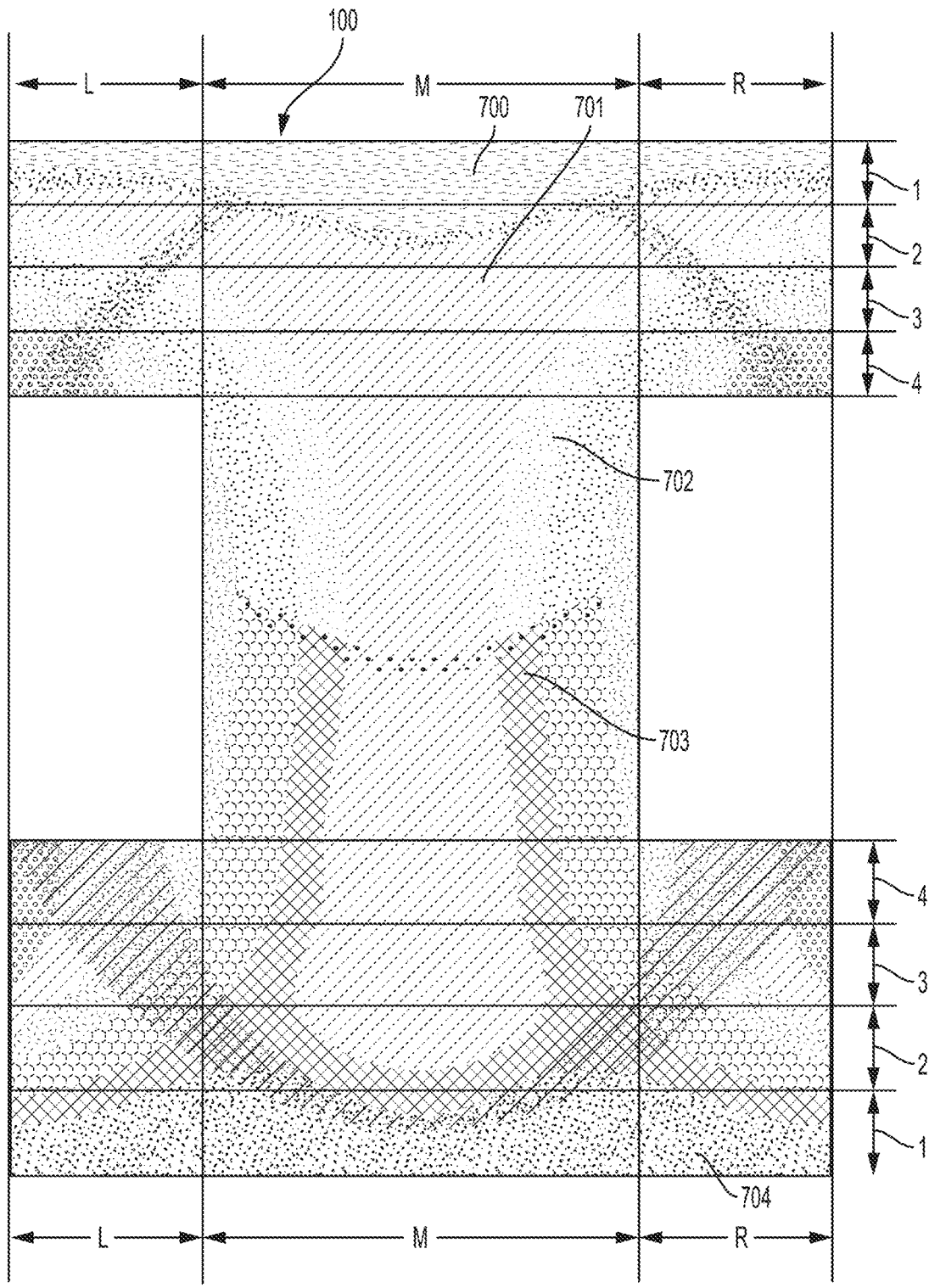
FIG. 3C is a plan view of a garment-facing surface of an optional embodiment of the pant of FIG. 1C comprising color fields and/or color patterns that compliment the different textures of FIG. 1C, prior to joining side edges of the belt to form the waist and leg openings.
Figure 3D:
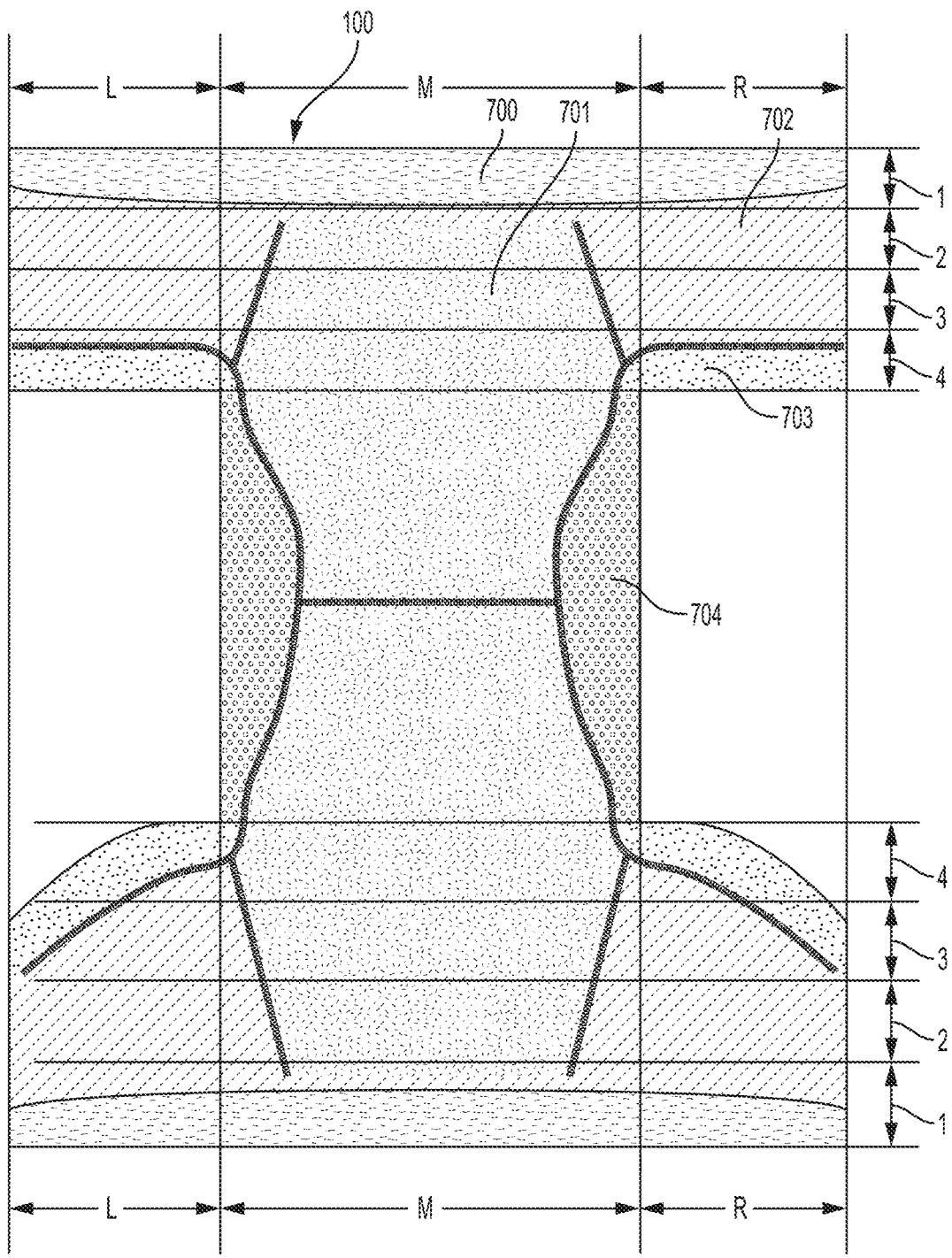
FIG. 3D is a plan view of a garment-facing surface of an optional embodiment of the pant of FIG. 1D comprising color fields and/or color patterns that compliment the different textures of FIG. 1D, prior to joining side edges of the belt to form the waist and leg openings.
Figure 3E:
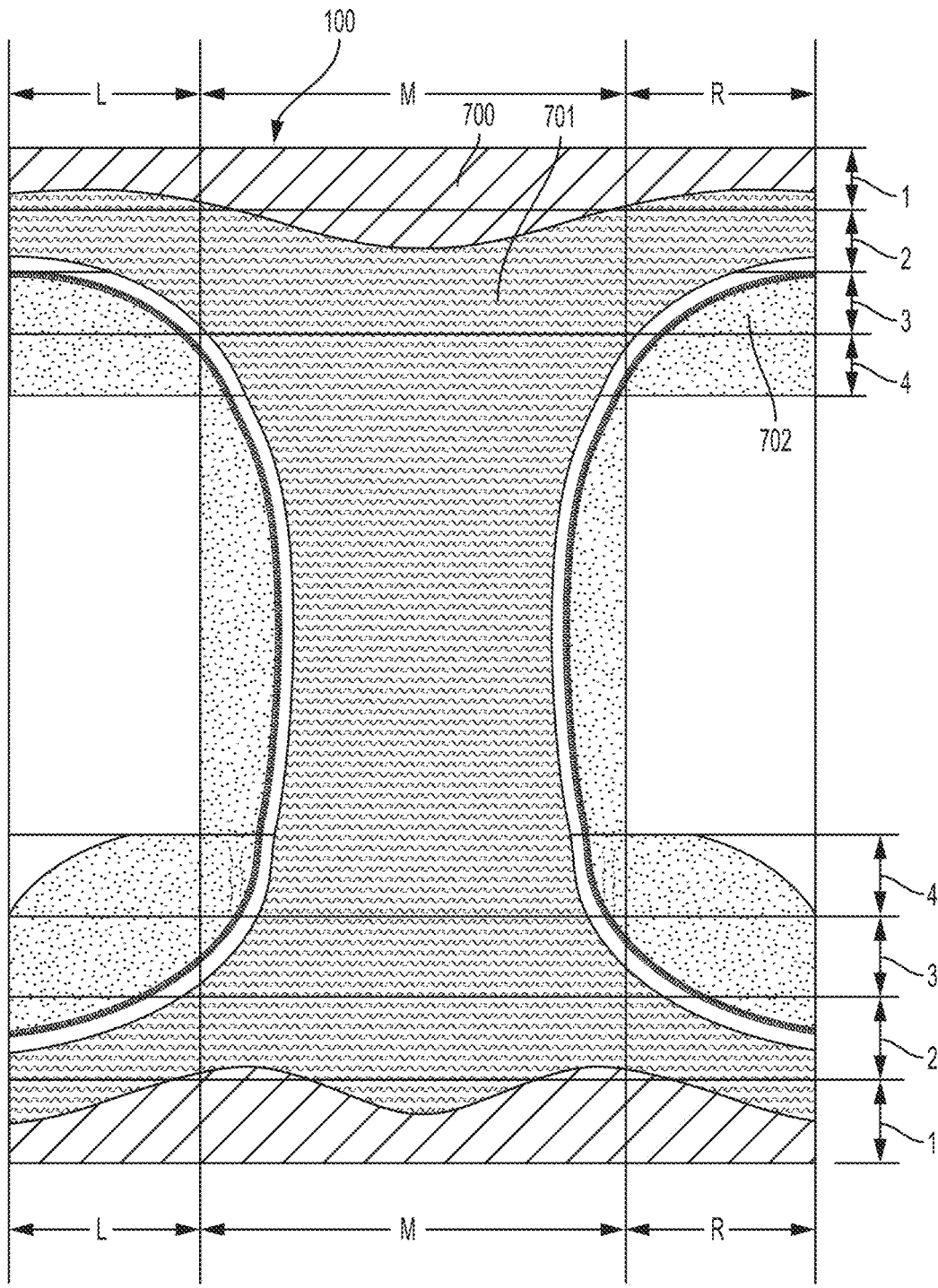
FIG. 3E is a plan view of a garment-facing surface of an optional embodiment of the pant of FIG. 1E comprising color fields and/or color patterns that compliment the different textures of FIG. 1E, prior to joining side edges of the belt to form the waist and leg openings.
Figure 3F:
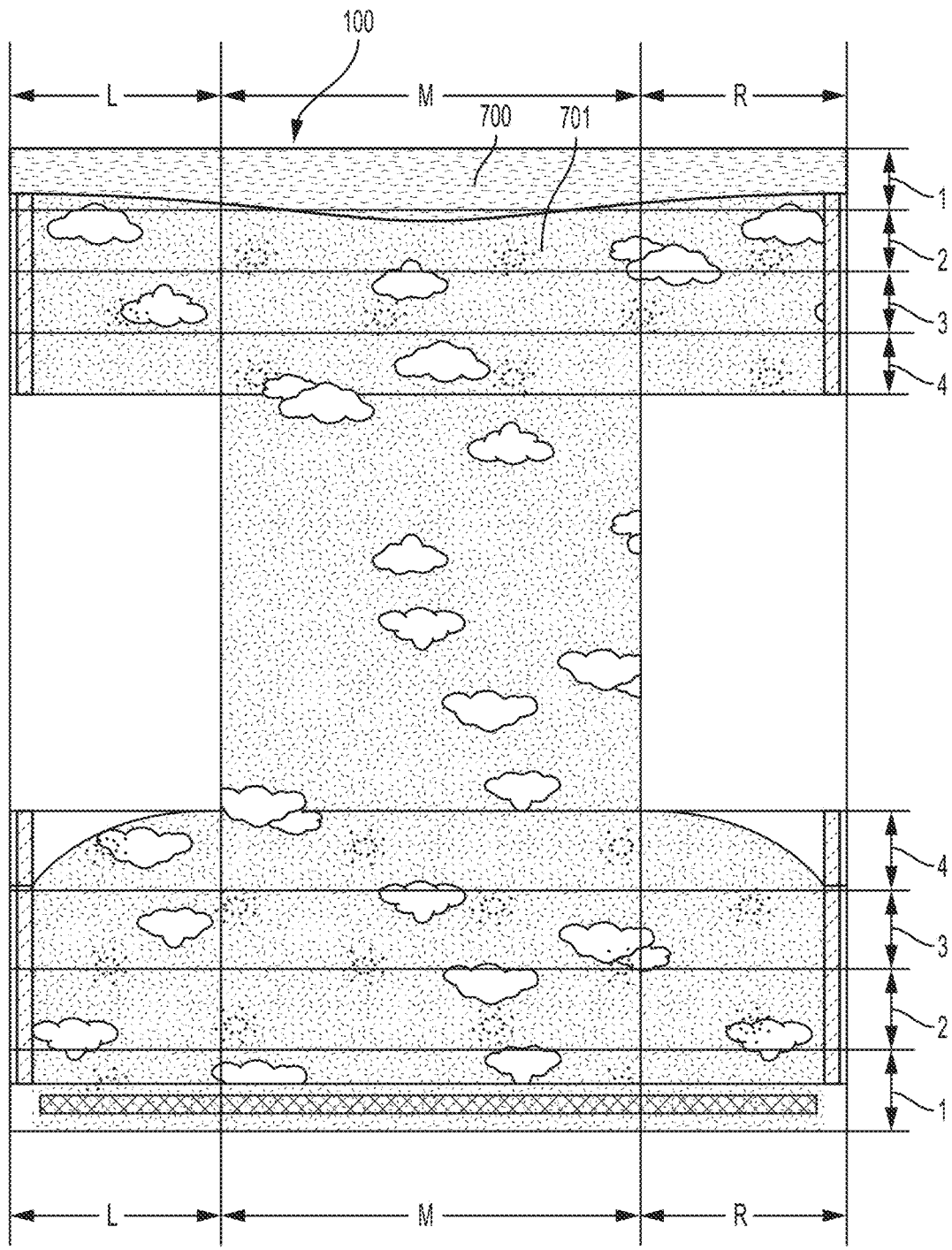
FIG. 3F is a plan view of a garment-facing surface of an optional embodiment of the pant of FIG. 1F comprising color fields and/or color patterns that compliment the different textures of FIG. 1F, prior to joining side edges of the belt to form the waist and leg openings.

It may also be desirable to have color fields and/or graphic patterns zones that overlap with texture zones that have little or no bonding, for example, the area 603 in FIG. 2B has no texture, but is overlapped with color field and/or graphic pattern 703 in FIG. 3B, such that the appearance of texture may coordinate with other areas that do have texture.

Figure 1G:
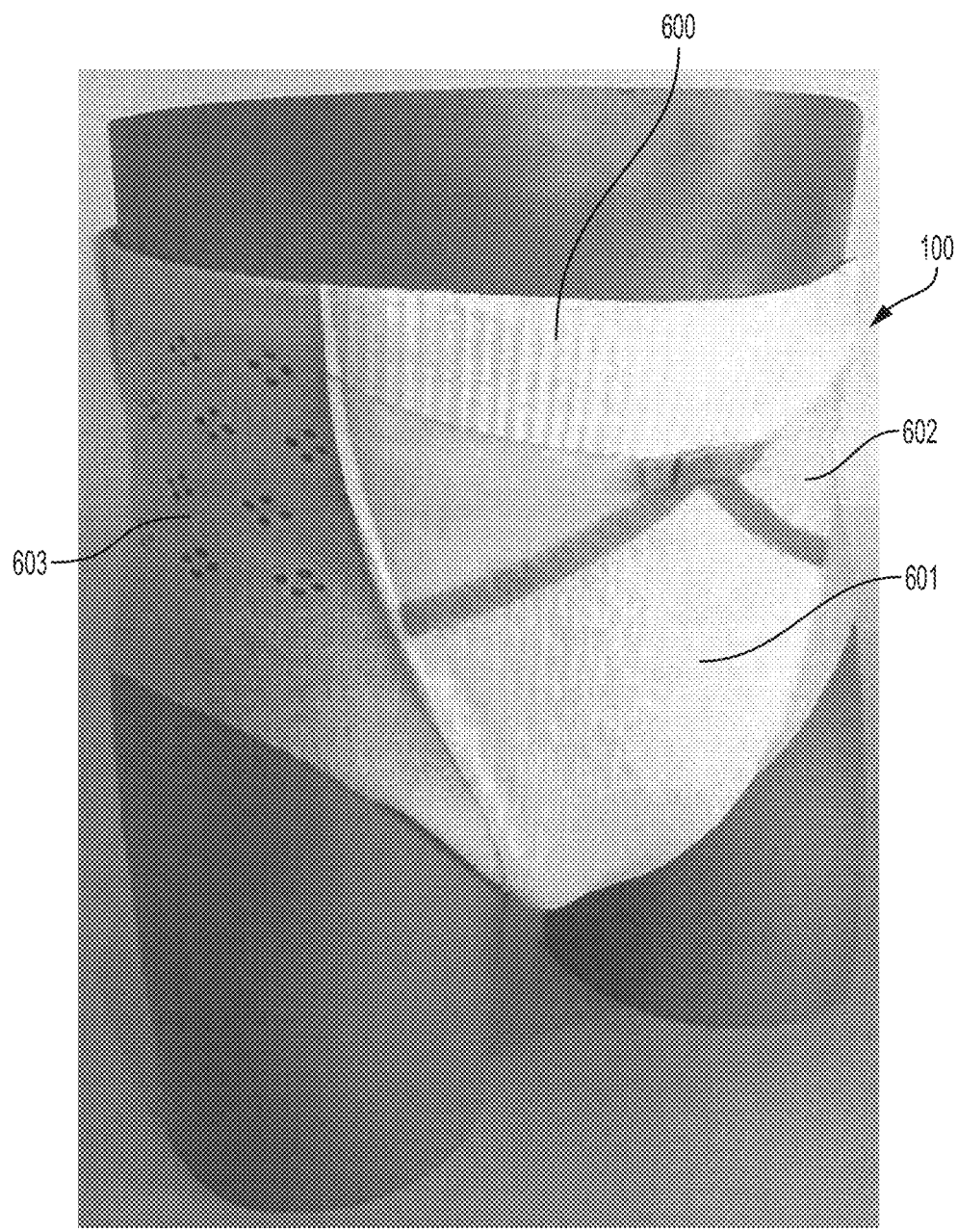
FIG. 1G is a perspective front view of a pant fitted onto a mannequin wearer comprising multiple texture zones.

FIG. 1G illustrates an absorbent article having a first relatively smooth texture, Percent-Contact-Area of greater than 40%, in Sections L and R wherein the elastomeric laminate is formed from 2 substrate layers with elastics bonded between via a substantially continuous adhesive layer. Section L and R may also comprise apertures 388 that are formed in the elastomeric laminate. The apertures may pass from the outer surface through the laminate to the interior surface and may be disposed in a random pattern or in an intentional pattern (as shown in FIG. 1G). Section M comprises a different texture than sections L and R. Sections L and R as shown in FIG. 1G have a higher Percent-Contact-Area, greater than 40%, than Section M (Percent-Contact-Area of less than 35%). Section M may be formed of a bi-laminate or tri-laminate and may comprise an intermittent pattern of bonds formed by thermal, pressure, heat, ultrasonic or adhesive. Alternatively, Section M may comprise an outer substrate layer formed of a nonwoven material comprising areas of varying basis weight or varying thickness.

Texture Parametrics

Relating to the characteristics of the texture, one or more of Sections 1, 2, 3, 4, L, M, and R may have: an Emtec-TS7-Value of less than about 12; an Emtec-TS750-Value of less than 60; a Rugosity-Frequency of from about 0.2 mm$^{-1}$ to about 1 mm$^{-1}$; a Rugosity-Wavelength of from about 0.5 mm to about 5 mm; and a 2%-98%-Height-Value of <1.6 mm. It should be understood that one or more of the Emtec, Rugosity-Frequency, Rugosity-Wavelength and/or 2%-98%-Height-Value in Sections L and R may be different from the Emtec, Rugosity-Frequency, Rugosity-Wavelength and/or 2%-98%-Height-Value in Section M.

Performance Parametrics

Texture zones of the present disclosure should not impact the desired performance of the article or the article components. As such, one or more of Sections 1, 2, 3, 4, L, M, and R may comprise a texture zone and may have: a Section-Modulus of from about 4 gf/mm to about 10 gf/mm; a Cantilever-Bending of less than about 40 mm; an Air-Permeability of at least one of: a) greater than about 40 cubic meters/square meter/minute Air-Permeability at 0 gf/mm (no extension); b) greater than about 60 cubic meters/square meter/minute Air-Permeability at 3 gf/mm (slight extension); and c) greater than about 80 cubic meters/square meter/minute Air-Permeability at 7 gf/mm (moderate extension); a Percent-Contact-Area of at least one of: a) greater than about 10% at 100 um, b) greater than about 20% at 200 um, and c) greater than about 30% at 300 um; a Force-Relaxation-Over-Time from about 5% to about 30%; less than 10% of the elastic strands are broken between adjacent bonds that are transversely spaced less than 20 mm from each other; less than 20% of the elastic filaments are broken between adjacent bonds that are transversely spaced less than 20 mm from each other; a Peel-Strength between first and second nonwoven layers greater than about 1 N/cm up to about 10 N/cm or up to and including substrate failure; greater than 70% of the elastic strands in one of the L and R article sections extends at least 50% of a lateral width (laid out flat, i.e., extended) of the respective L and R sections; and a Pressure-Under-Strand less than 1 psi (according to the conditions defined by the Pressure-Under-Strand Test).

Random Texture

Figure 4:
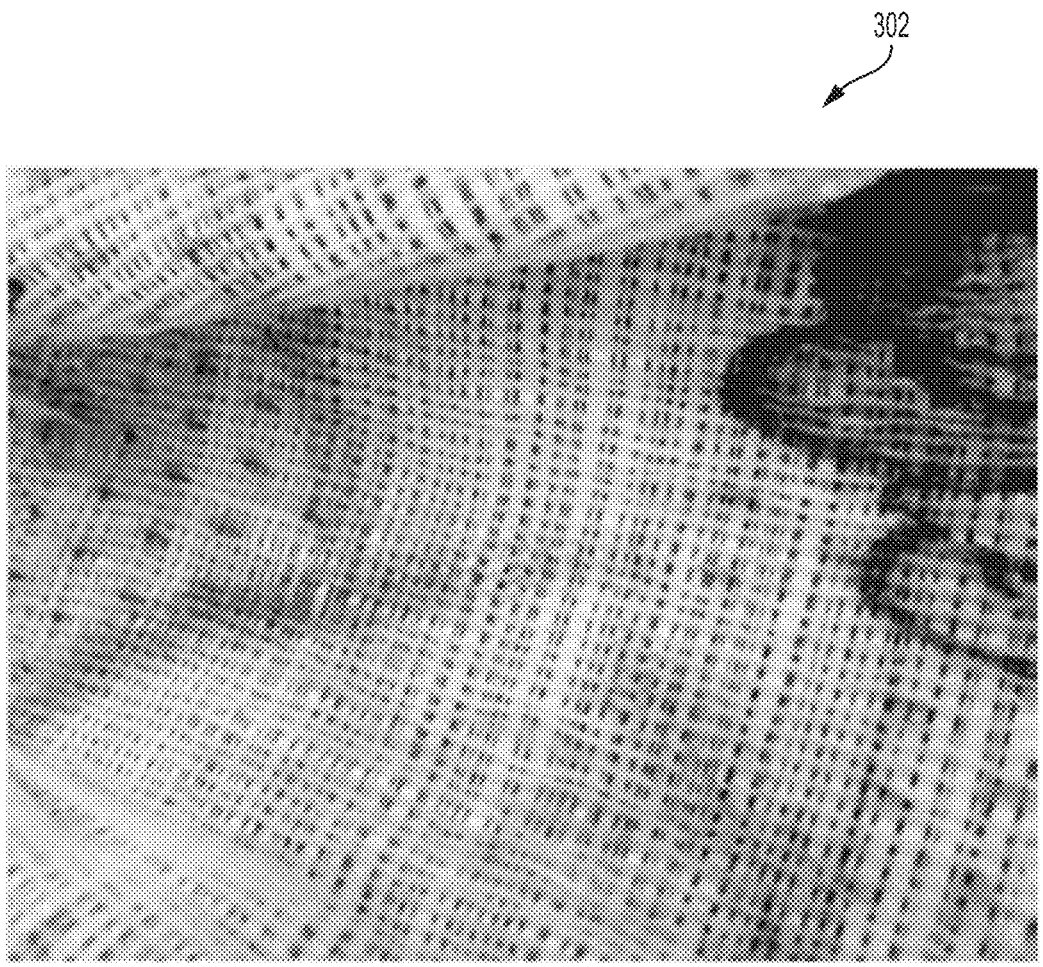
FIG. 4 is a top view of a garment-facing surface of a portion of an elastomeric laminate of the present disclosure illustrating color contrast between the elastic strands and a substrate layer of the laminate and assymetric elastic strand spacing.

As shown in FIG. 4, surprisingly unique textile visuals can be achieved by randomly spacing the plurality of elastics between substrate layers in combination with darker colored strands with a lighter colored nonwoven or lighter colored strands with a darker colored nonwoven. One way to achieve this effect is to have more strands (e.g., 5%, 10%, 15%) in one or more of Sections 1, 2, 3, or 4, versus one of the other sections. In a single section component, the strands may be asymmetrically spaced. The ΔE* of such a section may be greater than 7 and less than about 60.

This effect may be enhanced by using elastomeric laminates of the present disclosure (i.e., having an Average-Strand-Spacing from about 0.25 mm to about 4 mm, an Average Dtex of from about 20 to about 300, and an Average-Pre-Strain from about 50% to about 300%) and having elongate bonds or bond regions extending along the laminate (at about 90 degrees to the direction of the elastic strands), where the bonds or bond regions have an Average- Bond-Length of from about 5 mm to about 150 mm, and having an Average-Lateral-Bond-Spacing from about 2 mm to about 15 mm.

Multiple Beams

It should be appreciated that one or more texture zones may be formed from multiple beams of elastic. For example, separate beams may comprise a different number of elastics, and/or the beams may have elastics having different decitex, and/or the elastics of the two beams may be disposed at different spacing, and/or the separate beams may deliver elastics having different pre-strain, and/or the different beams may deliver elastics having different orientations in the product, e.g. liner, arcuate, angled, etc. The resultant portions created from such a multi-beam approach may have different textures.

Application-Force, Sustained-Fit-Load-Force, and Sustained-Fit-Unload Force of the Present Disclosure Absorbent articles comprising traditional stranded elastics and elastomeric laminates typically require high Application-Forces to ensure adequate Sustained-Fit-Load-Forces and Sustained-Fit-Unload-Forces to maintain the article's position on the wearer. The absorbent articles comprising traditional stranded elastics do not retain elastic forces as well as articles comprising beamed elastics and as such typically have significant consumer and performance trade-offs, i.e., difficult application for the consumers and good sustained fit and gasketing or ease of application for consumers and poor sustained fit, gasketing and leakage performance.

Higher decitex elastic of the traditional stranded elastic laminates have between 30 and 60 individual elastic filaments twisted together to form the elastic strand. Low decitex elastic of the beamed elastic laminate have between 3 and 7 elastic filaments. Without being bound by theory, the low decitex elastic used in the beamed elastic laminate have fewer individual filaments than the higher decitex elastic. In some cases the lower decitex may have as few as $^{1}/_{10}{}^{th}$ of the number of filaments. Given the elastic filaments are twisted to form the strands, the elastic comprising more filaments will have more filament to filament interaction as the strands extend and contract. This increase in interaction may adversely impact the retention of sustained fit load and unload forces. Furthermore, the larger bundle of twisted filaments also will likely result in different filaments being bonded to the substrates of the laminate at different points along the strand introducing additional constraints on various filaments in the bundle further impacting the filaments ability to extend and contract. The lower decitex elastic strands of the beamed elastic laminate comprise significantly fewer filaments and as such the filaments can extend and contract more independently of each other providing an elastic response closer to a monofilament strand.

An absorbent article comprising a beamed elastic laminate may have an Application-Force of between about 900 gf and about 1,600 gf, a Sustained-Fit-Load-Force of greater than about 30% of the Application-Force and a Sustained-Fit-Unload-Force of greater than about 25% of the Application-Force. Alternatively, an absorbent article comprising a beamed elastic laminate may have an Application-Force of between about 1,500 gf and about 3,000 gf, a Sustained-Fit-Load-Force of greater than about 35% of the Application-Force and a Sustained-Fit-Unload-Force of greater than about 30% of the Application-Force.

Figure 5A:
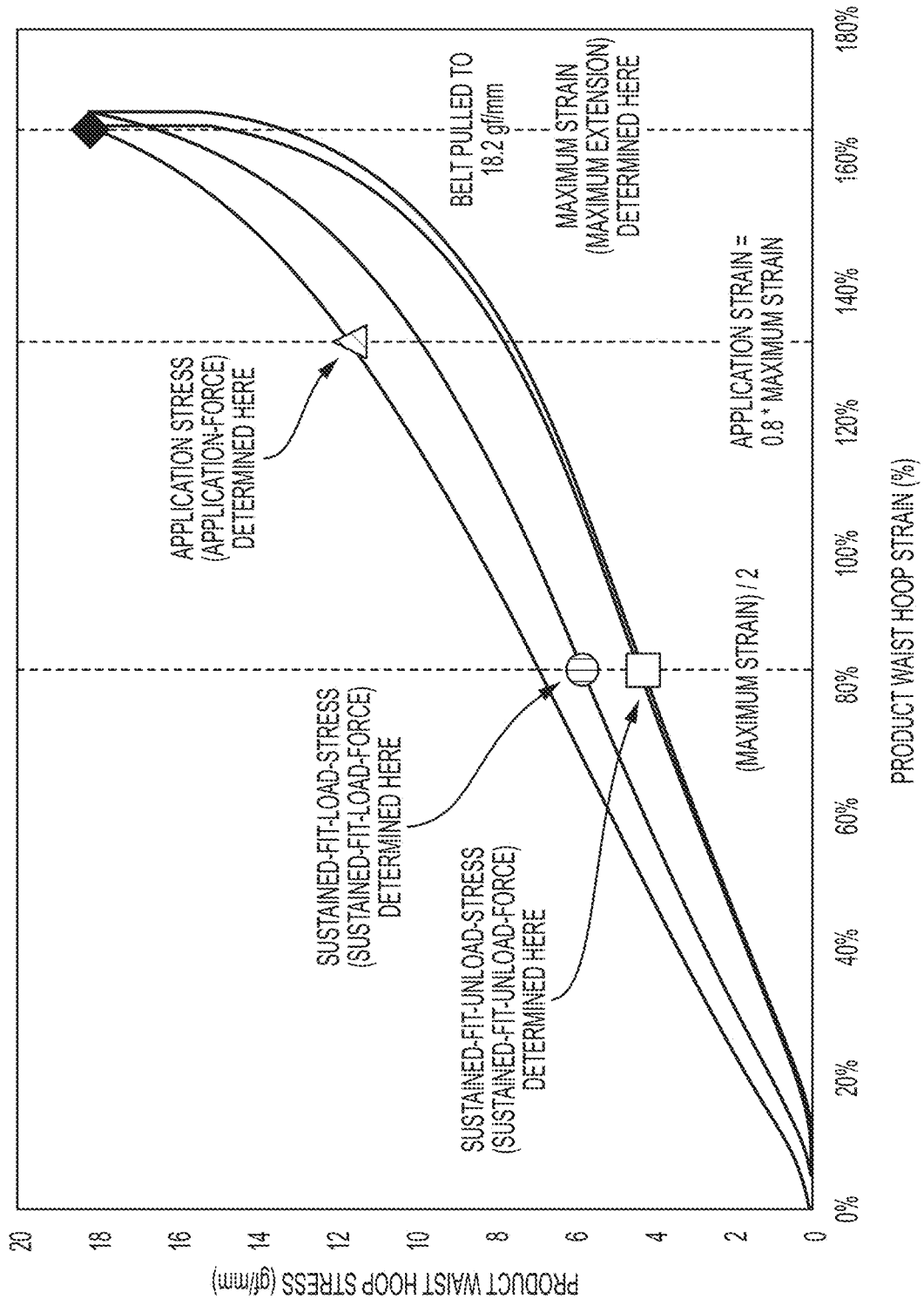
FIG. 5A illustrates a stress-strain curve with Maximum Extension, Application-Force, Sustained-Fit-Load-Force, and Sustained-Fit-Unload-Force.
Figure 5B:
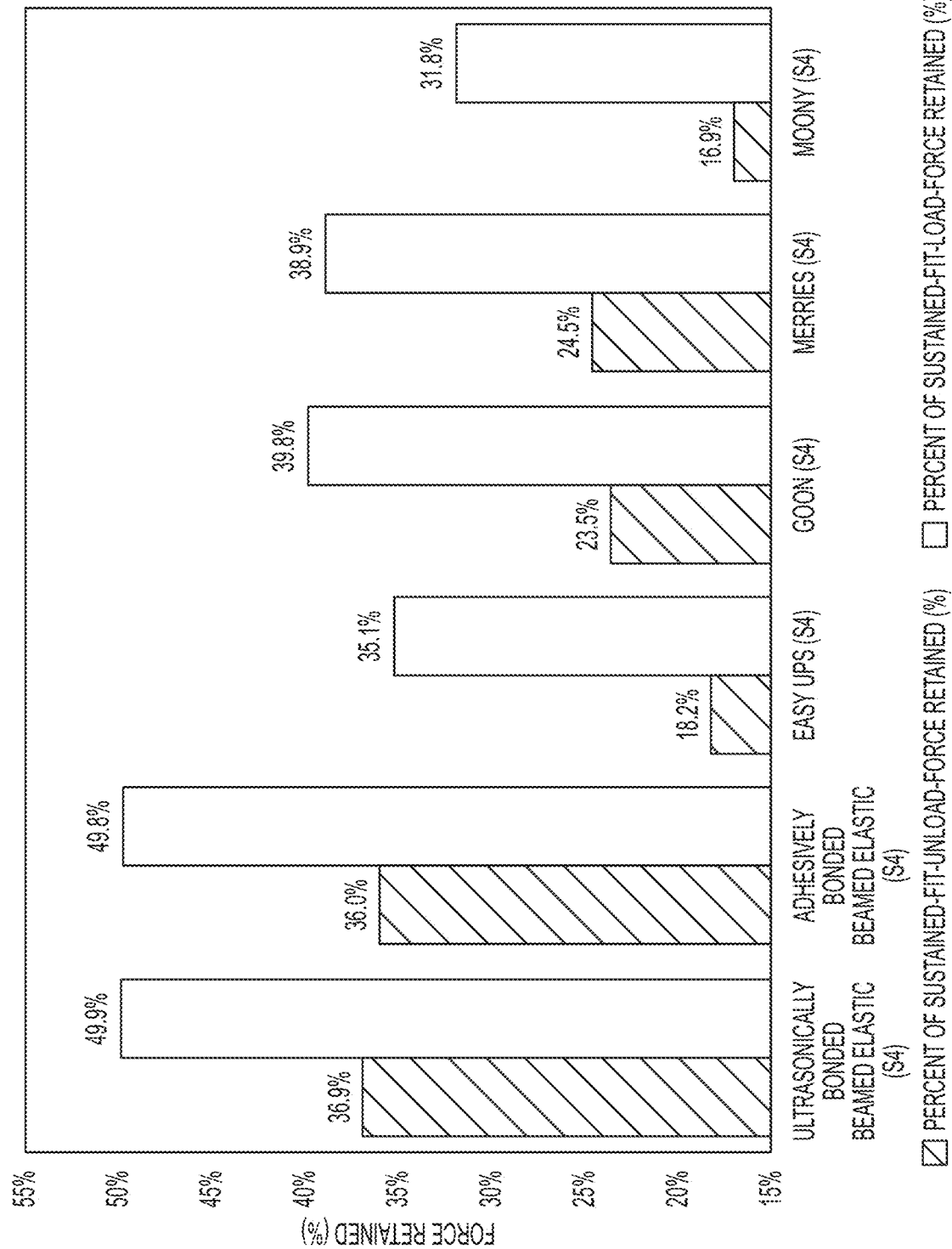
FIG. 5B illustrates Sustained-Fit-Load-Force and Sustained-Fit-Unload-Force across inventive and comparative products.
Figure 5C:
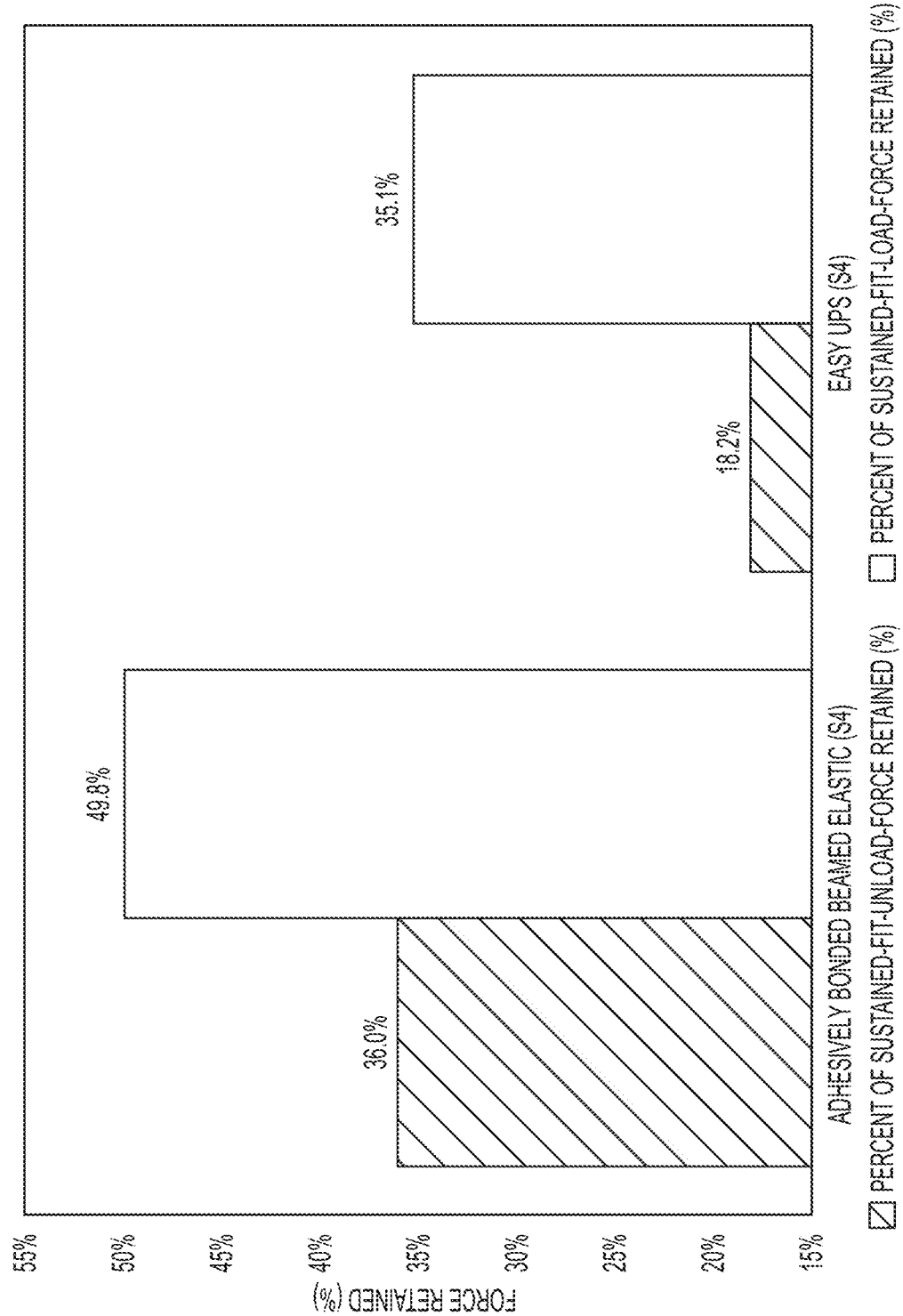
FIG. 5C illustrates Sustained-Fit-Load-Force and Sustained-Fit-Unload-Force of an inventive product and a comparative market product.
Figure 5D:
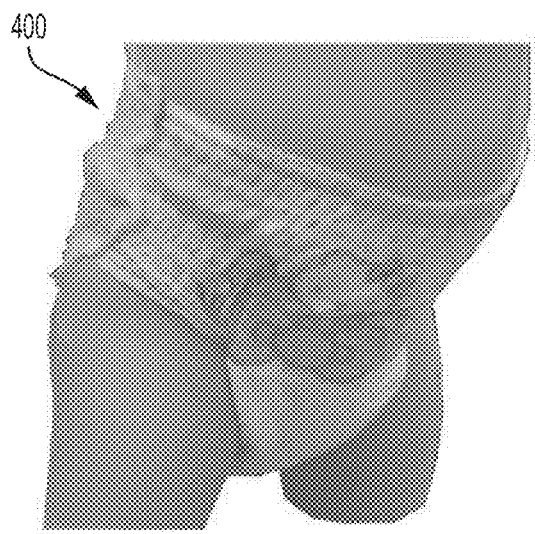
FIG. 5D is a perspective front view of the initial fit of the comparative market product of FIG. 5C (Easy Ups (Size 4)).
Figure 5D:
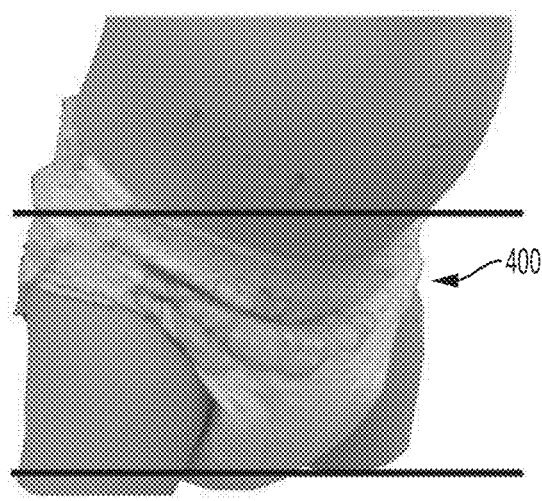
Figure 5E:
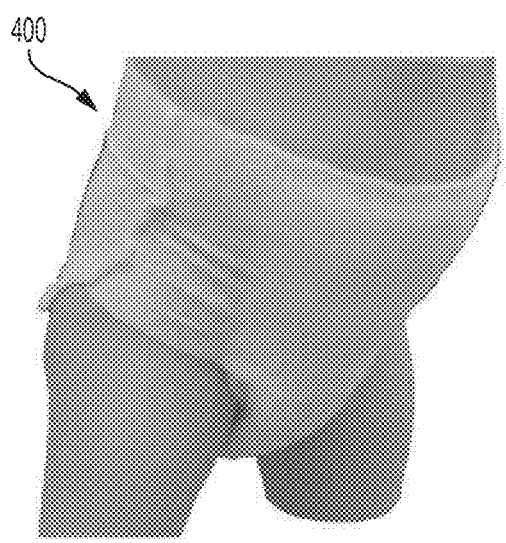
FIG. 5E is a perspective front view of the initial fit of the inventive product of FIG. 5C (Adhesively Bonded Beamed Elastic (Size 4)).
Figure 5E:
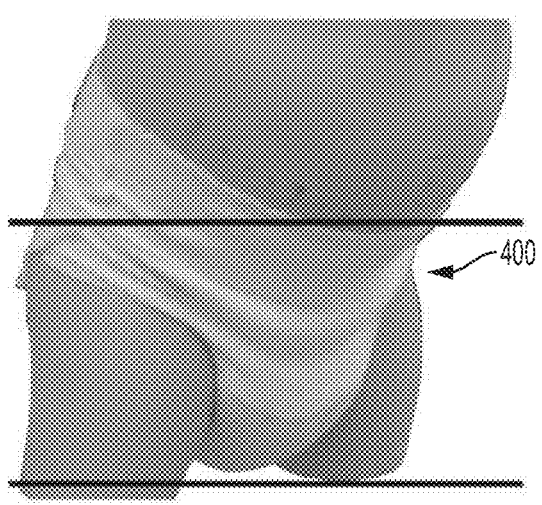
Figure 5F:
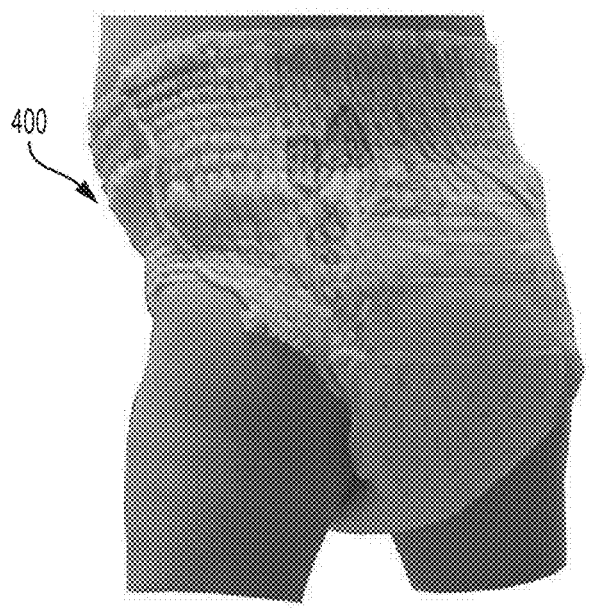
FIG. 5F is a perspective back view of the initial fit of the comparative market product of FIG. 5C (Easy Ups (Size 4)).
Figure 5F:
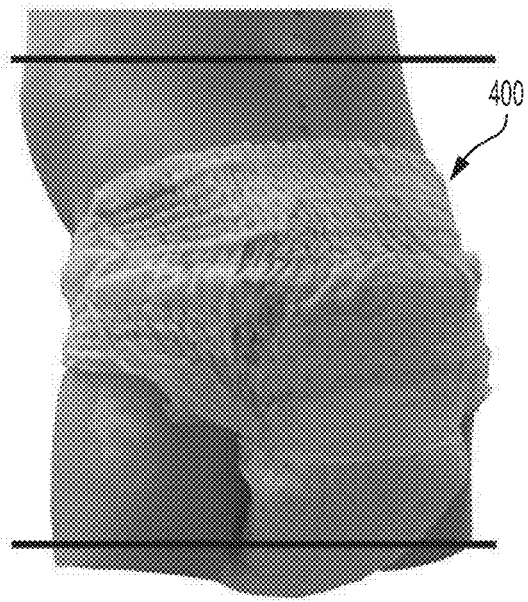
Figure 5G:
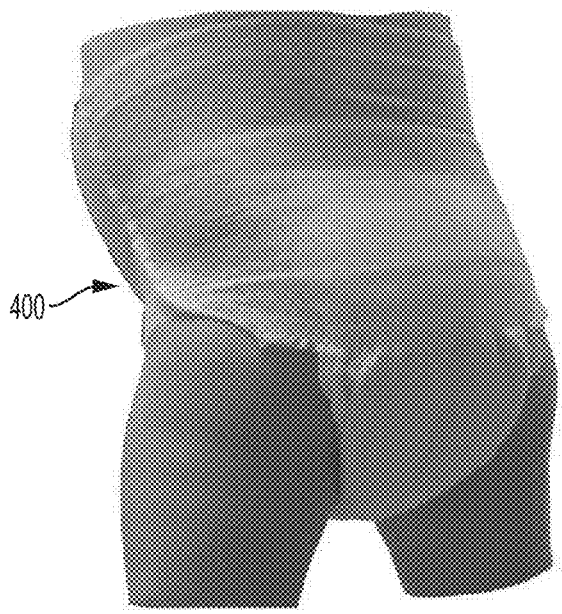
FIG. 5G is a perspective back view of the initial fit of the inventive product of FIG. 5C (Adhesively Bonded Beamed Elastic (Size 4)).
Figure 5G:
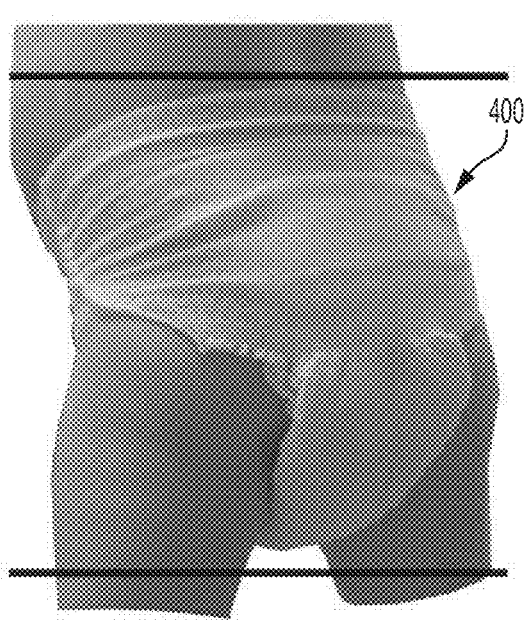
Figure 6A:
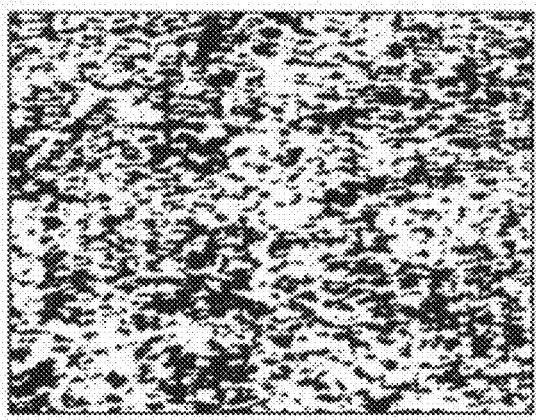
FIG. 6A is an image of inventive adhesively bonded elastomeric laminate of the present disclosure having an Average-Pre-Strain of 150% showing the Percent-Contact-Area taken from the Surface Topography Method.
Figure 6B:
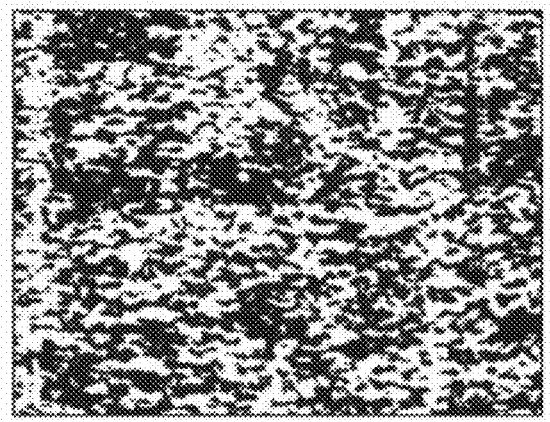
FIG. 6B is an image of inventive adhesively elastomeric laminate of the present disclosure having an Average-Pre-Strain of 120% showing the Percent-Contact-Area taken from the Surface Topography Method.
Figure 6C:
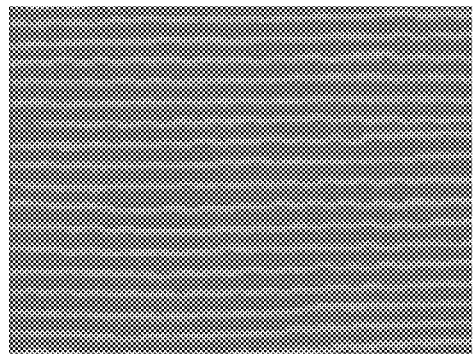
FIG. 6C is an image of inventive ultrasonically bonded elastomeric laminate of the present disclosure showing the Percent-Contact-Area taken from the Surface Topography Method.
Figure 6D:
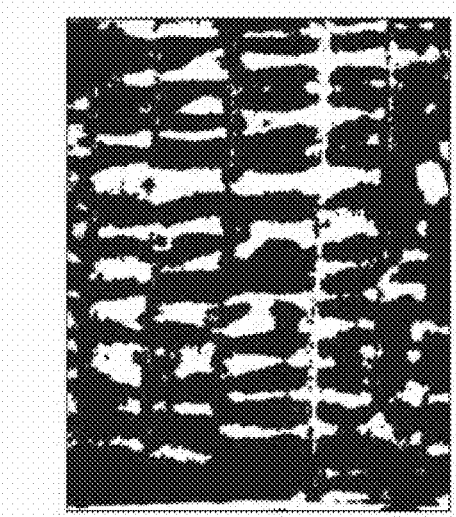
FIG. 6D is an image of a current market product of the present disclosure showing the Percent-Contact-Area taken from the Surface Topography Method.
Figure 6E:
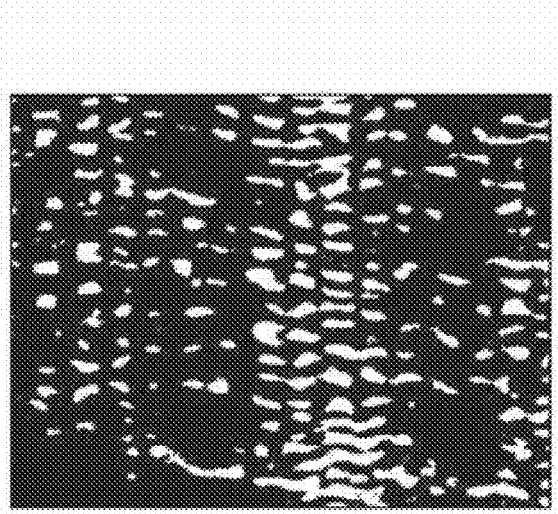
FIG. 6E is an image of a current market product of the present disclosure showing the Percent-Contact-Area taken from the Surface Topography Method.

In order to create the optimum usage experience it is desirable to provide an absorbent article having the right balance of Application-Force, Sustained-Fit-Load-Force and Sustained-Fit-Load-Force. FIG. 5A shows a force elongation curve that illustrates where these forces are taken along the curve. The desired outcome would be to have an article having an Application-Force that is equal to or lower than other comparative competitive products and a Sustained-Fit-Load-Force and Sustained-Fit-Unload-Force that are both higher than other comparative competitive products. For products having similar Application-Force the Sustained-Fit-Load-Force and Sustained-Fit-Unload-Force can also be reflected as a percentage relative to the Application-Force. Actual Application-Forces, Sustained-Fit-Load-Forces and Sustained-Fit-Unload-Forces of inventive embodiments, as well as competitive products, can be found in Table A (below). FIG. 5B is an illustration of the data from Table A which illustrates the superior Sustained-Fit-Load-Forces and Sustained-Fit-Unload-Forces of the inventive embodiments versus competitive products. Two products, Adhesively Bonded Beamed Elastic (inventive embodiment) and Easy Ups (Size 4), illustrated in FIG. 5C were selected to conduct on mannequin fit testing. During the mannequin fit test, the products were applied to a mechanically manipulated mannequin that underwent a fixed series of motions that simulate real baby movements. After application the initial position of where the pant article rests on the mannequin was measured: front waist initial position, back waist initial position, and initial rise (measured from a fixed point in the front through the crotch to a fixed point in the back). FIG. 5D shows the initial fit of Easy Ups from the front and FIG. 5F shows the initial fit of Easy Ups from the back. FIG. 5E shows the initial fit of an inventive embodiment from the front and FIG. 5G shows the initial fit of an inventive embodiment from the back. The article was then loaded with 75 mls of synthetic urine and then undergoes the mechanical manipulation steps. After the first cycle of mechanical manipulation the product was again loaded with another 75 mls of synthetic urine and then subjected to a second cycle of mechanical manipulation. After the second cycle, the product final position was measured, front waist final position, back waist final position, and final rise. FIG. 5D' shows the final fit of Easy Ups from the front and FIG. 5F' shows the final fit of Easy Ups from the back. FIG. 5E' shows the final fit of an inventive embodiment from the front and FIG. 5G' shows the final fit of an inventive embodiment from the back. The black lines on FIGS. 5D', 5E', 5F' and 5G' are included to provide a reference for comparison between the competitive market product and the inventive embodiment. From the charts, tables, and images it is clear that the inventive embodiment delivers superior sustained fit relative to the competitive market product as a result of the inventive Sustained-Fit-Load-Forces and Sustained-Fit-Unload-Forces of the beamed elastomeric belts. The actual measurements from the mannequin test are shown in Table B (below). The data shows that the competitive market product, Easy Ups had 162% more sagging at the front, 200% more sagging at the back and 202% more sagging in the rise than the inventive embodiment, adhesively bonded beamed elastic. In addition Easy Ups had 456% more slip than the adhesively bonded beamed elastic product.

TABLE A

| product | 1st Cycle Extension at 18.2 gf/mm (mm) | Application-Force (gf) | Sustained-Fit-Unload-Force (gf) | Sustained-Fit-Load-Force (gf) | Percent of Sustained-Fit-Unload-Force retained (%) | Percent of Sustained-Fit-load-Force retained (%) |
|---|---|---|---|---|---|---|
| Ultrasonically Bonded Beamed Elastic (S4) | 206 | 1280 | 472 | 639 | 36.9% | 49.9% |
| Adhesively Bonded Beamed Elastic (S4) | 200 | 1426 | 513 | 710 | 36.0% | 49.8% |
| Easy Ups (S4) | 196 | 1318 | 239 | 463 | 18.2% | 35.1% |
| Goon (S4) | 200 | 1364 | 321 | 542 | 23.5% | 39.8% |
| Merries (S4) | 203 | 1253 | 307 | 487 | 24.5% | 38.9% |
| Moony (S4) | 183 | 1455 | 246 | 463 | 16.9% | 31.8% |
| Always Discreet (S/M) | 558 | 1753 | 505 | 834 | 28.8% | 47.6% |
| Always Boutique (S/M) | 499 | 2326 | 644 | 1001 | 27.7% | 43.0% |

TABLE B

| Description | | Front Initial to Final Δ (mm) | Rise Initial to Final Δ (mm) | Back Initial to Final Δ (mm) | Total | SLIP | Crotch Sag |
|---|---|---|---|---|---|---|---|
| FIGS. 5D, 5D', 5F, 5F' | Easy Ups | −86 | −85 | −50 | −469 | −41 | −44 |
| FIGS. 5E, 5E', 5G, 5G' | Adhesively Bonded Beamed Elastic | −53 | −42 | −25 | 260 | −9 | −33 |
| Not Shown | Ultrasonically Bonded Beamed Elastic | −49 | −48 | −31 | 261 | −20 | −28 |
| Easy Ups Has Greater Sag than Adhesive Beamed Elastic (shown as a percentage) | | 162% | 202% | 200% | 180% | 456% | 133% |

Ratios of the Present Disclosure

Many absorbent articles comprising traditional elastic stranded laminates have used adhesive to bond the elastic materials to the substrates forming the elastomeric laminate. The approaches have included strand coating where the adhesive is directly applied to the elastic strands and surface coating where the adhesive is applied to one or both substrates of the elastomeric laminate and then the elastic is sandwiched between the substrates. Some attempts have been made to create thermal bonds spaced on either side of the elastic to trap it and hold it in place between the substrates.

The structure of beamed elastics, low decitex (small diameter), narrow spacing and low strain provide a unique combination of properties that enable the beamed elastic materials to be present inside of a thermal, mechanical or ultrasonic bond, in other words the elastic strands are so fine that the bond can be created continuously from one side of the elastic strand across the strand to the other side of the strand. In fact, the bond may extend continuously across multiple elastic strands. It has been discovered that in order to enable a fully ultrasonically bonded beamed elastic laminate a couple of relationships may be desirable: 1) a specific Dtex-to-Nonwoven-Basis-Weight-Ratio range may be maintained to ensure that in the bond area there is sufficient nonwoven material to encircle the elastic strand during the bonding process and 2) a specific range of Void-Area-to-Strand-Area-Ratio may also be maintained to ensure a dimensional lock around the elastic. The void area of the bond is created by formation of the bond around an elongated elastic having an elongated diameter (less than the relaxed strand diameter) when the elastic is allowed to relax, the elastic diameter increases as does the surface area thereby dimensionally locking the wider elastic strand in the narrower void space of the bond.

Another ratio that is relevant to forming a beamed elastic laminate with the right balance of Application-Force (ease of application), Sustained-Fit-Load-Force, and Sustained-Fit-Unload-Force for proper positioning and gasketing of the article is the Dtex-to-Spacing-Ratio ratio. As the decitex of the elastic increases the force to extend the elastic also increases. To maintain the proper balance of forces the spacing between the elastics may also be increased. As the decitex decreases, the elastic spacing should also decrease to ensure the proper balance of forces. Therefore, to maintain the proper balance of forces the Dtex-to-Spacing-Ratio may desirably be maintained.

The prior art does not define the boundaries of the ratios of Average-Strand-Spacing, Average-Dtex and Nonwoven-Basis-Weight of ultrasonically bonded stranded elastomeric laminates needed to deliver the desirable performance parametrics of article components, especially including Section-Modulus. Thus, the art fails to disclose the key for delivering how to reliably make elastomeric laminates where densified bonds overlap the elastic strands, such that the strands are dimensionally locked, in a way that prevents breakage of the strands. Thus, the art fails to disclose elastomeric laminates that are truly suitable for use as disposable absorbent article components. Key ratios disclosed herein yield desirable elastomeric nonwovens for use as disposable absorbent article components. The key ratios for ultrasonically bonded laminates include: Dtex-to-Spacing-Ratios, Dtex-to-Nonwoven-Basis-Weight-Ratios, and Void-Area-to-Strand-Area-Ratio.

Referring to FIG. 15A, the linkage of Dtex-to-Spacing-Ratio and Section-Modulus for Spandex strands is shown. Dtex-to-Spacing-Ratio's from about 65:1 to about 215:1 will result in a Section-Modulus of from about 4.0 gf/mm to about 9 gf/mm.

Referring to FIG. 15B, other desirable Dtex-to-Spacing-Ratios are shown. A Dtex-to-Spacing-Ratio of from about 40:1 to about 88:1 would deliver a very low Section-Modulus. This would be desirable for small babies i.e., preemies. This very soft feel would also result in very little force increase as the infant moves and stretches the garment.

Elastomeric laminates of the present disclosure may have a Dtex-to-Spacing-Ratio of from about 88:1 to about 140:1 would deliver a low to moderate Section-Modulus. This would be desirable for small babies who are not yet walking. It would deliver low to moderate force increase for additional applied stretch. It would also enables a broad fit range with few product offerings.

Elastomeric laminates of the present disclosure may have a Dtex-to-Spacing-Ratio of from about 140:1 to about 233:1 is desirable for most walking babies and adults. It would deliver a Section-Modulus that minimizes product sagging while providing a comfortable fit. It would also enable a broad fit range with few product offerings.

Elastomeric laminates of the present disclosure may have a Dtex-to-Spacing-Ratio of from about 233:1 to about 300:1 would mimic a film like Section-Modulus and feel. This is desirable when offering a more tailored fit, i.e., more sizes available over a target fit range.

Elastomeric laminates of the present disclosure may have a ratio of Average-Longitudinal-Bond-Spacing to Average-Bond-Width from about 1:2 to about 20:1, from about 5:1 to about 15:1, or from about 7:1 to about 13:1.

Elastomeric laminates of the present disclosure may have a ratio of Average-Lateral-Bond-Spacing to Average-Bond-Width from about 1:1 to about 50:1, from about 10:1 to about 30:1, or from about 15:1 to about 20:1.

Elastomeric laminates of the present disclosure may have a ratio of Average-Bond-Length to Average-Bond-Width from about 1:1 to about 300:1, from about 10:1 to about 200:1, or from about 20:1 to about 100:1.

Role of Parameters

Stranded elastomeric laminates of the present disclosure outperform stranded elastomeric laminates of the art in many of the relevant parameters that measure how laminates perform, including:

Hip-Hoop is relevant because it is the measure of the elongation and contraction of the closed circumference of an absorbent article. The data generated from this test can be used to determine the Application-Force, Sustained-Fit-Load-Force and the Sustained-Fit-Unload-Force.

Application-Force is relevant because it is the measure of the force that a wearer of caretaker might encounter while donning the absorbent article.

Sustained-Fit-Load-Force is relevant because it is the measure of the force that an article applies to the wearer when the wearer's waist extends for example during respiration or during wearer movement like when a wearer goes from a standing position to a sitting position.

Sustained-Fit-Unload-Force is relevant because it is the measure of the force that an article applies to the wearer when the wearer's waist contracts for example during respiration or during wearer movement like when a wearer goes from a sitting position to a standing position.

Surface Topography (Percent-Contact-Area, Rugosity-Frequency, Rugosity-Wavelength, and 2-98%-Height-Value) is relevant because it is the measure of the textural properties of the elastomeric laminates. The surface topography enables definition of Percent-Contact-Area which is the portion of the surface that may be in contact with the skin, Rugosity-Frequency, and Rugosity-Wavelength characterize the structural aspects of the texture and the 2-98%-Height-Value helps define the thickness of the elastomeric laminate.

Pressure-Under-Strand (Average-Pressure-Under-Strand) is relevant because it is the measure of the pressure the elastic will put on the skin. Lower pressure under strand correlates with less skin indentation and marking resulting in improved skin condition and comfort.

Air-Permeability is relevant because it is the measure of how easily air is passed through the elastomeric laminate, Air-Permeability is typically used to measure the breathability of various fabrics including water impermeable fabrics. Air-Permeability is typically measured in units of volume/surface area/unit time. The main influences on air permeability are the density of the material and its structure. Fabrics can be coated or otherwise treated to modify their air permeability either selectively or over the entirety of the fabric.

Force-Relaxation-Over-Time is relevant because it is the measure of an elastomeric laminates ability to retain its force over time under a fixed load. Certain Spandex materials can retain greater than 70% of their force over time while other elastic approaches like extruded strand elastics may lose as much as 70% of their force over time.

Emtec is relevant because it is an objective measuring instrument and the only existing device, which fulfills all the according requirements in the nonwoven and textile industry. It simultaneously gathers all single relevant parameters, which have an influence on the haptic characteristics of nonwovens and textiles, which are: softness, smoothness/roughness, and stiffness. The correlation of Emtec measured results to reliable hand panel numbers, determined by experienced hand panels, is excellent (up to 100%) according to the manufacturer.

Color-Contrast is relevant because it leverages small scale color measurements of elasticized laminate where the elastics strands are significantly different in color from the regions between the strands can be made from calibrated scanned images. These paired color measurements are then used to calculate a Color-Contrast for the laminate.

Section-Modulus is relevant because it is the measure of the slope of a force elongation curve within a given section of the elastomeric laminate. Relatively, if the force increases rapidly with elongation the material is higher modulus than one in which the force increases more slowly with elongation. It may be desired to have sections with differ.

Cantilever-Bending is relevant because it is the measure of flexural bending vs length. The test is run with a target deflection and the length of extension required to reach the target deflection is recorded. The shorter the length the more flexible the material is deemed to be.

These parameters are described in greater detail below. Also, please refer to the Methods section for details about performing tests for each of these parameters.

Section-Modulus

Figure 14:
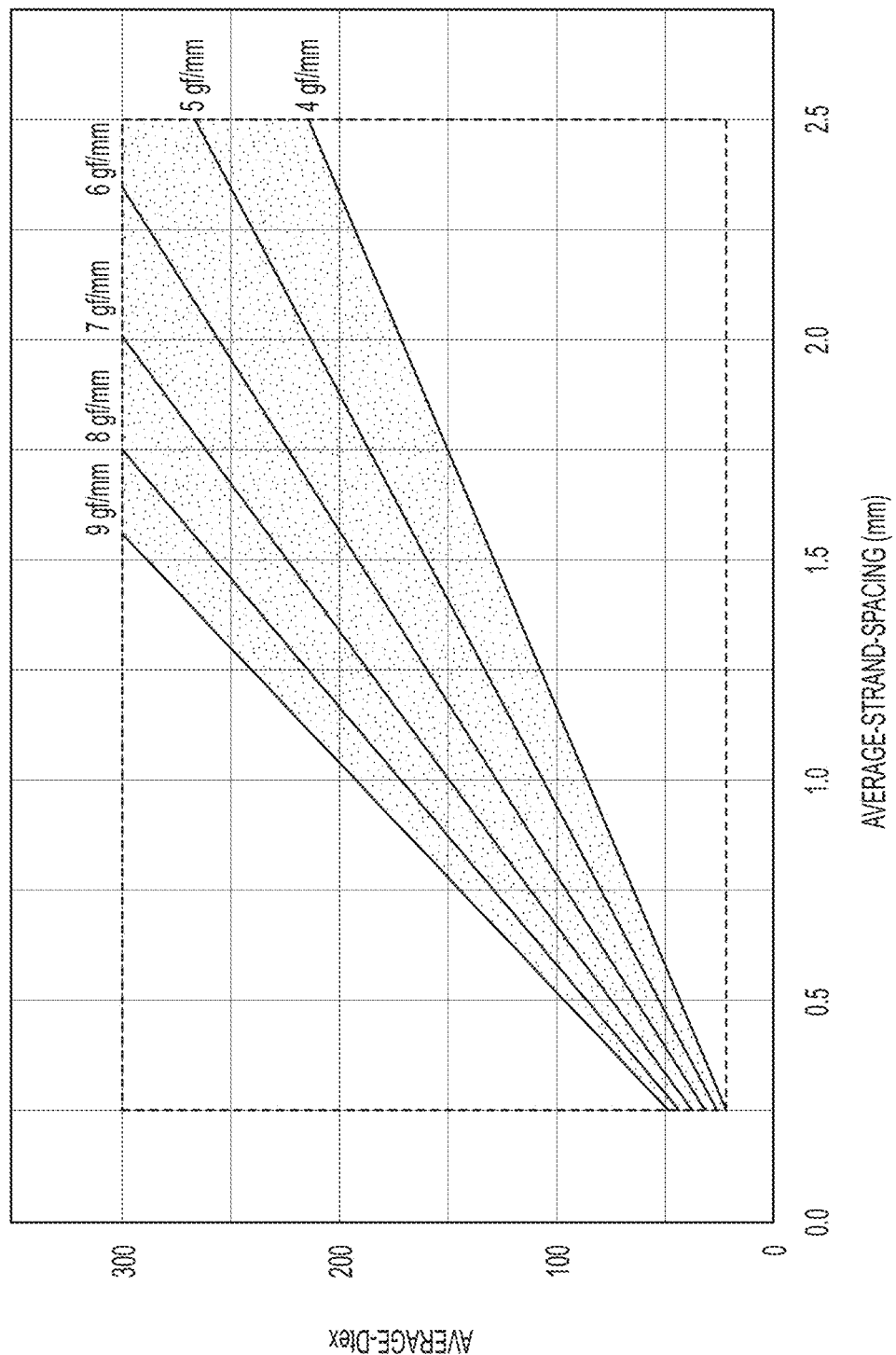
FIG. 14 is a graph illustrating the relationship linking Average-Strand-Spacing and Average-Dtex to Section-Modulus.

Referring to FIG. 14, the determination of Section-Modulus from any combination of Average-Strand-Spacing and Average-Dtex for Spandex strands is shown. The relevance of Section-Modulus to product performance and consumer perception is significant for two key reasons. First, Section-Modulus is how consumers perceive the ease of application, fit and comfort of a product. Section-Modulus conveys the ease and extent of elongation at a given applied force. Too high a Section-Modulus, and consumers perceive the product to be too small, too tight and uncomfortable with higher potential for skin marking. On the other hand, too low of a Section-Modulus and the consumer perceives the product to be too big, too loose and not able to stay in place nor able to properly gasket around the legs and waist. Consumer testing has revealed that a Section-Modulus of between from about 4 gf/mm to about 9 gf/mm are the preferred range for absorbent garments.

A second key impact of Section-Modulus is in the number of sizes that are needed within an array of products to fit a range of consumers. The higher the Section-Modulus, the more sizes that may need to be offered to achieve proper fit given the range over which consumers perceive the product to be comfortable.

Surface Topography

Surface Topography is the areal surface topology of the elastomeric laminate measured using optical profilometry. The 3D surface data are then sampled and processed to extract several parameters that describe the Percent-Contact-Area and 2-98% Height of the elastomeric laminate specimen surface as well as the Rugosity-Frequency and Rugosity-Wavelength.

Referring to FIGS. 6A-E and Table C (below), for comparison of various absorbent articles, we have selected a first setting to determine the Percent-Contact-Area corresponding with the thickness of the epidermis, 100 micrometers, a second setting at 2X the epidermis or 200 micrometers and a third setting at 3X the epidermis of 300 micrometers. It is apparent from the surface topography measurements that the beamed elastic laminates 302 (see FIGS. 6A-C) have significantly greater surface contact at 100 um (1.5× to 1.9×), 200 um (1.8× to 2.5×) and 300 um (1.9× to 2.7×) compared to the structures of the prior art (see FIGS. 6D and 6E). In addition, the 2%-98%-Height-Value which is derived from the surface topography data also shows a significant difference in surface smoothness for the beamed elastic laminate 302 versus the prior art structures. These differences in increased surface contact as well as surface smoothness will have a direct and significant impact on minimizing or eliminating skin marking of the various structures that can be created from beamed elastic laminates 302. In contrast, the data above 2% to 98% Height Value shows that the prior art product have a much rougher surface due in part to their larger decitex elastic and larger spacing which results in larger uncontrolled random rugosities. Combine the larger uncontrolled rugosities with the significantly lower Percent-Contact-Area and one can see that the pressure on the skin and skin marking is likely to be significantly greater for the prior art product executions and significantly lower for articles comprising the beamed elastic laminates.

Elastomeric laminates 302 of the present disclosure may have a Percent-Contact-Area at 100 um of greater than about 13% and/or a Percent-Contact-Area at 200 um of greater than about 27% and/or a Percent-Contact-Area at 300 um or greater than about 39%. In addition, the elastomeric laminates 302 of the present disclosure may have a 2%-98%-Height-Value of less than about 1.6.

Emtec

Emtec is an objective measuring instrument and the only existing device, which fulfills all the according requirements in the nonwoven and textile industry. It simultaneously gathers all single relevant parameters, which have an influence on the haptic characteristics of nonwovens and textiles, which are: Softness, Smoothness/Roughness, and Stiffness. The correlation of Emtec measured results to reliable hand panel numbers, determined by experienced hand panels, is excellent (up to 100%) according to the manufacturer. EMTEC has proven to be a valuable means to measure softness and tactile properties of various elastomeric laminates. Such elastomeric laminates, due to their complex construction, have a range of parameters that can affect the tactile properties of the laminate. For example, nonwoven basis weight, bond pattern, texture, elastic dtex, elastic pre-strain, elastic spacing, etc. can impact a panelists ability to discern softness and smoothness without the biases introduced by other visual or tactile elements. EMTEC has been proven to correlate with hand panel assessments and as such can provide an unbiased assessment of the elastomeric laminates themselves. It may be desirable to provide portions of an elastomeric laminate comprising an Emtec-TS7-Value of less than about 12 and an Emtec-TS750-Value of less than 60. It has also been determined that an Emtec-TS750-Value: Emtec-TS7-Value ratio of <8 is also particularly desirable.

Process of the Present Disclosure

Figure 9A:
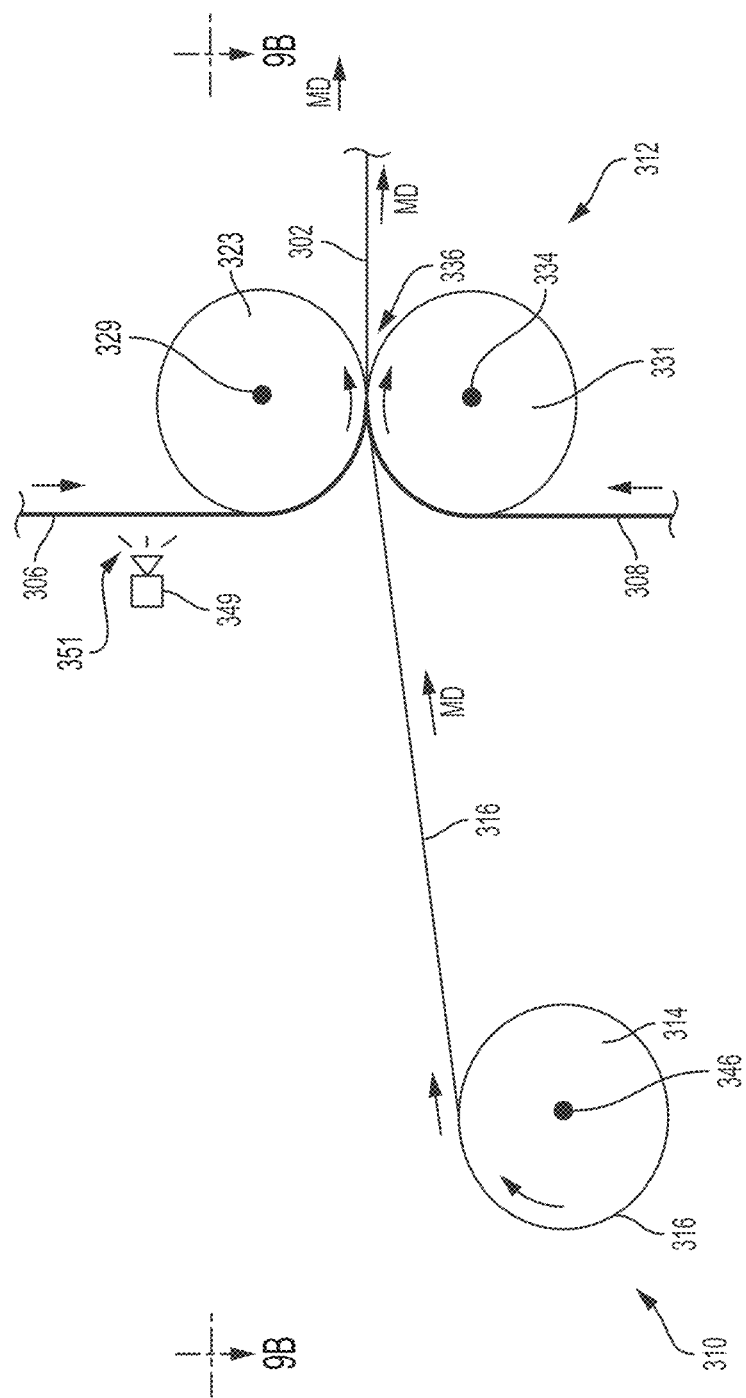
FIG. 9A is a schematic side view of a converting apparatus adapted to manufacture an elastomeric laminate including a first plurality of elastic strands positioned between a first substrate and a second substrate.
Figure 9B:
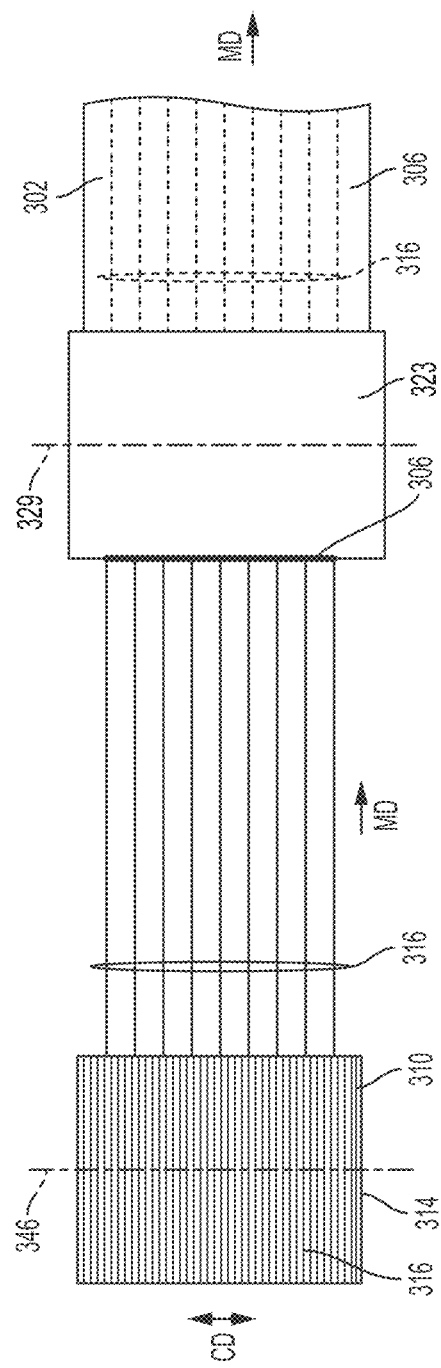
FIG. 9B is a view of the converting apparatus of FIG. 9A taken along line 9B-9B.

This section provides some details related to the process of making stranded elastomeric laminates of the present disclosure. Referring to FIGS. 9A and 9B, a plurality of elastic strands 316 (from about 10 strands to about 1500 strands having a decitex from about 10 to about 400) unwind about a first axis of rotation 346 from a first beam 314 (which is a first metering device 310) in the machine direction MD and transfer the plurality of elastic strands 316 from the first beam 314 (e.g., a warp beam) to a second metering device 312 (which includes a first roller 323 having a second axis of rotation 329 and a second roller 331 having a third axis of rotation 334, which form a nip 336). The plurality of elastic strands 316 may be stretched along the machine direction MD between the first metering device 310 and the second metering device 312 to prestrain the plurality of elastics 316 (from about 50% to about 300%). The stretched elastic strands 316 may be joined via an adhesive 351 from an adhesive applicator 349 (or the plurality of elastics 316 may be joined via other suitable means, such as ultrasonically) with a first substrate layer 306 and a second substrate layer 308 at the second metering device 312 to produce an elastomeric laminate 302, such that each of the strands are spaced (in the CD) in the elastomeric laminate from about 0.25 mm to about 4 mm. It is this process that forms the elastomeric laminate 302 of the present disclosure and that may be further incorporated into the various absorbent article components such as the belts, ear panels, side panels, transverse barriers, topsheets, backsheets, cuffs, waistbands, waistcaps, and/or chassis to offer the benefits described in this patent application. Further details of the process of creating beamed elastomeric laminate(s) for use in disposable absorbent articles are disclosed in U.S. Publication No. 62/436,589, titled "Methods and Apparatuses for Making Elastomeric Laminates with Elastic Strands Unwound from Beam," first-named inventor being Schneider, filed on Dec. 20, 2016. The elastomeric laminate 302 may be produced as part of the absorbent article manufacturing line, or may be produced offline, and unwound as an elastomeric laminate that is fed into the absorbent article manufacturing line.

Elastomeric Laminates of the Present Disclosure

An "elastomeric laminate 302" of the present disclosure may comprise a plurality of elastics 316 between a first substrate 306 and a second substrate layer 308, where the plurality of elastics 316 (often referred to as a "first plurality of elastics," a "second plurality of elastics," etc.) has an Average-Strand-Spacing from about 0.25 mm to about 4 mm, an Average-Dtex from about 10 to about 400, and an Pressure-Under-Strand from about 0.1 to about 1 psi. Said elastomeric laminate 302 may be used to form various article components or at least a portion of various absorbent article components, e.g. a belt, side panel, waistband or leg cuff. Further, the elastomeric laminate 302 may be used to form regions of the article or at least a portion of an article region, e.g. front waist region, crotch region or back waist region. When the elastomeric laminate 302 forms at least a portion of at least one of the group consisting of a belt, a chassis, a side panel, a topsheet, a backsheet, and an ear panel, and combinations thereof, the plurality of elastics 316 of the elastomeric laminate 302 may comprise from about 40 to about 1000 elastic strands. And, when the elastomeric laminate 302 forms at least a portion of at least one of the group consisting of a waistband, a waistcap, an inner leg cuff, an outer leg cuff, and combinations thereof, the first plurality of elastics 316 of the elastomeric laminate 302 may comprise from about 10 to about 400 elastic strands. Ultimately, "plurality of elastics" is a term of context, where certain properties (e.g., Average-Dtex, Average-Strand-Spacing, Pressure-Under-Strand, etc.), arrangements, attributes, characteristics, disposition, etc. of the elastics are referenced to define what a certain "plurality of elastics" is.

Further, the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having from about 40 to about 1000 elastic strands with an Average-Strand-Spacing from about 0.25 mm to about 4 mm, Average-Dtex from about 10 to about 400, an Average-Pre-Strain from about 50% to about 300%; and a first substrate 306 and a second substrate 308 each having a basis weight from about 6 grams per square meter to about 45 grams per square meter.

Further, when the elastomeric laminate 302 may form at least a portion of one or more of the group of article components including a belt 430, a side panel 330, chassis 200, a topsheet 124, backsheet 125, and an ear panel 530, the elastomeric laminate 302 may: comprise a plurality of elastics 316 having from about 50 to about 825, from about 100 to about 650 elastic strands, or from about 150 to about 475 elastic strands; comprise a plurality of elastics 316 having an Average-Strand-Spacing from about 0.5 mm to about 3.5 mm, or from about 0.75 mm to about 2.5 mm; comprise a plurality of elastics 316 having an Average-Dtex from about 30 to about 300, or from about 40 to about 200; comprise a plurality of elastics 316 having an Average-Pre-Strain which may be from about 75% to about 300%, or from about 100% to about 250%.

When the elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having from about 10 to about 400 elastic strands with an Average-Strand-Spacing from about 0.25 mm to about 4 mm, Average-Dtex from about 10 to about 400, an Average-Pre-Strain from about 50% to about 300% and a first substrate 306 and/or second substrate 308 each having a basis weight from about 6 grams per square meter to about 45 grams per square meter.

Further, when the elastomeric laminate 302 forms at least a portion of one or more of the group of article components including a waistband 122, waistcap 123, inner leg cuff 150, outer leg cuff 140 and a transverse barrier 16, the elastomeric laminate may: comprise a plurality of elastics 316 having from about 15 to about 300 elastic strands, from about 20 to about 225 elastic strands, or from about 25 to about 150 elastic strands; comprise a plurality of elastics 316 having an Average-Strand-Spacing from about 0.5 mm to about 3.0 mm, or from about 0.75 mm to about 2.5 mm; comprise a plurality of elastics 316 having an Average-Dtex from about 30 to about 300, or from about 40 to about 250; comprise a plurality of elastics 316 having an Average-Pre-Strain from about 75% to about 300%, or from about 100% to about 250%.

Any one of the belt 430, side panel 330, ear panel 530, chassis 200, topsheet 124, backsheet 125, waistband 122, waistcap 123, inner leg cuff 150, outer leg cuff 140 or transverse barrier may: comprise an elastomeric laminate 302 comprising a plurality of elastics 316 having Pressure-Under-Strand from about 0.1 psi to about 1 psi, or from about 0.2 psi to about 0.8 psi; comprise an elastomeric laminate comprising an Air-Permeability at 0 gf/mm (no extension) of greater than about 40 cubic meters/square meter/minute and/or a level of Air-Permeability at 3 gf/mm (slight extension) of greater than about 60 cubic meters/square meter/minute and/or a level of Air-Permeability at 7 gf/mm (moderate extension) of greater than about 80 cubic meters/square meter/minute; comprise an elastomeric laminate comprising a Cantilever-Bending of less than about 40 mm or alternatively less than about 35 mm in other embodiments the Cantilever-Bending may be less than 30 mm or alternatively less than 25 mm, or from about 15 mm to about 30 mm; comprise an elastomeric laminate comprising a Percent-Contact-Area of greater than about 13% at 100 um and/or greater than about 27% at 200 um and/or greater than about 39% at 300 um and/or a 2%-98%-Height-Value of <1.6 mm; comprise an elastomeric laminate comprising a Percent-Contact-Area of greater than about 13% at 100 um and/or greater than about 27% at 200 um and/or greater than about 36% at 300 um and/or a 2%-98%-Height-Value of <2.2 mm; comprise an elastomeric laminate comprising a Rugosity-Frequency of from about 0.2 $mm^{-1}$ to about 1 $mm^{-1}$ and a Rugosity-Wavelength of from about 0.5 mm to about 5 mm.

Beyond the beamed elastic strands 316 that may be used in each of the absorbent article components, other elastic components such as elastic nonwovens, elastomeric films, elastomeric foams, elastomeric scrims, and elastomeric ribbons, or combinations thereof, may be used with the beamed elastics 316.

Ultrasonic Bonds of the Present Disclosure
Forming Densified Bonds

Figure 10A:
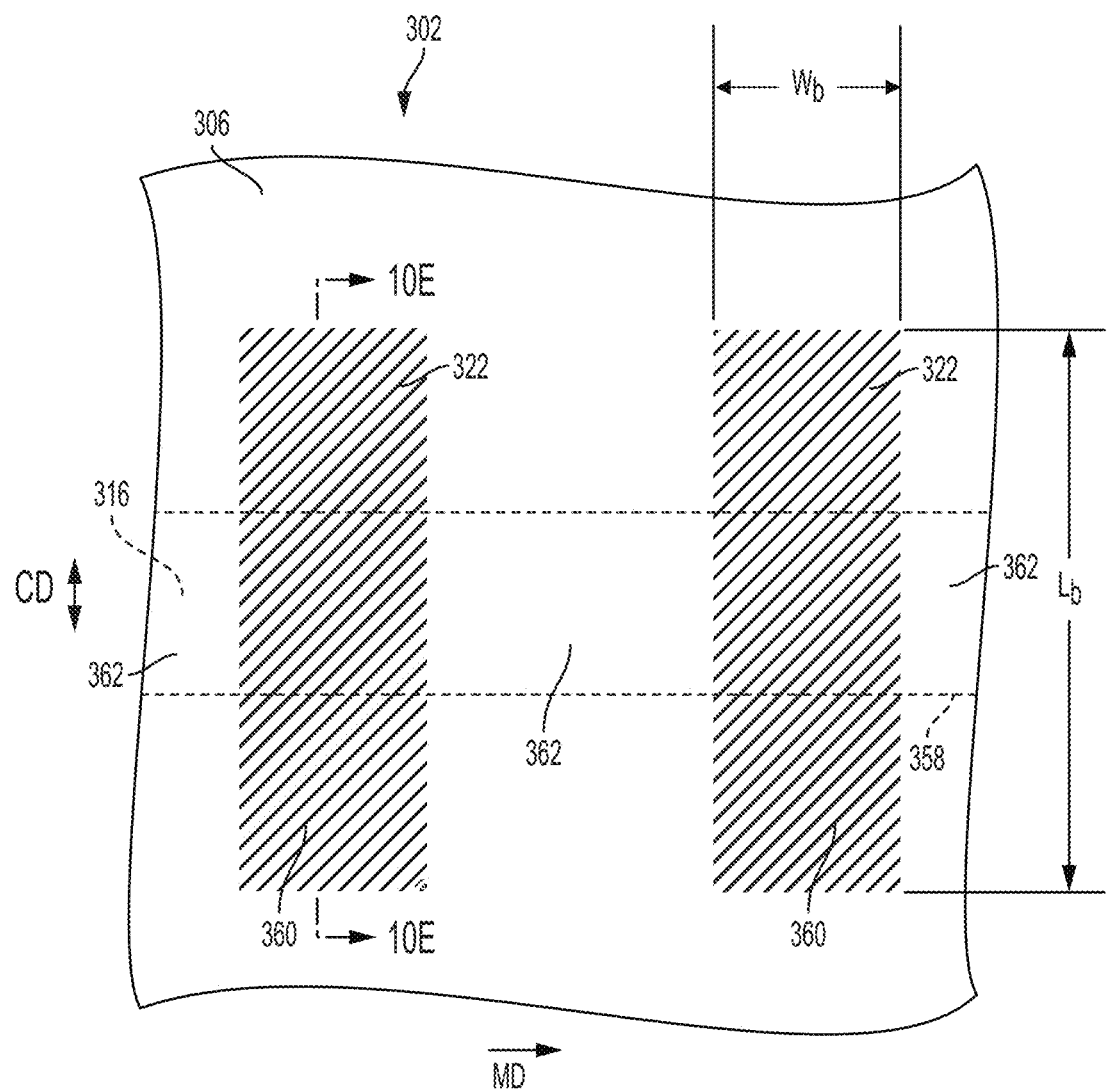
FIG. 10A is a detailed view of an elastic strand in a stretched state bonded between the first and second substrates.
Figure 10B:
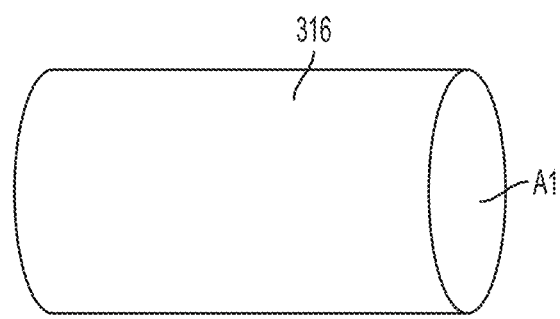
FIG. 10B shows a length of an elastic strand in a relaxed state with a first cross-sectional area.
Figure 10C:
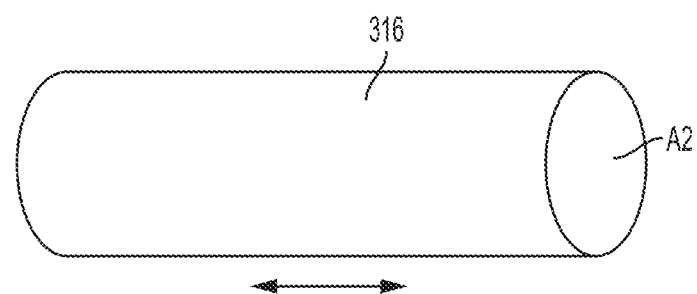
FIG. 10C shows a length of the elastic strand of FIG. 10B in a stretched state with a second cross-sectional area that is less than the first cross-sectional area of 10B.
Figure 10D:
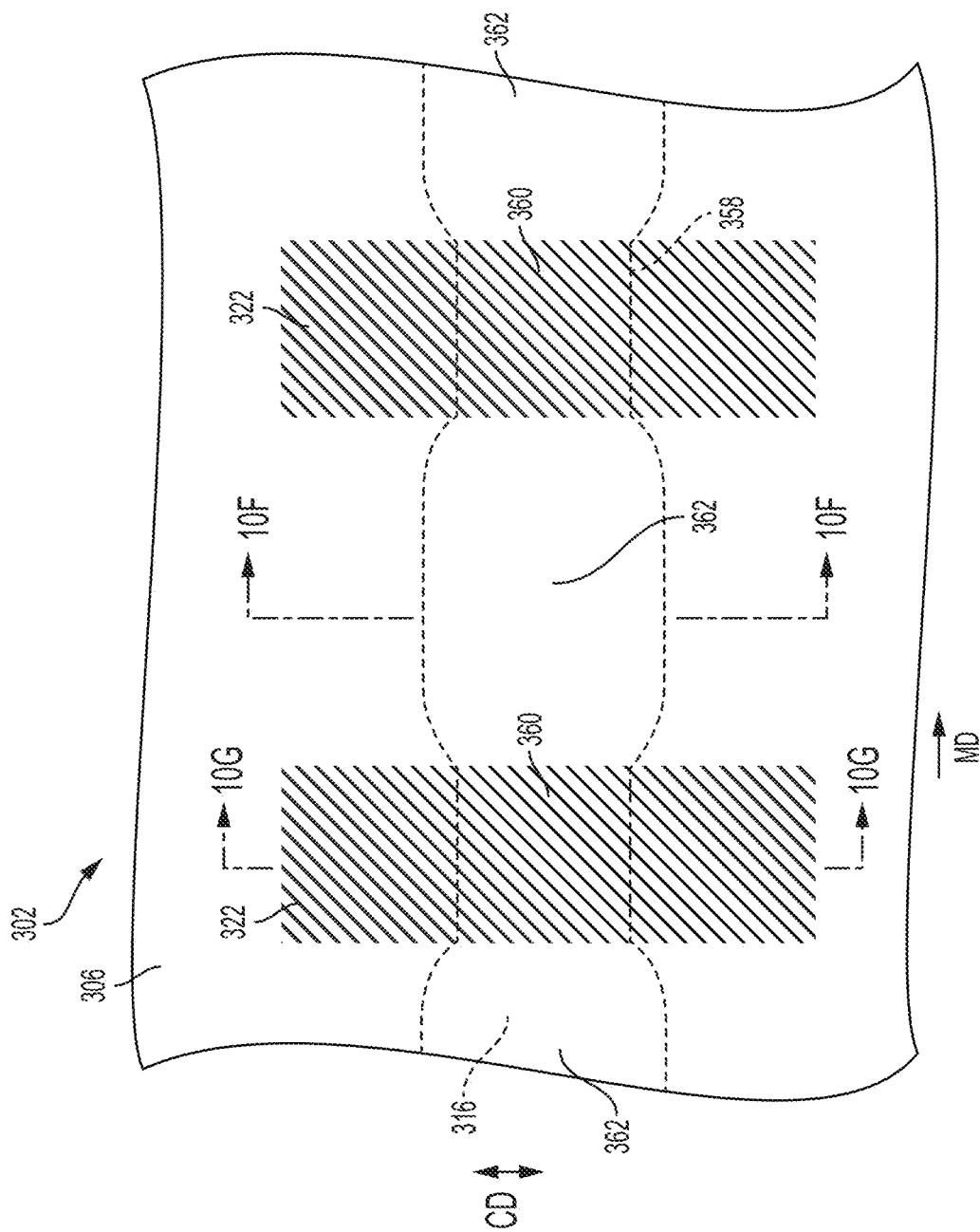
FIG. 10D is a detailed view of an elastic strand in a relaxed state bonded between the first and second substrates.
Figure 10E:
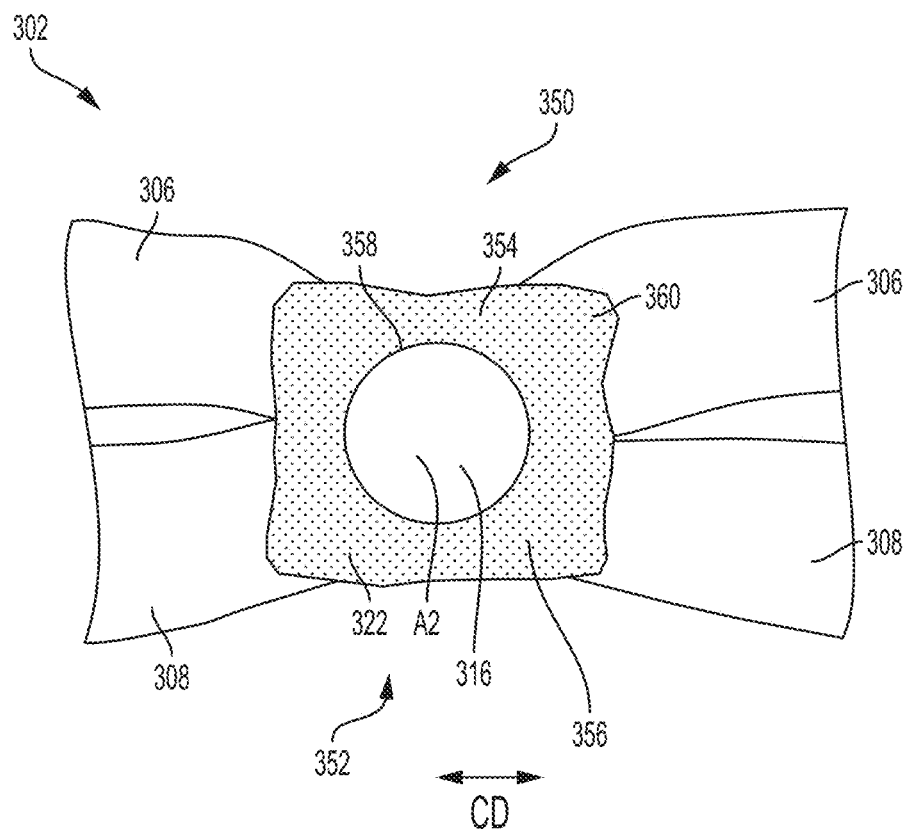
FIG. 10E is a sectional view of the elastic strand, bond, first substrate, and second substrate of FIG. 10A taken along line 10E-10E.
Figure 10F:
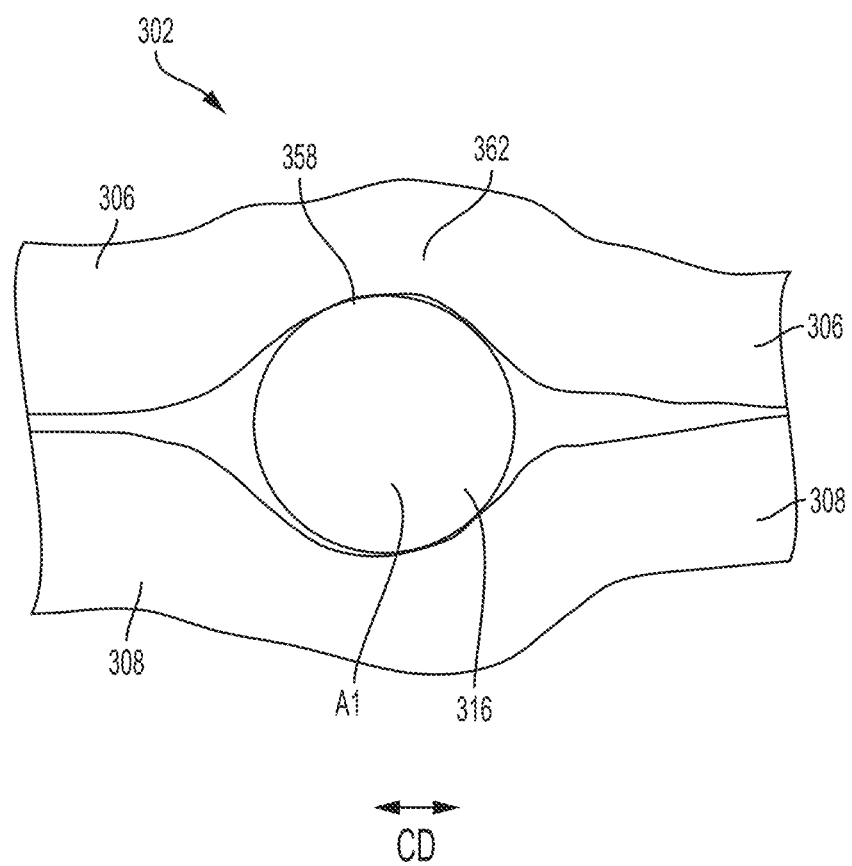
FIG. 10F is a sectional view of the elastic strand in a bonded region of FIG. 10D taken along line 10F-10F, wherein the elastic strand is in a relaxed state.
Figure 10G:
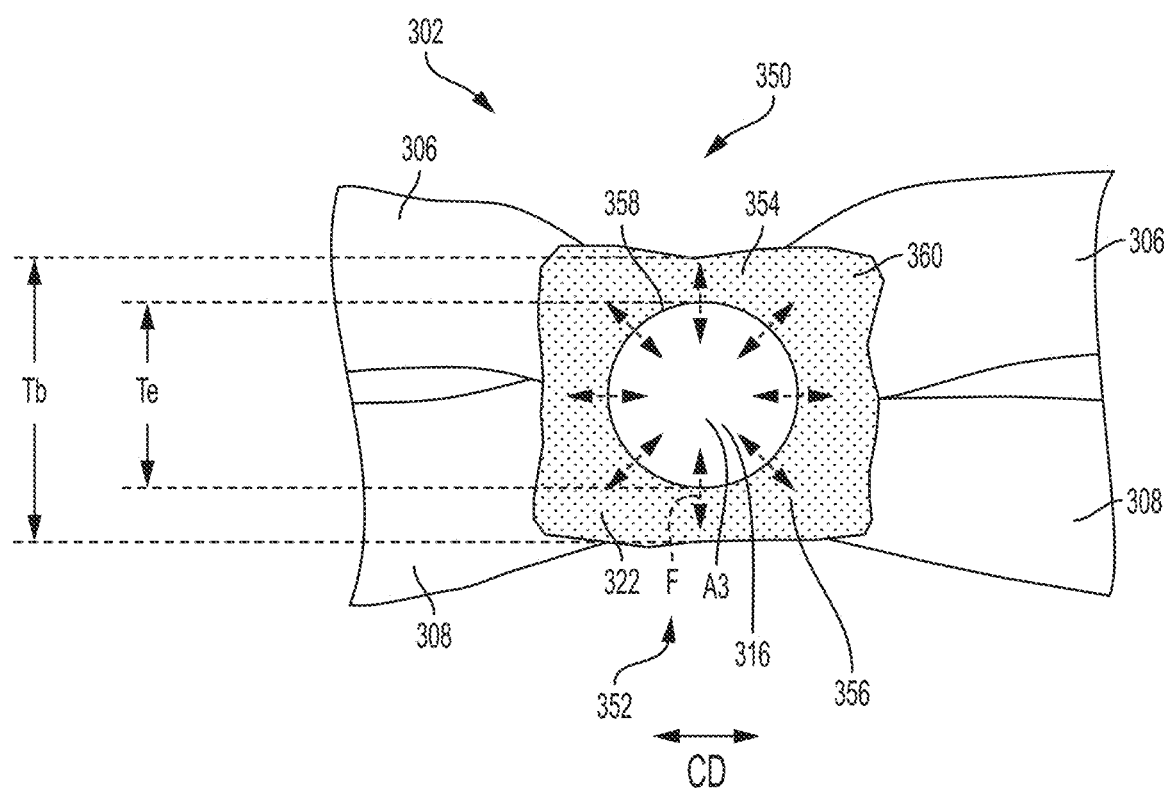
FIG. 10G is a sectional view of the elastic strand in an unbonded region of FIG. 10D taken along line 10G-10G, wherein the elastic strand is in a relaxed state.
Figure 10H:
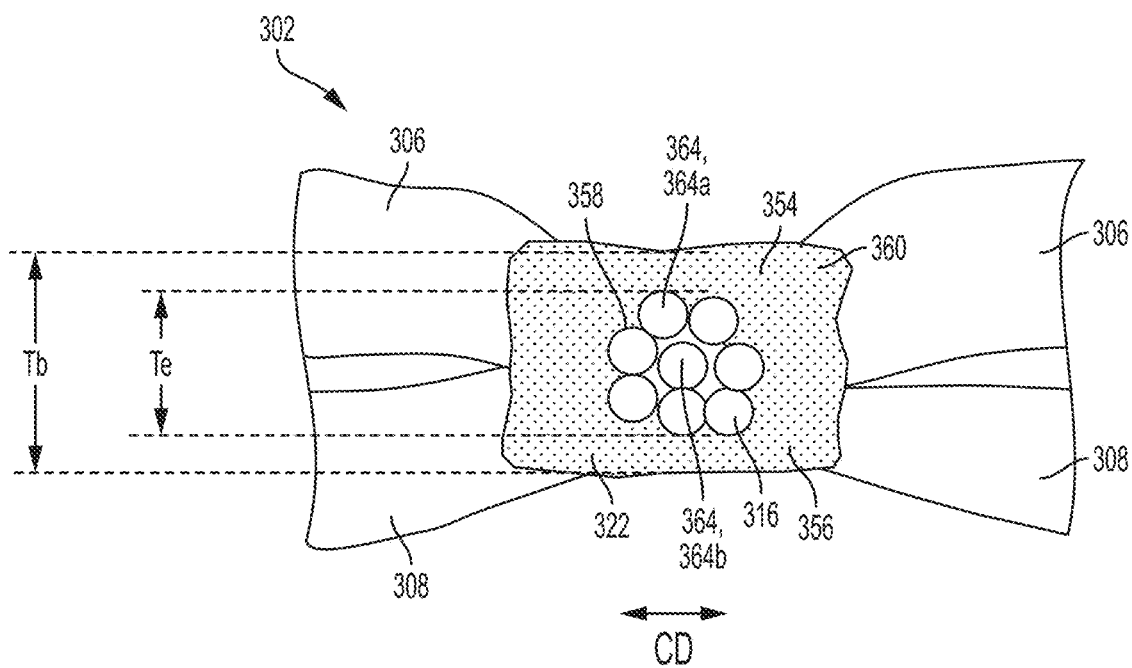
FIG. 10H is a sectional view of an elastic strand, bond, first substrate, and second substrate of FIG. 10A taken along line 10E-10E, wherein a plurality of filaments of the elastic strand are bonded in a first configuration.
Figure 10I:
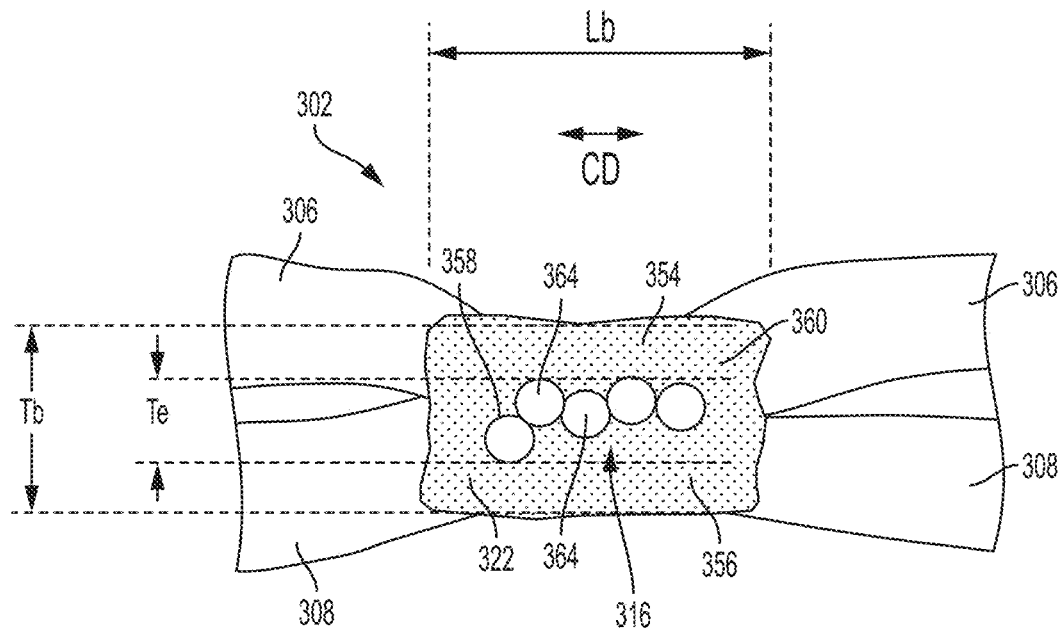
FIG. 10I is a sectional view of an elastic strand, bond, first substrate, and second substrate of FIG. 10A taken along line 10E-10E, wherein a plurality of filaments of the elastic strand are bonded in a second configuration.

Referring to FIG. 10I, a first material 354, such as a first substrate 306, may be bonded to a second material 356, such as a second substrate 308, via one or a plurality of bonds 322. The bond may be formed by melting the first material 354 and second material 356 together to form a densified region 311, that may be formed by ultrasonic bonding. The bond 322 may completely (or substantially) surround and conform with the outer perimeter of the elastic strand 316 to define a dimensional lock. In this way, the densified bonds 322 may be said to overlap one or a plurality of the elastic strands 316. The bond or plurality of densified bonds 322 may hold the first and second materials 354 and 356 together, such that the two materials have a Peel-Strength of from about of at least about 1 N/cm to about 5 N/cm or from about 2 N/cm up to about 10 N/cm or up to and including substrate failure of one or both of the nonwoven substrates. Thus, the bond or plurality of bonds 322 may dimensionally lock the elastic strands 316 and hold the first and second substrates together to so that the resulting elastomeric laminate 302 is useful as an article component. While one or more of the bonds 322 may overlap one or a plurality of the elastic strands 316, one or more of the bonds 322 may form a densified region holding the first and second materials 354 and 356 together, not overlap an elastic strand 316.

The first and second materials 354 and 356 (for example, inner and outer belt layers 432 and 434) may be melted together to form a densified region 311 around the elastic strand and to be bonded to each other; the densified region may be formed by ultrasonics such that a void having a Cross-Section-Bond-Void-Area corresponding substantially to the shape and dimensions of the tensioned elastic strand(s) or individual filaments making up the strand(s). As the elastic tension is released, the cross-sectional dimensions of the relaxed elastic (having a Cross-Sectional-Strand-Area) increase causing the now larger elastic to become dimensionally locked in place by the relatively smaller void. The dimensional lock holds the discrete length of the elastic strand in a fixed position in the bond region with the first and second substrates. Therefore, it is important that the cross-sectional area of the void space of the bond is less than the cross-sectional area of the relaxed elastic strand(s), i.e., a Void-Area-to-Elastic-Area-Ratio of less than 1. It may be desirable to have a Void-Area-to-Elastic-Area-Ratio of from about 0.25 to about 0.9, or from about 0.3 to about 0.7. In a contracted elastomeric laminate, the cross-sectional area of the void space of the bond is substantially the same as the cross-sectional area of the contracted elastic strand(s) 316 held within the bond. In most circumstances the cross-sectional shape of the void will be substantially the same as the cross-sectional shape of the elastic strand 316 held within the bond.

While the elastic strand 316 is overlapped and dimensionally locked by the densified bonds as described, the elastic strand 316 may be unbonded between densified bonds 322. Alternatively, the elastic strands may be bonded between the densified bonds 322 by adhesive. For instance, a first elastic strand may be overlapped by at least 3 densified bonds joining the first elastic strand to first and second nonwovens, and the first elastic strand may be unbonded between a first bond and a second bond of the at least 3 bonds and the first elastic strand may be unbonded between the second bond and a third bond of the at least three bonds. Further, the first strand may unbonded between a third bond and a fourth bond of the at least 3 bonds and the first elastic strand may be unbonded between the fourth bond and a fifth bond of the at least three bonds.

FIG. 10A is a detailed view of an elastic strand 316 in a stretched state secured with bonds 322 between the first and second substrates 306, 308. The bonding process, may apply heat, pressure, ultrasonics or combinations thereof, to a first region 350 of the first substrate 306 and a second region 352 of the second substrate 308 such that first material 354 of the first substrate 306 and second material 356 of the second substrate 308 become malleable. In turn, the malleable first and second materials 354, 356 deform and completely surround an outer perimeter 358 of a discrete length of the stretched elastic strand 316 in a bond region 360 forming a void that has substantially the same cross-sectional dimensions as the strained elastic strand 316.

A dimensional lock may be created between a portion of the elastic strand 316 and the bond between the first and second materials 354, 356 once the tension from the stretched elastic strand 316 is released. The dimensional lock acts to hold and/or secure the elastic strand 316 in a fixed position in the bond region 360. For the purposes of a general explanation, FIG. 10B shows a length of an elastic strand 316 in a unstretched or relaxed state, wherein the elastic strand 316 defines a first cross-sectional area A1. And FIG. 10C shows a length of the elastic strand 316 from FIG. 10B in a stretched state, wherein the elastic strand 316 defines a second cross-sectional area A2 that is less than the first cross-sectional area A1. Thus, the cross-sectional area of the stretched elastic strand 316 expands when tension is partially or fully released from the elastic strand 316. As discussed in more detail below, the tendency of the cross-sectional area of the elastic strand 316 to expand helps create the dimensional lock. An important factor in creation of the dimensional lock bond between the first and second material 354, 356 without cutting the stretched elastic strands 316 is the Dtex-to-Nonwoven-Basis-Weight-Ratio. In order for the bond to have sufficient bond strength to prevent separation of the first and second material layers 354 and 356, without application of excessive combining pressure that can cut the elastic strands 316 it is necessary to have enough total nonwoven basis weight to substantially or completely wrap the elastic strands and condense adequately to join the first and second materials 354 and 356 to form the nonwoven bond regions surrounding the elastic strands. The Dtex-to-Average-Nonwoven-Basis-Weight-Ratio may be from about 2 to about 13, from about 3 to about 10, or from about 4 to about 8.

Turning next to FIG. 10D, a detailed view of an elastic strand 316, such as shown in FIG. 10A, is provided wherein tension has been released (or reduced) on the elastic strand 316 and showing how the tendency of the elastic strand 316 to expand creates a dimensional lock in the bonded region 360. FIGS. 10D and 10F show the elastic strand 316 as having a first cross-sectional area A1 in an unbonded region 362 of the elastomeric laminate 302, wherein the first cross-sectional area A1 is greater than the second cross-sectional area A2 of the stretched elastic strand 316 shown in FIGS. 10A and 10E. And FIGS. 10D and 10G show the elastic strand 316 as having a third cross-sectional area A3 in the bond region 360 of the elastomeric laminate 302, wherein the third cross-sectional area A3 is the same or about the same as the second cross-sectional area A2 of the stretched elastic strand 316 shown in FIGS. 10A and 10E. As shown in FIG. 10G, the first and second materials 354, 356 in the bond region 360 help prevent the cross-sectional area of the elastic strand 316 from expanding fully when tension on elastic strand 316 has been reduced. As such, in some configurations, no adhesive may be applied to and/or present between the elastic strand 316 and the first and second materials 354, 356. It is also to be appreciated that in some configurations, adhesive may be applied to and/or present between the elastic strand 316 and the first and second materials 354, 356 to help the dimensional lock hold the discrete length of the elastic strand 316 in a fixed position in the bond region 360 together with the first and second substrates 306, 308. In some configurations, adhesive and the dimensional lock in the bond regions 360 may share the load exerted by elastic strand 316.

It is also to be appreciated that the elastic strands 316 herein bonded in accordance with the methods described herein may also be constructed from one or more filaments 364. For example, FIG. 10H shows a cross-sectional view of an elastic strand 316 in a bond region 360 wherein the elastic strand 316 comprises a plurality of individual filaments 364. As shown in FIG. 10H, the elastics strand 316 includes outer filaments 364a surrounding an inner filament 364b. The outer filaments 364a define the outer perimeter 358 of the elastic strand 316, and the outer filaments 364a may surround the inner filament 364b such that the inner filament 364b is not in contact with the first material 354 and the second material 356 in the bond 322. It is to be appreciated that the filaments 364 may be arranged in various positions within the bond region 360. For example, FIG. 10I shows a cross-sectional view of an elastic strand 316 in a bond region 360 wherein the plurality of individual filaments 364 together define a perimeter 358 that is elongated along the cross direction CD (i.e., cross-sectionally side-by-side such that other filaments of the elastic strand are not above or below them when viewed in cross-section (e.g., FIGS. 10I-L), and wherein all of the plurality of filaments 364 are in contact with the densified first and second materials 354 and 356.

Figure 10J:
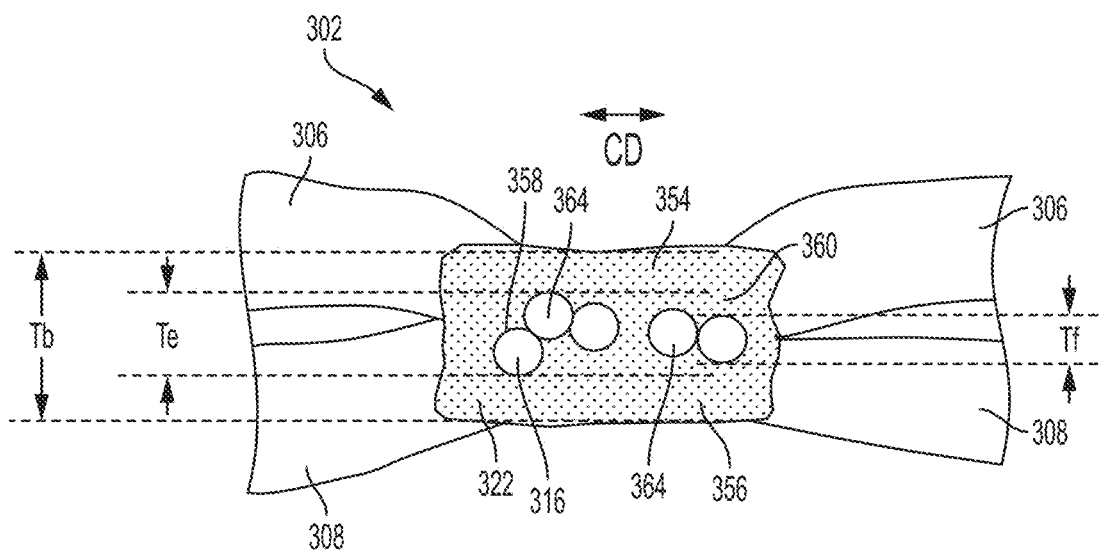
FIG. 10J is a sectional view of an elastic strand, bond, first substrate, and second substrate of FIG. 10A taken along line 10E-10E, wherein a plurality of filaments of the elastic strand are bonded in a third configuration.

In another example, FIG. 10J shows a cross-sectional view of an elastic strand 316 in a bond region 360 wherein at least two of the filaments 364 are separated from each other by at least one bond between the first material 354 and second material 356.

It is to be appreciated that different components may be used to construct the elastomeric laminates 302 in accordance with the methods and apparatuses herein. For example, the first and/or second substrates 306, 308 may include nonwovens and/or films and may be constructed from various types of materials, such as plastic films; apertured plastic films; woven or nonwoven webs of natural materials, such as wood or cotton fibers; synthetic fibers, such as polyolefins, polyamides, polyester, polyethylene, or polypropylene fibers or a combination of natural and/or synthetic fibers; or coated woven or nonwoven webs; polymeric films such as thermoplastic films of polyethylene or polypropylene, and/or a multi-layer or composite materials comprising a film and a nonwoven material.

It is also to be appreciated that the strands 316 and/or filaments 364 herein may define various different cross-sectional shapes. For example, in some configurations, strands 316 or filaments 364 may define circular, oval, or elliptical cross-sectional shapes or irregular shapes, such as dog bone and hourglass shapes. In addition, the elastic strands 316 may be configured in various ways and with various decitex values. In some configurations, the elastic strands 316 may be configured with decitex values ranging from about 10 decitex to about 400 decitex, specifically reciting all 1 decitex increments within the above-recited range and all ranges formed therein or thereby.

As previously mentioned, substrates 306, 308 with elastic strands 316 positioned therebetween can be bonded in accordance with methods herein without severing the elastics strands. For example, as shown in FIGS. 10G and 10H-10J, ultrasonics, heat, pressure, and combinations thereof may be applied to the substrates 306, 308 to create bonds 322 surrounding the elastic strand 316. The bond 322 is defined by a compressed region comprising first material 354 and second material 356 the compressed region having a minimum thickness Tb. In addition, the elastic strand 316 may have a thickness Te in the bond region 360. In some configurations, substrates 306, 308 that are bonded together to create a bond thickness Tb having a certain size relative to the elastic strand thickness Te, the elastic strand 316 may not be severed during the bonding process. In addition, the forces exerted between the elastic strand 316 and the first and second materials 354, 356 in the bond region 360 may be prevented from breaking the bond 322. Such a relationship between Te and Tb may be characterized by the decitex of elastic strands 316 and the bond thickness Tb. For example, substrates 306, 308 may be bonded together with an elastic strand having a decitex value less than or equal to about 78 positioned therebetween to create a bond 322 having a thickness Tb of at least about 100 μm ("microns") without severing the elastic strand 316. In another example, substrates 306, 308 may be bonded together with an elastic strand having a decitex value less than or equal to about 250 positioned therebetween to create a bond 322 having a thickness Tb of at least about 200 μm ("microns") without severing the elastic strand 316. In some configurations, such as shown in FIG. 10J, the bond thickness Tb may be at least 50% larger than the minimum cross-sectional thickness Tf of a filament 364. For example, as shown in FIG. 10J, the minimum cross-sectional thickness Tf of a filament 364 having a circular cross-section may be defined the diameter of such a filament.

Figure 10K:
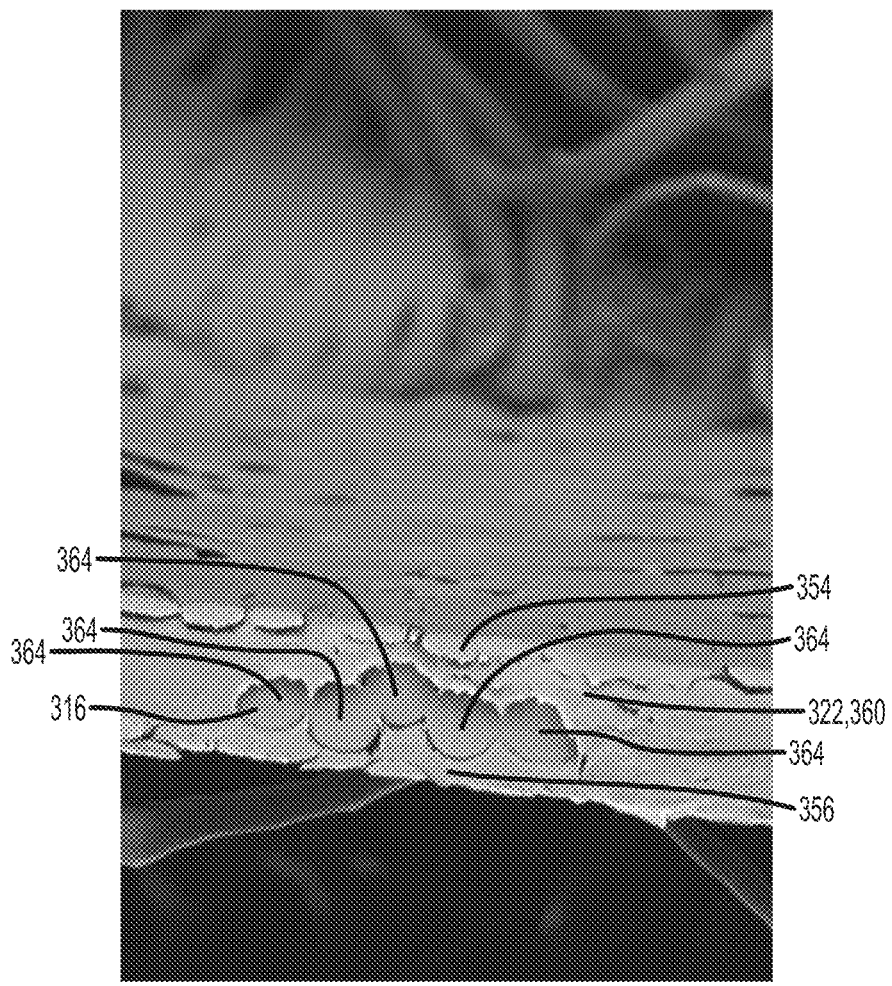
FIG. 10K is a scanning electron microscope ("SEM") photograph of a cross-sectional view of an elastic strand including five filaments in a bonded region and surrounded by hardened first and second substrate materials.
Figure 10L:
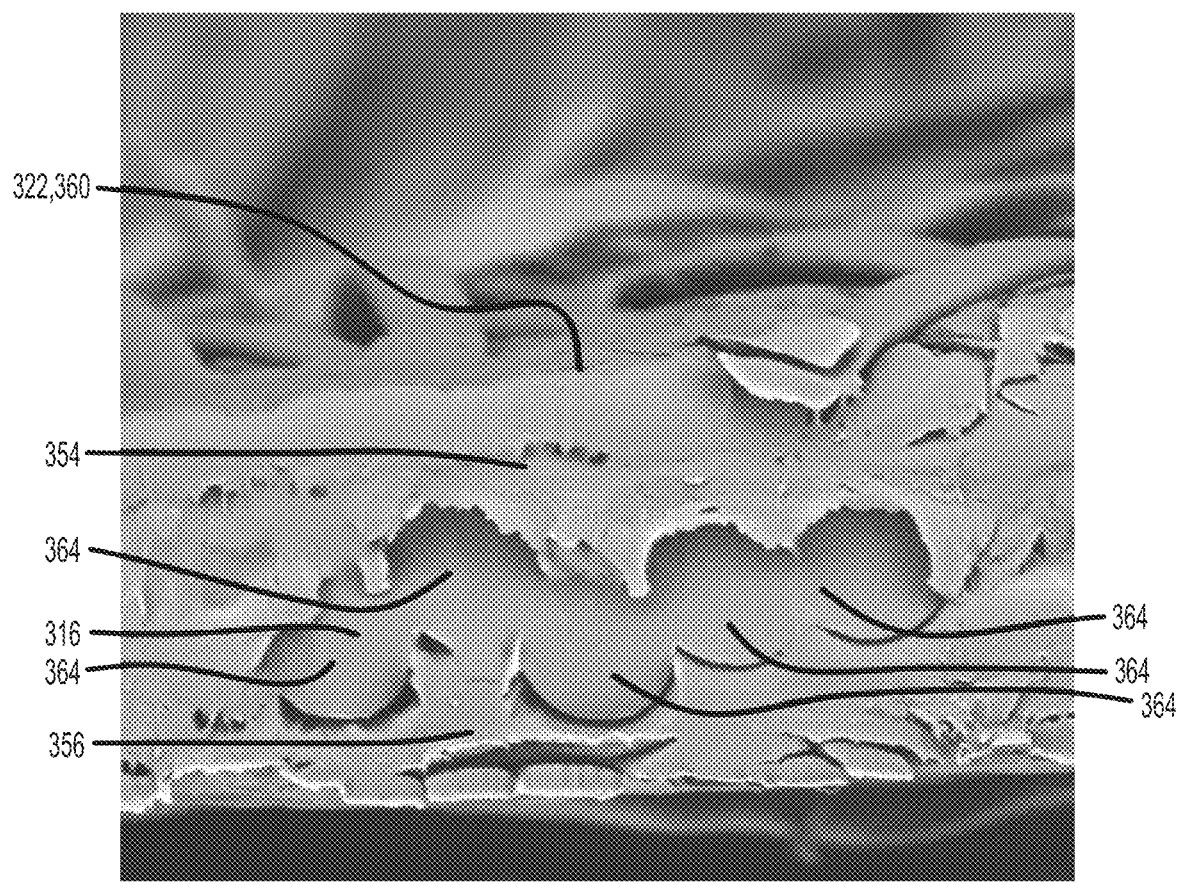
FIG. 10L is a scanning electron microscope ("SEM") photograph of a cross-sectional view of an elastic strand including five filaments in a bonded region and surrounded by hardened first and second substrate materials.
Figure 10M:
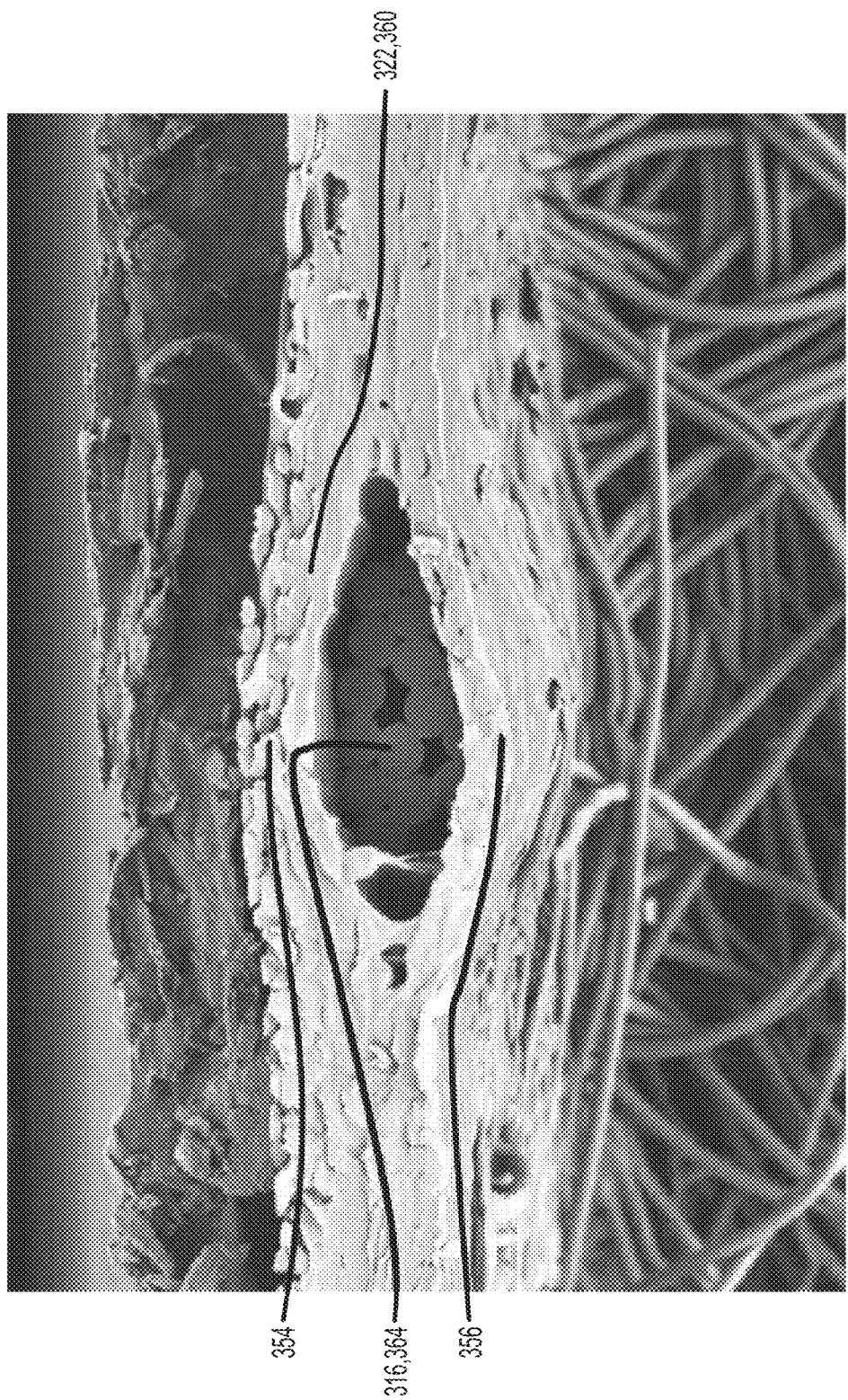
FIG. 10M is a scanning electron microscope ("SEM") photograph of a cross-sectional view of an elastic strand including fifteen filaments in a bonded region and surrounded by hardened first and second substrate materials.

FIGS. 10K-10M electron microscope photographs ("SEM") showing cross-sectional views of an elastic strand 316 in a bond region 360 surrounded by first and second materials 354, 356. In FIGS. 10K and 10L, the elastic strand 316 is a 78 decitex elastic strand including five filaments 364, wherein each filament 364 has a diameter of about 43 μm ("microns"). And the bond 322 defines a thickness Tb of about 80 μm ("microns"). In FIG. 10M, the elastic strand 316 is a 235 decitex elastic strand including fifteen filaments 364, wherein each filament 364 has a diameter of about 43 μm ("microns"). And the bond 322 defines a thickness Tb of about 200 μm ("microns").

Figure 10O:
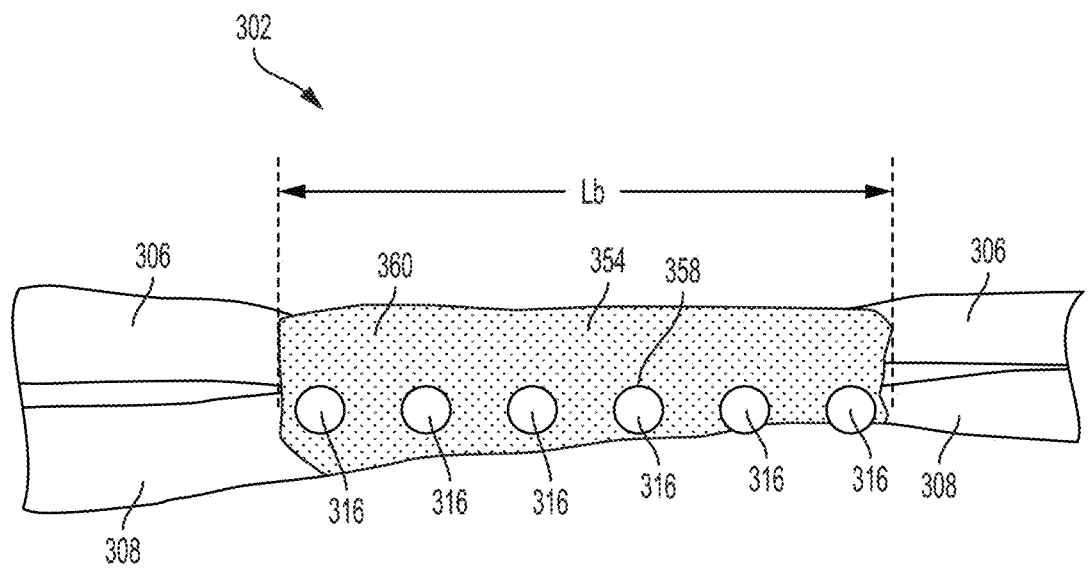
FIG. 10O is a sectional view of the elastic strand, bond, first substrate, and second substrate of FIG. 10N taken along line 10O-10O, such that the plurality of filaments are only partially surrounded by a densified bond 322.
Figure 10P:
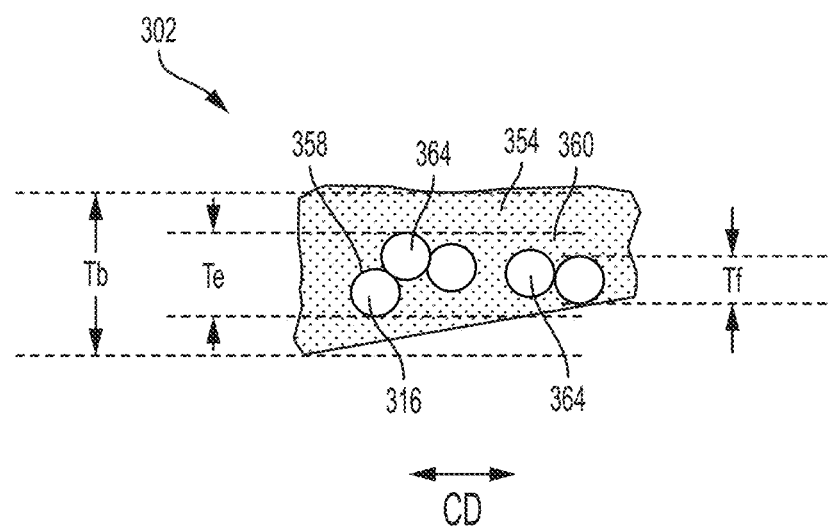
FIG. 10P is a sectional view of an elastic strand, bond, first substrate, and second substrate of FIG. 10A taken along line 10E-10E, wherein a plurality of filaments of the elastic strand are bonded in an alternative embodiment of the third configuration of FIG. 10J.

As shown in FIGS. 10N, 10O, and 10P, the densified bonds 322 may only partially surround some of the elastic strands such that either the top or the bottom of the bond 322 is much thicker than the other. This effect may be due to the process of ultrasonically bonding the elastomeric laminate with a stationary ultrasonic horn, which may drag a portion of the bond 322 while the bond 322 is being formed and in a molten state, creating a tail versus the boundary defined by the other of the top or bottom of the bond 322 and/or creating a wedge-shaped bond 322.

In certain embodiments, the bond 322 may be discrete and may surround only a portion of the filaments forming the strand. The discrete bond may surrounds at least about 10, at least about 20 filaments, at least about 30 filaments at least 10 elastic strands. Further, the plurality of elastic strands may comprise at least 100 elastic strands wherein each of the at least 100 elastic strands comprises at least 3 filaments wherein the plurality of densified bonds overlap at least 50 of the elastic strands making up the plurality of elastic strands and surrounds at least 150 filaments of the at least 100 elastic strands, and wherein substantial portions of the at least 100 elastic strands between the densified bonds are unbonded.

Elastomeric laminates of the present disclosure comprising a plurality of densified bonds as described above may be adhesive free. Alternatively, certain sections of the elastomeric laminates may comprise adhesive without densified bonds or certain sections may comprise the combination of adhesive and densified bonds. For instance, a first plurality of elastics between first and second nonwovens may be overlapped with a first plurality of densified bond and a second plurality of elastics between the first and second nonwovens may be overlapped with adhesive bonds. The first and/or second plurality of elastics may comprises from about 2 to about 20 elastic strands, may have an Average-Strand-Spacing of about 3 mm or greater, and/or may have an Average-Dtex of the second plurality of elastics is about 300 or greater.

Breakage

Elastomeric laminates of the present disclosure having Dtex-to-Spacing-Ratios, Dtex-to-Nonwoven-Basis-Weight-Ratios, and Void-Area-to-Elastic-Area-Ratios within the ranges disclosed above will result in minimal elastic strand breakage between densified portions of a plurality of bonds (i.e., minimal free ends 327 (see FIG. 10Q) of strands or free ends 328 of filaments between densified bonds). More particularly, less than 20%, or less than 15%, or less than 10%, or less than 5% of the strands between densified portions of the bonds may be broken in elastomeric laminates of the present disclosure. Further, less than 20%, or less than 15%, or less than 10%, or less than 5% of the filaments between densified portions of the bonds may be broken in elastomeric laminates of the present disclosure. Alternatively, lower breakage may be identified as greater than 70%, greater than 80%, or greater than 90% of the elastic strands in one of the L and R article sections extends at least 50% of a lateral width (laid out flat, i.e., extended) of the respective L and R sections.

It may, however, be desirable to have densified bonds in a section, but not have elastics in that section—like the section(s) over the chassis. The elastic strands may be purposefully cut or broken in this section, such that free ends of the cut or broken elastic strands overlap the chassis. When an elastomeric laminate comprises apertures, the apertures may cut or break the elastic strands.

Figure 10Q:
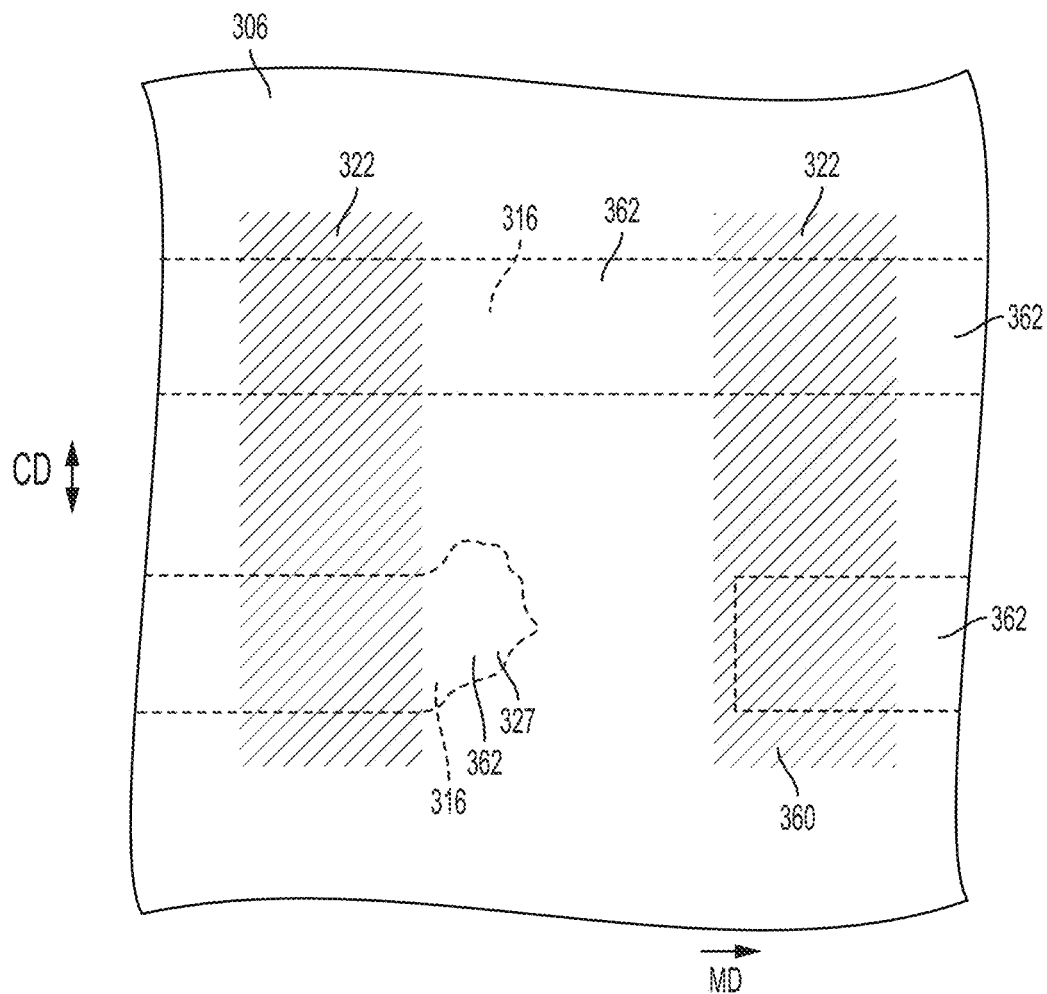
FIG. 10Q is a detailed view of multiple elastic strands in a stretched state bonded between the first and second substrates, illustrating a strand free-end 327.
Figure 10R:
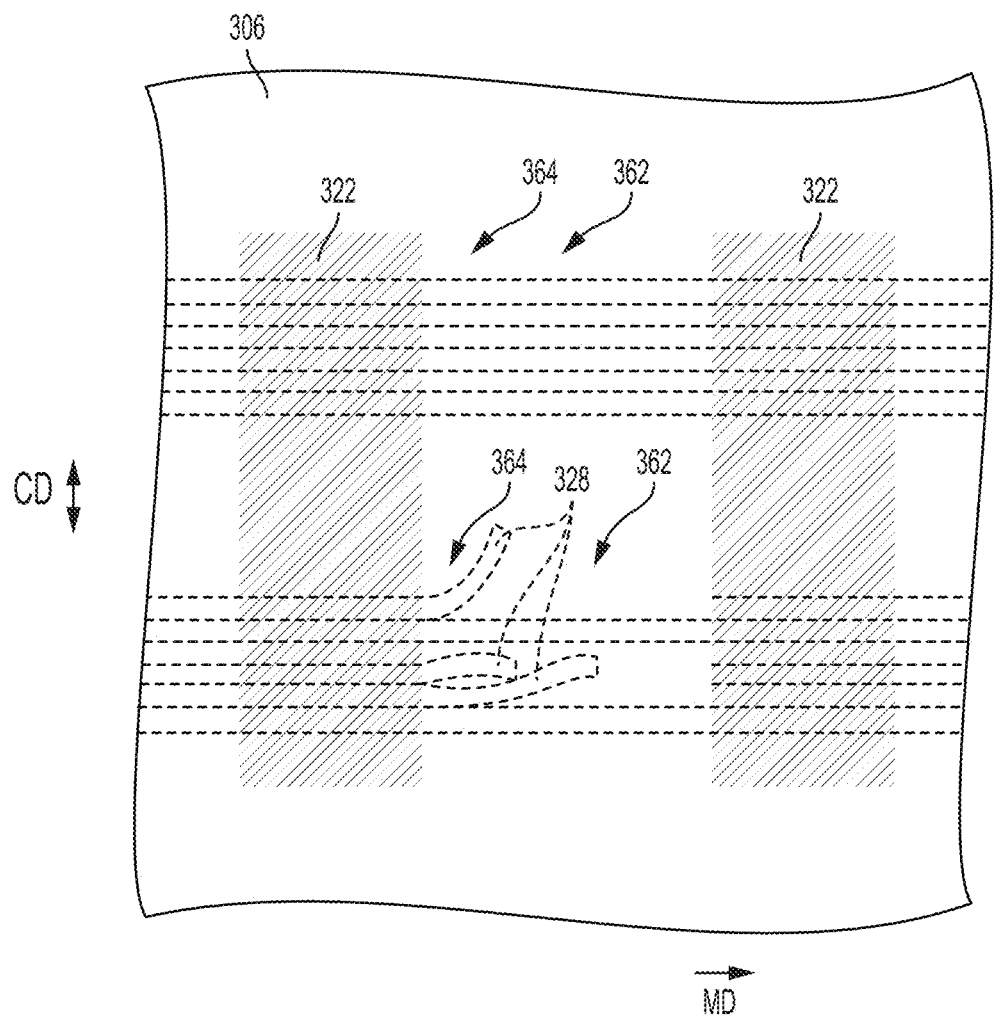
FIG. 10R is a detailed view of multiple elastic filaments in a stretched state bonded between the first and second substrates, illustrating filament free-ends 328.
Figure 11A:
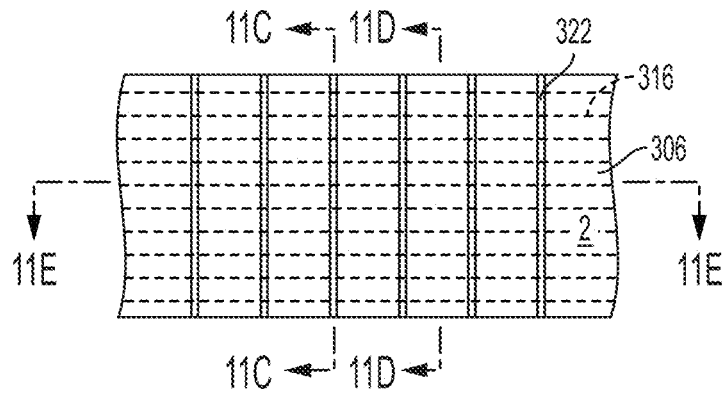
FIG. 11A is a plan view of a garment-facing surface or an exterior surface of an elastomeric bi-laminate.
Figure 11B:
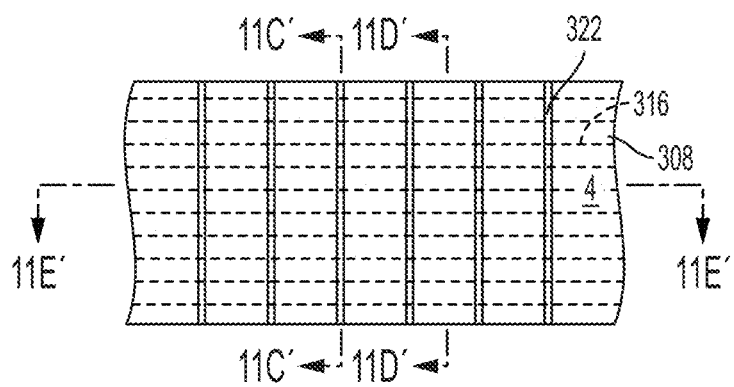
FIG. 11B is a plan view of a wearer-facing surface or an interior surface of the elastomeric bi-laminate of FIG. 11A.
Figure 11C:
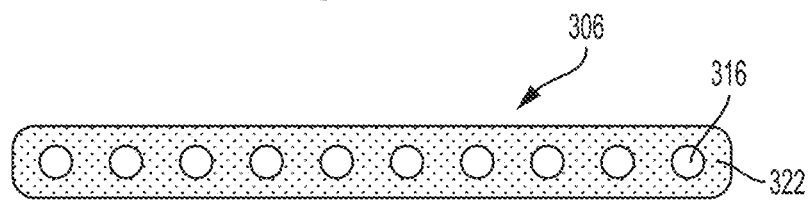
FIG. 11C is a cross-sectional view of the bi-laminate of FIG. 11A taken along line 11C-11C and is a cross-sectional view of the bi-laminate of FIG. 11B taken along line 11C'-11C'.
Figure 11D:
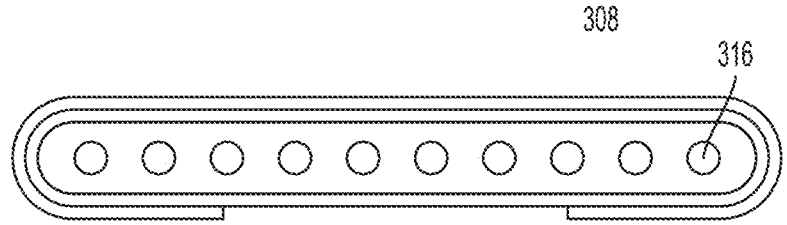
FIG. 11D is a sectional view of the bi-laminate of FIG. 11A taken along line 11D-11D and is a sectional view of the bi-laminate of FIG. 11B taken along line 11D'-11D'.
Figure 11E:
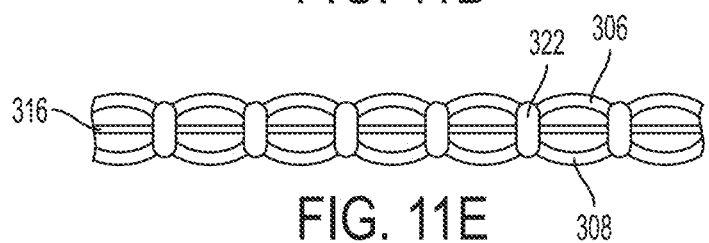
FIG. 11E is a cross-sectional view of the bi-laminate of FIG. 11A taken along line 11E-11E and is a cross-sectional view of the bi-laminate of FIG. 11B taken along line 11E'-11E'.

While elastomeric laminates of the present disclosure have minimal elastic strand breakage between densified portions of a plurality of bonds, a portion of the filaments making up the strand(s) may be broken between the densified portions of the plurality of bonds (see free end 327 of FIG. 10Q and fee ends 328 of FIG. 10R)

It may be desirable that less than 5%, 10%, 15%, or 20% of the elastic strands of a first plurality of strands are broken between adjacent densified bonds of the first plurality of bonds that are transversely spaced less than 20 mm from each other.

As an example, a first elastic strand may be overlapped by at least 3 densified bonds joining the first elastic strand to first and/or second nonwovens, where the first elastic strand is unbonded between the first bond and a second bond of the at least 3 bonds, and the first elastic strand is unbonded between the second bond and a third bond of the at least three bonds.

As another example, a first elastic strand may be overlapped by at least 5 densified bonds joining the first elastic strand to first and/or second nonwovens, where the first elastic strand is unbonded between the first bond and a second bond of the at least 3 bonds, and the first elastic strand is unbonded between the second bond and a third bond, and further, where the first strand is unbonded between the third bond and a fourth bond, and the first elastic strand is unbonded between the fourth bond and a fifth bond.

Bi-Laminates of the Present Disclosure

Figure 16A:
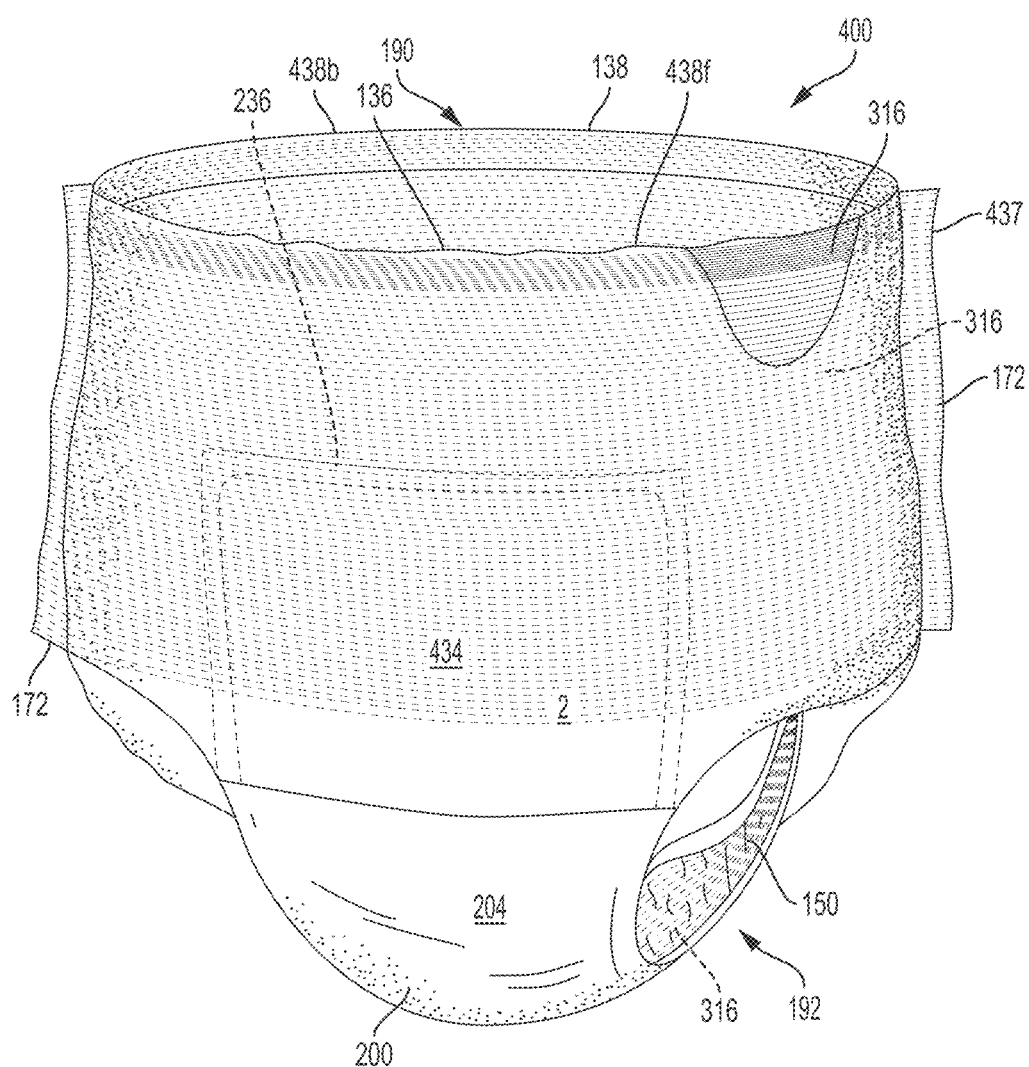
FIG. 16A is a perspective front view of a pant comprising discrete belts having continuous elastics.
Figure 16B:
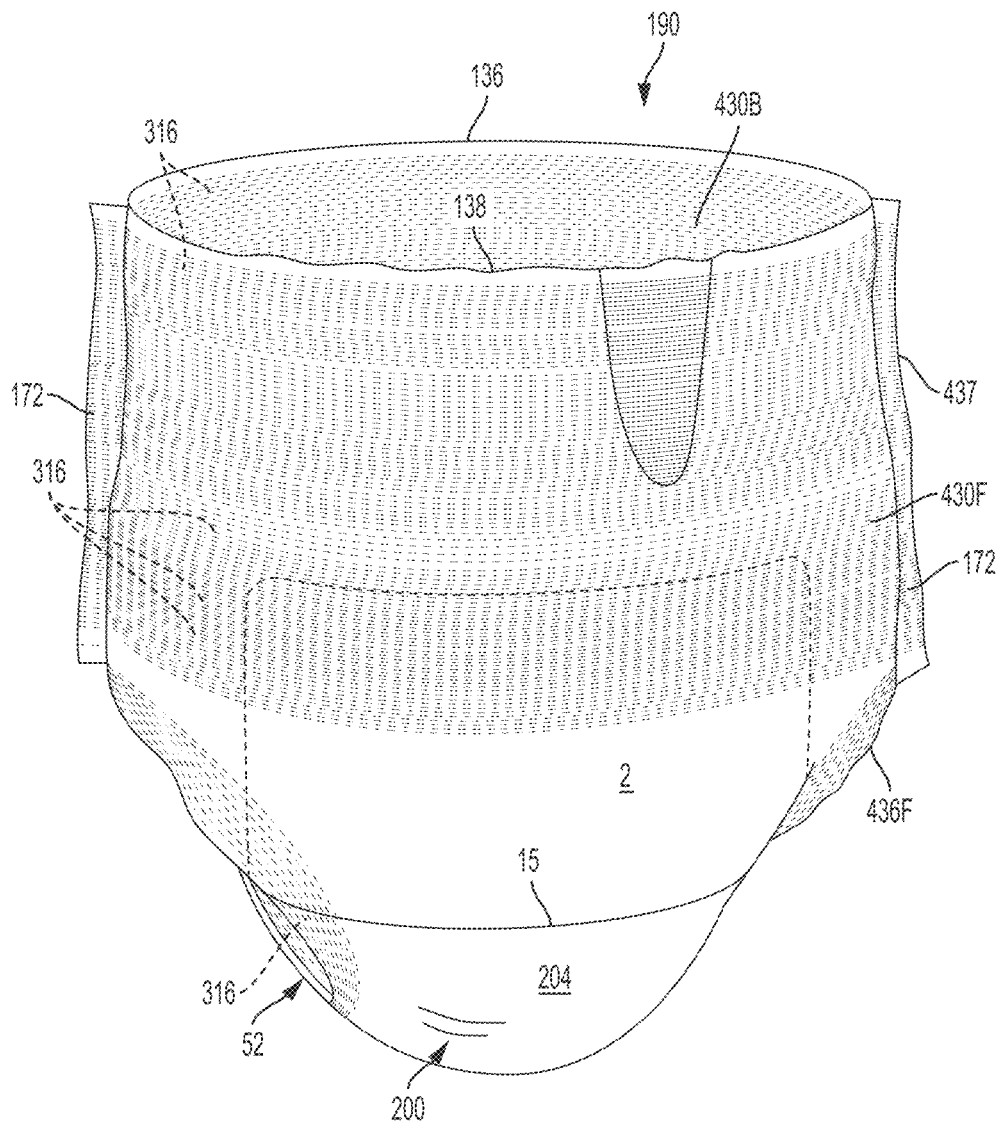
FIG. 16B is a perspective back view of the pant of FIG. 16A

As illustrated in FIGS. 11A-11E, and as described in detail in the Ultrasonic Bonds Section above, stranded elastomeric laminates of the present disclosure may be bi-laminates and may comprise beamed elastics 316. Bi-laminates may be bonded via densified regions, mechanically, thermally, by pressure, or via ultrasonics as described in the Ultrasonic Bonds Section above. Bi-laminates may also be bonded together via application of adhesives either in a defined pattern, random pattern or continuous pattern. Bi-laminates may comprise two nonwoven substrates having the same polymer composition, basis weight, formation type (spunbond, carded, spunbond-meltblown-spunbond, etc.). Alternatively, the nonwoven substrates forming the bi-laminate may be formed from nonwovens having different polymer composition, basis weight, formation type (spunbond, carded, spunbond-meltblown-spunbond, etc.). Each of the bi-laminates of FIGS. 11A-11E may be used to form the belts of FIGS. 16E-G.

Tri-Laminates of the Present Disclosure

Absorbent articles comprising beamed elastic laminates provide a step change in textural garment like appearance. The appearance can be further enhanced via a multi-layer (3 or more substrate layers) laminate configuration. These configurations lend themselves to distinct and different bonding approaches and patterns which enables the laminate to have a first texture on one surface and a second texture on the opposing surface. The textures may be the same, distinctly different, and/or complementary.

Figure 12A:
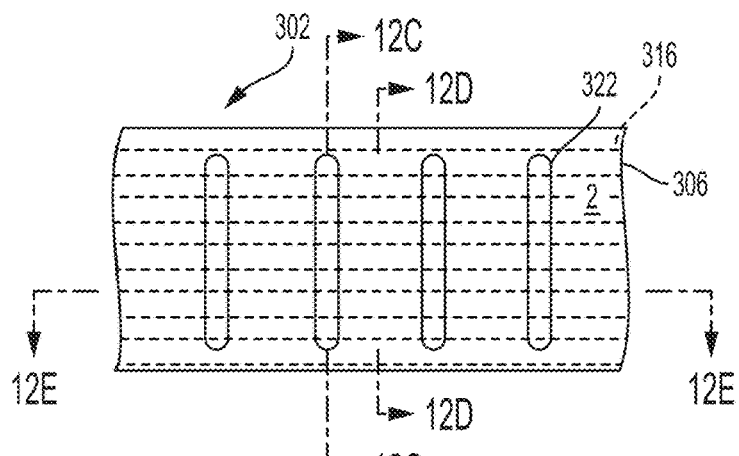
FIG. 12A is a plan view of a garment-facing surface of an elastomeric tri-laminate.
Figure 12B:
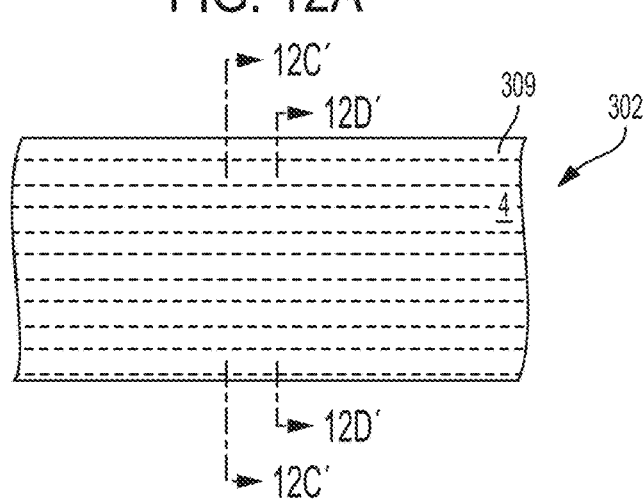
FIG. 12B is a plan view of a wearer-facing surface of the elastomeric tri-laminate of FIG. 12A.
Figure 12C:
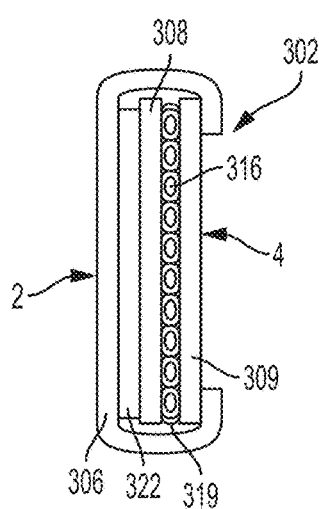
FIG. 12C is a cross-sectional view of the tri-laminate of FIG. 12A taken along line 12C-12C and is a cross-sectional view of the tri-laminate of FIG. 12B taken along line 12C'-12C'.
Figure 12D:
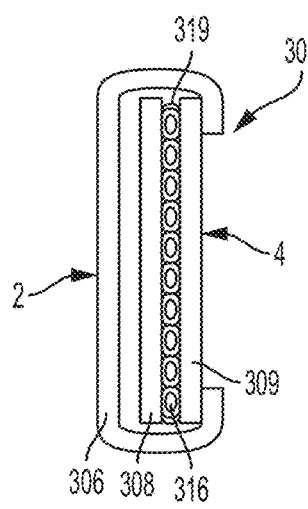
FIG. 12D is a sectional view of the tri-laminate of FIG. 12A taken along line 12D-12D and is a sectional view of the tri-laminate of FIG. 12B taken along line 12D'-12D'.
Figure 12E:
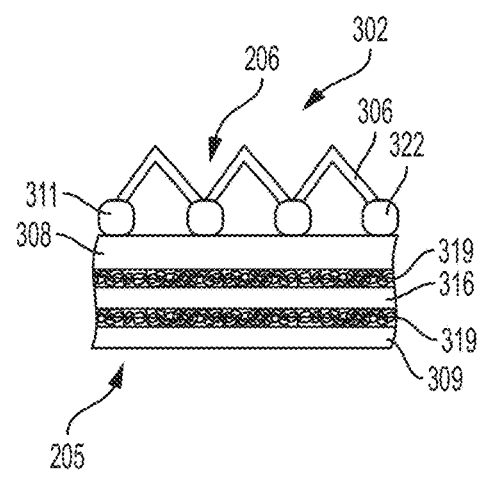
FIG. 12E is a cross-sectional view of the tri-laminate of FIG. 12A taken along line 12E-12E.
Figure 12F:
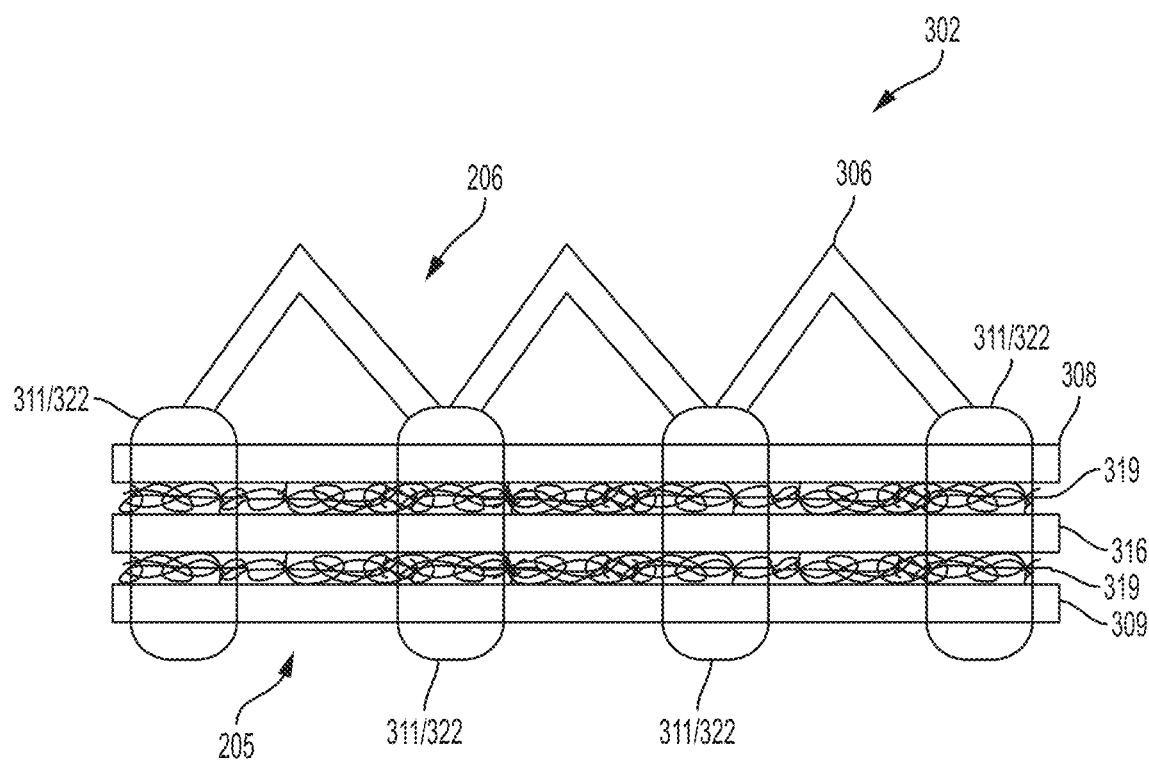
FIG. 12F is a cross-sectional view of an alternate embodiment of the tri-laminate of FIG. 12A taken along line 12E-12E.

When it is desirable to have different texture on the garment-facing surface 2 or exterior surface 206) versus the wearer-facing surface 4 or interior surface 205, elastomeric laminates of the present disclosure may be in the form of a tri-laminate. Referring to FIGS. 12A-13G, for example, first and second substrate layers 306 and 308 may be bonded with a different type of bond and/or bonding arrangement versus second and third substrate layers, 308 and 309. More particularly, as shown in FIGS. 12A-E, first and second substrate layers 306 and 308 may be ultrasonically bonded together with continuous (longitudinally or laterally) or discrete (longitudinally or laterally) bonds 322 comprising densified portions 311 (see FIGS. 12C and 12E), while the second and third substrates 308 and 309 may be joined via a substantially continuous adhesive 319 layer (see FIGS. 12C and 12E). FIG. 12F illustrates an alternative embodiment where a pattern of densified portions of ultrasonic bonds join the first, second, and third substrates together in addition to an adhesive layer joining the second and third substrates together. In another alternative embodiment, the bonds 322 joining the first and second substrates may be an adhesive instead of densified portions, such that discrete or patterned adhesive bonds join the first and second substrates and a continuous adhesive layer joins the second and third substrates. For each of these embodiments, the elastics 316 may be beamed elastics. The aforementioned configuration provides a smooth texture on one surface of the laminate and an intentional, well-defined and deliberate textural pattern on the opposing surface.

In FIGS. 12A-12E, the first and second substrates 306 and 308 may be joined by a first process step to form a bi-laminate, then the third substrate 309 may be joined by a second process step to the bi-laminate to form a tri-laminate. Alternatively, the second and third substrates 308 and 309 may be first joined to form a bi-laminate by a first process step, then the first substrate 306 may be joined to the bi-laminate to form a tri-laminate by a second process step.

In the alterative embodiment of FIG. 12F, the second and third substrates 308 and 309 may be first joined to form a bi-laminate via a first process step, then the first substrate 306 may be joined to the bi-laminate to form a tri-laminate via a second process step.

Figure 13E:
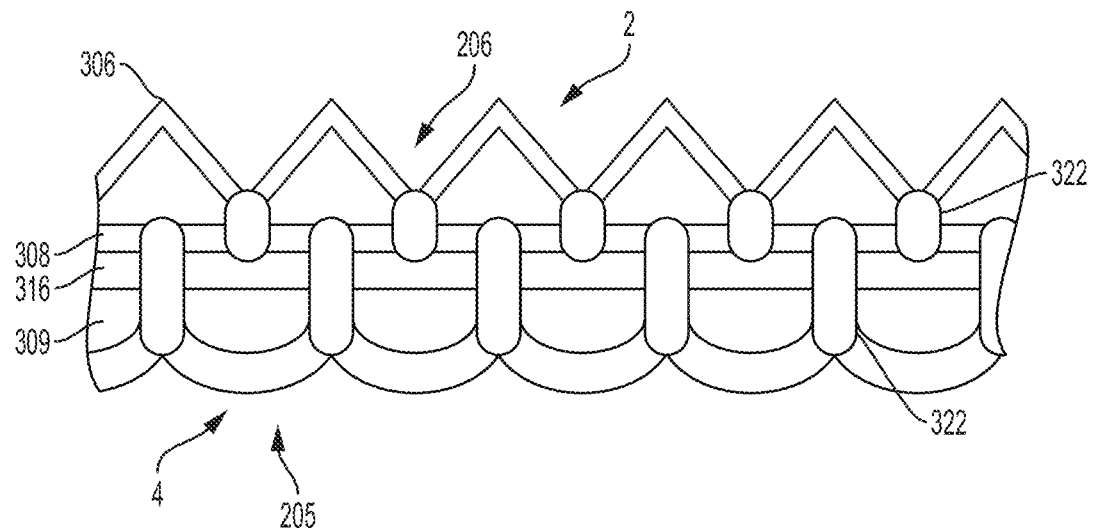
FIG. 13E is a cross-sectional view of the tri-laminate of FIG. 13A taken along line 13E-13E and is a cross-sectional view of the tri-laminate of FIG. 13B taken along line 13E'-13E'.

Referring to FIGS. 13A-13G, first and second substrate layers 306 and 308 may be ultrasonically bonded together with a pattern of continuous (longitudinally or laterally) or discrete (longitudinally or laterally) bonds 322 comprising densified portions 311 (see FIGS. 13C and 13E), while the second and third substrates 308 and 309 may be joined via a second pattern of continuous (longitudinally or laterally) or discrete (longitudinally or laterally) ultrasonic bonds (see FIGS. 13C and 13E). The bonds 322 joining the first and second substrates 306 and 308 together may alternatively form a pattern of continuous (longitudinally or laterally) or discrete (longitudinally or laterally) adhesive bonds, and the bonds 322 joining the second and third substrates 308 and 309 together may also form a pattern of continuous (longitudinally or laterally) or discrete (longitudinally or laterally) adhesive bonds such that one or both bond areas may be adhesive bonds. For each of these embodiments, the elastic strands 316 may be beamed elastics. In these embodiments, one surface of the laminate may be smooth while the opposing surface is textured. Alternatively, one surface of the laminate may have a first texture and the opposing surface of the laminate may have a second texture. In a third embodiment, both surfaces of the laminate may have a relatively smooth texture.

Figure 13F:
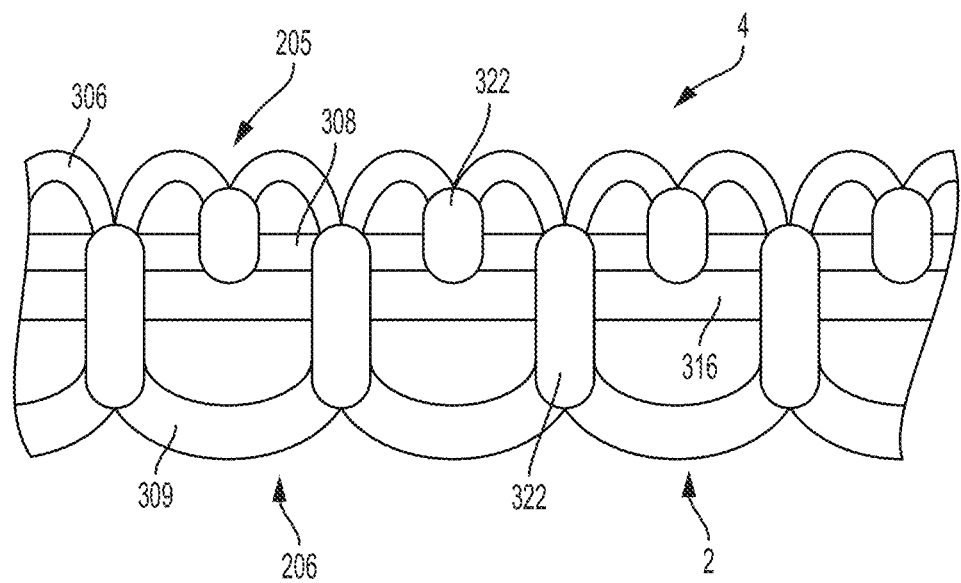
FIG. 13F is a cross-sectional view of an alternate embodiment of the tri-laminate of FIG. 13A taken along line 13E-13E and is a cross-sectional view of the tri-laminate of FIG. 13B taken along line 13E'-13E'.
Figure 13G:
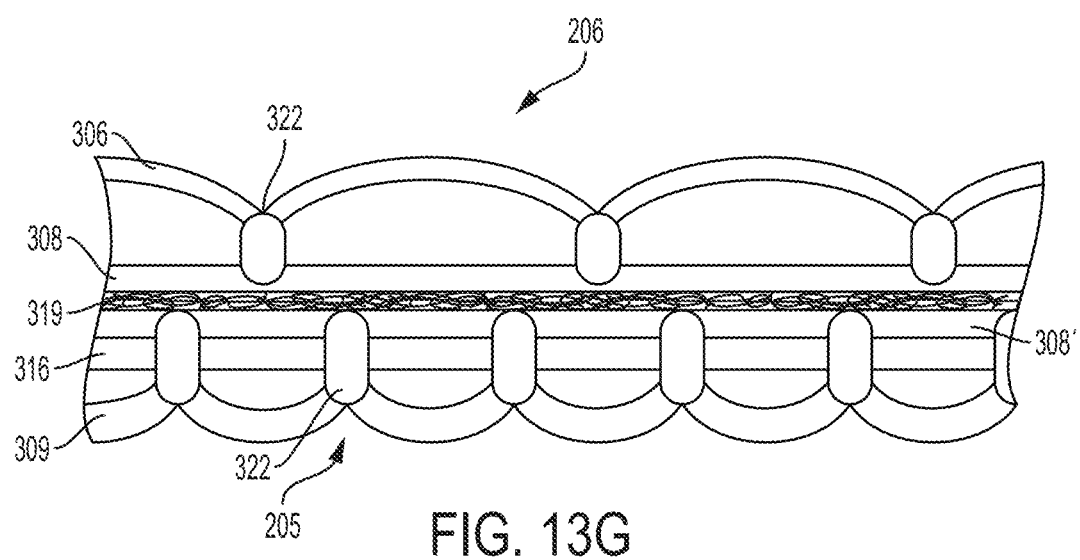
FIG. 13G is a cross-sectional view of an alternate embodiment of the tri-laminate of FIG. 13A taken along line 13E-13E and is a cross-sectional view of the tri-laminate of FIG. 13B taken along line 13E'-13E'.

FIG. 13F illustrates an alternative embodiment where densified portions of ultrasonic bonds join the first, second, and third substrates together. FIG. 13G illustrates an alternative embodiment where first and second substrates 306 and 308 are ultrasonically bonded together and where an additional inner second substrate 308' is ultrasonically bonded to the third substrate 309 and where the second inner substrates 308 and 308' are bonded together with an adhesive layer such that a quad-laminate is formed.

As shown in FIG. 13E, where the bonds joining the second and third substrates are ultrasonic, the second and third substrates may be joined by a first process step to form a bi-laminate, then the first substrate may be joined to the bi-laminate by a second process step.

As shown in FIG. 13F adhesive may be applied to one of the first substrate 306 to the second substrate 308 and subsequently, the first, second and third substrates are joined by ultrasonic bonds to form a tri-laminate. Alternatively, the first and second substrates 306 and 308 may be joined via a first process step, then the bi-laminate may be joined to the third substrate 309 with ultrasonic bonds that bond all three substrate layers via a second process step.

As shown in FIG. 12G, the first and second substrates may be joined to form a bi-laminate; separately, the additional second substrate 308' may be joined to the third substrate to form a bi-laminate; then the two bi-laminates may be joined together.

While the embodiments of 12A-13G illustrate a plurality of elastic strands disposed between the second and third nonwovens, it should be understood that the plurality of elastic strands may be disposed between the first and second nonwovens or between both the first and second nonwovens and the second and third nonwovens.

Beyond using a tri-laminate, different textures may also be accomplished on a garment-facing and wearer-facing surfaces of a two-layer laminate by using first and second substrates having different bonding arrangements of each of the nonwoven layers, or nonwoven layers having different basis weight arrangements as disclosed in P&G Docket No. 15271P, titled Stretch Laminate with Beamed Elastics and Formed Nonwoven Layer, and filed on Jun. 19, 2018.

It should also be understood that like tri-laminate structures of the prior art comprising traditional elastic strands due to their random, large, uncontrolled rugosities will not have the performance or appearance of the inventive tri-laminate structures because the inventive tri-laminate structures have beamed elastics, which form higher frequency lower amplitude controlled rugosities, disposed between at least the first and second or the second and third substrate layers. Particularly, the beamed elastics enable the inventive tri-laminates of this disclosure to yield the inventive properties disclosed herein (see Table C below), including inventive Percent-Contact-Areas, unique and inventive texture zones and a unique and inventive balance of Application-Force, Sustained-Fit-Load-Force and Sustained-Fit-Unload-Force. Each of the tri-laminates of FIGS. 12A-13G may be used to form the belts of FIGS. 16E-G.

TABLE C

| | Product | Average Filament Count | Average-Strand Spacing | Average-Dtex | Pressure-Under-Strand | WVTR ($g/m^2$/24 hr) | Rugosity Frequency (1/mml) | Rugosity Wavelength (mm) |
|---|---|---|---|---|---|---|---|---|
| Belt | Easy Ups | 55.7 | 8.5 | 940 | 1.578 | 5279 | 0.258 | 3.47 |
| | Merries | 55.4 | 5.2 | 625 | 1.344 | 5021 | 0.210 | 4.77 |
| | Mooney | | 5.3 | 448 | 1.626 | 4568 | 0.210 | 4.72 |
| | Goon | 55.6 | 4.8 | 350 | 1.323 | 4616 | 0.459 | 2.18 |
| | Depends | 42.2 | 6.8 | 459 | 1.987 | 4654 | 0.249 | 4.02 |
| | Always Discreet | 42.8 | 3.6 | 525 | 1.003 | 5234 | 0.524 | 1.27 |
| | Adhesively Bonded Beamed Elastic | 5.0 | 0.3 | 85 | 0.351 | 5212 | 0.616 | 1.62 |
| | Adhesively Bonded Beamed Elastic | 5.0 | 0.5 | 85 | 0.353 | 4684 | 0.721 | 1.39 |
| | Ultrasonically Bonded Beamed Elastic | 5.0 | 0.5 | 85 | 0.385 | 4670 | 0.367 | 2.73 |

| | Product | Contact Area 100 μm | Contact Area 200 μm | Contact Area 300 μm | 2.98% Height (mm) | Distortion (%) | Cantilever Bend (mm) |
|---|---|---|---|---|---|---|---|
| Belt | Easy Ups | 9.2% | 19.1% | 27.3% | 2.657 | 400% | 25.96 |
| | Merries | 7.0% | 15.8% | 24.5% | 3.092 | 367% | 38.06 |
| | Mooney | 6.5% | 16.1% | 24.7% | 2.292 | 300% | 35.27 |
| | Goon | 5.3% | 11.6% | 19.0% | 2.280 | 400% | 29.15 |
| | Depends | 6.2% | 24.9% | 24.4% | 1.841 | na | 36.57 |
| | Always Discreet | 7.3% | 16.2% | 26.9% | 1.629 | na | 25.95 |
| | Adhesively Bonded Beamed Elastic | 17.1% | 43.0% | 67.9% | 0.620 | 0% | 24.67 |
| | Adhesively Bonded Beamed Elastic | 17.1% | 53.0% | 67.9% | 0.624 | 0% | 23.13 |
| | Ultrasonically Bonded Beamed Elastic | 20.6% | 32.7% | 40.8% | 1.286 | na | na |

Adhesively Bonded Laminates of the Present Disclosure

It should be understood that Dtex-to-Spacing-Ratio is not only important for ultrasonically bonded laminates, but is also important for adhesively bonded laminates because the modulus that results from the Dtex-to-Spacing-Ratio is very similar between an ultrasonically bonded elastomeric laminate and an adhesively bonded elastomeric laminate. The adhesively bonded laminate comprising a broad coverage adhesive application will not, however, contract as much as an ultrasonically bonded laminate with equal dtex, spacing, and strain due to the high frequency, low amplitude folds that result in a stack up of nonwoven material that prevents the laminate from contracting fully. The ultrasonically bonded laminate will contract more due to the spaced bonds that result in lower frequency, higher amplitude folds which are less resistant to the contraction forces of the elastics in the laminate. These differences can be leveraged to create specific silhouettes or shapes of the absorbent article, as well as visually distinct textures. For example ultrasonics could be used at the waist or legs so that the openings contract more than the center (which may be adhesively bonded) of the article to aid in gasketing and fit around the waist (e.g., Section 1) and legs (e.g., Section 4), and will also provide for more garment-like textures around the waist and legs.

Chemistry and Structure of Elastomeric Strands of the Present Disclosure

Beamed elastics may be formed from Spandex fibers. One type of Spandex fiber is "PolyUrethane Urea" elastomer or the "high hard segment level PolyUrethane" elastomer, which may be formed into fibers using a solution (solvent) spinning process (as opposed to being processable in the molten state.) The Urea linkages in PolyUrethane Urea provides strong mutual chemical interactions crucial for providing "anchoring" that enables good stress relaxation performance at temperatures near body temperature on timescales corresponding to diaper wear, including overnight. This type of anchoring enables better Force-Relaxation-Over-Time (i.e., little force decay with time when held in stretched condition at body temperature) over many thermoplastic polyurethane (PolyUrethane with hard segment melting below 200 deg. C.) or thermoplastic Styrenic block copolymers. Elastomeric laminates of the present disclosure comprising elastic strands with this chemistry may have a Force-Relaxation-Over-Time from about 5% to about 30%, from about 5% to about 25%, from about 10% to about 25%, or from about 15% to about 20%.

Figure 8:
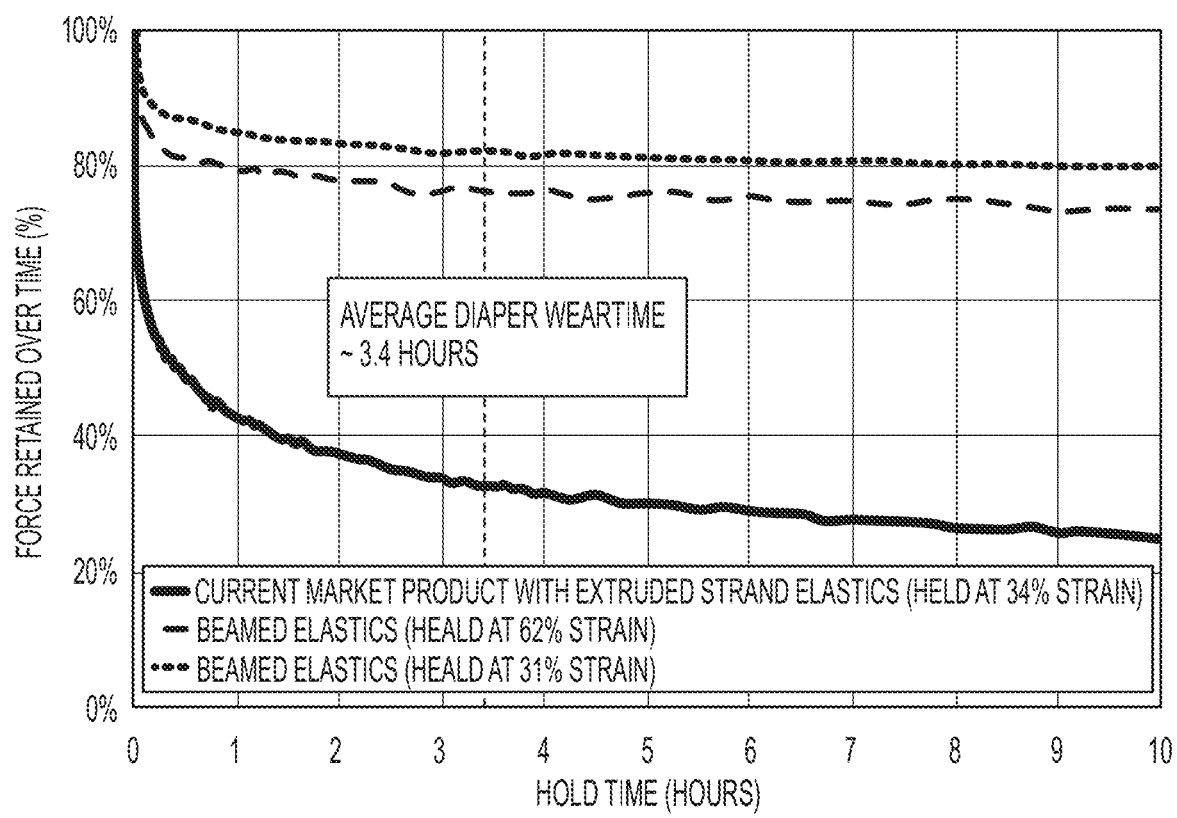
FIG. 8 is a chart showing Force-Relaxation-Over-Time for a laminate comprising extruded strand elastics and for an inventive elastomeric laminate of the present disclosure.

In contrast, extruded strands and scrims are typically made of Styrenic block copolymers or thermoplastic elastomers that can be formed in the molten state by conventional extrusion processes. Thermoplastic elastomers include compositions like polyolefin, polyurethane (PolyUrethane with hard segment melting below 200 deg. C.) elastomers, etc. Because these thermoplastic elastomers like Polyurethane (PolyUrethane with hard segment melting below 200 deg. C.) can be melted/remelted, and extruded it makes them susceptible to higher stress relaxation in use, which is a major negative. The styrenic block copolymers used in extruded strands comprise a comparatively long rubbery midblock situated between comparatively short end blocks. End blocks sufficiently short to enable good flow conventional extrusion processes often have a greater propensity to stress relax and undergo Force-Relaxation-Over-Time see FIG. 8.

The Urea linkage present in Spandex requires it to be made by spinning process. Spandex can't be melted/re-melted or extruded like Styrenic block copolymers. Spandex pre-polymer is combined with solvent and additives, and the solution is spun to make solid spandex fiber. Multiple fibers are then formed together to make one spandex strand. The Spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 40 fibers (or filaments), 30 fibers, 20 fibers, 15 fibers, 8 fibers, 5 fibers, 3 fibers or even as low as 2 fibers. Spandex fiber can be mono-component or bi-component (as disclosed in WO201045637A2).

Further related to the chemistry of beamed elastics, it may be desirable to coat the beamed elastics with an oil, such as a silicone oil or mineral oil, including about 10%, about 7%, about 5%, about 3%, or about 1% silicone oil or mineral oil. Treating the beamed elastics with silicone oil helps to prevent blocking (cross-linking) when the strands are wound to a spool or a beam and it also lowers the COF for the strand in textile machinery (for weaving, knitting and warping processes).

Commercially available Spandex strands may also be known as Lycra, Creora, Roica, or Dorlastan. Spandex is often referred as Elastan fiber or Polyurethane fiber.

LYCRA HYFIT strands, a product of Invista, Wichita, Kans., are a suitable for making the strands that make up the plurality of elastics 316 that make up the elastomeric laminate 302. Some strands, for example, the aforementioned LYCRA HYFIT, may comprise a number of individual fibers wound together to form the strand. With regard to elastic strands formed of a number of individual fibers it has been discovered that the individual fibers can move relative to each other changing the cross-sectional shape of the strand as well as becoming unraveled which can lead to poor control of the strands as well as poor bonding/adhering/joining of the elastic strands to one or both of the first substrate layer 306 and second substrate layer 308 of the elastomeric laminate 302. In order to minimize the negatives with regard to strands comprising a plurality of fibers it would be advantageous to minimize the number of fibers in a given strand. It would therefore be desirable to have less than about 40 fibers per strand, less than about 30 fibers per strand, less than about 20 fibers per strand, less than about 10 fibers per strand, less than about 5 fibers per strand and 1 fiber forming the strand. In the case of a single fiber forming the strand which can deliver comparable performance to the multi-fiber strands of the prior art it would be desirable for the fiber to have a fiber decitex from about 22 to about 300 and a fiber diameter from about 50 micrometers to about 185 micrometers.

Component Sections of the Present Disclosure

Components of absorbent articles comprising elastomeric laminates 302 may be sectioned to enable measurement and detailed characterization of the structure. Waistband 122 (see FIG. 17), waistcap 123 (see FIG. 18), inner leg cuff 150, outer leg cuff 140, and transverse barrier 165 all comprise 1 section. With regard to the waistband 122, waistcap 123, inner leg cuff 150, outer leg cuff 140 and transverse barrier 165 the section is defined as the region disposed between and including the distal most elastic and the proximal most elastic.

Other components such as the chassis 200, topsheet 124 (see FIGS. 16C, 16D, and 16E), backsheet 125 (see FIG. 16D), side panel 330 (see FIG. 17), ear panel 530 (FIG. 18), and belt panel (e.g., front and back belts) 430 (see FIGS. 1A-F, 16C and 16F) all comprise multiple sections as described herein. With regard to the side panel 330, ear panel 530 and belt panel 430 the portion of the component to be sectioned is defined as the region disposed between and including the distal most elastic of the elastomeric laminate 302 and the proximal most elastic of the elastomeric laminate 302 forming the component—except in cases where only a portion of the component is defined to be sectioned, then it is the region disposed between and including the distal most elastic of the defined portion of the elastomeric laminate 302 and the proximal most elastic of the defined portion elastomeric laminate 302 (see alternative back waist region 38' in FIG. 16C, which is a portion of the back belt component). The region is defined by a first line extending parallel to the lateral axis 44 (of the article that the component is part of) and passing through the distal most point of the distal most elastic and a second line extending parallel to the lateral axis and passing through the proximal most point of the proximal most elastic. For each of these elements, the region is then divided into 4 equal sections, defined by three lines disposed parallel to the lateral axis 44 and disposed at 25%, 50% and 75% of the distance between the first line and second line. The region comprises a first section, "1" or "Section 1," which includes the distal most elastic; a fourth section, "4" or "Section 4," which includes the proximal most elastic; a second section, "2" or "Section 2," disposed adjacent to Section 1; and a third section, "3" or "Section 3," disposed between the Sections 2 and 4.

Figure 23A:
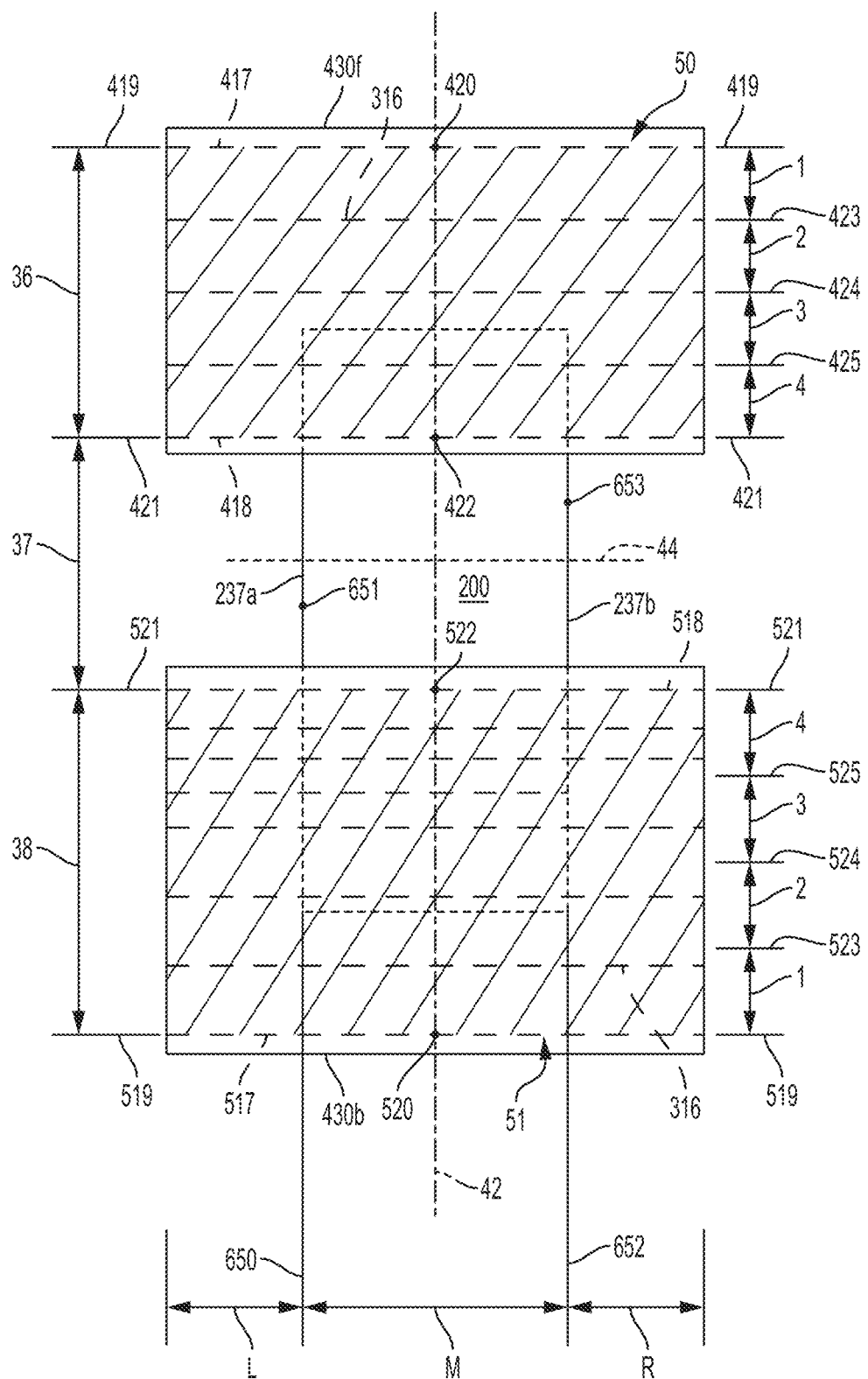
FIG. 23A is a plan view of the pant, prior to joining side edges of the belt to form the waist and leg openings, illustrating front and back component regions 50 and 51.

For example, a front waist region 36 comprising a front belt 430f may be sectioned as follows (see FIGS. 23A-C):

"Wherein the front waist region 36 comprises a front component region 50 disposed between and including a front distal most elastic strand 417 of the front waist region 36 and a proximal most elastic strand 418 of the front waist region 36;

wherein the front component region 50 is defined by a front distal component region line 419 extending parallel to the lateral axis 44 and passing through a distal most point 420 of the front distal most elastic strand 417 and a front proximal component region line 421 extending parallel to the lateral axis 44 and passing through a proximal most point 422 of the front proximal most elastic strand 418;

wherein the front component region 50 is then divided into 4 equal component sections, defined by first, second, and third component section lines 423, 424, and 425, each disposed parallel to the lateral axis 44 and disposed at 25%, 50% and 75% of the distance between the front distal component region line 419 and front proximal component region line 421;

wherein the front component region 50 comprises a first component section, Front Section 1, comprising the front distal most elastic strand 417, a fourth component section, Front Section 4, comprising the front proximal most elastic strand 418, a second component section, Front Section 2, adjacent to Front Section 1, and a third component section, Front Section 3, disposed between Front Sections 2 and 4."

For example, a back waist region 38 comprising a back belt 430f may be sectioned as follows (see FIGS. 23A-C):

"Wherein the back waist region 38 comprises a back component region 51 disposed between and including a back distal most elastic strand 517 of the back waist region 38 and a proximal most elastic strand 518 of the front waist region 38;

wherein the back component region 51 is defined by a back distal component region line 519 extending parallel to the lateral axis 44 and passing through a distal most point 520 of the back distal most elastic strand 517 and a back proximal component region line 521 extending parallel to the lateral axis 44 and passing through a proximal most point 522 of the back proximal most elastic strand 518;

wherein the back component region 51 is then divided into 4 equal component sections, defined by first, second, and third component section lines 523, 524, and 525, each disposed parallel to the lateral axis 44 and disposed at 25%, 50% and 75% of the distance between the back distal component region line 519 and back proximal component region line 521;

wherein the back component region 51 comprises a first component section, Back Section 1, comprising the back distal most elastic strand 517, a fourth component section, Back Section 4, comprising the back proximal most elastic strand 518, a second component section, Back Section 2, adjacent to Back Section 1, and a third component section, Back Section 3, disposed between Front Sections 2 and 4."

Figure 23B:
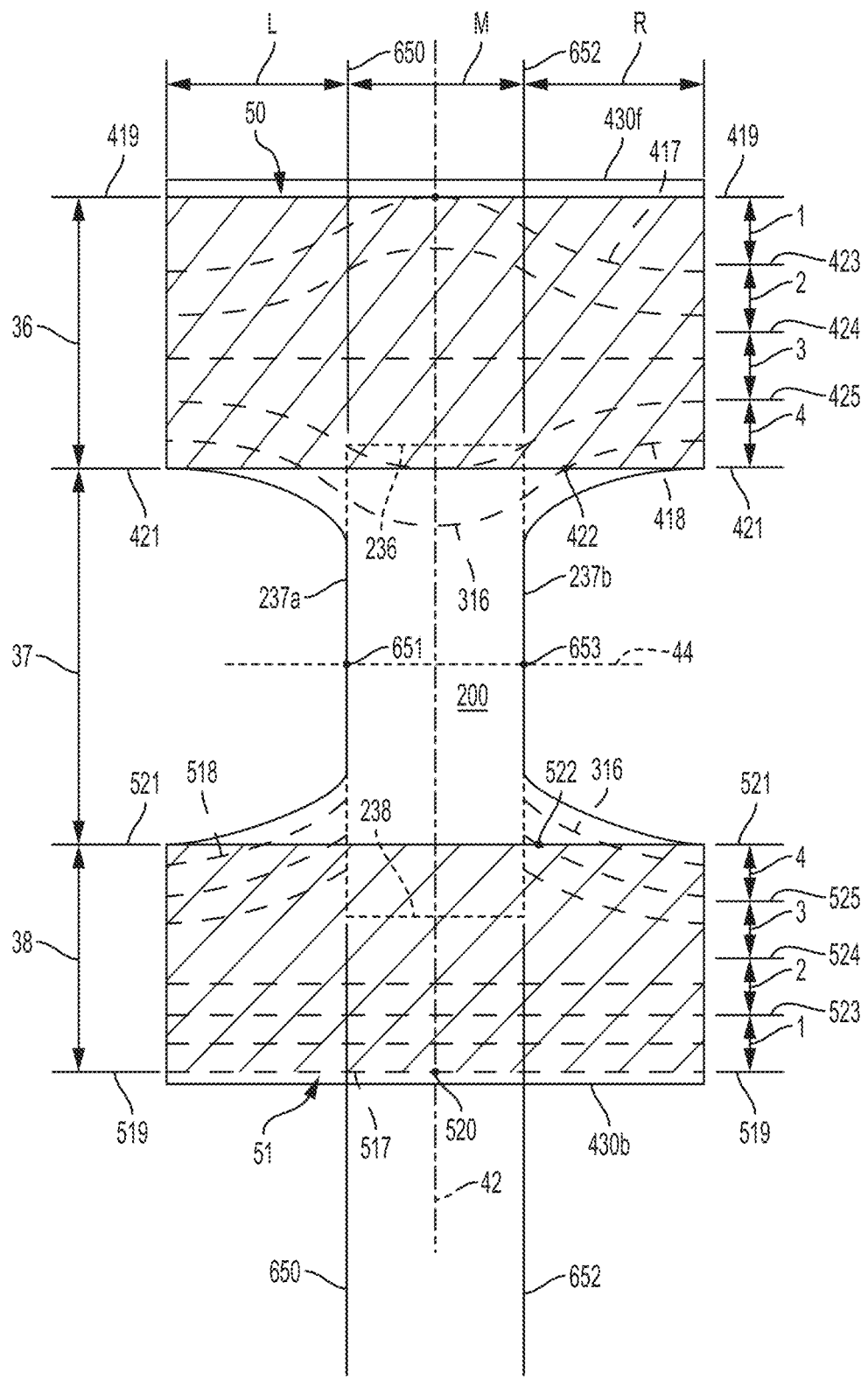
FIG. 23B is a plan view of the pant, prior to joining side edges of the belt to form the waist and leg openings, illustrating front and back component regions 50 and 51.
Figure 23C:
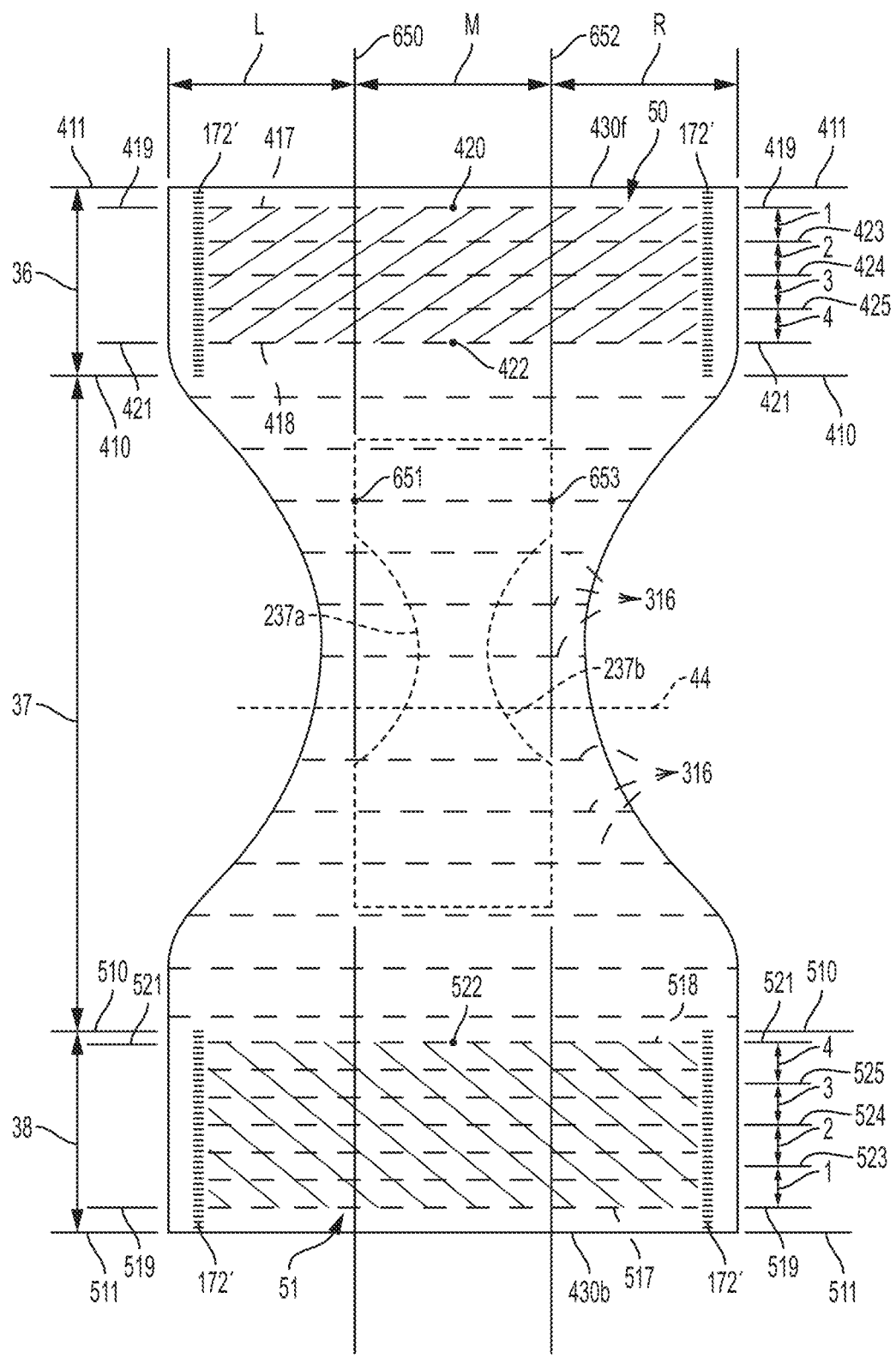
FIG. 23C is a plan view of the pant, prior to joining side edges of the belt to form the waist and leg openings, illustrating front and back component regions 50 and 51.

For embodiments wherein the laterally extending elastic disposed in one or both waist regions comprises and arcuate portion extending longitudinally inward of the proximal most point of the side seam, the proximal most point of the of the proximal most elastic is the point at which the elastic intersects a line extending laterally from the proximal most point of a first side seam to the proximal most point of the laterally opposing side seam as shown in FIG. 23B With regard to the chassis 200, topsheet 124 (see FIGS. 16C, 16D, and 16E), and backsheet 125 (see FIG. 16D) wherein the elastics 316 of the elastomeric laminate 302 extend in a substantially longitudinal orientation, the portion of the component to be sectioned is defined as the region disposed between and including the distal most elastic of the elastomeric laminate 302 on a first side of the longitudinal axis 42 and the distal most elastic of the elastomeric laminate 302 on a second side of the longitudinal axis 42. The region is defined by a first line extending parallel to the longitudinal axis 42 and passing through the distal most point of the distal most elastic on a first side of the longitudinal axis 42 and a second line extending parallel to the longitudinal axis 42 and passing through the distal most point of the distal most elastic on a second side of the longitudinal axis 42. For each of these elements, the region is then divided into 4 equal sections, defined by three lines disposed parallel to the longitudinal axis 42 and disposed at 25%, 50% and 75% of the distance between the first line and second line. The region comprises a first section, "1" or "Section 1," which includes the distal most elastic on the first side of the longitudinal axis; a fourth section, "4" or "Section 4," which includes the distal most elastic on the second side of the longitudinal axis; a second section, "2" or "Section 2," disposed adjacent to Section 1; and a third section, "3" or "Section 3," disposed between Sections 2 and 4.

With regard to the chassis 200, topsheet 124, and backsheet 125 (see FIG. 16E) wherein the elastics 316 of the elastomeric laminate 302 extend in a substantially lateral orientation, the portion of the component to be sectioned is defined as the region disposed between and including the distal most elastic of the elastomeric laminate 302 on a first side of the lateral axis 44 and the distal most elastic of the elastomeric laminate 302 on a second side of the lateral axis 44. The region is defined by a first line extending parallel to the lateral axis 44 and passing through the distal most point of the distal most elastic on a first side of the lateral axis 44 and a second line extending parallel to the lateral axis 44 and passing through the distal most point of the distal most elastic on a second side of the lateral axis 44. For each of these elements, the region is then divided into 4 equal sections, defined by three lines disposed parallel to the lateral axis 44 and disposed at 25%, 50% and 75% of the distance between the first line and second line. The region comprises a first section, "1" or "Section 1," which includes the distal most elastic on the first side of the lateral axis; a fourth section, "4" or "Section 4," which includes the distal most elastic on the second side of the lateral axis; a second section, "2" or "Section 2," disposed adjacent to Section 1; and a third section, "3" or "Section 3," disposed between Sections 2 and 4.

Absorbent Article Sections of the Present Disclosure

Beyond the absorbent article "component sections" described above, the absorbent article itself may be divided into "article sections" (see FIGS. 1A-3F, 16C, 17, 18, and 23A-C). Article sections may be used to enable characterization of the structure of article components that overlap the chassis and that extend laterally beyond the chassis. Particularly, a middle section "M" or "Section M" of the article region is defined by a left article region line 650 extending parallel to the longitudinal axis 42 and passing through a left laterally distal most point 651 of a left side edge 237a of the chassis 200 and by a right article region line 652 extending parallel to the longitudinal axis 42 and passing through a right laterally distal most point 653 of a right side edge 237b (laterally opposed from the left side edge 237a) of the chassis 200. Everything to one lateral side or the other of the M article section are the left article section "L" or "Section L" and laterally opposed right article section "R" or "Section R." Sections L and R can be more particularly referred to by referencing whether Sections L, R, or M are in the front, back, or crotch regions 33, 38, and 37, and, as appropriate, which article section it overlaps with. For instance, with regard to a belt 430, it may be referred to as having a Section 1 (adjacent a waist opening 190) in Section L of the front waist region 36. As another example, a portion of the belt 430 may be referenced that is longitudinally beyond the chassis 200 in the Section M in the back waist region 38.

Beamed Elastomeric Laminate Examples of the Present Disclosure

Consumer interactions and research has shown that a longstanding unmet consumer need exists to provide absorbent articles comprising textile garment-like textures, while maintaining the right balance of force and modulus for application and removal ease and freedom of movement while providing an article with the right balance of sustained fit forces and low elastic pressure on skin (relative to today's stranded products) in order to provide a comfortable wearing experience free from skin marks. Elastomeric laminate structures having a Section-Modulus of between about 2 gf/mm and 15 gf/mm or between 3 gf/mm and 12 gf/mm or between 4 gf/mm and 10 gf/mm are most desirable for ease of application, ease of removal, conforming fit and freedom of movement. Combining Section-Modulus with Application-Force, Sustained-Fit-Unload-Force and Sustained-Fit-Load-Force wherein the Application-Force is less than about 1,600 gf, a Sustained-Fit-Load-Force of greater than 30% of the Application-Force and a Sustained-Fit-Unload-Force of greater than 25% of the Application-Force helps ensure ease of use, and superior sustained fit and gasketing. Absorbent articles of the present disclosure may also comprise a beamed elastic laminate having an Application-Force of greater than about 1,500 gf, a Sustained-Fit-Load-Force of greater than 30% of the Application-Force and a Sustained-Fit-Unload-Force of greater than 30% of the Application-Force. Traditional elastic material configurations may exhibit very high pressures under each elastic element, e.g., elastic strands, leading to increased skin marking and reduced comfort. One approach to reduce the pressure of the elastic on the skin is to increase the number of elastics for a given area, e.g., beamed elastics. Increasing the number of elastics within a given area alone may reduce the pressure under each elastic, however, if that is the only change it can also significantly increase the overall modulus of the elastomeric laminate structure. In order to achieve the right balance of modulus and pressure on the skin it is necessary to reduce the elastic decitex and/or the elastic strain as the spacing between the elastics is reduced thereby increasing the elastic number in order to balance the modulus and pressure on the skin and maintain these parameters within the consumer preferred range. In order to deliver the desired Section-Modulus a unique balance of elastic decitex, elastics with a decitex of less than 400, and strand spacing, when the spacing is less than 4 mm, is desirable.

The relationship between decitex and spacing to achieve the desired results can be characterized as a ratio. The Dtex-to-Spacing-Ratio may be greater than 60:1 and less than 300:1, greater than 60:1 and less than 250:1, greater than 65:1 and less than 215:1, or greater than 60:1 and less than 150:1. The ratio may also be greater than 80:1 and less than 300:1, greater than 80:1 and less than 250:1, or greater than 65:1 and less than 300:1. This breakthrough has been enabled through delivery of very low decitex elastic at very low strain levels and with very tight elastic spacing that have never before been seen in disposable absorbent articles. Delivery of such low decitex elastic at low strain and tight spacing is enabled via a new to absorbent article technology created from the textile warp beam technology approach. The examples below illustrate such elastomeric structures.

The elastomeric laminate forming part of the absorbent article may comprise two or more nonwoven layers with elastic material disposed between wherein a first portion of the elastic material is joined to the nonwoven layers by one or more of adhesive bonding, pressure bonding, thermal bonding or ultrasonic bonding.

The elastomeric laminate forming part of the absorbent article may comprise two or more nonwoven layers with elastic material disposed between at least two of the nonwoven layers where the elastic material is joined to one or both of the nonwoven layers by one or more of adhesive bonding, pressure bonding, thermal bonding or ultrasonic bonding. An elastomeric laminate having a first texture region that may be formed in part by adhesive bonding, pressure bonding, thermal bonding or ultrasonic bonding disposed in an arcuate pattern/shape. Alternatively the first texture region may be formed in part by adhesive bonding, pressure bonding, thermal bonding or ultrasonic bonding and disposed in a vertical (longitudinal) linear orientation. Alternatively, a first region may be formed in part by adhesive bonding, pressure bonding, thermal bonding or ultrasonic bonding and disposed in an array of closed shapes and in certain embodiments the adhesive bonding, pressure bonding, thermal bonding or ultrasonic bonding may be disposed angularly relative to one or both of the longitudinal or lateral centerlines. Alternatively, the elastomeric laminate may comprise an inner belt layer and an outer belt layer formed by two separate nonwoven layers bonded to each other via adhesive bonding, pressure bonding, thermal bonding or ultrasonic bonding with elastics disposed between the inner belt layer and the dual layer outer belt layer. It should be understood that one or both of the nonwoven materials forming the elastomeric laminate may comprise a plurality of apertures, disposed randomly or in a defined pattern, extending through one or both of the nonwoven layers.

Example 1: Pant with Ultrasonically Bonded Belts

| Pant Details: | |
|---|---|
| Overall Product Length | 450 mm |
| Seam to Seam Belt Pitch | 355 mm |
| Center Chassis Length | 403 mm |
| Laminate Details: | |
| Average-Bond-Width (Ultrasonic) | 0.5 mm |
| Average-Lateral-Bond-Spacing (Ultrasonic) | 4.5 mm |
| Average-Bond-Length (Ultrasonic) | 150 mm |
| Average-Dtex | 140 |
| Average-Strand-Spacing | 1.5 mm |
| Average-Pre-Strain | 180% |
| Outer Belt NW Basis-Weight | 20 gsm |
| Outer Belt NW Type | Carded |
| Inner Belt NW Basis-Weight | 20 gsm |
| Inner Belt NW Type | Carded |

Example 2: Pant with Ultrasonically Bonded Belts

| Pant Details: | |
|---|---|
| Overall Product Length | 450 mm |
| Seam to Seam Belt Pitch | 355 mm |
| Center Chassis Length | 403 mm |
| Laminate Details: | |
| Average- Bond-Width (Ultrasonic) | 0.7 mm |
| Average-Lateral-Bond-Spacing (Ultrasonic) | 4.0 mm |
| Average-Bond-Length (Ultrasonic) | 150 mm |
| Average-Dtex | 45 |
| Average-Strand-Spacing | 0.5 mm |
| Average-Pre-Strain | 150% |
| Outer Belt NW Basis-Weight | 15 gsm |
| Outer Belt NW Type | Spunbond |
| Inner Belt NW Basis-Weight | 15 gsm |
| Inner Belt NW Type | Spunbond |

Example 3: Pant with Adhesively Bonded Belts

| Pant Details: | |
|---|---|
| Overall Product Length | 450 mm |
| Seam to Seam Belt Pitch | 355 mm |
| Center Chassis Length | 403 mm |
| Laminate Details: | |
| Adhesive Application | Slot |
| Adhesive Basis-Weight | 8 gsm |
| Average-Dtex | 210 |
| Average-Strand-Spacing | 2.5 mm |
| Average-Pre-Strain | 150% |
| Outer Belt NW Basis-Weight | 13 gsm |
| Outer Belt NW Type | Spunbond |
| Inner Belt NW Basis-Weight | 13 gsm |
| Inner Belt NW Type | Spunbond |

Example 4: Tri-Laminate Belt Providing Smooth Texture Inside and Lofty Texture Outside

| Pant Details: | |
|---|---|
| Overall Product Length | 450 mm |
| Seam to Seam Belt Pitch | 355 mm |
| Center Chassis Length | 403 mm |
| Laminate Details: | |
| Outer Belt NW Basis-Weight | 13 gsm |
| Outer Belt NW Type | Spunbond |
| Intermediate Belt NW Basis-Weight | 8 gsm |
| Intermediate Belt NW Type | Spunbond |
| Ultrasonic Bonding of Outer NW to Intermediate NW | |
| Average-Lateral-Bond-Spacing (Ultrasonic) | 10 mm |
| Average-Bond-Length (Ultrasonic) | Variable (non-uniform) |
| Average-Bond-Width (Ultrasonic) | 1 mm |
| Inner Belt NW Basis-Weight | 13 gsm |
| Inner Belt NW Type | Spunbond |
| Adhesive Bonding of Inner NW to Intermediate NW and Elastic | |
| Adhesive Application | Slot |
| Adhesive Basis-Weight | 8 gsm |
| Average-Dtex | 78 |
| Average-Spacing | 1 mm |
| Average-Pre-Strain | 150% |

Example 5: Belt Having Multiple Texture Zones

| Pant Details: | |
|---|---|
| Overall Product Length | 450 mm |
| Seam to Seam Belt Pitch | 355 mm |
| Center Chassis Length | 403 mm |
| Laminate Details: | |
| Outer Belt NW Basis-Weight | 20 gsm |
| Outer Belt NW Type | Spunbond |
| Inner Belt NW Basis-Weight | 15 gsm |
| Inner Belt NW Type | Spunbond |
| 1$^{st}$ Belt Section: Ultrasonic Bonding of Outer Belt NW to Inner Belt NW and Elastic | |
| Average-Lateral-Bond-Spacing (Ultrasonic) | 4 mm |
| Average-Bond-Length (Ultrasonic) | Variable |
| Average-Bond-Width (Ultrasonic) | 0.75 mm |
| Average-Dtex | 78 |
| Average-Strand-Spacing | 1 mm |
| Average-Pre-Strain | 150% |
| 2$^{nd}$ and 3$^{rd}$ Belt Sections: Adhesive Bonding of Outer Belt NW to Inner Belt NW and Elastic | |
| Adhesive Application | Slot |
| Adhesive Basis-Weight | 8 gsm |
| Average-Dtex | 78 |
| Average-Strand-Spacing | 1 mm |
| Average-Pre-Strain | 150% |
| 4$^{th}$ Belt Section: Ultrasonic Bonding of Outer Belt NW to Inner Belt NW and Elastic | |
| Average-Lateral-Bond-Spacing (Ultrasonic) | 4 mm |
| Average-Bond-Length (Ultrasonic) | Variable |
| Average-Bond-Width (Ultrasonic) | 0.75 mm |
| Average-Dtex | 78 |
| Average-Strand-Spacing | 1 mm |
| Average-Pre-Strain | 150% |

Example 6 (Hypothetical): Belt Having Multiple Texture Zones

| Pant Details: | |
|---|---|
| Overall Product Length | 450 mm |
| Seam to Seam Belt Pitch | 355 mm |
| Center Chassis Length | 403 mm |

| Laminate Details: | |
|---|---|
| Outer Belt NW Basis-Weight | 20 gsm |
| Outer Belt NW Type | Spunbond |
| Inner Belt NW Basis-Weight | 15 gsm |
| Inner Belt NW Type | Spunbond |

1$^{st}$ Belt Section (Front and Back Belt): Ultrasonic Bonding of Outer and Inner Belt NWs and Elastic

| | |
|---|---|
| Average-Lateral-Bond-Spacing (Ultrasonic) | 4 mm |
| Average-Bond-Length (Ultrasonic) | Variable (non-uniform) |
| Average-Bond-Width (Ultrasonic) | 0.75 mm |
| Average-Bond-Disposition (Ultrasonic) | Angular (between 5 and 80 degrees relative to longitudinal axis) |
| Average-Dtex | 78 |
| Average-Strand-Spacing | 0.75 mm |
| Average-Pre-Strain | 150% |

2$^{nd}$ and 3$^{rd}$ Belt Section in Sections L and R (Front and Back Belt): Ultrasonic Bonding of Outer Belt NW to Inner Belt NW and Elastic

| | |
|---|---|
| Average-Lateral-Bond-Spacing (Ultrasonic) | Variable |
| Average-Bond-Length (Ultrasonic) | Variable |
| Average-Bond-Width (Ultrasonic) | 0.75 mm |
| Average-Bond-Disposition (Ultrasonic) | Closed Shape s |
| Average-Dtex | 78 |
| Average-Strand-Spacing | 0.75 mm |
| Average-Pre-Strain | 150% |

2$^{nd}$ and 3$^{rd}$ Belt Section in Section M (Front and Back): Ultrasonic Bonding of Outer Belt NW to Inner Belt NW and Elastic

| | |
|---|---|
| Average-Lateral-Bond-Spacing (Ultrasonic) | 3 mm |
| Average-Bond-Length (Ultrasonic) | 180 mm |
| Average-Bond-Width (Ultrasonic) | 0.5 mm |
| Average-Bond-Disposition (Ultrasonic) | Laterally Extending (Herring bone) |
| Average-Dtex | 78 |
| Average-Strand-Spacing | 0.75 mm |
| Average-Pre-Strain | 150% |

4$^{th}$ Belt Section Front: Ultrasonic Bonding of Outer Belt NW to Inner Belt NW and Elastic

| | |
|---|---|
| Average-Lateral-Bond-Spacing (Ultrasonic) | 4 mm |
| Average-Bond-Length (Ultrasonic) | 25 mm |
| Average-Bond-Width (Ultrasonic) | 0.75 mm |
| Average-Bond-Disposition (Ultrasonic) | Longitudinally Extending |
| Average-Dtex | 78 |
| Average-Strand-Spacing | 0.75 mm |
| Average-Pre-Strain | 150% |

4$^{th}$ Belt Section Back: Adhesive Bonding of Outer Belt NW to Inner Belt NW and Elastic

| | |
|---|---|
| Adhesive Application | Continuous Slot |
| Adhesive Basis-Weight | 8 gsm |
| Average-Dtex | 640 |
| Average-Strand-Spacing | 3 mm |
| Average-Pre-Strain | 180% |

Example 7 (Hypothetical): Belt Having Multiple Texture Zones

| Pant Details: | |
|---|---|
| Overall Product Length | 450 mm |
| Seam to Seam Belt Pitch | 355 mm |
| Center Chassis Length | 403 mm |
| Laminate Details: | |
| Outer Belt NW Basis-Weight | 22 gsm |
| Outer Belt NW Type | Spunbond |
| Inner Belt NW Basis-Weight | 13 gsm |
| Inner Belt NW Type | Spunbond |
| 1st Belt Section (Front and Back Belt): Ultrasonic Bonding of Outer Belt NW to Inner Belt NW and Elastic | |
| Average-Lateral-Bond-Spacing (Ultrasonic) | 4 mm |
| Average-Bond-Length (Ultrasonic) | Variable (non-uniform) |
| Average-Bond-Width (Ultrasonic) | 0.75 mm |
| Average-Bond-Disposition (Ultrasonic) | Angular (between 5 and 80 degrees relative to longitudinal axis) |
| Average-Dtex | 78 |
| Average-Strand-Spacing | 0.75 mm |
| Average-Pre-Strain | 150% |
| 2nd and 3rd Belt Section in Sections L and R (Front and Back Belt): Ultrasonic Bonding of Outer Belt NW to Inner Belt NW and Elastic | |
| Average-Lateral-Bond-Spacing (Ultrasonic) | Variable |
| Average-Bond-Length (Ultrasonic) | Variable |
| Average-Bond-Width (Ultrasonic) | 0.75 mm |
| Average-Bond-Disposition (Ultrasonic) | Arcuate |
| Average-Dtex | 78 |
| Average-Strand-Spacing | 0.75 mm |
| Average-Pre-Strain | 150% |
| 2nd and 3rd Belt Section in Section M (Front and Back): Ultrasonic Bonding of Outer Belt NW to Inner Belt NW and Elastic | |
| Average-Lateral-Bond-Spacing (Ultrasonic) | 3 mm |
| Average-Bond-Length (Ultrasonic) | 180 mm |
| Average-Bond-Width (Ultrasonic) | 0.5 mm |
| Average-Bond-Disposition (Ultrasonic) | Laterally Extending (Herring bone) |
| Average-Dtex | 78 |
| Average-Strand-Spacing | 0.75 mm |
| Average-Pre-Strain | 150% |
| 4th Belt Section Front: Ultrasonic Bonding of Outer Belt NW to Inner Belt NW and Elastic | |
| Average-Lateral-Bond-Spacing (Ultrasonic) | 4 mm |
| Average-Bond-Length (Ultrasonic) | 25 mm |
| Average-Bond-Width (Ultrasonic) | 0.75 mm |
| Average-Bond-Disposition (Ultrasonic) | Longitudinally Ex tending |
| Average-Dtex | 78 |
| Average-Strand-Spacing | 0.75 mm |
| Average-Pre-Strain | 150% |
| 4th Belt Section Back: Adhesive Bonding of Outer Belt NW to Inner Belt NW and Elastic | |
| Adhesive Application Continuous Slot | |
| Adhesive Basis-Weight | 8 gsm |
| Average-Dtex | 640 |
| Average-Strand-Spacing | 3 mm |
| Average-Pre-Strain | 180% |

Example 8: Belt Having Multiple Texture Zones (Inner Smooth Texture and Outer Lofty Texture)

| Pant Details: | |
|---|---|
| Overall Product Length | 450 mm |
| Seam to Seam Belt Pitch | 355 mm |
| Center Chassis Length | 403 mm |
| Laminate Details: | |
| Outer Belt NW Basis-Weight | 13 gsm |
| Outer Belt NW Type | Bico |
| Intermediate Belt NW Layer Basis-Weight | 8 gsm |
| Intermediate Belt NW Type | Spunbond |
| Inner Belt NW Basis-Weight | 13 gsm |
| Inner Belt NW Type | Spunbond |
| Ultrasonic Bonding of Outer Belt NW to Intermediate Belt NW | |
| Average-Lateral-Bond-Spacing (Ultrasonic) | Variable |
| Average-Bond-Length (Ultrasonic) | Variable |
| Average-Bond-Width (Ultrasonic) | 0.7 mm |
| Adhesive Bonding of intermediate Belt NW to Inner Belt NW and Elastic | |
| Adhesive Application Continuous | Slot |
| Adhesive Basis-Weight | 8 gsm |

| | |
|---|---|
| Average-Dtex | 78 |
| Average-Strand-Spacing | 0.75 mm |
| Average-Pre-Strain | 120% |

Inventive examples 1-8 above will have one or more of the following properties:
  a) A Peel-Strength between the first and second nonwovens from about 1 N/cm to about 10 N/cm or upto and including substrate failure;
  b) A Dtex-to-Spacing-Ratio from about 65:1 to about 200:1;
  c) A Pressure-Under-Strand of from about 0.1 to about 1.2 psi;
  d) An Application-Force of from about 900 gf to about 1600 gf;
  e) A Sustained-Fit-Load-Force greater than about 30% of the Application-Force;
  f) A Sustained-Fit-Unload-Force greater than about 25% of the Application-Force;
  g) A Section-Modulus of from about 3 gf/mm to about 12 gf/mm;
  h) A Cantilever-Bending of less than about 40 mm;
  i) A Percent-Contact-Area of one or both surfaces of the laminate of at least one of: 1) greater than about 10% at 100 um, 2) greater than about 20% at 200 um, and 3) greater than about 30% at 300 um; and
  j) A Force-Relaxation-Over-Time of the elastomeric laminate from about 5% to about 40%.

Absorbent Articles of the Present Disclosure

Products comprising elastomeric laminates of the present disclosure may comprise absorbent articles 100 of differing structure and/or form that are generally designed and configured to manage bodily exudates such as urine, menses, and/or feces, such as disposable taped and pants, including baby and adult disposable absorbent articles.

As shown in the figures, the absorbent articles 100 of the present disclosure may comprise a chassis 200 comprising a topsheet 124, a backsheet 125, and an absorbent core 128 disposed at least partially between the topsheet 124 and the backsheet 125. The chassis 200 may further comprise an inner leg cuff 150 and an outer leg cuff 140 (the cuffs generally referred to as 52).

One end portion of an absorbent article 100 may be configured as a front waist region 36 and the longitudinally opposing end portion may be configured as a back waist region 38. An intermediate portion of the absorbent article 100 extending longitudinally between the front waist region 36 and the back waist region 38 may be configured as a crotch region 37. The length of each of the front waist region 36, the back waist region 38 and the crotch region 37 may be about ⅓ of the length of the absorbent article 100, for example (see, for example, FIG. 18). Alternatively, the length of each of the front waist region 36, the back waist region 38, and the crotch region 37 may have other dimensions (e.g., defined by the longitudinal dimension of the belt immediately adjacent the side seam or the longitudinal dimension of the ear panel/side panel immediately adjacent the center chassis—see, for example, FIGS. 16C and 17; or in the case where an article has a continuous component such as the pant in FIGS. 16G and 23C, the side seam 172 (or where the side seam will be or was 172') may define the boundaries between the front and back waist regions and the crotch region (see the alternative component sections 1 '-4' and alternative front and back waist regions 36' and 38' and crotch region 37' in FIG. 16C, where the back belt is longitudinally longer than the front belt).

When the side seams are used to define the front and back waist regions and crotch region, such may be described as follows:

"The front waist region 36 is a region between a) a proximal most front axis 410 extending parallel to the lateral axis 44 and passing through proximal most points of the laterally opposed front side seams 172 or 172'; and b) a distal most front axis 411 extending parallel to the lateral axis and passing through distal most points of the laterally opposed front side seams 172 or 172'; and the back waist region 38 is a region between a) a proximal most back axis 510 extending parallel to the lateral axis 44 and passing through proximal most points of the laterally opposed back side seams 172 or 172'; and b) a distal most back axis 511 extending parallel to the lateral axis and passing through distal most distal points of the laterally opposed back side seams 172 or 172'."

The absorbent article 100 may have a laterally extending front waist end edge 136 in the front waist region 36 and a longitudinally opposing and laterally extending back waist end edge 138 in the back waist region 38.

The chassis 200 of the absorbent article 100 may comprise a first longitudinally extending side edge 237a and a laterally opposing and second longitudinally extending side edge 237b. Both of the side edges 237 may extend longitudinally between the front waist end edge 136 and the back waist end edge 138. The chassis 200 may form a portion of the laterally extending front waist end edge 136 in the front waist region 36 and a portion of the longitudinally opposing and laterally extending back waist end edge 138 in the back waist region 38. Furthermore, the chassis 200 may comprise a chassis interior surface 202 (forming at least a portion of the wearer-facing surface 4), a chassis exterior surface 204 (forming at least a portion of the garment-facing surface 2), a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 237a and through a midpoint of the second side edge 237b.

Figure 16C:
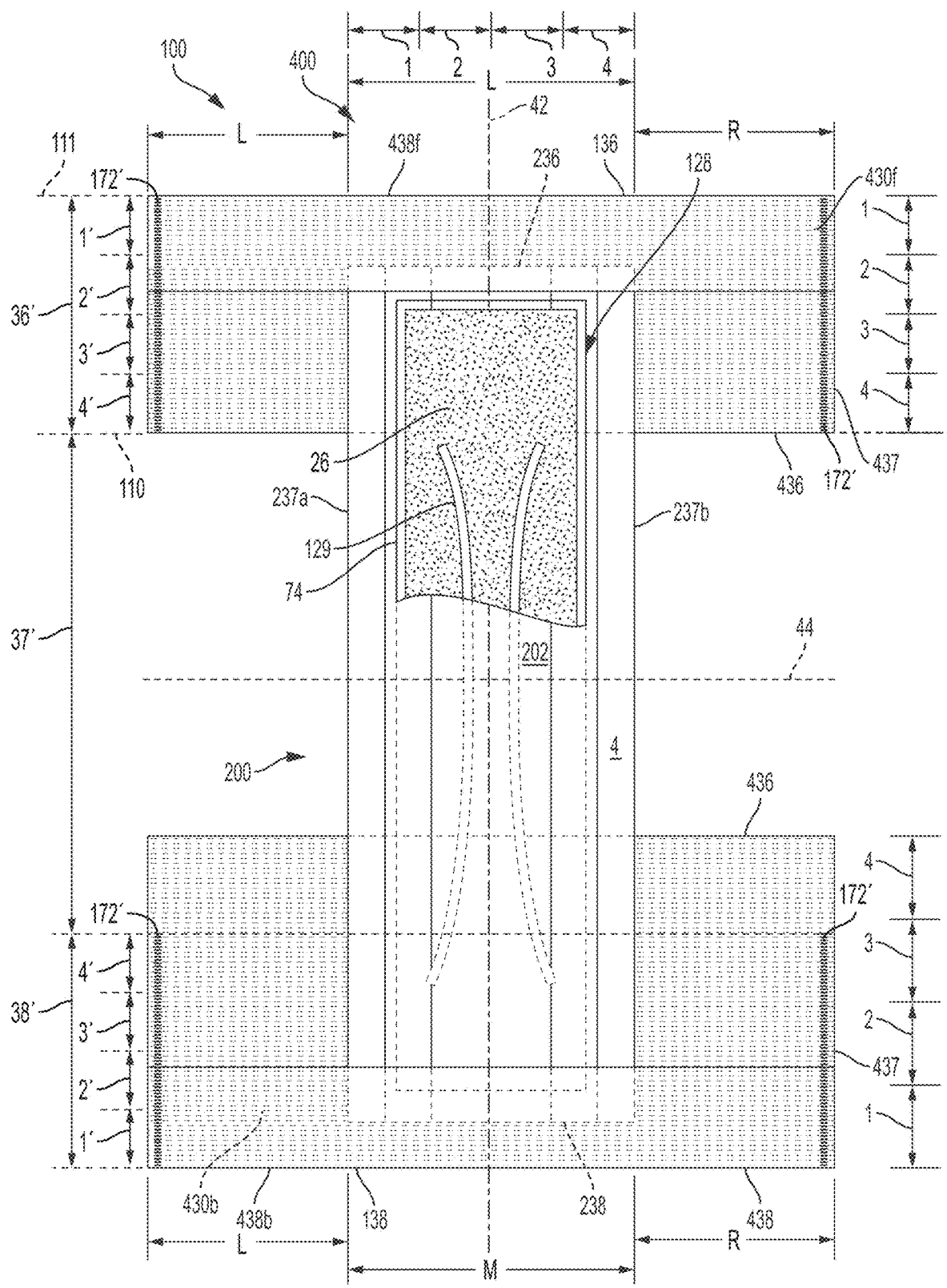
FIG. 16C is a plan view of the pant of FIG. 16A, prior to joining side edges of the belt to form the waist and leg openings.

Referring to FIG. 16C, often true for belted absorbent articles, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38.

Figure 16D:
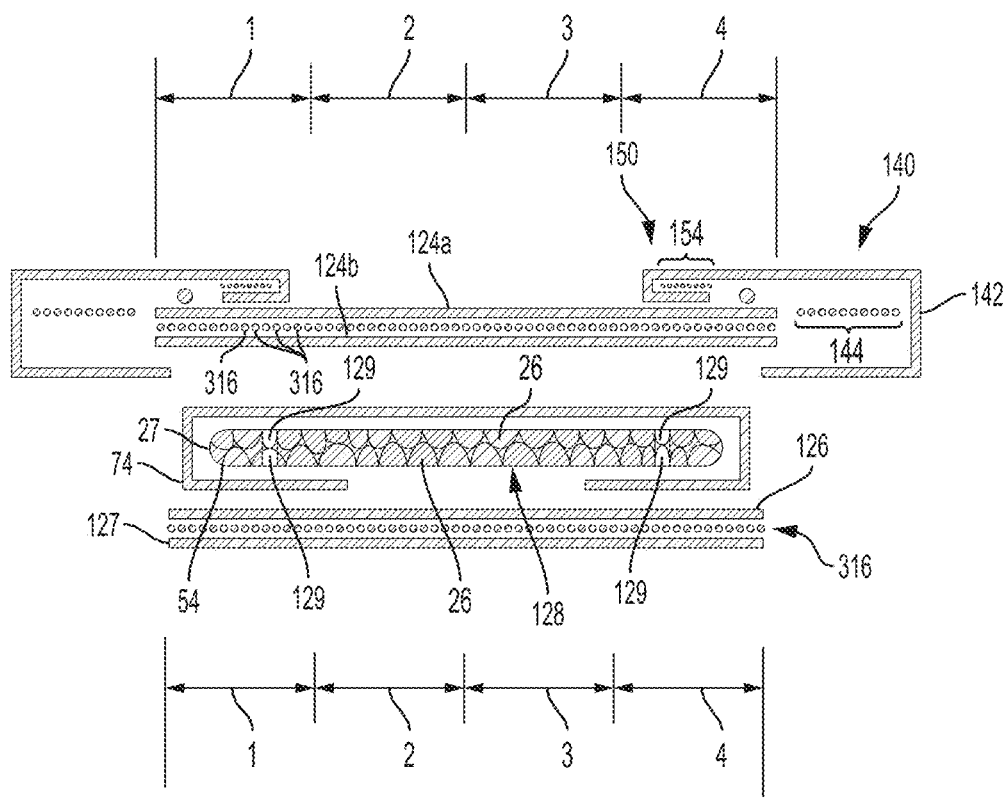
FIG. 16D is a cross-section view of the pant of FIG. 16C taken along the transverse axis, illustrating the elasticized topsheet (showing elastics 316 oriented parallel to the longitudinal axis 42) and the elasticized backsheet (showing elastics 316 oriented parallel to the longitudinal axis 42).
Figure 16E:
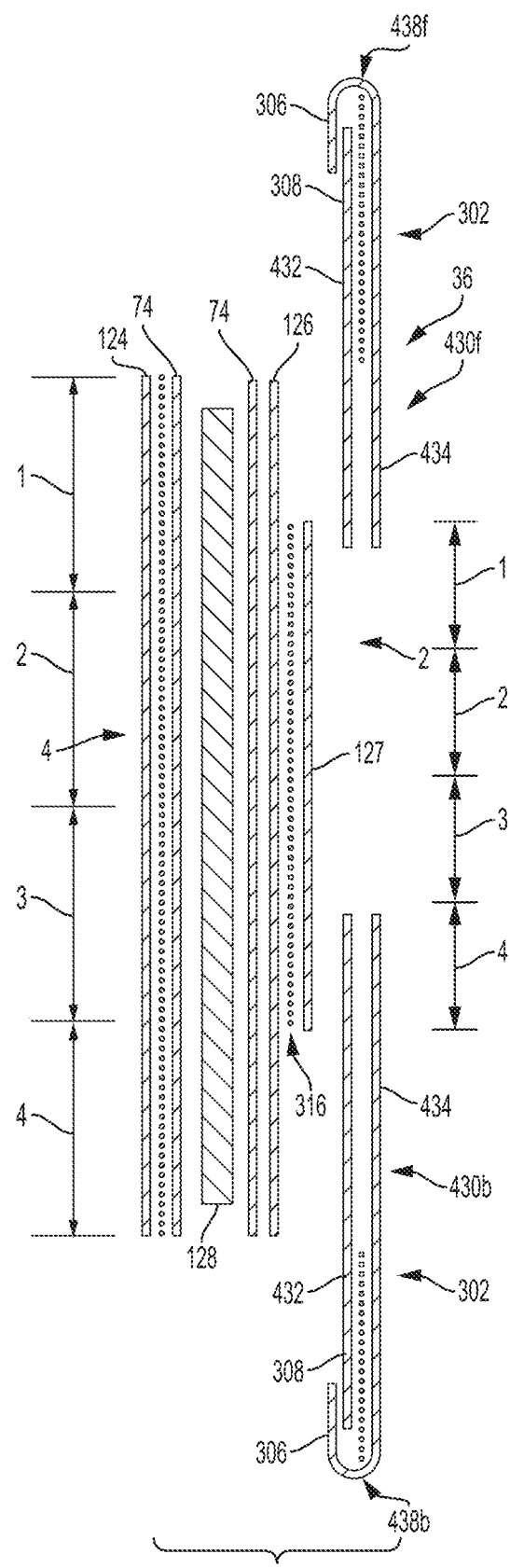
FIG. 16E is a cross-section view of an alternate embodiment of the pant of FIG. 16C taken along the longitudinal axis 42, showing longitudinally opposing discrete belts, wherein elastics 316 are oriented parallel to the lateral axis 44 between the core wrap 74 and the topsheet 124 and oriented parallel to the lateral axis 44 between the backsheet film 126 and the backsheet nonwoven 127.

Referring to FIG. 16D, the chassis 200 may comprise elastics 316 oriented parallel to the longitudinal axis 42 between the backsheet nonwoven 127 and backsheet film 126. Alternatively, the chassis 200 may have elastics 316 oriented parallel to the longitudinal axis 42 between the core wrap 74 and the backsheet 125. Still further, in FIG. 16E the chassis 200 comprises elastics 316 oriented parallel with the lateral axis 44 between the backsheet film 126 and the backsheet nonwoven 127. FIG. 16D also shows elastics 316 oriented parallel with the longitudinal axis 42 between a first topsheet layer 124a and a second topsheet layer 124b. Still further, FIG. 16E shows elastics 316 oriented parallel with the lateral axis 44 between the topsheet 124 and the core wrap 74.

A portion or the entirety of the absorbent article 100 may be made to be laterally elastically extensible. The extensibility of the absorbent article 100 may be desirable in order to allow the absorbent article 100 to conform to a body of a wearer during movement by the wearer. The extensibility may also be desirable, for example, in order to allow the caregiver to extend the front waist region 36, the back waist region 38, the crotch region 37, and/or the chassis 200 to provide additional body coverage for wearers of differing size, i.e., to tailor the fit of the absorbent article 100 to the individual wearer and to aide in ease of application. Such extension may provide the absorbent article 100 with a generally hourglass shape, so long as the crotch region 37 is extended to a relatively lesser degree than the waist regions 36 and/or 38. This extension may also impart a tailored appearance to the absorbent article 100 during use.

Figure 17:
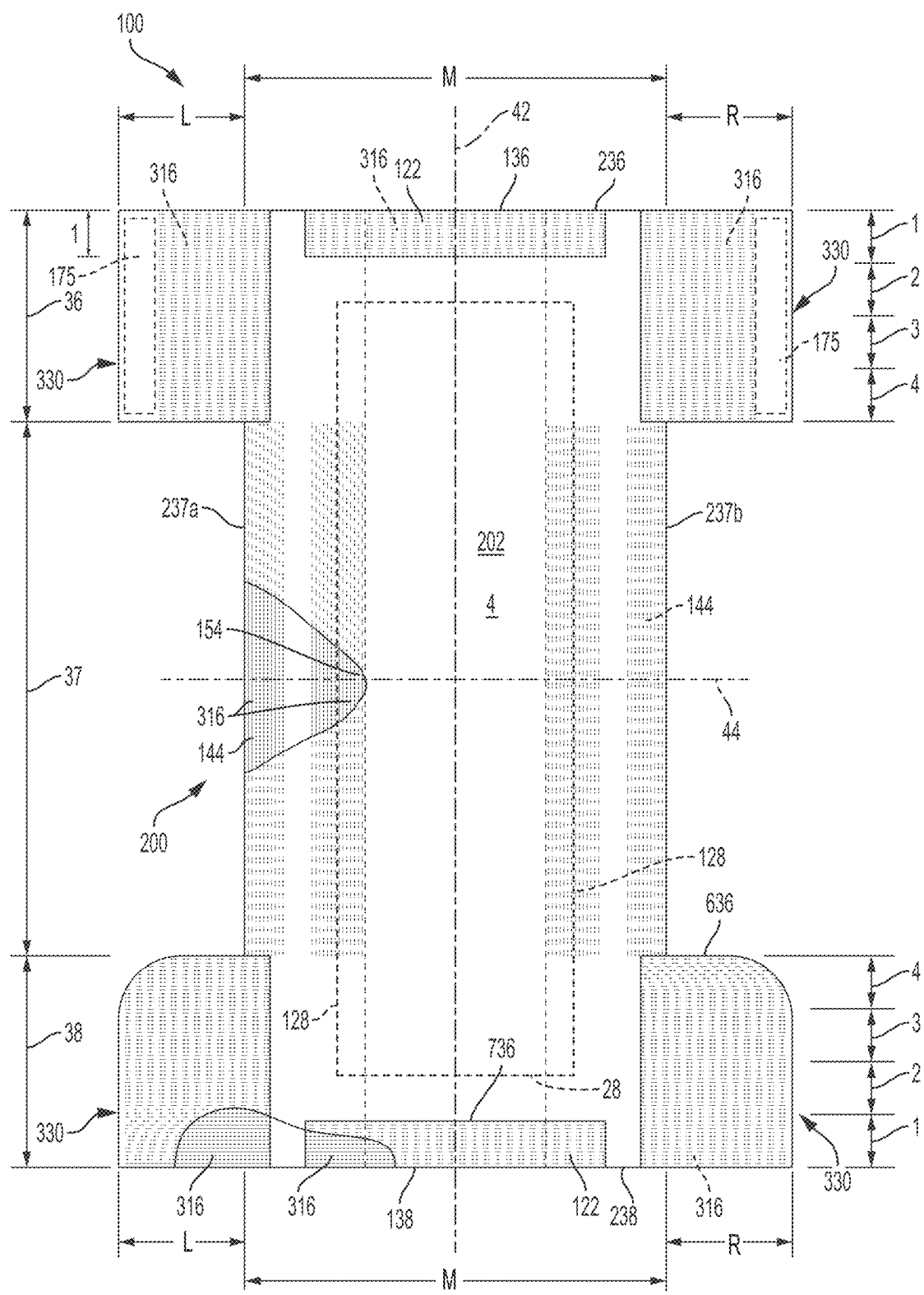
FIG. 17 is a plan view of a pant prior to joining the side panels to form the waist and leg openings.
Figure 18:
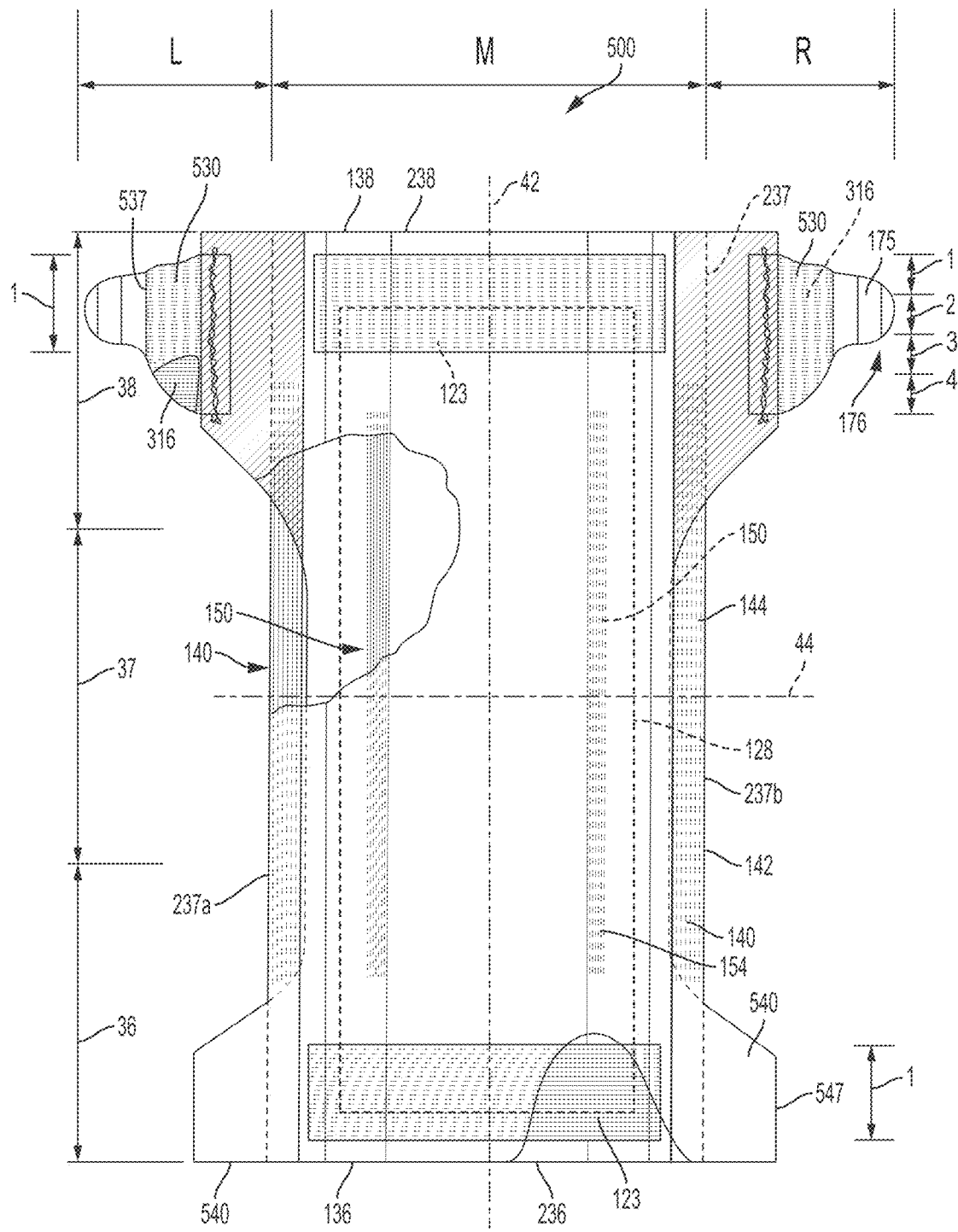
FIG. 18 is a plan view of a taped diaper comprising a pair of shaped discrete elastomeric ear panels 530 and a pair of non-elastomeric ear panels 540.
Figure 19A:
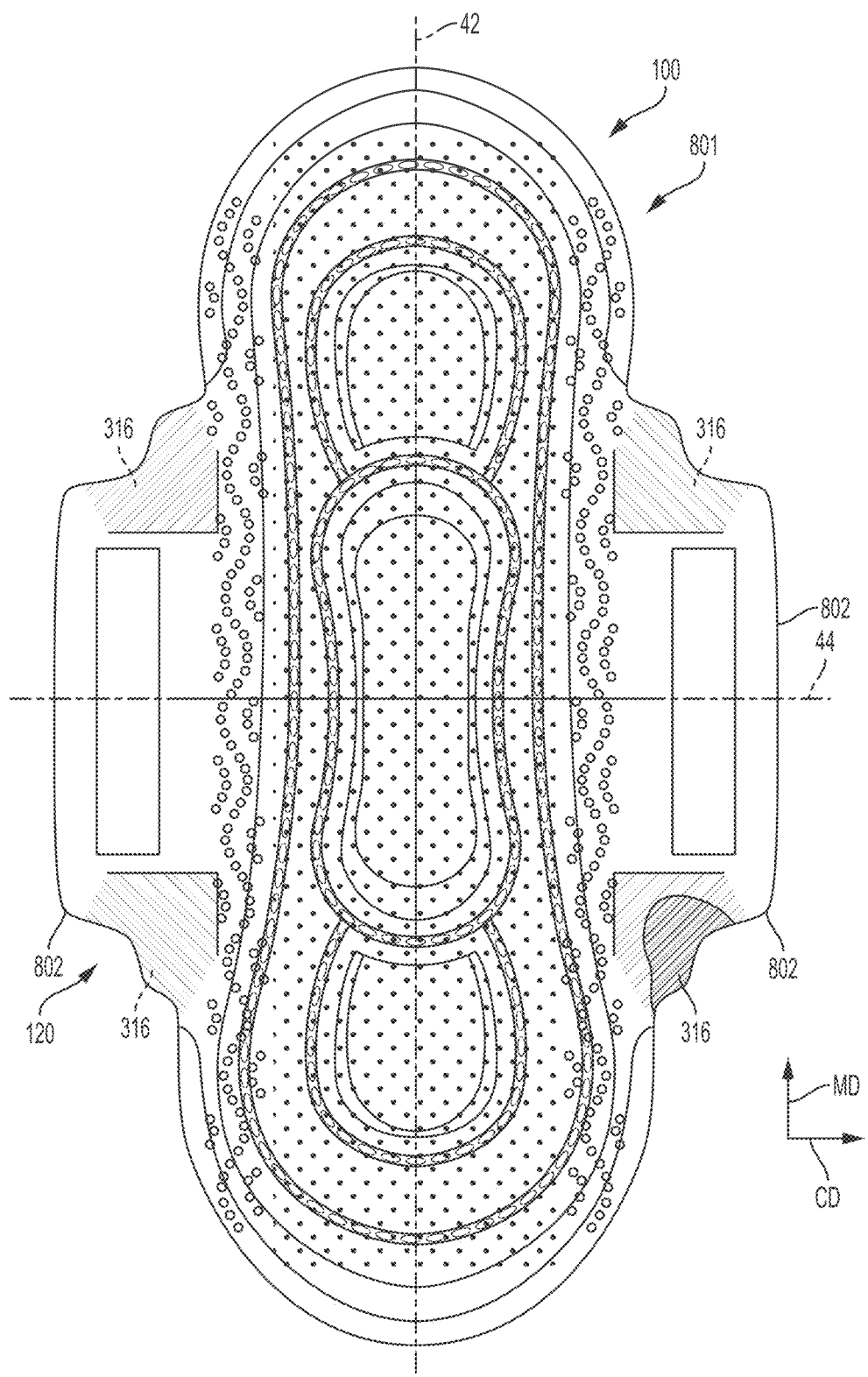
FIG. 19A is an interior plan view of a feminine hygiene article 801, specifically a pad, illustrating elasticized wings 802, where the elastics 316 are at approximately 45 degree angles relative to the longitudinal axis 42 and lateral axis 44.
Figure 19B:
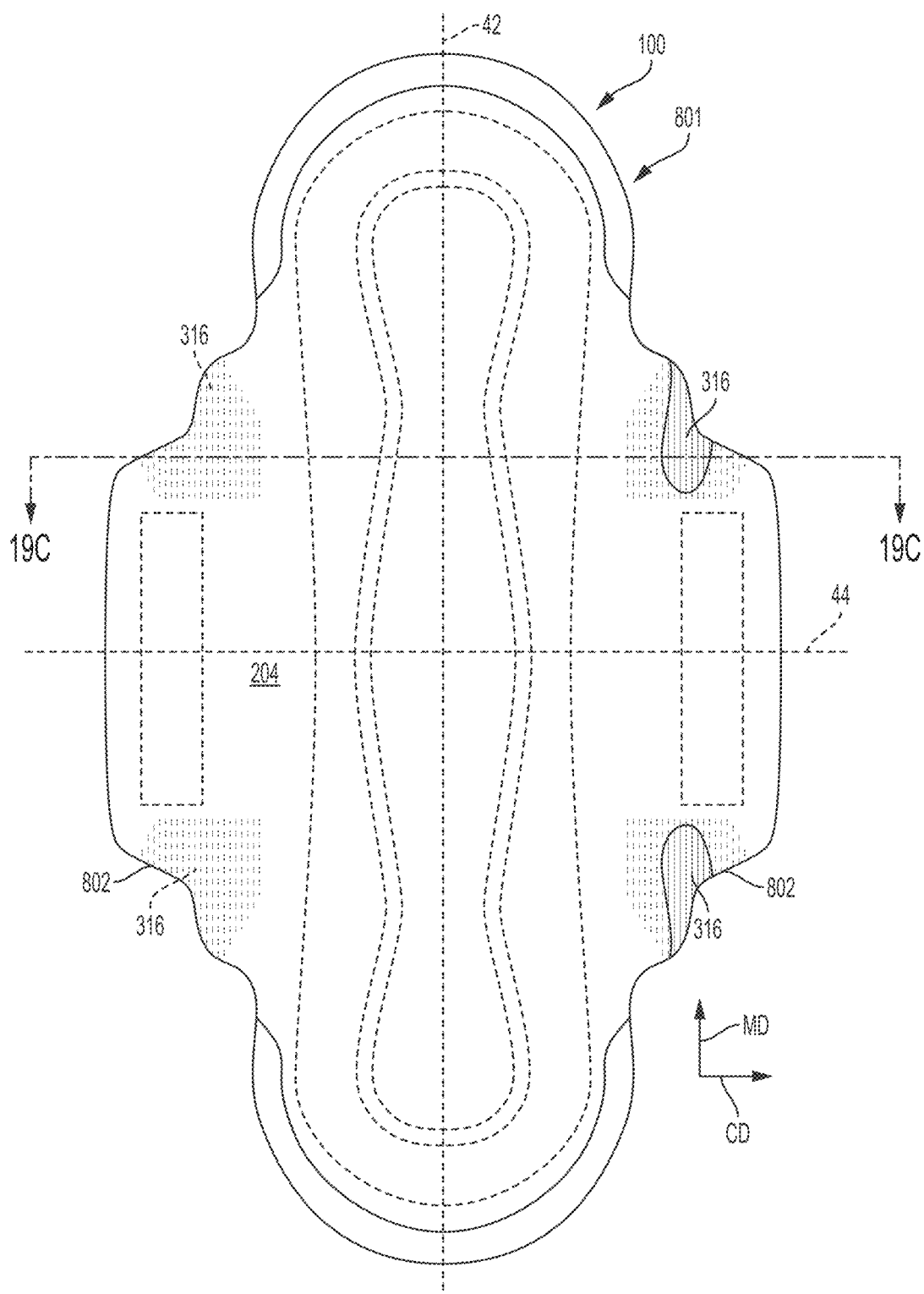
FIG. 19B is an exterior plan view of an alternative embodiment of the feminine hygiene article 801 of FIG. 19A illustrating elasticized wings 802, wherein the elastics 316 are oriented parallel to the longitudinal axis 42.
Figure 19C:
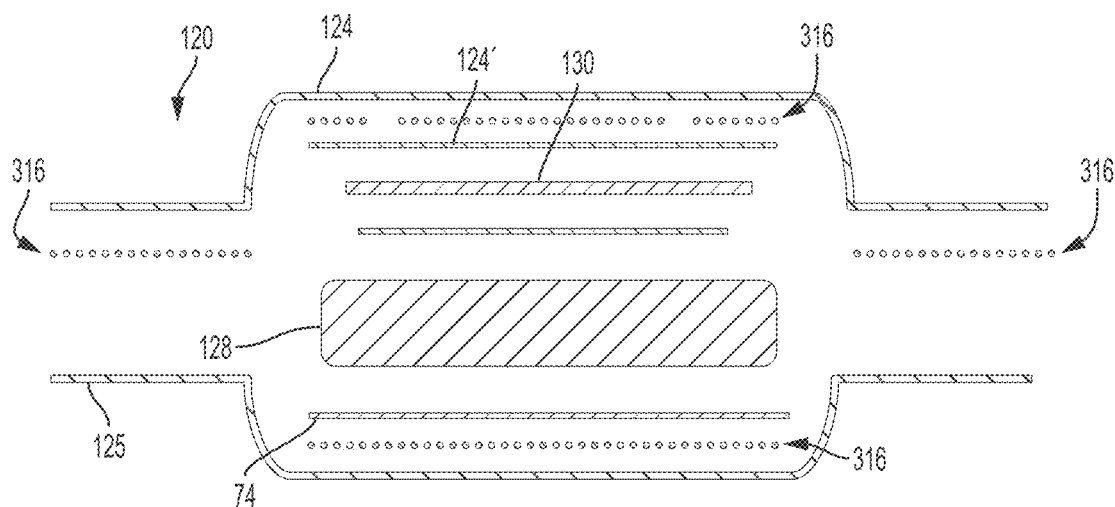
FIG. 19C is a cross-section view of an alternative embodiment of the feminine hygiene article 801, along line 19C-19C of the feminine hygiene article 801 of FIG. 19A, illustrating only one layer of strands between the layers making up the wings, as well as strands underlying or forming a portion of the topsheet 124 and secondary topsheet 124'.

The chassis 200 may be substantially rectangular and may have discrete side panels 330 (FIG. 17), extensible ear panels 530 (FIG. 18) and/or non-extensible ear panels 540 (FIG. 18) joined to the chassis 200 at or adjacent the chassis side edges 237 in one or both of the front waist region 36 and back waist region 38. Portions of one or more of the chassis side edges 237, the chassis front end edge 236 and the chassis back end edge 238 may be arcuate or curved either convexly or concavely as shown in FIG. 19A. The chassis 200 may comprise integral side panels 330, integral extensible ear panels, integral belts 430 or integral non-extensible ear panels 540 formed by one or more of the outer cover nonwoven, backsheet film, outer leg cuff material, topsheet or core wrap 74 disposed in one or both of the front and back waist regions (FIG. 18). Alternatively, the chassis 200 may comprise discrete side panels 330 (see FIG. 17), discrete extensible ear panels 530 (see FIG. 18), or discrete belts 430 or belt layers (FIGS. 1A-F, 2A-F, 3A-F, 16E, and 16F (inner belt layers 432)). The chassis may be shaped or non-rectangular, in one waist region and substantially rectangular in the opposing waist region. Alternatively, the chassis may be substantially rectangular in one or both of the waist regions and non-rectangular in the crotch region.

Absorbent articles of the present disclosure may comprise a plurality of laterally extending elastic elements wherein the elastic elements are present in a first waist region, the crotch region and in the opposing second waist region.

Closed-Form Pant Article

Closed-form, pant-style, absorbent articles are generally disclosed in FIGS. 1A-F, 2A-F, 3A-3F, 16A-17, and 23A-C and are designed to be packaged in closed-form having a waist opening 190 and two leg openings 192, and designed to be donned onto the wearer like a pair of durable underwear. The pant may comprise discrete elastomeric side panels 330 (FIG. 17) and/or discrete belts 430 (FIGS. 1A-F, 2A-F, 3A-F, 16A-C, 16E, 16F (inner belts), and 23A) in one or both of the front waist region 36 and back waist region 38. Alternatively, the side panels 330 and/or belts 430 may be formed integrally with other elements of the article such as the chassis 200.

When the absorbent article comprises front and back belts 430, the sides of front and back belts 430 on one side of the article may be joined permanently or refastenably to each other and the front and back side panels on the opposing side of the article may be joined permanently or refastenably to each other to create a waist opening 190 and a pair of leg openings 192 (FIGS. 16A and 16B). The belts 430 provide an elastically extensible feature that provides a more comfortable and contouring fit by initially conformably fitting the article 100 to the wearer and sustaining this fit throughout the time of wear well past when the pant has been loaded with exudates since the elastomeric side panels allow the sides of the pant to expand and contract. Further, the elastomeric belts 430 provide ease of application and develop and maintain wearing forces and tensions to maintain the article 100 on the wearer and enhance the fit, especially when beamed elastomeric laminates are used to form the belts 430. The elastomeric side panels enable ease of application allowing the pant to be pulled conformably over the hips of the wearer and positioned at the waist where the belts 430 conform to the body and provide tension sufficient to maintain the articles position on the wearer. The tension created by the side panels is transmitted from the elastic belts 430 along the waist opening 190 and along at least a portion of the leg opening 192. Typically, particularly regarding discrete side panels 330, the chassis 200 is disposed between the side panels 330 and extends to form a portion of the waist edge 136 and/or 138 of the pant comprising side panels 330. In other words, a portion of the waist edge 136 and/or 138 in one or both of the front waist region 36 and back waist region 38 may be formed in part by the side panels 330 and in part by the chassis 200.

The pant comprising side panels 330 may also comprise a pair of laterally opposing refastenable seams 174. The refastenable side seam 174 may be formed by refastenably joining an interior surface of a portion of the article, e.g. a side panel 330, to an exterior surface of another portion of the article 100, e.g., a longitudinally opposing side panel 330 or the chassis 200 to form the refastenable side seam 174.

The pant comprising belts 430 may also comprise a first permanent side seam 172 and a laterally opposing second permanent side seam 172 as illustrated, for example, in FIGS. 16A and 16B. The permanent side seam 172 may be formed by joining an interior surface of a portion of the article 100, e.g. belt 430, to an exterior surface of another portion of the article 100, e.g. a longitudinally opposing belt 430 or the chassis 200 to form the permanent side seam 172. Alternatively, the permanent side seam 172 may be formed by joining an interior surface of a portion of the article 100, e.g. a belt 430, to an interior surface of another portion of the article 100, e.g. a longitudinally opposing belt 430 to form the permanent side seam 172. Any pants comprising side panels 330 configurations described above may comprise a waistband 122 wherein at least a portion of the waistband 122 (as illustrated in FIG. 17) is disposed at or immediately adjacent the waist edge 136 and/or 138 and overlaps a portion of the center chassis 200. The waistband 122 may extend laterally to overlap portions of the inner leg cuffs 150 and/or portions of the elastomeric side panels 330. The waistband 122 may be disposed on the interior surface 202 of the chassis 200 or alternatively between the topsheet 124 and the backsheet 125.

Figure 16F:
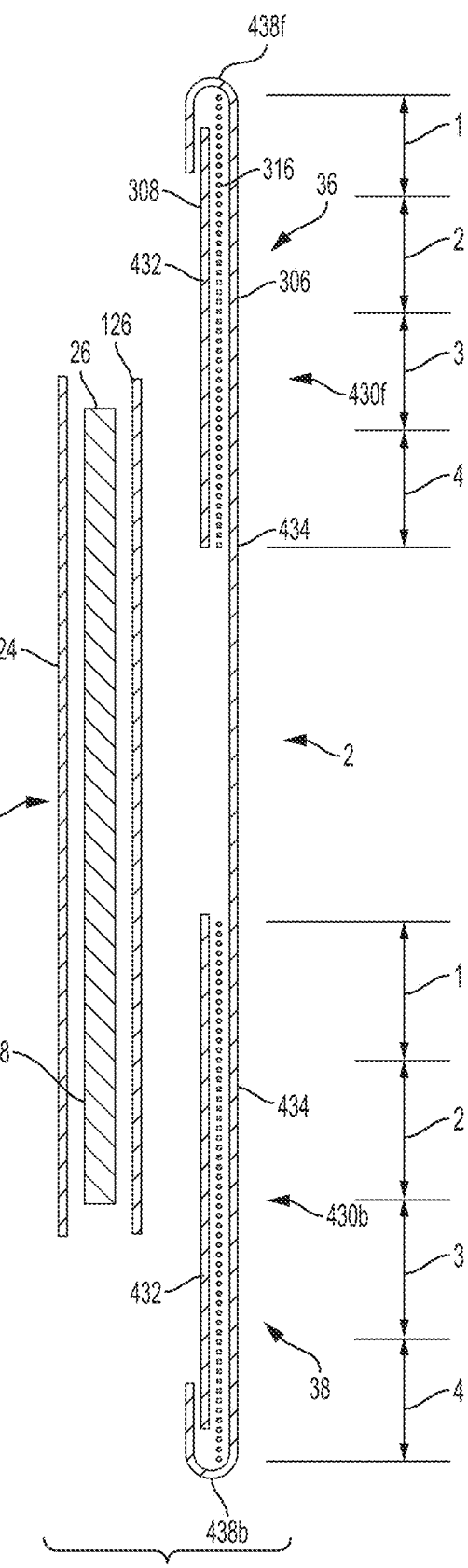
FIG. 16F is a cross-section view of an alternate embodiment of the belt pant of FIG. 16C taken along the longitudinal axis 42, showing longitudinally opposing discrete inner belt layers 432 and a common outer belt layer 434, and showing elastic strands 316 extending continuously across the core.
Figure 16G:
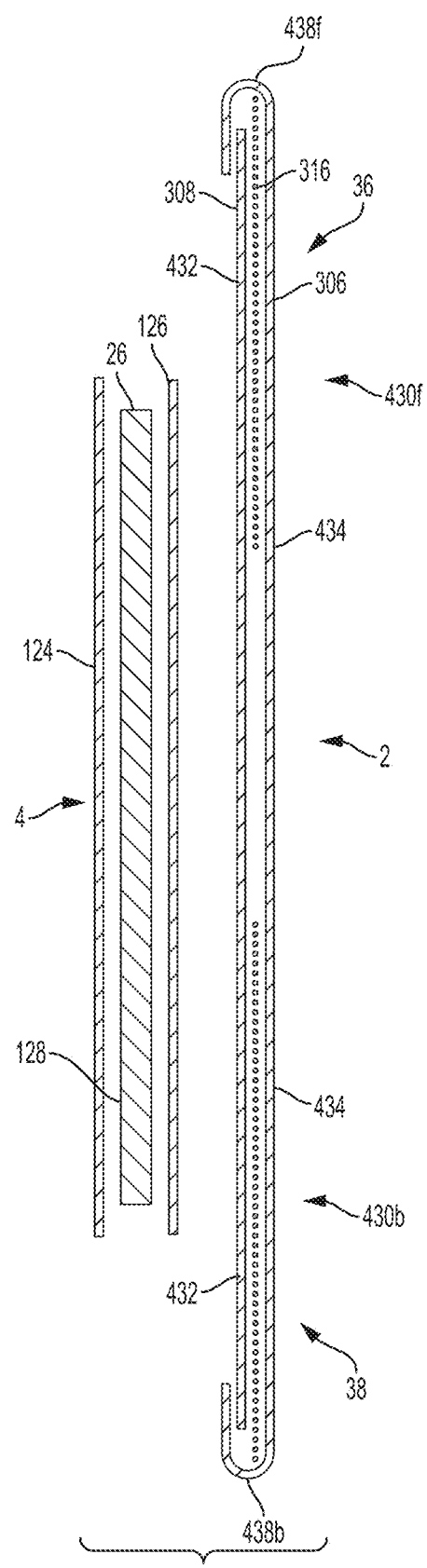
FIG. 16G is a cross-section view of an alternate embodiment of the belt pant of FIG. 16C taken along the longitudinal axis 42, showing a common inner belt layer 432 and common outer belt layer 434.

Particularly regarding belts 430, as illustrated in FIG. 16F, the inner belt layer 432 and/or the outer belt layer 434 of the first and second elastomeric belts 430 may be formed by a common belt layer as shown in FIG. 16F. When the first and second elastomeric belts 430 have a common belt layer, the common belt layer may extend from a first waist edge in a first waist region to a longitudinally opposing second waist edge in a second waist region, i.e. front waist edge 136 to back waist edge 138.

Also, particularly regarding belted pants 400, as illustrated in FIG. 16C, the belt pant 400 may have a first elastomeric belt 430 disposed in a first waist region having a first longitudinal length and a second elastomeric belt 430 disposed in a second waist region having a second longitudinal length wherein the longitudinal length of the first belt is greater than the longitudinal length of the second belt along the side edge of the belt at or adjacent the side seam. This length difference helps provide buttock coverage in the back of the pant providing a more underwear-like appearance. And, while this advantage is disclosed for belted pants 400, there is also an advantage in having longitudinally longer side panels 330 in the back waist region 38.

Open-Form Taped Article

Open-form, taped-style, absorbent articles are generally disclosed in FIG. 18. The taped diaper 500, open-form article, may comprise elastomeric ear panels 530 in one or both of the front waist region 36 and back waist region 38. The elastomeric ear panels 530 may be unitary structurally with other elements of the article 100 or as a separate element joined to another element of the article 100. The elastomeric ear panels 530 provide an elastically extensible feature that provides a more comfortable and contouring fit by initially conformably fitting the article 100 to the wearer and sustaining this fit throughout the time of wear well past when the taped diaper 500 has been loaded with exudates since the elastomeric ear panels 530 allows the diaper to expand and contract to fit the wearer. Further, the elastomeric ear panels 530 develop and maintain wearing forces (tensions) and enhance the tensions developed and maintained by the fastening system 179 (including the fasteners 175 (e.g., hooks) that may be releasably engaged with a mating fasteners 178 (e.g., loops)), to maintain the article 100 on the wearer and enhance the fit. The elastomeric ear panels 530 especially assist in maintaining the primary line of tension formed by the fastening system 179 allowing the diaper to conformably fit over the hips of the wearer where there is dynamic motion, and initially pre-tensioning the waist opening 190 and leg opening 192 since the diaperer typically stretches the elastomeric ear panels 530 when applying the taped diaper 500 on the wearer so that when the elastomeric ear panels 530 contract, tension is transmitted from the elastomeric ear panels 530 along the waist opening 190 and along at least a portion of the leg opening 192. While the open-form article of the present disclosure may have the elastomeric ear panels 530 disposed in the back waist region 38, alternatively, the taped diaper 500 may be provided with elastomeric ear panels 530 disposed in the front waist region 36 or in both the front waist region 36 and the back waist region 38. The open-form article may also have elastomeric ear panels 530 disposed in a first waist region and elastomeric ear panels 530 or non-elastomeric ear panels 540 disposed in a second waist region.

Alternatively, the open-form, taped-style, absorbent articles may comprise an elastomeric belt 430 disposed in one of the waist regions. The elastomeric belt 430 may be joined and/or positioned in a particular place or position and may be unitary structurally with other elements of the article 100 or as a separate element joined to another element of the article 100. A belted taped diaper the elastomeric belt 430 may be disposed in the back waist region 38. The elastomeric belt 430 may have fasteners disposed at or adjacent the laterally opposing ends of the belt. Fasteners 175 may be disposed on the interior surface of the belt 430 to engage with a discrete mating fastening component 178 or with the exterior surface 204 of the article (like the backsheet nonwoven 127) to fasten the article on the wearer.

Outer Cover Material

The backsheet 125 may comprise a backsheet film 126 and backsheet nonwoven 127. The backsheet nonwoven 127 may also be referred to as the outer cover material. The outer cover material forms at least a portion of the garment-facing surface of the absorbent article 100 and effectively "covers" the backsheet film 126 so that the film is not present on the garment-facing surface. The outer cover material may comprise a bond pattern, apertures, and/or three-dimensional features.

Absorbent Core

As used herein, the term "absorbent core" 128 refers to the component of the absorbent article 100 having the most absorbent capacity and that comprises an absorbent material. Referring to FIGS. 16C and 16D in some instances, absorbent material (e.g., 26 and 53) may be positioned within a core bag or a core wrap 74. The absorbent material may be profiled or not profiled, depending on the specific absorbent article. The absorbent core 128 may comprise, consist essentially of, or consist of, a core wrap, absorbent material, and glue enclosed within the core wrap. The absorbent material may comprise superabsorbent polymers, a mixture of superabsorbent polymers and air felt, only air felt, and/or a foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt—in such cases the AGM 26 may be held in place by an adhesive 54, such as a thermoplastic adhesive. And, for swim diapers, the article may be free of superabsorbent polymers. The absorbent core periphery, which may be the periphery of the core wrap, may define any suitable shape, such as rectangular, "T," "Y," "hour-glass," or "dog-bone" shaped, for example. An absorbent core periphery having a generally "dog bone" or "hour-glass" shape may taper along its width towards the crotch region 37 of the absorbent article 100.

Referring to FIGS. 16C and 16D the absorbent core 128 may have areas having little or no absorbent material, where a wearer-facing surface of the core bag 74 may be joined to a garment-facing surface of the core bag 74. These areas having little or no absorbent material may be referred to as "channels" 129. These channels can embody any suitable shapes and any suitable number of channels may be provided. In other instances, the absorbent core may be embossed to create the impression of channels. The absorbent core in FIGS. 16C and 16D is merely an example absorbent core. Many other absorbent cores with or without channels are also within the scope of the present disclosure.

As used herein, a loaded absorbent core is one holding (or capable of holding) a load of at least 50, 100, or 200 milliliters (mls) for diapers, pants, and adult incontinence articles. The disposable absorbent articles of the present disclosure comprising an absorbent core are designed to fit the wearer with an empty absorbent core (i.e., one that is not loaded), as well as being capable of fitting the wear for an appreciable time (2 or more hours) even when the core is loaded.

Acquisition Materials

One or more acquisition materials (e.g., 130) may be present at least partially intermediate the topsheet 124 and the absorbent core 128. The acquisition materials are typically hydrophilic materials that provide significant wicking of bodily exudates. These materials may dewater the topsheet 124 and quickly move bodily exudates into the absorbent core 128. The acquisition materials 130 may comprise one or more nonwoven materials, foams, cellulosic materials, cross-linked cellulosic materials, air laid cellulosic nonwoven materials, spunlace materials, or combinations thereof, for example. In some instances, portions of the acquisition materials may extend through portions of the topsheet 124, portions of the topsheet 124 may extend through portions of the acquisition materials, and/or the topsheet 124 may be nested with the acquisition materials. Typically, an acquisition material or layer may have a width and length that are smaller than the width and length of the topsheet 124. The acquisition material may be a secondary topsheet in the feminine pad context. The acquisition material may have one or more channels as described in the absorbent core 128 section (including the embossed version). The channels in the acquisition material may align or not align with channels in the absorbent core 128. In an example, a first acquisition material may comprise a nonwoven material and as second acquisition material may comprise a cross-linked cellulosic material.

Topsheets

The absorbent articles 100 of the present disclosure may comprise a topsheet 124. The topsheet 124 is the part of the absorbent article 100 that is in contact with the wearer's skin. The topsheet 124 may be joined to portions of the backsheet 125, the absorbent core 128, the leg cuffs 52, and/or any other layers as is known to those of ordinary skill in the art. The topsheet 124 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheet may comprise a bond pattern, apertures, and/or three-dimensional features.

Backsheets

The absorbent article 100 of the present disclosure may comprise a backsheet 125. The backsheet 125 is generally that portion of the absorbent article 100 positioned proximate to the garment-facing surface of the absorbent core 128. The backsheet 125 may be joined to portions of the topsheet 124, the backsheet nonwoven 127, the absorbent core 128, and/or any other layers of the absorbent article by any attachment methods known to those of skill in the art. The backsheet film 126 prevents, or at least inhibits, the bodily exudates absorbed and contained in the absorbent core 128 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet. The backsheet may comprise a bond pattern, apertures, and/or three-dimensional features.

Leg Cuffs

The absorbent articles 100 of the present disclosure may comprise leg cuffs 52, which include inner leg cuffs 150 and outer leg cuffs 140. The inner leg cuffs 150 may be positioned laterally inboard of outer leg cuffs 140. Each of the leg cuffs 52 may be formed by a piece of material which is bonded to the absorbent article 100 so it can extend upwards from a wearer-facing surface of the absorbent article 100 and provide improved containment of body exudates approximately at the junction of the torso and legs of the wearer. The inner leg cuffs 150 are delimited by an edge joined directly or indirectly to (or formed by) the topsheet and/or the backsheet and a free terminal edge, which is intended to contact and form a seal with the wearer's skin. The inner leg cuffs 150 may extend longitudinally at least partially (or fully) between the front end edge 136 and the back end edge 138 of the absorbent article 100 on opposite sides of the chassis and may be at least present in the crotch region 37. The inner leg cuffs 150 may each comprise one or more elastics 316 (e.g., elastic strands or strips) near or at the free terminal edge. These elastics 316 cause the inner leg cuffs 150 to help form a seal around the legs and torso of a wearer. The outer leg cuffs 140 extend at least partially between the front end edge 136 and the back end edge 138. The outer leg cuffs 140 essentially cause portions of the absorbent article 100 proximate to the chassis side edges 237a and 237b to help form a seal around the legs of the wearer. The outer leg cuffs 140 may extend at least within the crotch region 37.

Waistbands/Waistcaps

The absorbent articles 100 of the present disclosure may comprise one or more elastic waistbands 122. The elastic waistbands 122 may be positioned on the garment-facing surface or the wearer-facing surface, or may be formed therebetween. As an example, a first elastic waistband 122 may be present in the front waist region 36 near the front waist edge 136 and a second elastic waistband 122 may be present in the back waist region 38 near the back waist edge 138. The elastic waistbands 122 may aid in sealing the absorbent article 100 around a waist of a wearer and at least inhibiting bodily exudates from escaping the absorbent article 100 through the waist opening circumference. In some instances, an elastic waistband may fully surround the waist opening 190 of the absorbent article 100. A waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g., center chassis 200 of the absorbent article 100 along the longitudinally distal edge of the waist cap 123 and/or along the laterally opposing side edges of the waist cap 123.

Belts

Beyond what was disclosed about belts in the Open-Form Taped Article and Closed-Form Pant Article Sections above, the front and back belts 430f and 430b may comprise front and back inner belt layers 432 and front and back outer belt layers 434 having an elastomeric material (e.g., strands 316 or a film (which may be apertured)) disposed at least partially therebetween. The elastic strands 316 or the film may be relaxed (including being cut) to reduce elastic strain over the absorbent core 128 or, may alternatively, run continuously across the absorbent core 128. The elastics strands 316 may have uniform or variable spacing therebetween in any portion of the belts. The elastic strands 316 may also be pre-strained the same amount or different amounts. The front and/or back belts 430f and 430b may have one or more elastic element free zones where the chassis 200 overlaps the belts 430f and 430b. In other instances, at least some of the elastic strands 316 may extend continuously across the chassis 200. The inner and/or outer belt layer may comprise a bond pattern, apertures, and/or three-dimensional features.

The front and back inner belt layers 432 and the front and back outer belt layers 434 may be joined using adhesives, heat bonds, pressure bonds, ultrasonic, or thermoplastic bonds. Various suitable belt layer configurations can be found in U.S. Pat. Appl. Pub. No. 2013/0211363.

Front and back belt end edges 438f and 438b may extend longitudinally beyond the front and back chassis end edges 236 and 238 or they may be co-terminus. The front and back belt side edges 437 may extend laterally beyond the chassis side edges 237a and 237b. The front and back belts 430f and 430b may be continuous (i.e., having at least one layer that is continuous (see 434 in FIG. 16F) from belt end edge 438f to the opposite belt end edge 438b). Alternatively, the front and back belts 430f and 430b may be discontinuous from belt end edge 438f to the opposite belt end edge 438b (see 432 and 434 in FIG. 16E), such that they are discrete.

As disclosed in U.S. Pat. No. 7,901,393, the longitudinal length (along the central longitudinal axis 42) of the back belt 430b may be greater than the longitudinal length of the front belt 430f, and this may be particularly useful for increased buttocks coverage when the back belt 430b has a greater longitudinal length versus the front belt 430f adjacent to or immediately adjacent to the side seams 172. Alternatively, the bottom corners of the longer back belt may be trimmed in diagonal lines or curves.

The front and back belts 430f and 430b may include slits, holes, and/or perforations providing increased breathability, softness, and a garment-like texture. Underwear-like appearance can be enhanced by substantially aligning the waist and leg edges at the side seams 172.

Packaged Absorbent Articles of the Present Disclosure

Assembled absorbent articles, especially including disposable diaper and pants, from the converter are transferred into stacker chain and form a stack. The stack of absorbent articles is then compressed in two stations:

1) Pre-compression (PC): that squeezes majority of air out of the diapers. The strain reaches about 0.45 but the force is normally less than 200N.
2) Main-compression (MC): the stack is further compressed to a strain about 0.7. Even though the strain increase is small compared to PC, the force on the stack peaks in MC. Depending on the midrange and the product formulation, the MC force on the stack soars to a few kN and sometimes over 10 kN. This puts the diapers under a pressure of 100-500 kPa in a quarter second at a strain rate around 1/s.

The stack is normally over compressed followed by a release before transporting through shuttle into the bag. Over compression is needed for smooth stack transportation in the shuttle as it reduces the normal contact force (therefore the frictions) between the absorbent articles of the stack and the shuttle surfaces. These high forces in MC may have potential negative impacts to product performance, such as glue bleed through, AGM poke through, loss of softness and 3D structure (including texture), etc.

Beyond this, there is still a long and harsh way ahead, from palletization to transportation and warehouse handling, until the package of absorbent articles finally reaches the shelf or the consumer's home. During the transportation, the packages of absorbent articles are exposed to a wide range of dynamic load in all three directions and dramatic changes in temperatures and humidity which alter the material properties. After production, absorbent articles may be confined in bags for several months before usage.

Of course, the absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. As noted above, the absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

It has been found that the stranded elastomeric laminates of the present disclosure withstand the negative forces associated making absorbent article and with being packaged under high compression for an extended period of time. Of particular importance, the stranded elastomeric laminates of the present disclosure maintain the important properties disclosed herein, including those associated with texture (e.g., Percent-Contact-Area, Rugosity-Frequency, Rugosity-Wavelength, and 2-98%-Height-Value).

Accordingly, packages of the absorbent articles of the present disclosure may have an In-Bag Stack-Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag-Stack-Height of from about 70 mm to about 110 mm, from about 70 mm to about 105 mm, from about 70 mm to about 100 mm, from about 75 mm to about 95 mm, from about 80 mm to about 95 mm, from about 80 mm to about 90 mm, from about 85 mm to about 90 mm, or from about 88 mm to about 90 mm, specifically reciting all 0.1 mm increments within the specified ranges and all ranges formed therein or thereby, according to the In-Bag Stack Height Test described herein.

Figure 20:
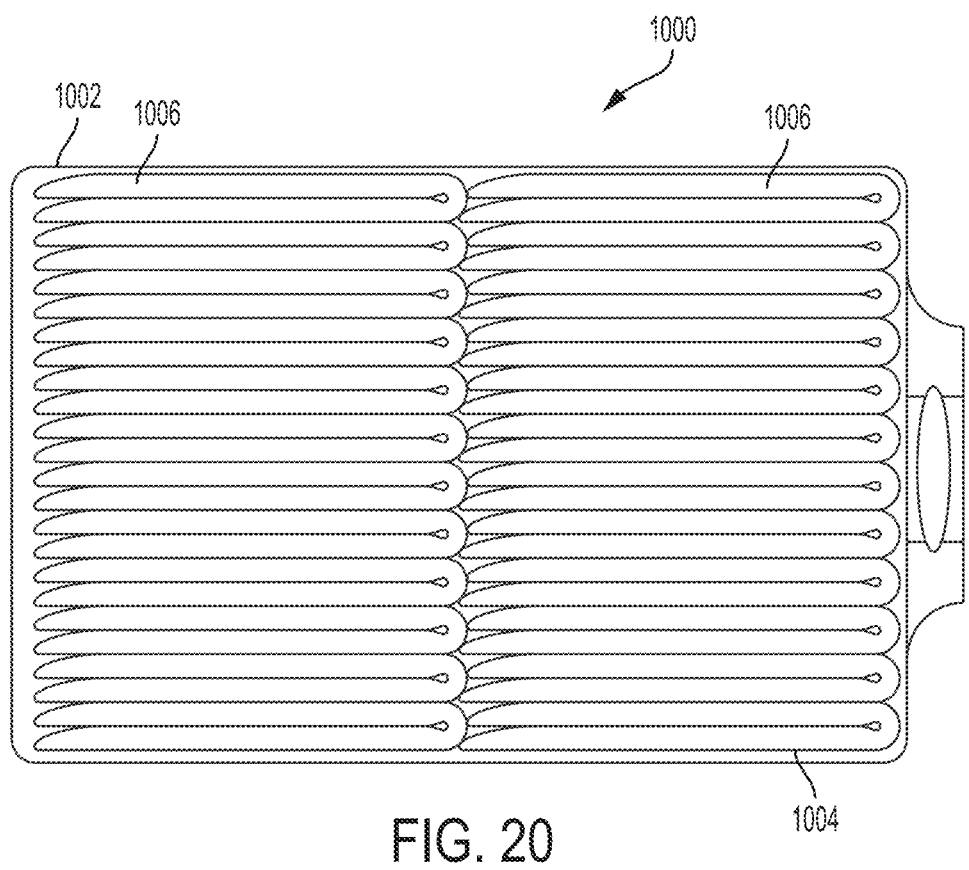
FIG. 20 illustrates packaged disposable absorbent articles of the present disclosure.

FIG. 20 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006. As indicated above, each of the absorbent articles 1004 may be disposable absorbent pant articles, and, may particularly be belted pant articles.

EXAMPLE CLAIM EMBODIMENTS OF THE PRESENT DISCLOSURE

Example Claim Set 1

1. An elastomeric laminate, comprising:
a plurality of elastic strands between of first and second nonwovens;

wherein the plurality of elastic strands has an Average-Strand-Spacing from about 0.25 mm to about 4 mm;

wherein the plurality of elastic strands has an Average-Dtex from about 10 to about 400;

wherein the plurality of elastic strands has an Average-Pre-Strain from about 50% to about 300%;

wherein a plurality of densified bonds joins the first and second nonwovens together;

wherein the plurality of densified bonds is discrete and spaced from each other;

wherein the plurality of densified bonds overlaps and at least partially surround portions of the plurality of elastic strands;

wherein a Peel-Strength between the first and second nonwovens is from about 1 N/cm to about 15N/cm; and wherein a Dtex-to-Nonwoven-Basis-Weight-Ratio of a first elastic strand and of at least one of the first and second nonwovens is from about 1.5 to about 15.

2. The elastomeric laminate according to claim 1, wherein a first elastic strand of the first plurality of elastic strands comprises from about 2 to about 40 filaments, including first and second filaments, wherein the first and second filaments are disposed cross-sectionally side-by-side of each other, and wherein at least one discrete bond of the plurality of discrete bonds surrounds at least the first and second filaments.

3. The elastomeric laminate according to any of the preceding claims, wherein the at least one discrete bond overlaps at least 10 elastic strands of the first plurality of elastic strands.

4. The elastomeric laminate according to any of the preceding claims, wherein the at least one discrete bond surrounds at least 20 filaments of the at least 10 elastic strands.

5. The elastomeric laminate according to any of the preceding claims, wherein the plurality of elastic strands has an Average-Strand-Spacing from about 0.5 mm to about 2.5 mm.

6. The elastomeric laminate according to any of the preceding claims, wherein at least one of the densified bonds making up the plurality of densified bonds has a Void-Area-to-Strand-Area-Ratio of less than 1.

7. The elastomeric laminate according to any of the preceding claims, wherein a Dtex-to-Spacing-Ratio of the plurality of elastic strands is from about 65:1 to about 150:1.

8. The elastomeric laminate according to any of the preceding claims, wherein the plurality of elastic strands comprises at least 100 elastic strands, and wherein each of the at least 100 elastic strands comprises at least 3 filaments, and wherein the plurality of densified bonds overlap at least 50 of the elastic strands making up the plurality of elastic strands and surround at least 150 filaments of the at least 100 elastic strands, and wherein substantial portions of the at least 100 elastic strands between the densified bonds are unbonded.

9. The elastomeric laminate according to any of the preceding claims, wherein the elastomeric laminate forms at least a portion of at least one of the group consisting of a belt, a chassis, a side panel, a topsheet, a backsheet, an ear panel, and combinations thereof, wherein the plurality of elastic strands comprises from about 40 to about 1000 elastic strands, wherein each of the elastic strands making up the about 40 to about 1000 elastic strands are overlapped by and partially surrounded by the plurality of discrete bonds.

10. The elastomeric laminate according to any of the preceding claims, wherein a third nonwoven is joined to the second nonwoven such that a tri-laminate is formed, and wherein an exterior surface of the third nonwoven and an exterior surface of the first nonwoven have different Percent-Contact-Area.

11. The elastomeric laminate according to claim 10, wherein the third nonwoven is joined to the second nonwoven via adhesive.

12. The elastomeric laminate according to any of the preceding claims, wherein the first nonwoven layer has a basis weight from about 6 grams per square meter to about 35 grams per square meter, and wherein the second nonwoven layer has a basis weight from about 6 grams per square meter to about 35 grams per square meter.

13. The elastomeric laminate according to any of the preceding claims, further comprising at least one of:

a) a Percent-Contact-Area of at least one of: a) greater than about 10% at 100 um, b) greater than about 20% at 200 um, and c) greater than about 30% at 300 um;

b) a Force-Relaxation from about 5% to about 30%;

c) a Cantilever-Bending of less than about 40 mm;

d) a 2%-98%-Height-Value of <2.2 mm;

e) a Pressure-Under-Strand from about 0.1 to about 1 psi; and f) a Section-Modulus of from about 2 gf/mm to about 15 gf/mm.

14. The elastomeric laminate according to any of the preceding claims, wherein the plurality of elastic strands has an Average-Strand-Spacing from about 0.75 mm to about 2.5 mm.

15. The elastomeric laminate according to any of the preceding claims, wherein the plurality of elastic strands has an Average-Dtex from about 40 to about 250.

16. The elastomeric laminate according to any of the preceding claims, wherein the plurality of elastic strands has an Average-Pre-Strain from about 100% to about 250%.

Example Claim Set 2

1. An elastomeric laminate, comprising:

a plurality of elastic strands between first and second nonwovens;

wherein the plurality of elastic strands has an Average-Strand-Spacing from about 0.25 mm to about 4 mm;

wherein the plurality of elastic strands has an Average-Dtex from about 10 to about 400;

wherein the first and second nonwovens are joined together, and wherein a third nonwoven is joined to the second nonwoven, such that the second nonwoven is an intermediate nonwoven;

wherein a Dtex-to-Spacing-Ratio of the plurality of elastic strands is from about 65:1 to about 200:1;

wherein the first and second nonwovens are joined together via an adhesive, and wherein the adhesive overlaps and at least partially surrounds a portion of the plurality of elastic strands;

wherein the second and third nonwovens are joined together via a plurality of bonds, wherein the plurality of bonds are discrete and laterally spaced from each other; and wherein an exterior surface of the third nonwoven and an exterior surface of the first nonwoven have different Percent-Contact-Areas.

2. The elastomeric laminate according to claim 1, wherein elastic strands are not present between the second and third nonwovens.\*\*\*

3. The elastomeric laminate according to any of the preceding claims, wherein a Dtex-to-Spacing-Ratio of the plurality of elastic strands is from about 65:1 to about 150:1.

4. The elastomeric laminate according to any of the preceding claims, wherein the first nonwoven layer has a basis weight from about 6 grams per square meter to about 35 grams per square meter, and wherein the second nonwoven layer has a basis weight from about 6 grams per square meter to about 35 grams per square meter.

5. The elastomeric laminate according to any of the preceding claims, further comprising at least one of:

a) a Percent-Contact-Area of at least one of: a) greater than about 10% at 100 um, b) greater than about 20% at 200 um, and c) greater than about 30% at 300 um;

b) a Force-Relaxation from about 5% to about 30%;

c) a Cantilever-Bending of less than about 40 mm;

d) a 2%-98%-Height-Value of <2.2 mm;

e) a Pressure-Under-Strand from about 0.1 to about 1 psi; and f) a Section-Modulus of from about 2 gf/mm to about 15 gf/mm.

6. The elastomeric laminate according to any of the preceding claims, wherein the plurality of elastic strands has an Average-Strand-Spacing from about 0.75 mm to about 2.5 mm.

7. The elastomeric laminate according to any of the preceding claims, wherein the plurality of elastic strands has an Average-Dtex from about 40 to about 250.

8. The elastomeric laminate according to any of the preceding claims, wherein the plurality of elastic strands has an Average-Pre-Strain from about 100% to about 250%.

Example Claim Set 3

1. A disposable absorbent pant article, wherein the disposable absorbent pant article comprises:

a chassis comprising a topsheet, a backsheet and an absorbent core disposed between the topsheet and the backsheet;

a first plurality of elastic strands disposed in a front waist region;

a second plurality of elastic strands disposed in a back waist region;

wherein the front and back waist regions are joined together at laterally opposed side seams to form a waist and leg openings;

wherein each of the first and second pluralities of elastic strands have an Average-Strand-Spacing from about 0.25 mm to about 4 mm;

wherein each of the of the first and second pluralities of elastic strands have Average-Dtex is from about 10 to about 400;

wherein at least a portion of each of the first and second pluralities of elastic strands has a Pressure-Under-Strand of from about 0.1 to about 1 psi;

wherein the pant article has an Application-Force of from about 900 gf to about 1600 gf, and a Sustained-Fit-Load-Force greater than 30% of the Application-Force; and wherein the pant article has a Sustained-Fit-Unload-Force greater than 25% of the Application-Force.

2. The disposable absorbent pant article according to claim 1, wherein the front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams;

wherein the back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams;

wherein the front waist region comprises a front component region disposed between and including a front distal most elastic strand of the front waist region and a proximal most elastic strand of the front waist region;

wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;

wherein the front component region is then divided into 4 equal component sections, defined by first, second, and third component section lines, each disposed parallel to the lateral axis and disposed at 25%, 50% and 75% of the distance between the front distal component region line and front proximal component region line;

wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4; and wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R.

3. The disposable absorbent pant article according to claim 2, wherein at least one of Front Sections 2 and 3 within Section L comprise a different bonding arrangement than Front Section 1 within Section L, and wherein at least one of Front Sections 2 and 3 within Section L comprise a different bonding arrangement than Front Section 4 within Section L.

4. The disposable absorbent pant article according to any of claims 2-3, wherein Front Sections 3 and 4 within Section L comprise a different bonding arrangement than Front Sections 3 and 4 within Section M, and wherein Section L comprises at least 3 different bonding arrangements within Front Sections 1-4.

5. The disposable absorbent pant article according to any of claims 2-4, wherein a portion of the chassis is contiguous with the Front Section 4 within Section M and has the same bonding arrangement and/or the same graphics pattern as Front Section 4 within M.

6. The disposable absorbent pant article according to any of claims 2-5, wherein Front Section 1 comprises 5% more or 5% fewer elastic strands than Front Section 2 within Section L, and wherein Front Section 2 comprises 5% more or 5% fewer elastic strands than Front Section 3 within Section L; and wherein the ΔE* of Front Sections 1 and 2 within Section L is greater than about 7 and less than about 60.

7. The disposable absorbent pant article according to any of claims 2-6, wherein at least one discrete bond making up the plurality of discrete bonds is disposed in portions at least three of Front Sections 1-4 within Section L.

8. The disposable absorbent pant article according to any of claims 2-8, wherein greater than 70% of the elastic strands in at least one of Sections L and R extends at least 50% of a lateral width (when the absorbent article is laid out flat) of the respective at least one of Sections L and R.

9. The disposable absorbent pant article according to any of the preceding claims, wherein the disposable absorbent pant article has an Application-Force of greater than about 1500 gf, a Sustained-Fit-Load-Force greater than 30% of the Application-Force, and a Sustained-Fit-Unload-Force greater than 30% of the Application-Force.

10. The disposable absorbent pant article according to any of the preceding claims, wherein the disposable absorbent pant article has an Application-Force of from about 900 gf to about 1600 gf, a Sustained-Fit-Load-Force from about 400 gf to about 800, and a Sustained-Fit-Unload-Force from about 325 to about 600 gf.

11. The disposable absorbent pant article according to any of the preceding claims, wherein each of the first and second plurality of elastic strands has an Average-Strand-Spacing from about 0.75 mm to about 2.5 mm.

12. The disposable absorbent pant article according to any of the preceding claims, wherein each of the first and second plurality of elastic strands has an Average-Dtex from about 40 to about 250.

13. The disposable absorbent pant article according to any of the preceding claims, wherein each of the first and second plurality of elastic strands has an Average-Pre-Strain from about 100% to about 250%.

Example Claim Set 4

1. A packaged product comprising:
 a package having height, width and depth dimensions, an interior space and an exterior surface, the package comprising a film;
 a plurality of disposable absorbent articles, which are bi-folded and arranged to form a stack of disposable absorbent articles, wherein the stack of disposable absorbent articles is compressed along a compression axis and disposed within the interior space of the package such that the compression axis of the stack of disposable absorbent articles is oriented substantially along the width dimension of the package, each of the folded disposable absorbent articles comprising:
 a topsheet;
 a backsheet;
 an absorbent core located between the topsheet and the backsheet;
 wherein each of the disposable absorbent articles comprises an elastomeric laminate comprising:
 a plurality of elastic strands between first and second nonwovens;
 wherein the plurality of elastic strands has an Average-Strand-Spacing from about 0.25 mm to about 4 mm;
 wherein the plurality of elastic strands has an Average-Dtex from about 10 to about 400;
 wherein the plurality of elastic strands has an Average-Pre-Strain from about 50% to about 300%; and
 wherein the packaged product exhibits an In-Bag-Stack-Height from 70 mm to 110 mm wherein the In-Bag-Stack-Height is the width of the package divided by the number of the disposable articles per stack and then multiplied by ten.

2. The packaged product according to claim 1, wherein a plurality of densified bonds joins the first and second nonwovens together;
 wherein the plurality of densified bonds is discrete and spaced from each other;
 wherein the plurality of densified bonds overlaps and at least partially surround a portion of the plurality of elastic strands; and
 wherein a Dtex-to-Nonwoven-Basis-Weight-Ratio of a first elastic strand and of at least one of the first and second nonwoven layers is from about 1.5 to about 7.

3. The packaged product according to any of the preceding claims, wherein one elastomeric laminate of at least one absorbent article of the plurality of absorbent articles has at least one of:
 a) a Percent-Contact-Area of at least one of: a) greater than about 13% at 100 um, b) greater than about 27% at 200 um, and c) greater than about 36% at 300 um;
 b) a Rugosity-Frequency of from about 0.2 mm$^{-1}$ to about 1 mm$^{-1}$;
 c) a Rugosity-Wavelength of from about 0.5 mm to about 5 mm; and
 d) a 2-98%-Height-Value of between 0.3 to about 3.0.

4. The packaged product according to any of the preceding claims, wherein the plurality of elastic strands has an Average-Strand-Spacing from about 0.75 mm to about 2.5 mm.

5. The packaged product according to any of the preceding claims, wherein the plurality of elastic strands has an Average-Dtex from about 40 to about 250.

6. The packaged product according to any of the preceding claims, wherein the plurality of elastic strands has an Average-Pre-Strain from about 100% to about 250%.

7. The packaged product according to any of the preceding claims, wherein the absorbent article is a disposable taped diaper.

8. The packaged product according to any of the preceding claims, wherein the absorbent article is a disposable pant.

9. The elastomeric laminate according to any of the preceding claims, further comprising at least two distinct texture zones, including a first texture zone comprising a first bonding arrangement, and including a second texture zone comprising a second bonding arrangement, wherein the first and second bonding arrangements are different.

10. The elastomeric laminate according to claim 9, wherein the first and second texture zones have different Percent-Contact-Areas.

11. The elastomeric laminate according to any of the preceding claims, wherein the elastomeric laminate forms at least a portion of a disposable absorbent pant article, and wherein the disposable absorbent pant article has an Application-Force of from about 900 gf to about 1600 gf, and a Sustained-Fit-Load-Force greater than 30% of the Application-Force, and wherein the pant article has a Sustained-Fit-Unload-Force greater than 25% of the Application-Force.

12. The elastomeric laminate according to any of the preceding claims, wherein the packaged product exhibits an In-Bag-Stack-Height from 75 mm to about 95 mm.

Example Claim Set 5

1. A disposable absorbent pant article, comprising:

a chassis comprising a topsheet, a backsheet and an absorbent core disposed between the topsheet and the backsheet;

a first plurality of elastic strands disposed in a front waist region;

a second plurality of elastic strands disposed in a back waist region;

wherein the front and back waist regions are joined together at laterally opposed side seams to form a waist and leg openings;

wherein the front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams;

wherein the back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams;

wherein the front waist region comprises a front component region disposed between and including a front distal most elastic strand of the front waist region and a proximal most elastic strand of the front waist region;

wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;

wherein the front component region is then divided into 4 equal component sections, defined by first, second, and third component section lines, each disposed parallel to the lateral axis and disposed at 25%, 50% and 75% of the distance between the front distal component region line and front proximal component region line;

wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4;

wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R;

wherein each of the first and second pluralities of elastics have an Average-Strand-Spacing from about 0.5 mm to about 3 mm;

wherein each of the of the first and second pluralities of elastics have Average-Dtex is from about 40 to about 300;

wherein at least a portion of each of the first and second pluralities of elastics has a Pressure-Under-Strand of from about 0.1 to about 1.2 psi;

wherein the pant article has an Application-Force of from about 900 gf to about 1600 gf, and a Sustained-Fit-Load-Force greater than 30% of the Application-Force, and a Sustained-Fit-Unload-Force greater than 25% of the Application-Force;

wherein Section L and Section R have a first texture having a first Percent-Contact-Area and Section M has a second texture having a second Percent-Contact-Area wherein the first Percent-Contact-Area is greater than the second Percent-Contact-Area;

wherein at least a portion of the plurality of elastics disposed in Section L and Section R are joined to the laminate substrates via adhesive bonding; and wherein Section M comprises thermal, mechanical, pressure, or ultrasonic bonds or a substrate having non-uniform basis weight or non-uniform thickness to form a portion of the texture on an exterior surface of Section M.

Example Claim Set 6

1. An elastomeric laminate, comprising:

a plurality of elastic strands between of first and second nonwovens;

wherein the plurality of elastic strands has an Average-Strand-Spacing from about 0.25 mm to about 4 mm;

wherein the plurality of elastic strands has an Average-Dtex from about 10 to about 400;

wherein the plurality of elastic strands has an Average-Pre-Strain from about 50% to about 300%;

wherein a Peel-Strength between the first and second nonwovens is from about 1 N/cm to about 15N/cm;

wherein the first and second nonwovens are joined together via an adhesive;

wherein the adhesive overlaps and at least partially surrounds a portion of the plurality of elastic strands;

wherein a Dtex-to-Spacing-Ratio of the plurality of elastic strands is from about 65:1 to about 200:1; and wherein the elastomeric laminate forms at least a portion of a disposable absorbent article.

2. The elastomeric laminate according to claim 1, wherein a Dtex-to-Spacing-Ratio of the plurality of elastic strands is from about 65:1 to about 150:1.

3. The elastomeric laminate according to any of the preceding claims, further comprising at least one of:

a) a Percent-Contact-Area of at least one of: a) greater than about 10% at 100 um, b) greater than about 20% at 200 um, and c) greater than about 30% at 300 um;

b) a Force-Relaxation from about 5% to about 30%;

c) a Cantilever-Bending of less than about 40 mm;

d) a 2%-98%-Height-Value of <2.2 mm;

e) a Pressure-Under-Strand from about 0.1 to about 1 psi; and f) a Section-Modulus of from about 2 gf/mm to about 15 gf/mm.

4. The elastomeric laminate according to any of the preceding claims, wherein the plurality of elastic strands comprises from about 40 to about 1000 elastic strands.

5. The elastomeric laminate according to any of the preceding claims, wherein a third nonwoven is joined to the second nonwoven such that a tri-laminate is formed, and wherein an exterior surface of the third nonwoven and an exterior surface of the first nonwoven have different Percent-Contact-Areas.

6. The elastomeric laminate according to any of the preceding claims, further comprising at least two distinct texture zones, including a first texture zone comprising a first bonding arrangement, and including a second texture zone comprising a second bonding arrangement, wherein the first and second bonding arrangements are different.

7. The elastomeric laminate according to claim 6, wherein the first and second texture zones have different Percent-Contact-Areas.

8. The elastomeric laminate according to claim 5, wherein the third nonwoven is joined to the second nonwoven via adhesive.

9. The elastomeric laminate according to claim 5, wherein the third nonwoven is joined to the second nonwoven via heat, pressure, and ultrasonic bonds.

10. The elastomeric laminate according to claim 5, 8, or 9, wherein the third nonwoven is joined to the second nonwoven via laterally and/or longitudinally discrete bonds.

11. The elastomeric laminate according to claim 1, wherein the elastomeric laminate forms at least a portion of a belt, a chassis, a side panel, a topsheet, a backsheet, an ear panel, and combinations thereof.

12. The elastomeric laminate according to claim 1, wherein the elastomeric laminate has a Pressure-Under-Strand of from about 0.1 to about 1 psi.

13. The elastomeric laminate according to any of claims 5 and 8-10, wherein elastic strands are not present between the second and third nonwovens.

14. The elastomeric laminate according to any of the preceding claims, wherein the elastomeric laminate forms at least a portion of a disposable absorbent pant article comprising a front waist region and a back waist region;
wherein the front and back waist regions are joined together at seams to form a waist and leg opening;
wherein the front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams;
wherein the back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams;
wherein the front waist region comprises a front component region disposed between and including a front distal most elastic strand of the front waist region and a proximal most elastic strand of the front waist region;
wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;
wherein the front component region is then divided into 4 equal component sections, defined by first, second, and third component section lines, each disposed parallel to the lateral axis and disposed at 25%, 50% and 75% of the distance between the front distal component region line and front proximal component region line;
wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4;
wherein the disposable absorbent pant article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R.

15. The elastomeric laminate according to claim 14, wherein at least one of Front Sections 2 and 3 within Section L comprise a different bonding arrangement than Front Section 1 within Section L, and wherein at least one of Front Sections 2 and 3 within Section L comprise a different bonding arrangement than Front Section 4 within Section L.

16. The elastomeric laminate according to any of claims 14 and 15, wherein Front Sections 3 and 4 within Section L comprise a different bonding arrangement than Front Sections 3 and 4 within Section M, and wherein Section L comprises at least 3 different bonding arrangements within Front Sections 1-4.

17. The elastomeric laminate according to any of claims 14-16, wherein a portion of the chassis is contiguous with the Front Section 4 within Section M and has the same bonding arrangement and/or the same graphics pattern as Front Section 4 within M.

18. The elastomeric laminate according to any of claims 14-17, wherein Front Section 1 comprises 5% more or 5% fewer elastic strands than Front Section 2 within Section L, and wherein Front Section 2 comprises 5% more or 5% fewer elastic strands than Front Section 3 within Section L; and wherein the $\Delta E^*$ of Front Sections 1 and 2 within Section L is greater than about 7 and less than about 60.

19. The disposable absorbent pant article according to any of claims 14-18, wherein at least one discrete bond is disposed in portions at least three of Front Sections 1-4 within Section L.

20. The disposable absorbent pant article according to any of claims 14-19, wherein greater than 70% of the elastic strands in at least one of Sections L and R extends at least 50% of a lateral width (when the absorbent article is laid out flat) of the respective at least one of Sections L and R.

21. The elastomeric laminate of any of the preceding claims, wherein the elastomeric laminate forms at least a portion of a disposable absorbent pant article, and wherein the disposable absorbent pant article has an Application-Force of from about 900 gf to about 1600 gf, and a Sustained-Fit-Load-Force greater than 30% of the Application-Force, and wherein the pant article has a Sustained-Fit-Unload-Force greater than 25% of the Application-Force.

22. The disposable absorbent pant article according to claim 21, wherein the disposable absorbent pant article has an Application-Force of greater than about 1500 gf, a Sustained-Fit-Load-Force greater than 30% of the Application-Force, and a Sustained-Fit-Unload-Force greater than 30% of the Application-Force.

23. The disposable absorbent pant article according to any of claims 21-22, wherein the disposable absorbent pant article has an Application-Force of from about 900 gf to about 1600 gf, a Sustained-Fit-Load-Force from about 400 gf to about 800, and a Sustained-Fit-Unload-Force from about 325 to about 600 gf.

24. The elastomeric laminate according to any of the preceding claims, wherein the elastomeric laminate forms at least a portion of each disposable absorbent article of a plurality of disposable absorbent articles;

wherein each disposable absorbent article making up the plurality of disposable absorbent articles is bi-folded and arranged to form a stack of disposable absorbent articles;

wherein the stack of disposable absorbent articles is compressed along a compression axis and disposed within an interior space of a package such that the compression axis of the stack of disposable absorbent articles is oriented substantially along a width dimension of the package to form a packaged product; and wherein each of the folded disposable absorbent articles comprise a topsheet, a backsheet, and an absorbent core located between the topsheet and the backsheet;

wherein the packaged product exhibits an In-Bag-Stack-Height from 70 mm to 110 mm, and wherein the In-Bag-Stack-Height is the width of the package divided by the number of the disposable articles per stack and then multiplied by ten.

25. The elastomeric laminate according to claim 24, wherein the packaged product exhibits an In-Bag-Stack-Height from 75 mm to about 95 mm.

Example Claim Set 7

1. An absorbent article, comprising:
a chassis comprising a topsheet, a backsheet and an absorbent core disposed between the topsheet and the backsheet;
an elastomeric laminate joined to the chassis, the elastomeric laminate comprising a plurality of elastics between first and second nonwoven layers;
wherein the elastomeric laminate forms at least a portion of the absorbent article, and wherein the elastomeric laminate comprises a plurality of bonds overlapping at least a portion of elastics strands making up the plurality of elastics;
wherein the plurality of bonds consist of densified bonds, and wherein each of the plurality of bonds join the first and second nonwoven layers together via a densified portion;
wherein a first elastic strand of the plurality of elastics is overlapped by a first bond of the plurality of bonds;
wherein the first elastic strand of the plurality of strands comprises from about 2 to about 40 filaments;
wherein the first bond contacts at least a first and a second filament of the from about 2 to about 40 filaments, and wherein the first and second filaments are disposed longitudinally side-by-side of each other; and
wherein a Dtex-to-Nonwoven-Ratio of the first elastic strand and first and second nonwoven layers is from about 1.5 to about 10.

2. An absorbent article, comprising:
a chassis comprising a topsheet, a backsheet and an absorbent core disposed between the topsheet and the backsheet;
an elastomeric laminate joined to the chassis, the elastomeric laminate comprising a plurality of elastics between first and second nonwoven layers;
wherein the elastomeric laminate forms at least a portion of the absorbent article; wherein the first elastomeric laminate comprises a plurality of bonds overlapping at least a portion of elastics strands making up the plurality of elastics;
wherein the plurality of bonds consist of densified bonds, and wherein each of the plurality of bonds join the first and second nonwoven layers together via a densified portion;
wherein a first elastic strand of the plurality of elastics is overlapped by a first bond of the plurality of bonds;
wherein the first elastic strand of the plurality of strands comprises from about 2 to about 40 filaments;
wherein the first bond contacts at least a first and a second filament of the from about 2 to about 40 filaments, and wherein the first and second filaments are disposed longitudinally side by side of each other; and
wherein a Dtex-to-Spacing-Ratio of the first plurality of elastics is from about 65:1 to about 215:1.

3. An absorbent article, comprising:
a chassis comprising a topsheet, a backsheet and an absorbent core disposed between the topsheet and the backsheet;
a first elastomeric laminate joined to the chassis, the elastomeric laminate comprising a plurality of elastics between first and second nonwoven layers;
wherein the elastomeric laminate forms at least a portion of the absorbent article, wherein the elastomeric laminate comprises an adhesive overlapping at least a portion of elastics strands making up the first plurality of elastics;
wherein the adhesive joins the first and second nonwoven layers together;
wherein a first elastic strand of the first plurality of elastics is overlapped by the adhesive;
wherein the first elastic strand of the first plurality of strands comprises from about 2 to about 40 filaments; and
wherein the elastomeric laminate has a Dtex-to-Spacing-Ratio of the first plurality of elastics is from about 65:1 to about 215:1.

4. The absorbent article according to any of the preceding claims, wherein the first elastic strand has a Dtex from about 30 to about 400.

5. The absorbent article according to any of the preceding claims, wherein the first nonwoven layer has a basis weight from about 8 grams per square meter to about 45 grams per square meter; and wherein the second nonwoven layer has a basis weight from about 8 grams per square meter to about 45 grams per square meter.

6. The absorbent article according to any of the preceding claims, wherein the plurality of elastics comprise from about 40 to about 1000 elastic strands.

7. The absorbent article according to any of the preceding claims, wherein the plurality of elastics have an Average-Pre-Strain from about 50% to about 400%.

8. The absorbent article according to any of the preceding claims, wherein the plurality of elastics have an Average-Strand-Spacing from about 0.25 mm to about 4 mm.

9. The absorbent article according to claim 1, 2, or 4-8, wherein a Dtex-to-Spacing-Ratio of the f plurality of elastics is from about 65:1 to about 300:1.

10. The absorbent article according to any of the preceding claims, wherein the elastomeric laminate has a Section-Modulus of from about 3 gf/mm to about 12 gf/mm.

11. The absorbent article of claim 1, wherein the elastomeric laminate has a Void-Area-to-Strand-Area-Ratio of less than 1.

12. The absorbent article according to any of claims 1, 2, and 4-11, wherein the elastomeric laminate comprises adhesive.

13. The absorbent article according to any of claims 1, 2, and 4-11, wherein the absorbent article further comprises:
a second plurality of elastics between the first and second substrates;

wherein the second plurality of elastics comprises from about 10 to about 50 elastic strands;

wherein the second plurality of elastics have an Average-Strand-Spacing of about 3 mm or greater;

wherein an Average-Dtex of the second plurality of elastics is about 300 or greater; and wherein the second plurality are adhered to the first and second substrates via an adhesive.

14. The absorbent article according to any of the preceding claims, wherein the Pressure-Under-Strand of the plurality of elastics is from about 0.1 to about 1 psi.

15. The absorbent article of claim 1, wherein the elastomeric laminate has a Percent-Contact-Area of at least one of: a) greater than about 10% at 100 um, b) greater than about 20% at 200 um, and c) greater than about 30% at 300 um.

Example Claim Set 8

1. An absorbent article, comprising:
a lateral axis and a longitudinal axis;
a front waist region and a back waist region;
wherein the front and back waist regions are joined together at laterally opposed front and back side seams to form a waist and leg openings;
a chassis comprising a topsheet, a backsheet and an absorbent core disposed between the topsheet and the backsheet;
an elastomeric laminate comprising a plurality of elastics between first and second nonwoven layers, wherein the plurality of elastics comprises a first elastic strand and a second elastic strand;
the elastomeric laminate comprises a plurality of bonds overlapping at least a portion of elastic strands making up the plurality of elastics, and wherein each of the plurality of bonds join the first and second nonwoven layers together;
wherein the plurality of bonds comprise densified bonds comprising a densified portion, and wherein at least a portion of the densified bonds overlaps and at least partially surrounds the first and second elastic strands;
wherein the elastomeric laminate forms an article component;
wherein the front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams;
wherein the back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams;
wherein the front waist region comprises a front component region disposed between and including a front distal most elastic strand of the front waist region and a proximal most elastic strand of the front waist region;
wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;
wherein the front component region is then divided into 4 equal component sections, defined by first, second, and third component section lines, each disposed parallel to the lateral axis and disposed at 25%, 50% and 75% of the distance between the front distal component region line and front proximal component region line;
wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4; and
wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R;
wherein Front Section 1 comprises longitudinally extending bonds or bond regions transversely spaced from each other at an Average-Lateral-Bond-Spacing; and
wherein at least one of Front Sections 2 and 3 comprise longitudinally extending bonds or bond regions transversely spaced from each other at a different Average-Lateral-Bond-Spacing than Front Section 1.

2. An absorbent article, comprising:
a lateral axis and a longitudinal axis;
a front waist region and a back waist region;
wherein the front and back waist regions are joined together at laterally opposed front and back side seams to form a waist and leg openings;
a chassis comprising a topsheet, a backsheet and an absorbent core disposed between the topsheet and the backsheet;
an elastomeric laminate comprising a plurality of elastics between first and second nonwoven layers, wherein the plurality of elastics comprises a first elastic strand and a second elastic strand;
the elastomeric laminate comprises a plurality of bonds overlapping at least a portion of elastic strands making up the plurality of elastics, and wherein each of the plurality of bonds join the first and second nonwoven layers together;
wherein the plurality of bonds comprise densified bonds comprising a densified portion, and wherein at least a portion of the densified bonds overlaps and at least partially surrounds the first and second elastic strands;
wherein the elastomeric laminate forms an article component;
wherein the front waist region is a region between a) a proximal most front axis extending parallel to the lateral axis and passing through proximal most points of the laterally opposed front side seams; and b) a distal most front axis extending parallel to the lateral axis and passing through distal most points of the laterally opposed front side seams;
wherein the back waist region is a region between a) a proximal most back axis extending parallel to the lateral axis and passing through proximal most points of the laterally opposed back side seams; and b) a distal most back axis extending parallel to the lateral axis and passing through distal most points of the laterally opposed back side seams;
wherein the front waist region comprises a front component region disposed between and including a front distal most elastic strand of the front waist region and a proximal most elastic strand of the front waist region;

wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;

wherein the front component region is then divided into 4 equal component sections, defined by first, second, and third component section lines, each disposed parallel to the lateral axis and disposed at 25%, 50% and 75% of the distance between the front distal component region line and front proximal component region line;

wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4; and wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R;

wherein Front Section 1 comprises a first bonding arrangement in at least one of Sections L and R;

wherein Front Section 2 comprises a second bonding arrangement in at least one of Sections L and R;

wherein Front Section 3 comprises a third bonding arrangement in at least one of Sections L and R;

wherein Front Section 4 comprises a fourth bonding arrangement in at least one of Sections L and R;

wherein the first bonding arrangement is different than the fourth bonding arrangement; and wherein the first and fourth bonding arrangements are different than at least one of the second and third bonding arrangements.

3. An absorbent article, comprising:

a lateral axis and a longitudinal axis;

a front waist region and a back waist region;

a chassis comprising a topsheet, a backsheet and an absorbent core disposed between the topsheet and the backsheet;

an elastomeric laminate comprising a plurality of elastics between first and second nonwoven layers, wherein the plurality of elastics comprises a first elastic strand and a second elastic strand;

the elastomeric laminate comprises a plurality of bonds overlapping at least a portion of elastic strands making up the plurality of elastics, and wherein each of the plurality of bonds join the first and second nonwoven layers together;

wherein the plurality of bonds comprise densified bonds comprising a densified portion, and wherein at least a portion of the densified bonds overlaps and at least partially surrounds the first and second elastic strands;

wherein the elastomeric laminate forms an article component;

wherein the front waist region is a front ⅓ of the absorbent article;

wherein the back waist region is a back ⅓ of the absorbent article;

wherein the front waist region comprises a front component region disposed between and including a front distal most elastic strand of the front waist region and a proximal most elastic strand of the front waist region;

wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;

wherein the front component region is then divided into 4 equal component sections, defined by first, second, and third component section lines, each disposed parallel to the lateral axis and disposed at 25%, 50% and 75% of the distance between the front distal component region line and front proximal component region line;

wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4; and wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R;

wherein a Percent-Contact-Area in Front Section 1 within Section M is at least 15% different than a Percent-Contact-Area in Front Section 1 within Section L.

4. The absorbent article according to any of the preceding claims, wherein at least a portion of the plurality of the bonds or bond regions in Front Section 1 extend into Section 2.

5. The absorbent article according to any of the preceding claims, wherein at least a plurality of the bonds or bond regions in Section 2 extend into Section 3.

6. The absorbent article according to any of the preceding claims, wherein at least one bond making up the plurality of bonds extends longitudinally.

7. The absorbent article according to claim 6, wherein the at least one bond extending longitudinally is angled relative to the longitudinal axis.

8. The absorbent article according to any of claims 6 and 7, the at least one bond extending longitudinally is disposed in Front Section 1.

9. The absorbent article according to any of the preceding claims, wherein a bond or a bond region making up the plurality of bonds cooperate to form arcuate bonds or arcuate bond regions.

10. The absorbent article according to any of the preceding claims, comprising at least one of the following:
  a) the Average-Lateral-Bond-Spacing of Front Section 1 is from about 2 mm to about 15 mm;
  b) the Average-Lateral-Bond-Spacing of Front Section 2 is from about 2 mm to about 15 mm;
  c) the Average-Lateral-Bond-Spacing of Front Section 3 is from about 2 mm to about 15 mm; and
  d) the Average-Lateral-Bond-Spacing of Front Section 4 is from about 2 mm to about 15 mm.

11. The absorbent article according to claims any of the preceding claims, comprising at least one of the following:
  a) the longitudinally extending bonds or bond regions of Front Section 1 have an Average-Bond-Width from about 0.25 mm to about 5 mm;
  b) the longitudinally extending bonds or bond regions of Front Section 2 have an Average-Bond-Width from about 0.25 mm to about 5 mm;
  c) the longitudinally extending bonds or bond regions of Front Section 3 have an Average-Bond-Width from about 0.25 mm to about 5 mm; and
  d) the longitudinally extending bonds or bond regions of Front Section 4 have an Average-Bond-Width from about 0.25 mm to about 5 mm.

12. The absorbent article according to any of the preceding claims, wherein at least one of Front Sections 1, 2, 3, or 4 have an Emtec-TS7-Value of less than about 12 and an Emtec-TS750-Value of less than 60.

13. The absorbent article according to any of the preceding claims, wherein at least two of Sections 1, 2, 3, or 4 have an Air-Permeability of at least one of: a) greater than about 40 cubic meters/square meter/minute Air-Permeability at 0 gf/mm (no extension); b) greater than about 60 cubic meters/square meter/minute Air-Permeability at 3 gf/mm (slight extension); and c) greater than about 80 cubic meters/square meter/minute Air-Permeability at 7 gf/mm (moderate extension).

14. The absorbent article according to any of the preceding claims, wherein at least two of Sections 1, 2, 3, or 4 have a Percent-Contact-Area of at least one of: a) greater than about 13% at 100 um, b) greater than about 27% at 200 um, and c) greater than about 36% at 300 um.

Methods of the Present Disclosure
General Sample Preparation

The General Sample Preparation is intended to be used for methods that do not have specific sample preparation instructions within the method itself.

When collecting a specimen for testing, the specimen must contain a plurality of elastic strands and/or an elastic material, elastic scrim, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared. And, depending on the method, the portion or area of the stranded elastomeric laminate that should be tested will include a plurality of elastic strands between an area of first and second nonwovens, excluding any cut window (such as an elastic-free zone or area overlapping with the core or center chassis, and excluding any seams joining multiple article components together. Certain methods, however, may require testing of the absorbent article component, including cut windows and seams (e.g., Hip Hoop Test).

For pants, remove the side panels where they are attached to the chassis and separate the side panels at the side seams. Identify the elastic material that transverses the entire width of the panel. Identify the longitudinally distal most edge of the elastic material or elastic strand (closest to the waist edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs are tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final length to the nearest 1 mm. Calculate the elongation as (Final Length−Initial Length)/Initial length.

Cantilever-Bending

The Bending Length and Flexural Rigidity at the waist is measured as the Cantilever-Bending value as determined using ASTM Method D1388, Option A Cantilever Test with the modifications described below. The test apparatus described in the D1388 is used without modification. Articles are conditioned at 23° C.±2 C.° and 50%±2% relative humidity for 2 hrs. prior to analysis and then tested under the same environmental conditions.

The method is applied to a dry nonwoven laminate specimen dissected from an absorbent article rather than a fabric. For a belted article cut the belt at the side seams and remove the belt from the rest of the article using for example a cryogenic spay (e.g. Quick-Freeze, Miller-Stephenson Company, Danbury, Conn.). For pants, remove the side panel from the chassis and separate/cut along the side seam. The specimen is cut as a 25.4 mm strip parallel to the longitudinal axis of the product, starting at the waist and extending toward the crotch of the product. The length of the specimen can be less than the 200 mm cited in D1388, but must be at least 10 mm longer than the overhang length determined during testing. If the waist of the specimen is folded over, leave the fold intact for testing.

The specimen is placed on the platform with the garment facing side down and the end proximal to the waist as the leading edge. The bend is performed as described in D1388. Record the overhang length (OL) to the nearest 1 mm. Calculate the Bending Length (BL) as the Overhang Length divided by 2 and report to the nearest 1 mm. Take the specimen and measure the overhang length from the leading edge and cut across the strip. Measure and record the mass of the overhang piece and record to the nearest 0.001 g. From the mass and the dimensions of the overhang piece calculate the basis weight (BW) and record to the nearest 0.01 g/m².

Average-Strand-Spacing Using a ruler calibrated against a certified NIST ruler and accurate to 0.5 mm, measure the distance between the two distal strands within a section to the nearest 0.5 mm, and then divide by the number of strands in that section−1

Average-Strand-Spacing=d/(n−1) where n>1 report to the nearest 0.1 mm.

Pressure-Under-Strand (Also Referred to as Average-Pressure-Under-Strand)

Figure 21:
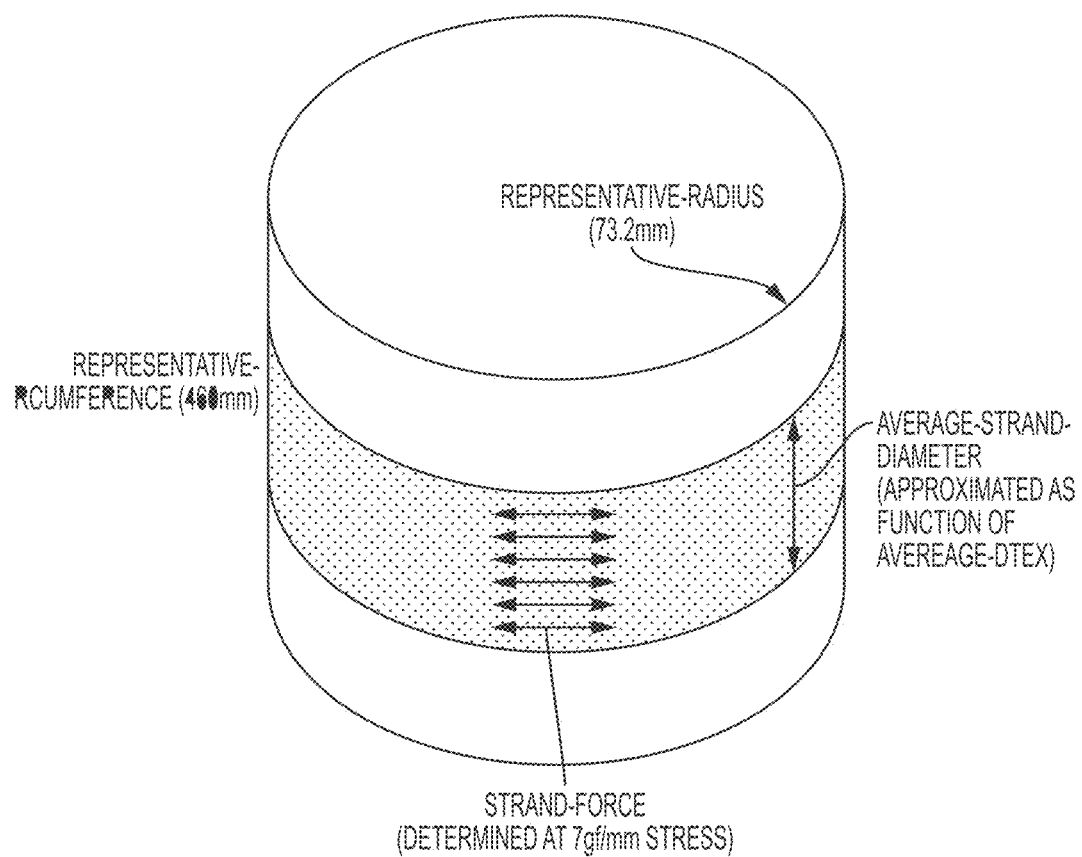
FIG. 21 illustrates Pressure-Under-Strand.

Defined as the average pressure imparted by each individual elastic strand of a section under specific conditions. These conditions are defined as (refer to FIG. 21):

The section is pulled to a Stress of 7 gf/mm (within a consumer preferred range of stresses as determined experimentally)

The section is pulled over a cylinder whose circumference is defined as a Representative-Circumference Where:

Pressure-Under-Strand (psi)=1.422*Strand-Force/ (2*Representative-Radius*Average-Strand-Diameter)

Representative-Radius (mm)=Representative-Circumference/(2*pi)

Representative-Circumference (mm)=460 mm

Stress (gf/mm)=(Summation of Strand-Forces within a section)/(Section-Width)

Section-Width (mm)=(Number of Elastics in the section)*Average-Strand-Spacing (mm)

Strand-Force (gf)=Strand-Strain (%)*0.046875*Average-Dtex

Strand-Strain (%)=strain in each elastic strand within a section

Average-Strand-Diameter (mm)=2*sqrt (Strand-Cross-Sectional-Area/pi)

Strand-Cross-Sectional-Area (mm²)=Average-Dtex/ Strand-Density/10,000

Strand-Density (g/cc)=1.15 g/cc (industry standard for PolyUrethaneUrea based spandex elastics)

Dtex (g/10,000m)=Standard textile unit of measure. Dtex is weight in grams for 10,000m of the material Average-Pre-Strain=Amount of stretch in elastic strands in a section prior to combining with substrate layer(s).

Maximum-Strain=Average-Pre-Strain. This is the maximum amount of strain each section can be pulled to. It cannot exceed the Average-Pre-Strain.

Maximum-Section-Force=Summation of each strand in the section pulled to the Maximum-Strain.

Section-Modulus

Figure 7:
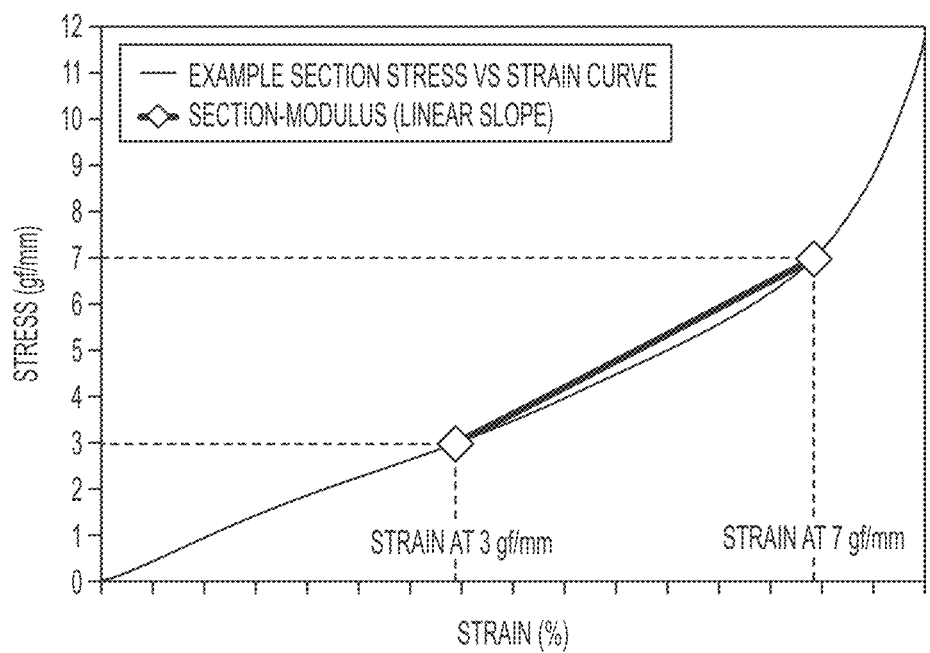
FIG. 7 illustrates the Section-Modulus.

Defined as the modulus of a given section. Section-Modulus (also referred to as modulus) is the linear slope of the stress vs strain data of the section between 3 gf/mm and 7 gf/mm (refer to FIG. 7). Section-Modulus is calculated as:

Section-Modulus=[7 gf/mm−3 gf/mm]/[(section strain at 7 gf/mm)−(section strain at 3 gf/mm)]

Where:

section strain at 7 gf/mm=7 gf/mm*(Average-Strand-Spacing)/DTEX-FACTOR section strain at 3 gf/mm=3 gf/mm*(Average-Strand-Spacing)/DTEX-FACTOR Average-Strand-Spacing (mm)=d/(n−1)

d is the distance (mm) between the two distal strands of the section n is the number of strands, when n>1

DTEX-FACTOR=37.5*Average-Dtex/800 (dtex as measured, specified)

Section-Modulus is reported in units of (gf/mm)

Average-Decitex (Average-Dtex)

The Average-Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastomeric laminates containing elastic fibers is often reported by manufacturers as part of a specification for an elastic fiber or an elastomeric laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g. Quick-Freeze, Miller-Stephenson Company, Danbury, Conn.), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-}Dtex = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross-sections exposed are mounted on an SEM sample holder in a relaxed state, sputter coated with gold, introduced into an SEM for analysis, and imaged at a resolution sufficient to clearly elucidate fiber cross-sections. Fiber cross-sections are oriented as perpendicular as possible to the detector to minimize any oblique distortion in the measured cross-sections. Fiber cross-sections may vary in shape, and some fibers may consist of a plurality of individual filaments. Regardless, the area of each of the three fiber cross-sections is determined (for example, using diameters for round fibers, major and minor axes for elliptical fibers, and image analysis for more complicated shapes), and the average of the three areas $a_k$ for the elastic fiber, in units of micrometers squared ($\mu m^2$), is recorded to the nearest 0.1 $\mu m^2$. The decitex $d_k$ of the kth elastic fiber measured is calculated by:

$$d_k = 10000 \text{ m} \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). For any elastic fiber analyzed, the experimentally determined $L_k$ and $d_k$ values are subsequently used in the expression above for Average-Dtex.

Surface Topography (Percent-Contact-Area, Rugosity-Frequency, Rugosity-Wavelength, and 2-98%-Height-Value)

In the Surface Topography Method, an elastomeric laminate specimen is removed from an absorbent article and extended across and in contact with the convex surface of a transparent horizontal cylindrical tubing segment, allowing the areal surface topology of the wearerfacing side of the laminate to be measured through the transparent tubing segment using optical profilometry. The 3D surface data are then sampled and processed to extract several parameters that describe the Percent-Contact-Area and height of the elastomeric laminate specimen surface as well as the frequency and wavelength of its associated rugosities. All sample preparation and testing is performed in a conditioned room maintained at about 23±2° C. and about 50±2% relative humidity, and samples are equilibrated in this environment for at least 24 hours prior to testing.

Sample Preparation

Each elastomeric laminate specimen extracted from an article is mounted on a horizontal tubing segment as described below. The tubing segment is cut from a sufficient length of optically clear, colorless cast acrylic cylindrical tubing having an outer diameter of 8.0 inches (203 mm) and a wall thickness of 0.1875 inches (4.76 mm). The segment has a dimension of 4.0 inches (102 mm) along an axis parallel to the central cylindrical axis of the parent tubing and a circumferential outer arc length of 5.5 inches (140 mm).

The elastomeric laminate specimen is extended in its primary stretch direction to a ratio corresponding to its extension at 3 g/mm (mass per linear width), where its width is determined by the Span Corrected Width metric as defined in the Caliper Test Method, and in which the extension is the average ratio measured under static load for the first ten seconds during which it is applied. In this extended state, the extended elastomeric laminate specimen is oriented such that its wearer-facing surface is in contact with the convex surface of the tubing segment and that the axis of extension is oriented around the circumference of the tubing segment. The extended laminate is secured at both ends to the transparent tubing segment such that the wearer-facing surface of the laminate is viewable through the concave side of the transparent tubing segment.

Five replicate elastomeric laminate specimens are isolated and prepared in this way from five equivalent absorbent articles for analysis.

3D Surface Image Acquisition

A three-dimensional (3D) surface topography image of the wearerfacing surface of the extended elastomeric laminate specimen is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with Mountains Map technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (XY) plane. This 3D data set can also be thought of as an image in which every pixel in the image there is associated an XY displacement, and the value of the pixel is the recorded Z-axis height value. The system has a field of view of 60×45 mm with an XY pixel resolution of approximately 37 microns, and a height resolution of 0.5 microns, with a total possible height range of 32 mm.

The instrument is calibrated according to manufacturer's specifications using the calibration plates for lateral (XY plane) and vertical (Z-axis) available from the vendor.

The elastomeric laminate specimen mounted on the transparent tubing segment is positioned with the concave surface of the tubing segment surface facing upward so that the wearerfacing surface is facing upward and visible through the transparent material. The tubing segment is placed on a stand such that the convex (downward-facing) specimen surface in the region to be analyzed is suspended freely and not resting on a surface. The tubing segment is oriented such that its circumferential direction (that direction or axis along which the laminate is stretched) is centered and perpendicular relative to the long axis of the camera's field of view (or either of the central axes if the field of view is square). A 3D surface topology image of the elastomeric laminate specimen is collected by following the instrument manufacturer's recommended measurement procedures, which may include focusing the measurement system and performing a brightness adjustment. No pre-filtering options are used. The collected height image file is saved to the evaluation computer running the surface texture analysis software.

If the field of view of the 3D surface topography measurement system exceeds the evaluation region on the elastomeric laminate specimen the image may be cropped to remove extraneous areas and retain a rectangular field of view of the relevant portion, while maintaining the XY resolution, prior to performing the analysis.

3D Surface Image Analysis

The 3D surface topography image is opened in the surface texture analysis software. The following filtering procedure is then performed on each image: 1) removal of invalid or non-measured points; 2) a 5×5 pixel median filter to remove noise; 3) a 5×5 pixel mean filter to smooth the surface; and 4) subtraction of a two-dimensional, second-order polynomial (determined via least-squares fit of the surface topology image) to remove the general form and flatten the surface. The second-order polynomial is defined by the following equation:

$$f(x,y) = c_1 + c_2 x + c_3 y + c_4 x^2 + c_5 y^2 + c_6 xy$$

Each data set that has been processed to this point as described above is referred to as a "preprocessed specimen data set." The highest points of the resulting topology image correspond to those areas in contact with the convex surface of the tubing segment, and the lowest points are those points most distal below the convex surface of the tubing segment.

Percent-Contact-Area and 2-98%-Height-Value

For each of the 3D surface topography images of the five replicate specimens, the following analysis is performed on preprocessed specimen data sets. The Percent-Contact-Area and 2-98% Height measurements are derived from the Areal Material Ratio (Abbott-Firestone) curve described in the ISO 13565-2:1996 standard extrapolated to surfaces. This curve is the cumulative curve of the surface height distribution histogram versus the range of surface heights measured. A material ratio is the ratio, expressed as a percent, of the area corresponding to points with heights equal to or above an intersecting plane passing through the surface at a given height, or cut depth, to the cross-sectional area of the evaluation region (field of view area). The height at a material ratio of 2% is initially identified. A cut depth of 100 µm below this height is then identified, and the material ratio at this depth is recorded as the Percent-Contact-Area at 100 µm. This procedure is repeated at a cut depth of 200 µm and 300 µm below the identified height at a material ratio of 2%, and the material ratio at these depths are recorded as the Percent-Contact-Area at 200 µm and the Percent-Contact-Area at 300 µm respectively. All of the Percent-Contact-Area values are recorded to the nearest 0.1%. The 2-98%-Height-Value of the specimen surface is defined as the difference in heights between two material ratios that exclude a small percentage of the highest peaks and lowest valleys. The 2-98% Height of the specimen surface is the height between the two cutting depths corresponding to a material ratio value of 2% to the material ratio of 98%, and is recorded to the nearest 0.01 mm.

Rugosity-Frequency and Rugosity-Wavelength

The preprocessed 3D surface topology images for each specimen are subjected to Fourier transform spatial frequency analysis to determine Rugosity-Frequency and Rugosity-Wavelength.

Each 3D surface topology image is deconstructed into individual line profiles by isolating each entire row of single data points that run in the dimension parallel to the elastic strands (if present and evident) of the elastomeric laminate, or, more generally, perpendicular to the rugosity exhibited by the elastomeric laminate in the relaxed state. These line profiles are therefore data sets in the form of height (in millimeters) versus distance (in millimeters).

For each replicate 3D surface topology image deconstructed, each line profile is mean centered, and a fast Fourier transform (FFT) is applied to calculate the frequency amplitude spectrum of each line profile. The Fourier transform amplitude versus spatial frequency spectra of all extracted line profiles are averaged, and the resulting average amplitude versus spatial frequency spectrum is defined as $F(1/d)$, where $1/d$ is reciprocal distance in units of $mm^{-1}$. Finally, the function $P(1/d) = d \times F^2(1/d)$, the spatial frequency power spectral density with a prefactor of distance d to correct for the expected 1/d noise, is plotted versus 1/d. The value of reciprocal distance 1/d at which P(1/d) is at a maximum is defined as the Rugosity-Frequency and is recorded in units of $mm^{-1}$ to the nearest 0.001 $mm^{-1}$. The reciprocal of the Rugosity-Frequency is defined as the Rugosity-Wavelength and is recorded in units of mm to the nearest 0.01 mm.

Reporting of Method Parameters

After the 3D surface image analysis described above is performed on 3D surface topology images of all five specimen replicates, the following output parameters are defined and reported. The arithmetic mean of all five Percent-Contact-Area at 100 µm measurements is defined as the Average Percent-Contact-Area at 100 µm and is reported to the nearest 0.1%. The arithmetic mean of all five Percent-Contact-Area at 200 µm measurements is defined as the Average Percent-Contact-Area at 200 µm and is reported to the nearest 0.1%. The arithmetic mean of all five Percent-Contact-Area at 300 µm measurements is defined as the Average Percent-Contact-Area at 300 µm and is reported to the nearest 0.1%. The arithmetic mean of all five 2-98% Height measurements is defined as the Average 2-98% Height and is reported in units of mm to the nearest 0.01 mm. The arithmetic mean of all five Rugosity-Frequency measurements is defined as the Average Rugosity-Frequency and is reported in units of mm to the nearest 0.001 $mm^{-1}$. The arithmetic mean of all five Rugosity-Wavelength measurements is defined as the Average Rugosity-Wavelength and is reported in units of mm to the nearest 0.01 mm.

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Force-Relaxation-Over-Time

The Force-Relaxation-Over-Time of a specimen is measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions. Prepare a sample size such that it enables a gauge length of 25.4 mm (parallel to the elastic stretch) at a width of 12.7 mm.

Program the tensile tester to perform an elongation to determine the engineering strain at which the tensile force reaches 0.0294 N/mm.

Prepare and condition a second sample as described above for the Force-Relaxation-Over-Time over time test. The test is performed on the same equipment as described above. It is performed at a temperature of 37.8° C. Extend the sample to the strain as determined above. Hold the sample for 10 hours and record the force at a rate of 100 Hz throughout the experiment a chart showing the data for an extruded strand prior art product and an inventive elastomeric laminate comprising beam elastic as described herein is show in FIG. 8.

Air-Permeability

Air-Permeability is tested using a TexTest FX3300 Air-Permeability Tester (available from Advanced Testing Instruments, Greer, S.C.) with a custom made 1 $cm^2$ aperture (also available from Advanced Testing Instruments). Standardize the instrument according to the manufacturer's procedures. Precondition the articles at about 23° C.±2 C.° and about 50%±2% relative humidity for two hours prior to testing. Articles are preconditioned at 23° C.±2 C.° and 50%±2% relative humidity for two hours prior to testing and all testing is performed under the same environmental conditions.

The test is intended for use with stretch laminate of the sample article such as belts, side panels, ears, waist bands, etc. Stretch components are removed from the article using, for example, cryogenic spay (e.g. Quick-Freeze, Miller-Stephenson Company, Danbury, Conn.) or cutting. Specimens are dissected from the laminate avoiding material seams or other structures not integral to the stretch. Stretch laminates are harvested from 3 articles for each test set.

Cut a specimen from the stretch region of the laminate that is 25 mm by 25 mm. For a specimen with unevenly spaced strands, a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Using the Span Corrected Width determine the elongation need to achieve 3 g/mm SCW and 7 g/mm SCW by hanging weights on a substantially similar specimen and measuring the elongation.

The on the instrument's air pressure is set for 125 Pa. Place a specimen in its relaxed state with the wearer-facing side downward on the port plate. The stretch region must completely cover the instruments port. Close the sample ring and adjust the measuring range until it is within specification. Record the Air-Permeability for the un-extended specimen to the nearest 0.1 m³/m²/min.

Select one of the edges of laminate that is perpendicular to the machine direction (MD) and secure it to the port plate of the instrument using adhesive tape. The specimen is then extended in the machine direction to a length equivalent to 3 gf/mm and secured. The stretch region must completely cover the port. Close the sample ring and adjust the measuring range until the it is within specification. Record the Air-Permeability for the 3 g/mm to the nearest 0.1 m³/m²/min. Repeat in like fashion for the 7 g/mm extension and record the Air-Permeability for the 3 g/mm to the nearest 0.1 m³/m²/min.

A total of five measures are made on replicate specimens for each stretch laminate. Calculate and report the arithmetic average for Air-Permeability at the 0 gf/mm, 3 gf/mm, and 7 gf/mm elongation and report each to the nearest 0.1 m3/m2/min.

PEEL-STRENGTH (Value from the "180 Degree Peel Test Method")

Tensile properties are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced flat grips, wider than the width of the test specimen. Air pressure supplied to the jaws should be sufficient to prevent specimen slippage. All testing is performed in a conditioned room maintained at about 23° C.±2 C.° and about 50%±2% relative humidity.

Program the tensile tester to perform a 180 degree peel test. Raise the crosshead at a rate of 150 mm/min until the laminate separates. Return the crosshead to its starting position. Force and extension data are collected at a rate of 100 Hz throughout the experiment.

Condition samples at about 23° C.±2 C.° and about 50%±2% relative humidity for at least two hours before testing. Prepare an elastic laminate as described in General Sample Preparation from above corresponding locations on five (5) replicate products. Trim samples to 60 mm long by 25.4 mm wide. If the sample is not 60 mm long the length can be adjusted. Repeat in like fashion for all five (5) specimen strips Set the gage length to 25.4 mm using a calibrated caliper block and zero the crosshead. Manually peel 15 mm of one end of the specimen strip apart. Place the first of the peeled tail into the upper grip and close. Place the second tail into the lower grip and close. The specimen should have minimal slack but less than 0.05 N of force on the load cell. Start the test program and collected data.

From the Force (N) versus Extension (mm) curve calculate the average force between the initiation of the peel and the termination of the peel and record to the nearest 0.01 N. Repeat in like fashion for each of the 4 remaining sample strips. Calculate an average for the 5 samples and report as the Peel Force to the nearest 0.01 N/cm.

Color-Contrast ("ΔE*") (Value from the Strand Color Contrast Measurement)

Small scale color measurements of elasticized laminate where the elastics strands are significantly different in color from the regions between the strands can be made from calibrated scanned images. These paired color measurements are then used to calculate a Color-Contrast for the laminate.

A flatbed scanner capable of scanning a minimum of 24 bit color at 1200 dpi is used. For calibration, the automatic color management of the scanner must be disabled. If it cannot, the scanner is not appropriate for this application. A suitable scanner is an Epson Perfection V750 Pro from Epson America Inc., Long Beach Calif., or equivalent. The scanner is calibrated against a color reflection target compliant to a color standard (such as ANSI method ITS.7/2-1993, or equivalent) using color management software (a suitable package is MonacoEZColor available from X-Rite Grand Rapids, Mich.) to construct an ICC scanner profile. The resulting calibrated scanner profile is opened within an imaging program that supports sampling in CIE L*a*b* (a suitable program is Photoshop available from Adobe Systems Inc., San Jose, Calif.) to measure the color of elastic strands within a scanned image of the sample.

Using the calibration software, acquire a scan of the color standard in 24 bit color and build an ICC profile following the vender's instructions. Save the profile for use in the image analysis software. Prepare a sample of the elastic laminate that is at least 25.4 mm in the CD as described under General Sample Preparation above from a corresponding location on three replicate products. Secure a sample at a length equivalent to 7 g/mm SCW on the scanner glass. Back the sample with a white plate (herein white is defined as L*>95, −2<a*<2, and −2<b*<2) and acquire a 25 mm square, 24 bit color image at 1200 dpi. Open the image in the image analysis program and select a site over a strand bundle. Select L*a*b* as the color mode. Adjust the diameter of the "eyedropper" tool to a diameter slightly smaller than the width of the strand and take a L*a*b* reading overtop the strand. Take a second L*a*b* reading at an adjacent site between strands where the laminate is not ultrasonically bonded. In like fashion, acquire 19 more measurement pairs spaced throughout the image. Calculate the ΔE* value between each pair using the following equation:

$$\Delta E^* = \sqrt{(L_1^* - L_2^*)^2 + (a_1^* - a^*)^2 + (b_1^* - b_2^*)^2}$$

Acquire 20 paired readings from the next two replicate samples and calculate the ΔE* for each pair. Calculate the average of the 60 ΔE* values and report as the Strand Contrast to the nearest 0.01 units.

EMTEC (Including Emtec-TS7-Value and Emtec-TS750-Value) (Also Called the Emtec Test)

The Emtec Test is performed on a portion of interest of elastic laminate material. In this test, TS7, TS750, and D values are measured using an Emtec Tissue Softness Analyzer ("Emtec TSA") (Emtec Electronic GmbH, Leipzig, Germany) interfaced with a computer running Emtec TSA software (version 3.19 or equivalent). The Emtec TSA includes a rotor with vertical blades which rotate on the test sample at a defined and calibrated rotational speed (set by manufacturer) and contact force of 100 mN. Contact between the vertical blades and the test sample creates vibrations both in the blades and in the test sample, and the resulting sound is recorded by a microphone within the instrument. The recorded sound file is then analyzed by the Emtec TSA software to determine TS7 and TS750 values. The D value is a measure of sample stiffness and is based on the vertical distance required for the contact force of the blades on test sample to be increased from 100 mN to 600 mN. The sample preparation, instrument operation, and testing procedures are performed according the instrument manufacturer's specifications.

Sample Preparation

A test sample is prepared by cutting a square portion of interest from an absorbent article. Test samples are cut to a length and width of no less than about 90 mm and no greater than about 120 mm to ensure the sample can be clamped into the Emtec TSA instrument properly. If the construction of the laminate is such that the elastic strands are able to move independently of the nonwovens when the laminate is cut (evidenced, for example, by the retraction of the elastic strands into a cut sample when it is stretched), the laminate is thermally welded (prior to cutting out the sample) perpendicularly to the elastic strands and just inside the intended edge of the sample so as to immobilize the ends of the elastic strands. (If an absorbent does not contain a sufficiently large area of the substrate of interest to extract a sample of the size specified above, it is acceptable to sample equivalent material from roll stock, similarly thermally welding around the perimeter of the cut sample if needed.) Test samples are selected to avoid unusually large creases or folds within the testing region. Six substantially similar replicate samples are prepared for testing.

All samples are equilibrated at TAPPI standard temperature and relative humidity conditions (23° C.±2 C.° and 50%±2%) for at least 2 hours prior to conducting the Emtec TSA testing, which is also conducted under TAPPI conditions.

Testing Procedure

The instrument is calibrated according to the Emtec's instructions using the 1-point calibration method with the appropriate reference standards (so-called "ref.2 samples," or equivalent, available from Emtec).

A test sample is mounted in the instrument with the surface of interest facing upward, and the test is performed according to the manufacturer's instructions. The software displays values for TS7, TS750, and D when the automated instrument testing routine is complete. TS7 and TS750 are each recorded to the nearest 0.01 dB $V^2$ rms, and D is recorded to the nearest 0.01 mm/N. The test sample is then removed from the instrument and discarded. This testing procedure is performed individually on the corresponding surfaces of interest of each of the six of the replicate samples.

The value of TS7, TS750, and D are each averaged (arithmetic mean) across the six sample replicates. The average values of TS7 and TS750 are reported to the nearest 0.01 dB $V^2$ rms. The average value of D is reported to the nearest 0.01 mm/N. HIP-HOOP (value from the Hip Hoop Test or the Whole Outer Cover Waist Opening Circumference Extension Force Test)

This method is a 2 cycle hysteresis test, with is used for determining: the maximum extension of the product waist at a stress of 18.2 gf/mm (and maximum strain); the Application-Force (and Application-Stress); the Sustained-Fit Load-Force (and Sustained-Fit-Load-Stress); and Sustained-Fit-Unload-Force (and Sustained-Fit-Unload-Stress) of a disposable article with a continuous waist. The article can be a pant or a closable article that has been pre-fastened.

Whole product waist opening circumference extension forces (and stresses) are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 10% to 90% of the limit of the cell. Initial waist circumference is measured using a flexible tape measure. The accuracy of the tape is either traceable to NIST or other standards organization, or verified for accuracy against a traceable ruler. All testing is performed in a conditioned room maintained at about 23° C.±2 C.° and about 50%±2% relative humidity. Samples are condition under the same conditions for 2 hours prior to testing. Five replicate articles are analyzed and the results averaged.

For this test, a custom hook fixture 1510 (FIG. 22) is used. The hook fixture 1510 comprises a pair of J-shaped hooks 1512, each with an attachment member 1514 designed to mount to the tester's stationary base and upper movable crosshead (via the load cell). Each J-shaped hook 1512 has a substantially circular cross-sectional shape with a diameter, D, of about 1 cm. The hooks 1512 have a width, W, of about 25 cm. If the elastic side panel to be tested extends past the end of the engaging arm, or bunches at the J curve of the fixture, W is lengthened to accommodate the longer side panel. The hooks 1512 exhibit a smooth curvature to form the two engaging arms 1516 that are perpendicular to the attachment member 1514. Each attachment member is fitted with a locking collar 1513 which fixes the engagement arms 1516 of the hooks parallel to one another and perpendicular to the pull axis of the tensile tester.

The stress in the product waist is calculated by first determining the narrowest longitudinal length within the closed waist hoop. For a disposable article with a continuous waist, this is typically the length of the side seam. For a pant that is prefastened, this is typically the longitudinal length of the attaching fastener. For example, a closed form product with the narrowest longitudinal length within the hoop being an 11 cm side panel, the maximum stress to pull to, 18.2 gf/mm, would be 2000 gf.

Figure 22:
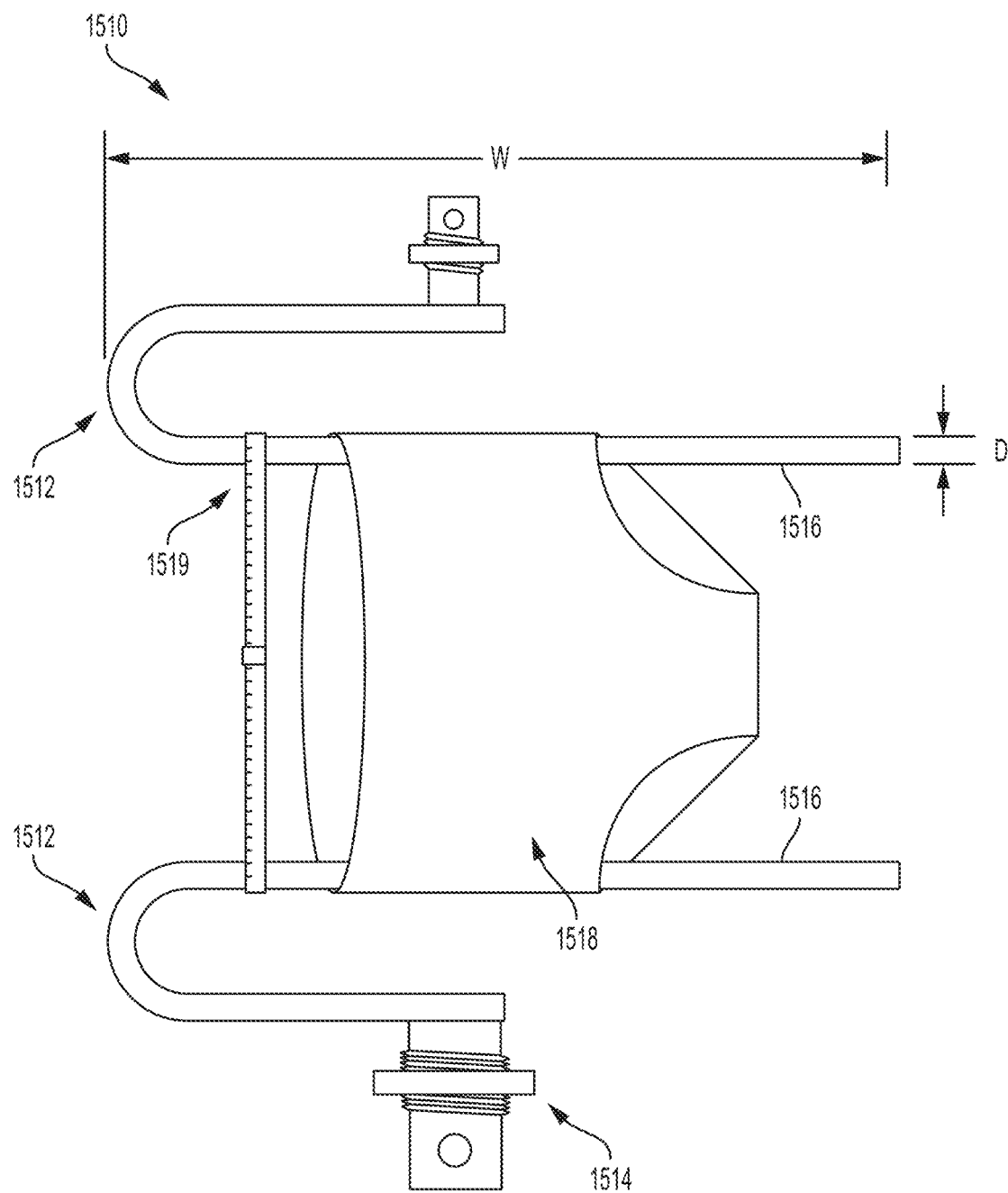
FIG. 22 is a front view of a hook fixture for performing the Hoop Extension Test

Manually move the crosshead up. Hang the article from the top engaging arm 1516 such that the article is solely supported from the top arm, and zero the load cell. Lower the top engaging arm so that the article 1518 can be slid onto the engaging arms 1516 with the elastic sides centered along the pull axis of the tester, as illustrated in FIG. 22. Adjust the engaging arms 1516 to remove any slack from the article, but ensure that no more than 5 grams of force is measured on the load cell. Zero the crosshead. With a flexible measuring tape, graduated in mm, measure the relaxed waist opening circumference by wrapping the tape 1519 around the engaging arms 1516 proximate to the waist opening of the article of FIG. 22. Record the Initial Circumference to the nearest 1 mm. Remove the measuring tape from the arms 1516.

The test consists of 7 distinct steps.

1. This is called the first load. Program the tensile tester to move the crosshead up at a rate of 254 mm/min. Extend the crosshead until a stress of 18.2 gf/mm is reached. At this point, record the extension as the maximum extension. The maximum strain is also calculated using the Initial Circumference. maximum strain=(maximum extension)/(Initial Circumference/2).
2. Hold at this crosshead extension for 30 seconds.
3. This is called the first unload. Return the crosshead at a rate of 254 mm/min to the starting position.
4. Hold at this crosshead extension for 60 seconds.
5. This is called the second load. Move the crosshead up at a rate of 254 mm/min. Extend until a stress of 18.2 gf/mm is reached.
6. Hold at this crosshead extension for 30 seconds.
7. This is called the second unload. Return the crosshead at a rate of 254 mm/min to the starting position.

Collect data at an acquisition rate of 100 Hz throughout the experiment.

In like fashion repeat for the remaining four replicates.

Maximum Strain (Maximum Extension)=(maximum extension at 18.2 gf/mm)/(Initial Circumference/2)

Application-Strain (Application Extension)=Maximum Strain multiplied by 80%.

Application-Force (Application-Stress)=Force (gf/mm) (Stress) at Application-Strain in the first load (step 1 of Hip Hoop test).

Sustained-Fit-Load-Force (Sustained-Fit-Load-Stress) =Force (gf/mm) (Stress) at (Maximum Strain/2) in the second load (step 5 of Hip Hoop test) cycle.

Sustained-Fit-Unload-Force (Sustained-Fit-Unload-Stress)=Force (gf/mm) (Stress) at (Maximum Strain/2) in the second unload (step 7 of Hip Hoop test) cycle.

Melting-Point

Melting point of a polymer specimen can be determined by Differential Scanning calorimetry (DSC) using ASTM 794, Standard Test Method for Melting and Crystallization Temperatures by Thermal Analysis. Melting point is reported as $T_p$ (melting peak) from the endothermic curve to the nearest 0.1° C.

In-Bag-Stack-Height

The In-Bag-Stack-Height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 20). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag-Stack-Height"=(package width/absorbent article count per stack)×10 is calculated and reported to within ±0.5 mm.

CONCLUSION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An elastomeric laminate, comprising:
a plurality of elastic strands between of first and second nonwovens;
wherein the plurality of elastic strands has an Average-Strand-Spacing from about 0.25 mm to about 4 mm;
wherein the plurality of elastic strands has an Average-Dtex from about 10 to about 400;
wherein the plurality of elastic strands has an Average-Pre-Strain from about 50% to about 300%; and
wherein a Dtex-to-Nonwoven-Basis-Weight-Ratio of a first elastic strand and of at least one of the first and second nonwovens is from about 1.5 to about 15.

2. The elastomeric laminate of claim 1, wherein a first elastic strand of the first plurality of elastic strands comprises from about 2 to about 40 filaments, including first and second filaments, wherein the first and second filaments are disposed cross-sectionally side-by-side of each other, and wherein at least one discrete bond surrounds at least the first and second filaments.

3. The elastomeric laminate of claim 2, wherein the at least one discrete bond overlaps at least 10 elastic strands of the first plurality of elastic strands.

4. The elastomeric laminate of claim 3, wherein the at least one discrete bond surrounds at least 20 filaments of the at least 10 elastic strands.

5. The elastomeric laminate of claim 1, wherein the plurality of elastic strands has an Average-Strand-Spacing from about 0.5 mm to about 2.5 mm.

6. The elastomeric laminate of claim 1, wherein a Dtex-to-Spacing-Ratio of the plurality of elastic strands is from about 65:1 to about 150:1.

7. The elastomeric laminate of claim 1, wherein the plurality of elastic strands comprises at least 100 elastic strands, and wherein each of the at least 100 elastic strands comprises at least 3 filaments.

8. The elastomeric laminate of claim 1, further comprising at least one of:
   a) a Percent-Contact-Area of at least one of: a) greater than about 10% at 100 um, b) greater than about 20% at 200 um, and c) greater than about 30% at 300 um;
   b) a Force-Relaxation-Over-Time from about 5% to about 30%;
   c) a Cantilever-Bending of less than about 40 mm;
   d) a 2%-98%-Height-Value of <2.2 mm;
   e) a Pressure-Under-Strand from about 0.1 to about 1 psi; and
   f) a Section-Modulus of from about 2 gf/mm to about 15 gf/mm.

9. The elastomeric laminate of claim 1, wherein the elastomeric laminate forms at least a portion of at least one of the group consisting of a belt, a chassis, a side panel, a topsheet, a backsheet, an ear panel, and combinations thereof, wherein the plurality of elastic strands comprises from about 40 to about 1000 elastic strands, wherein each of the elastic strands making up the about 40 to about 1000 elastic strands are overlapped by and partially surrounded by a plurality of discrete bonds.

10. The elastomeric laminate of claim 1, wherein a third nonwoven is joined to the second nonwoven such that a tri-laminate is formed, and wherein an exterior surface of the third nonwoven and an exterior surface of the first nonwoven have different Percent-Contact-Areas.

11. The elastomeric laminate of claim 10, wherein the third nonwoven is joined to the second nonwoven via adhesive.

12. The elastomeric laminate of claim 1, wherein the first nonwoven layer has a basis weight from about 6 grams per square meter to about 35 grams per square meter, and wherein the second nonwoven layer has a basis weight from about 6 grams per square meter to about 35 grams per square meter.

13. The elastomeric laminate of claim 1, wherein a Peel-Strength between the first and second nonwovens is from about 1 N/cm to about 15N/cm.

* * * * *